United States Patent
Finlay et al.

(10) Patent No.: US 11,884,671 B2
(45) Date of Patent: Jan. 30, 2024

(54) PURINONE COMPOUNDS AND THEIR USE IN TREATING CANCER

(71) Applicants: ASTRAZENECA AB, Södertälje (SE); CANCER RESEARCH TECHNOLOGY LIMITED, London (GB)

(72) Inventors: Maurice Raymond Verschoyle Finlay, Cambridge (GB); Frederick Woolf Goldberg, Cambridge (GB); Martin Richard Howard, Cambridge (GB); Attilla Kuan Tsuei Ting, Cambridge (GB)

(73) Assignees: AstraZeneca AB, Södertälje (SE); Cancer Research Technology Limited, London (GB)

( * ) Notice: Subject to any disclaimer, the term of this patent is extended or adjusted under 35 U.S.C. 154(b) by 642 days.

(21) Appl. No.: 16/973,862

(22) PCT Filed: Jun. 14, 2019

(86) PCT No.: PCT/EP2019/065686
§ 371 (c)(1),
(2) Date: Dec. 10, 2020

(87) PCT Pub. No.: WO2019/238929
PCT Pub. Date: Dec. 19, 2019

(65) Prior Publication Data
US 2021/0171525 A1    Jun. 10, 2021

Related U.S. Application Data

(60) Provisional application No. 62/685,325, filed on Jun. 15, 2018.

(51) Int. Cl.
| | |
|---|---|
| *C07D 473/32* | (2006.01) |
| *A61K 9/127* | (2006.01) |
| *A61K 31/437* | (2006.01) |
| *A61K 31/502* | (2006.01) |
| *A61K 31/522* | (2006.01) |
| *A61K 31/5377* | (2006.01) |
| *A61K 31/704* | (2006.01) |
| *A61N 5/10* | (2006.01) |

(52) U.S. Cl.
CPC ............ *C07D 473/32* (2013.01); *A61K 9/127* (2013.01); *A61K 31/437* (2013.01); *A61K 31/502* (2013.01); *A61K 31/522* (2013.01); *A61K 31/5377* (2013.01); *A61K 31/704* (2013.01); *A61N 5/10* (2013.01); *C07B 2200/13* (2013.01)

(58) Field of Classification Search
None
See application file for complete search history.

(56) References Cited

FOREIGN PATENT DOCUMENTS

| WO | 2009024824 A1 | 2/2009 |
|---|---|---|
| WO | 2018114999 A1 | 6/2018 |

OTHER PUBLICATIONS

International Search Report dated Sep. 2, 2019, and Written Opinion dated Sep. 2, 2019, for International Application PCT/EP2019/065686.

*Primary Examiner* — Nannette Holloman

(57) ABSTRACT

The specification generally relates to compounds of Formula (I): (I) and pharmaceutically acceptable salts thereof, where R, $A^1$, $A^2$ and $A^3$ have any of the meanings defined herein. The specification also relates to the use of such compounds and salts thereof to treat or prevent DNA-PK mediated disease, including cancer. The specification further relates to pharmaceutical compositions comprising such compounds and salts; kits comprising such compounds and salts; methods of manufacture of such compounds and salts; intermediates useful in the manufacture of such compounds and salts; and to methods of treating DNA-PK mediated disease, including cancer, using such compounds and salts.

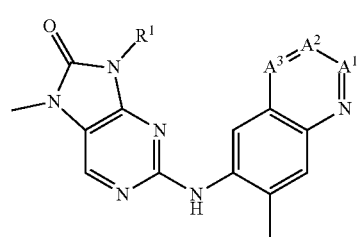

22 Claims, 5 Drawing Sheets

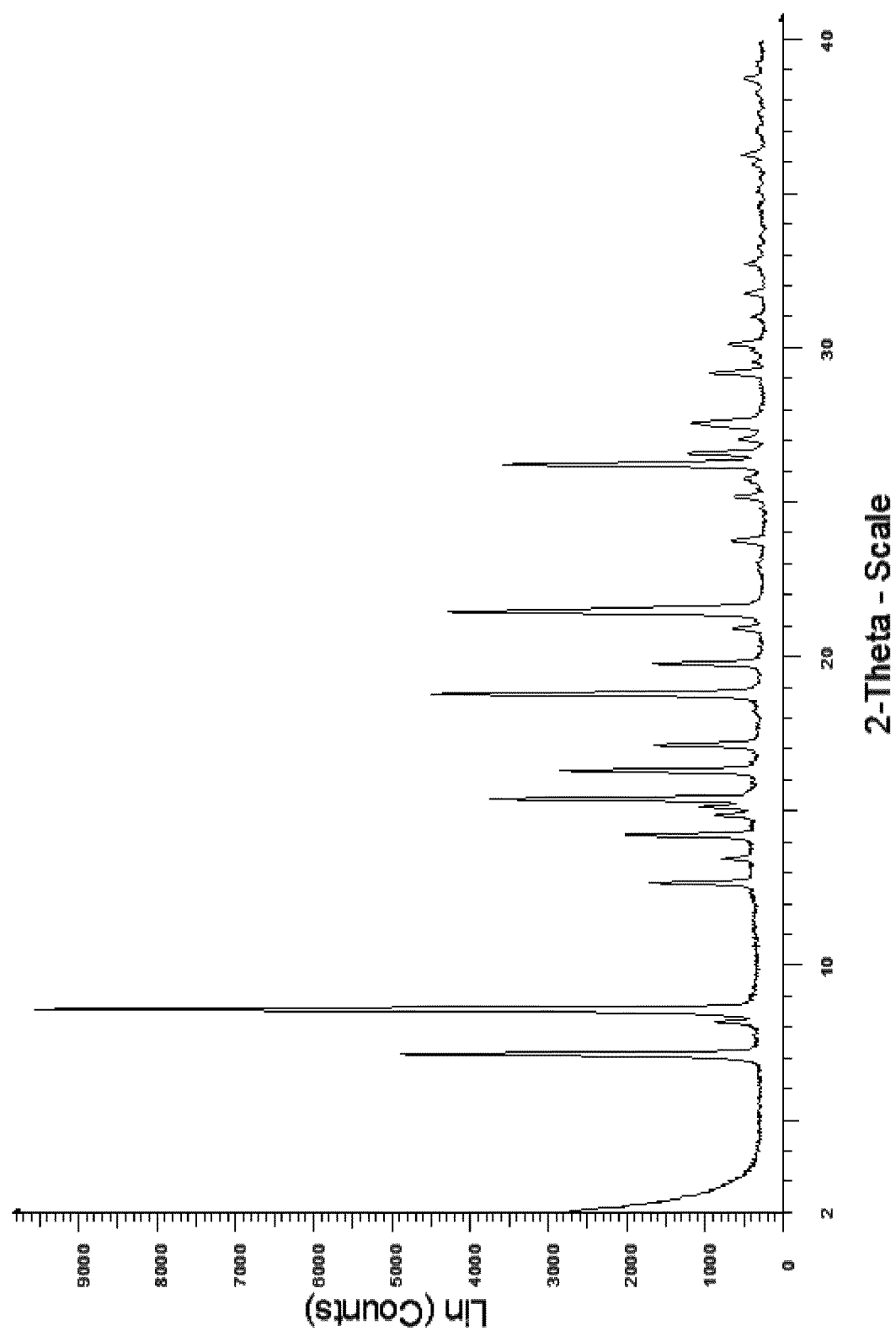
Figure 1: X-Ray Powder Diffraction Pattern Compound A Form A

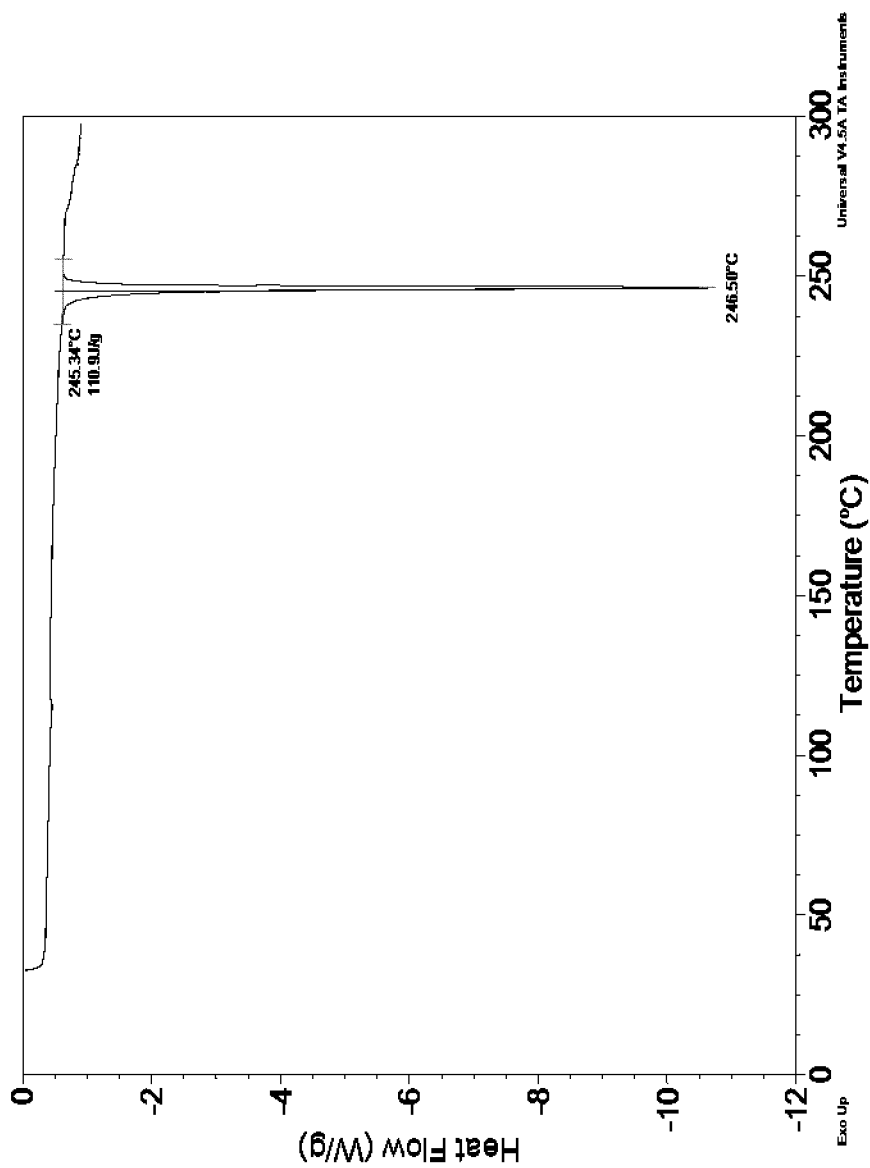
Figure 2: DSC thermogram of Compound A Form A

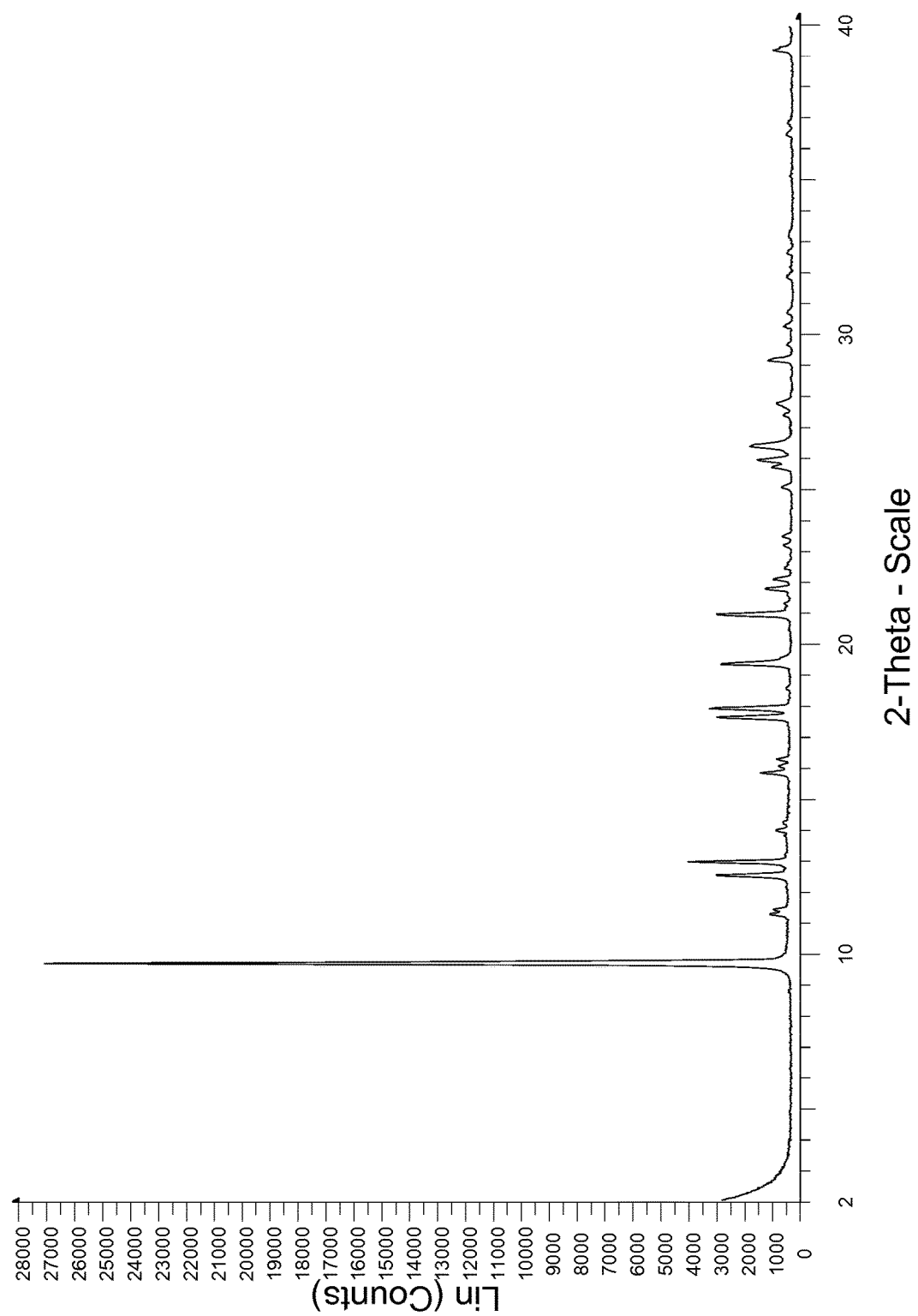
Figure 3: X-Ray Powder Diffraction Pattern Compound B Form A

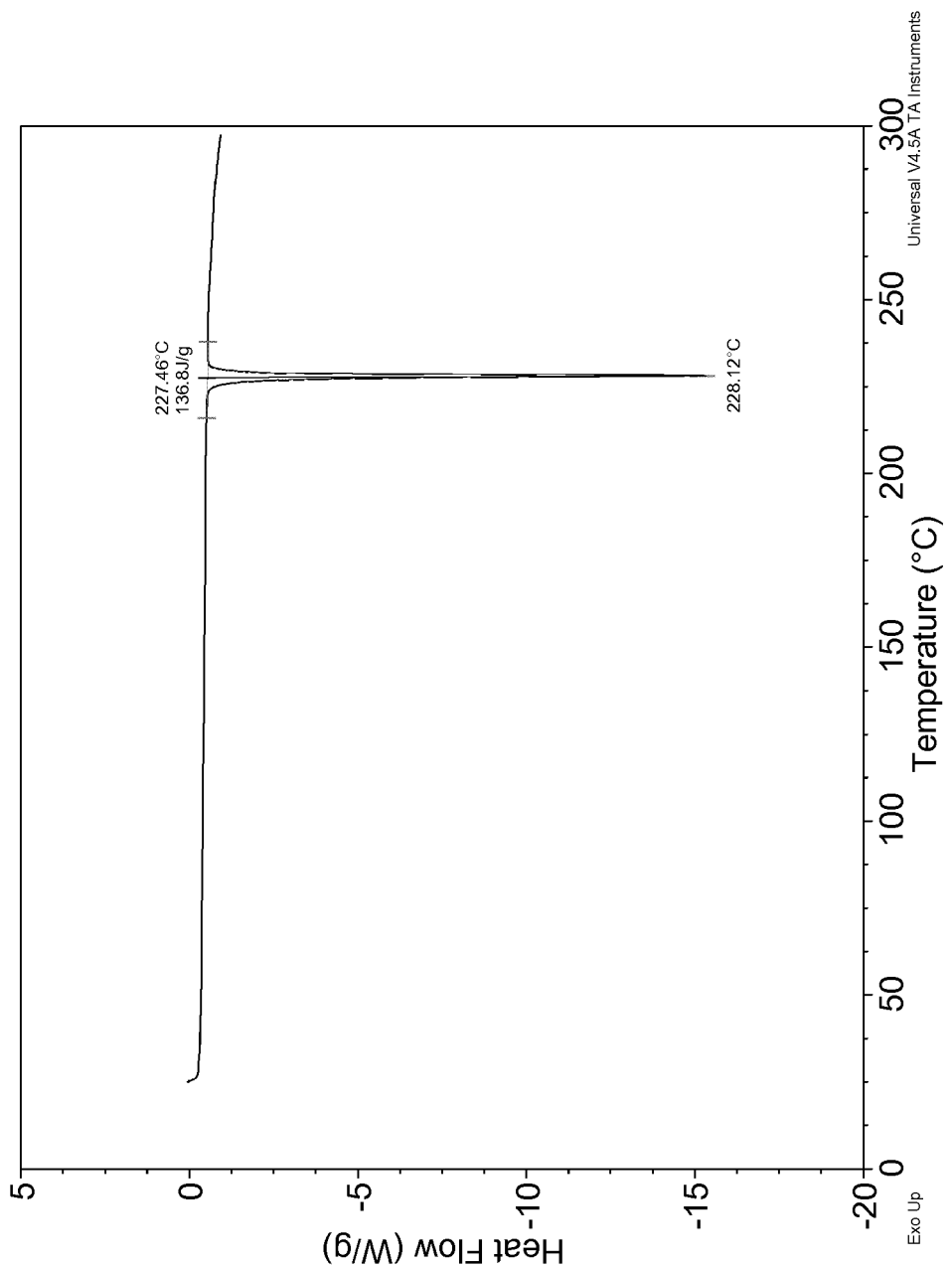
Figure 4: DSC thermogram of Compound B Form A

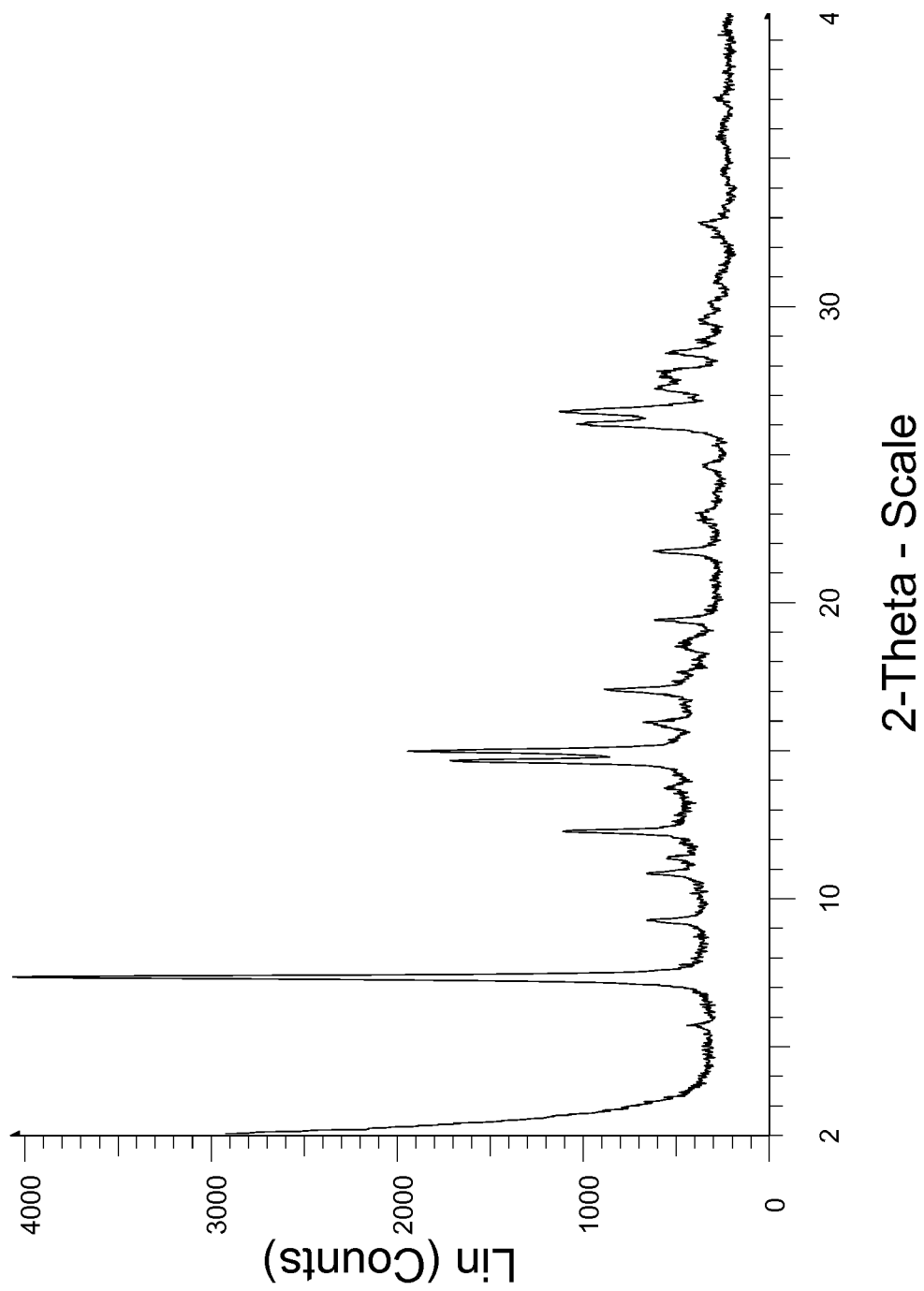
Figure 5: X-Ray Powder Diffraction Pattern Compound C Form A

PURINONE COMPOUNDS AND THEIR USE IN TREATING CANCER

CROSS-REFERENCE TO RELATED APPLICATIONS

This application is a U.S. National Phase Application of International Application No. PCT/EP2019/065686, filed on Jun. 14, 2019, which claims the benefit under 35 U.S.C. § 119(e) of U.S. Provisional Application No. 62/685,325, filed on Jun. 15, 2018. Each of the above-listed applications is incorporated by reference herein in their entirety.

FIELD

The specification generally relates to substituted purinone compounds and pharmaceutically acceptable salts thereof. These compounds and their pharmaceutically acceptable salts selectively modulate DNA-dependent protein kinase ("DNA-PK"), and the specification therefore also relates to the use of such compounds and salts thereof to treat or prevent DNA-PK mediated disease, including cancer. The specification further relates to crystalline forms of purinone compounds and pharmaceutically acceptable salts thereof; pharmaceutical compositions comprising such compounds and salts; kits comprising such compounds and salts; methods of manufacture of such compounds and salts; intermediates useful in the manufacture of such compounds and salts; and to methods of treating DNA-PK mediated disease, including cancer, using such compounds and salts.

BACKGROUND

DNA-PK is a nuclear serine/threonine protein kinase complex composed of the catalytic subunit DNA-PKcs and a heterodimer of Ku proteins (Ku70/Ku80). DNA-PK plays a crucial role in the repair of DNA double strand breaks (DSBs), serving to maintain genomic integrity, and in the process of V(D)J recombination, resulting in the highly diverse repertoire of antibodies/immunoglobulins and T cell receptors found on B- and T-cells respectively. DNA-PK has also been implicated in a range of other biological processes, including modulation of chromatin structure, telomere maintenance, transcriptional regulation, and the response to replication stress (Smith and Jackson, 1999; Goodwin and Knudsen, 2014).

DNA DSBs are regarded as the most lethal lesion a cell can encounter. To combat the serious threats posed by DNA DSBs, eukaryotic cells have evolved several mechanisms to mediate their repair. In higher eukaryotes, the predominant mechanism is DNA non-homologous end-joining (NHEJ). This is an error-prone DSB repair pathway involving direct ligation of the broken ends of DSBs that occurs during all phases of the cell cycle, and is preferentially used during the early G1/S phases, where no template sister chromatid is available (Hartlerode and Scully, 2009). This is in contrast to the second major pathway of DSB repair, homologous recombination (HR), which occurs primarily in G2/M phases of the cell cycle when undamaged sister chromatids are available (San Filippo et al., 2008). Other mechanisms underlying the selection of NHEJ or HR for DSB repair are incompletely defined, although blunt, minimally processed DNA ends are repaired by NHEJ, whereas 3' end resection is required for HR to occur (Symington and Gautier, 2011). End resection is controlled by an interplay of BRCA1 and 53BP1, with 53BP1 supporting NHEJ by suppressing end resection (Escribano-Diaz et al., 2013).

NHEJ is initiated through the recognition and binding of broken DNA ends by the ring-shaped Ku70/Ku80 heterodimer, followed by recruitment of DNA-PKcs through its interaction with Ku and DNA. Recruitment of DNA-PKcs facilitates movement of the Ku heterodimer into the DNA duplex, allowing DNA-PKcs to serve as a tether for the broken DNA ends and prevent degradation by exonucleases (Yoo and Dynan, 1999). Binding to DNA promotes activation of DNA-PKcs catalytic activity. Perhaps the most important substrate of DNA-PK is the kinase subunit itself, as autophosphorylation is critical for the regulation of DNA end processing, enzyme inactivation and complex dissociation (Chan et al., 2002). The most well characterized autophosphorylation sites are Ser2056 and Thr2609 (Douglas et al., 2002). DNA-PKcs phosphorylates and alters the activity of a wide range of substrates that mediate NHEJ, including Artemis, Ku70, Ku80, and DNA ligase 4 (Neal and Meek, 2011); it also phosphorylates Ser139 on histone variant H2AX (7H2AX); this is a well known marker of DNA double strand breaks (An et al., 2010).

Double strand breaks can be generated endogenously via production of reactive oxygen species during metabolism or via developmental V(D)J recombination in the immune system, and exogenously by ionizing radiation, radiomimetic drugs such as bleomycin, and topoisomerise II inhibitors such as etoposide and doxorubicin. Therefore, DNA-PK inhibitors are likely to increase the lethality of these agents. DNA-PK inhibitors may also be effective as single agents in tumours with high endogenous levels of DNA damage resulting from defects in other DNA repair pathways such as HR and mismatch repair. For example, DNA-PK inhibitors have been shown to be effective as single agents against ATM defective lymphomas (Riabinska et al., 2013). ATM is important in HR repair, and when cancer cells are deficient in ATM the cells are "addicted" to NHEJ to enable their survival. A synthetic lethal interaction has also been demonstrated between DNA-PK and MSH3 (Deitlein et al., 2014). DNA-PK is a member of the phosphatidylinositol 3-kinase-related kinase (PIKK) family of protein kinases and older generation DNA-PK inhibitors such as NU7026, NU7441, KU-0060648 and CC-115 have suffered from poor selectivity against other PIKK family members. However, these compounds have demonstrated the therapeutic potential of targeting DNA-PK consistent with the known mechanisms of action of the DNA-PK protein. For example, NU7026 and KU-0060648 can potentiate the cytotoxicity of topoisomerase II inhibitors (Willmore et al, 2004; Munck et al., 2012) and NU7441 potentiated the effect of ionizing radiation in breast cancer models (Ciszewski et al., 2014).

Accordingly there is a need for DNA-PK inhibitors that are selective, demonstrate good bioavailability and are suitable for dosing. Furthermore, there is a need for DNA-PK inhibitors with a longer half-life for providing increased duration of cover upon chronic dosing.

SUMMARY

Briefly, this specification describes, in part, a compound of Formula (I):

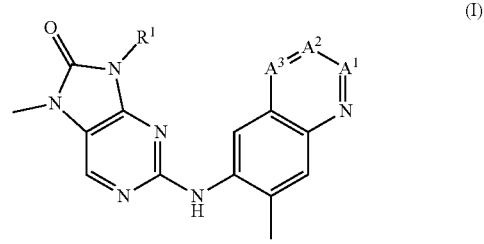

or a pharmaceutically acceptable salt thereof, where:

A¹ represents N or CR²ᴬ, A² represents N or CR²ᴮ and A³ represents N or CR²ᶜ, where no more than one of A¹, A² and A³ represents N;

R¹ represents $C_{4-6}$ cycloalkyl or a 4 to 6 membered heterocycloalkyl containing one heteroatom selected from O, S and N, wherein the $C_{4-6}$ cycloalkyl or 4 to 6 membered heterocycloalkyl is optionally substituted with one or more groups selected from fluoro, $C_{1-3}$ alkyl (optionally substituted with a group selected from hydroxyl and $C_{1-2}$ alkoxy), cyclopropyl, hydroxyl, $NH_2$, dioxo, $C(O)C_{1-2}$ alkyl, azetidinyl and oxetanyl;

R²ᴬ, R²ᴮ and R²ᶜ each independently represent hydrogen, methyl or methoxy.

This specification also describes, in part, a pharmaceutical composition which comprises a compound of Formula (I), or a pharmaceutically acceptable salt thereof, and at least one pharmaceutically acceptable excipient.

This specification also describes, in part, a compound of Formula (I), or a pharmaceutically acceptable salt thereof, for use in therapy.

This specification also describes, in part, a compound of Formula (I), or a pharmaceutically acceptable salt thereof, for use in the treatment of cancer.

This specification also describes, in part, a compound of Formula (I), or a pharmaceutically acceptable salt thereof, for the manufacture of a medicament for the treatment of cancer.

This specification also describes, in part, a method for treating cancer in a warm-blooded animal in need of such treatment, which comprises administering to said warm-blooded animal a therapeutically effective amount of a compound of Formula (I), or a pharmaceutically acceptable salt thereof.

BRIEF DESCRIPTION OF THE FIGURES

FIG. 1 shows the XRPD for Form A of 7-methyl-9-(1-methylpiperidin-4-yl)-2-((7-methylquinolin-6-yl)amino)-7,9-dihydro-8H-purin-8-one (Compound A, Example 44).

FIG. 2 shows the DSC for Form A of 7-methyl-9-(1-methylpiperidin-4-yl)-2-((7-methylquinolin-6-yl)amino)-7,9-dihydro-8H-purin-8-one (Compound A, Example 44).

FIG. 3 shows the XRPD for Form A of (S)-7-methyl-2-((7-methylcinnolin-6-yl)amino)-9-(tetrahydrofuran-3-yl)-7,9-dihydro-8H-purin-8-one (Compound B, Example 21).

FIG. 4 shows the DSC for Form A of (S)-7-methyl-2-((7-methylcinnolin-6-yl)amino)-9-(tetrahydrofuran-3-yl)-7,9-dihydro-8H-purin-8-one (Compound B, Example 21).

FIG. 5 shows the XRPD for Form A of 9-((3R,4R)-4-fluoropyrrolidin-3-yl)-7-methyl-2-((7-methylquinolin-6-yl)amino)-7,9-dihydro-8H-purin-8-one (Compound C, Example 52).

DESCRIPTION OF ILLUSTRATIVE EMBODIMENTS

Many embodiments of the disclosure are detailed throughout the specification and will be apparent to a reader skilled in the art. The disclosure is not to be interpreted as being limited to any particular embodiment(s) thereof.

In the first embodiment there is provided a compound of Formula (I):

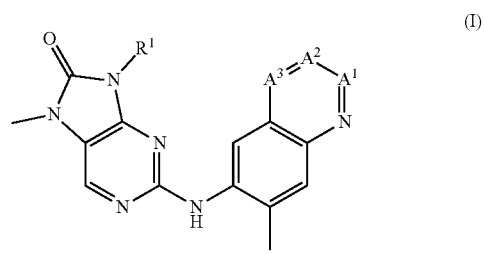

or a pharmaceutically acceptable salt thereof, where:

A¹ represents N or CR²ᴬ, A² represents N or CR²ᴮ and A³ represents N or CR²ᶜ, where no more than one of A¹, A² and A³ represent N;

R¹ represents $C_{4-6}$ cycloalkyl or a 4 to 6 membered heterocycloalkyl containing one heteroatom selected from O, S and N, wherein the $C_{4-6}$ cycloalkyl or 4 to 6 membered heterocycloalkyl is optionally substituted with one or more groups selected from fluoro, $C_{1-3}$ alkyl (optionally substituted with a group selected from hydroxyl and $C_{1-2}$ alkoxy), cyclopropyl, hydroxyl, $NH_2$, dioxo, $C(O)C_{1-2}$ alkyl, azetidinyl and oxetanyl;

R²ᴬ, R²ᴮ and R²ᶜ each independently represent hydrogen, methyl or methoxy.

$C_{4-6}$ cycloalkyl is a saturated non-aromatic carbocyclic ring containing no heteroatoms. $C_{4-6}$ cycloalkyl is any such carbocyclic ring containing 4 to 6 carbon atoms. $C_{4-6}$ cycloalkyl groups include cyclobutyl, cyclopentyl and cyclohexanyl, for example cyclohexanyl.

The term "cyclohexanyl" refers to a carbocyclic ring containing six carbon atoms. 1-hydroxycyclohex-4-yl groups and 4-hydroxycyclohex-1-yl groups have the same structure, as shown below.

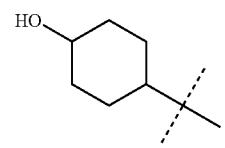

A cis-1-hydroxy-cyclohex-4-yl group is equivalent to a cis-4-hydroxy-cyclohex-1-yl and has the following structure:

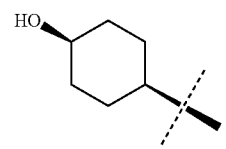

In the above structures the dashed line indicates the bonding position of the relevant group.

A 4 to 6 membered heterocycloalkyl is a saturated non-aromatic ring comprising one heteroatom independently selected from nitrogen, oxygen or sulphur with the remaining ring members being carbon. 4 to 6 membered heterocycloalkyl groups include piperidinyl, tetrahydropyranyl, tetrahydrothiopyranyl, pyrrolidinyl, tetrahydrofuranyl, tetrahydrothiophenyl, azetidinyl and oxetanyl, for example piperidinyl, tetrahydrofuranyl, tetrahydropyranyl, tetrahydrothiopyranyl, oxetanyl and pyrrolidinyl. For the avoidance of doubt, substituents on the heterocycloalkyl ring may be linked via either a carbon atom or a heteroatom.

The term "dioxo" means two oxo substituents which are attached to the same atom. Examples of dioxo substitution include instances where $R^1$ represents thianyl, which may also be referred to as tetrahydrothiopyranyl, where the sulphur ring atom is substituted with two oxo groups, i.e. tetrahydrothiopyran 1,1-dioxide.

The prefix $C_{p-q}$ in $C_{p-q}$ alkyl and other terms (where p and q are integers) indicates the range of carbon atoms that are present in the group and unless otherwise stated alkyl and alkoxy groups containing the requisite number of carbon atoms can be branched or unbranched. $C_{1-3}$ alkyl groups include methyl (Me), ethyl (Et), n-propyl and i-propyl, for example methyl and ethyl.

The term $C_{p-q}$ alkoxy comprises —O—$C_{p-q}$ alkyl groups. $C_{1-2}$ alkoxy groups include methoxy and ethoxy, for example methoxy.

Where the term "optionally" is used, it is intended that the subsequent feature may or may not occur. As such, use of the term "optionally" includes instances where the feature is present, and also instances where the feature is not present. For example, a group "optionally substituted by one methoxy group" includes groups with and without a methoxy substituent.

The term "substituted" means that one or more hydrogens (for example 1 or 2 hydrogens, or alternatively 1 hydrogen) on the designated group is replaced by the indicated substituent(s) (for example 1 or 2 substituents, or alternatively 1 substituent), provided that any atom(s) bearing a substituent maintains a permitted valency. Substituent combinations encompass only stable compounds and stable synthetic intermediates. "Stable" means that the relevant compound or intermediate is sufficiently robust to be isolated and have utility either as a synthetic intermediate or as an agent having potential therapeutic utility. If a group is not described as "substituted", or "optionally substituted", it is to be regarded as unsubstituted (i.e. that none of the hydrogens on the designated group have been replaced).

The term "pharmaceutically acceptable" is used to specify that an object (for example a salt, dosage form or excipient) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Ziirich:Wiley-VCH/VHCA, 2002.

A further embodiment provides any of the embodiments defined herein (for example the embodiment of claim 1) with the proviso that one or more specific Examples (for instance one, two or three specific Examples) selected from the group consisting of Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 and 52 is individually disclaimed.

In one embodiment, $R^1$ represents cyclohexanyl or a 4 to 6 membered heterocycloalkyl containing one heteroatom selected from O, N or S.

In another embodiment, $R^1$ represents a 4 to 6 membered heterocycloalkyl containing one heteroatom selected from O or N.

In another embodiment, $R^1$ represents a 4 to 6 membered heterocycloalkyl containing one N heteroatom.

In another embodiment, $R^1$ is selected from cyclohexanyl, oxetanyl, tetrahydrofuranyl, tetrahydropyranyl, pyrrolidinyl, piperidinyl and tetrahydrothiopyranyl.

In another embodiment, $R^1$ is selected from pyrrolidinyl and piperidinyl.

In another embodiment, $R^1$ is selected from cyclohexanyl, oxetan-3-yl, tetrahydrofuran-3-yl, tetrahydropyran-3-yl, tetrahydropyran-4-yl, pyrrolidin-3-yl, piperidin-4-yl and tetrahydrothiopyran-4-yl.

In another embodiment, $R^1$ is selected from pyrrolidin-3-yl and piperidin-4-yl.

In one embodiment, $R^1$ is optionally substituted with one or two substituents selected from fluoro, methyl, ethyl, hydroxyl, $NH_2$, dioxo, C(O)Me and oxetanyl, wherein the ethyl is optionally substituted with hydroxyl or methoxy. In one embodiment, $R^1$ is optionally substituted with fluoro, methyl, ethyl, hydroxyl, $NH_2$ and oxetanyl. In one embodiment, $R^1$ is optionally substituted with fluoro or methyl.

In one embodiment, $R^1$ represents pyrrolidinyl or piperidinyl and is optionally substituted with one or two substituents selected from fluoro, methyl, ethyl, hydroxyl, $NH_2$ and oxetanyl.

In one embodiment, $R^1$ represents cyclohexanyl optionally substituted with hydroxyl, methyl or $NH_2$.

In another embodiment, $R^1$ represents oxetan-3-yl.

In another embodiment, $R^1$ represents tetrahydrofuran-3-yl.

In another embodiment, $R^1$ represents tetrahydropyran-3-yl or tetrahydropyran-4-yl.

In another embodiment, $R^1$ represents pyrrolidin-3-yl optionally substituted with methyl.

In another embodiment, $R^1$ represents pyrrolidin-3-yl optionally substituted with fluoro.

In another embodiment, $R^1$ represents 4-fluoropyrrolidin-3-yl.

In another embodiment, $R^1$ represents piperidin-4-yl optionally substituted with a group selected from methyl, ethyl (unsubstituted or substituted with methoxy or hydroxyl), C(O)Me and oxetan-3-yl. In another embodiment, $R^1$ represents piperidin-4-yl optionally substituted with methyl.

In another embodiment, $R^1$ represents 1-methylpiperidin-4-yl.

In another embodiment, $R^1$ represents dioxidotetrahydro-2H-thiopyran-4-yl.

In one embodiment, $A^1$ represents $CR^{2A}$, $A^2$ represents $CR^{2B}$ and $A^3$ represents $CR^{2C}$.

In another embodiment, $A^1$ represents N, $A^2$ represents $CR^{2B}$ and $A^3$ represents $CR^{2C}$.

In another embodiment, $A^2$ represents N, $A^1$ represents $CR^{2A}$ and $A^3$ represents $CR^{2C}$.

In another embodiment, $A^3$ represents N, $A^1$ represents $CR^{2A}$ and $A^2$ represents $CR^{2C}$.

In another embodiment, $A^1$ represents $CR^{2A}$ or N, $A^2$ represents $CR^{2B}$ and $A^3$ represents $CR^{2C}$.

In one embodiment, $R^{2A}$ represents hydrogen. In one embodiment, $R^{2B}$ represents hydrogen. In one embodiment, $R^{2C}$ represents hydrogen.

In another embodiment, one, two or three groups selected from $R^{2A}$, $R^{2B}$ and $R^{2C}$ is/are independently selected from methyl and methoxy, and any remaining $R^{2A}$, $R^{2B}$ and/or $R^{2C}$ groups represent hydrogen.

In another embodiment, one, two or three groups selected from $R^{2A}$, $R^{2B}$ and $R^{2C}$ represent methyl.

In another embodiment, one, two or three groups selected from $R^{2A}$, $R^{2B}$ and $R^{2C}$ represent methoxy.

In another embodiment, one or two groups selected from $R^{2A}$, $R^{2B}$ and $R^{2C}$ are independently selected from methyl and methoxy.

In another embodiment, one or two groups selected from $R^{2A}$, $R^{2B}$ and $R^{2C}$ represent methyl.

In another embodiment, one or two groups selected from $R^{2A}$, $R^{2B}$ and $R^{2C}$ represent methoxy.

In another embodiment, one group selected from $R^{2A}$, $R^{2B}$ and $R^{2C}$ represents methyl.

In another embodiment, one group selected from $R^{2A}$, $R^{2B}$ and $R^{2C}$ represents methoxy.

The present disclosure also provides compounds of Formula (I), wherein:
- $A^1$ represents N or $CR^{2A}$, $A^2$ represents N or $CR^{2B}$ and $A^3$ represents N or $CR^{2C}$, wherein no more than one of $A^1$, $A^2$ and $A^3$ represents N;
- $R^1$ represents cyclohexanyl, oxetanyl, tetrahydrofuranyl, tetrahydropyranyl, pyrrolidinyl, piperidinyl or tetrahydrothiopyranyl and is optionally substituted with one or two groups selected from fluoro, methyl, ethyl, hydroxyl, $NH_2$, dioxo, C(O)Me and oxetanyl, wherein the ethyl is optionally substituted with hydroxyl or methoxy; and
- $R^{2A}$, $R^{2B}$ and $R^{2C}$ each independently represent hydrogen, methyl or methoxy.

The present disclosure also provides compounds of Formula (I), wherein:
- $A^1$ represents N or $CR^{2A}$, $A^2$ represents N or $CR^{2B}$ and $A^3$ represents N or $CR^{2C}$, wherein no more than one of $A^1$, $A^2$ and $A^3$ represents N;
- $R^1$ represents pyrrolidinyl or piperidinyl and is optionally substituted with one or two groups selected from fluoro, methyl, ethyl, hydroxyl, $NH_2$, dioxo and oxetanyl, wherein the ethyl is optionally substituted with hydroxyl or methoxy; and
- $R^{2A}$, $R^{2B}$ and $R^{2C}$ each independently represent hydrogen, methyl or methoxy.

In one embodiment, $A^1$ represents N or $CR^{2A}$, $A^2$ represents $CR^2$ and $A^3$ represents $CR^{2C}$; $R^1$ represents cyclohexanyl, oxetanyl, tetrahydrofuranyl, tetrahydropyranyl, pyrrolidinyl, piperidinyl or tetrahydrothiopyranyl and is optionally substituted with one or two groups selected from fluoro, methyl, ethyl, hydroxyl, $NH_2$, dioxo, C(O)Me and oxetanyl, wherein the ethyl is optionally substituted with hydroxyl or methoxy; and $R^{2A}$, $R^{2B}$ and $R^{2C}$ each independently represent hydrogen, methyl or methoxy.

In one embodiment, $A^1$ represents $CR^{2A}$ or N, $A^2$ represents $CR^{2B}$ and $A^3$ represents $CR^{2C}$; $R^1$ represents pyrrolidinyl or piperidinyl and is optionally substituted with one or two groups selected from fluoro, methyl, ethyl, hydroxyl, $NH_2$, dioxo and oxetanyl, wherein the ethyl is optionally substituted with hydroxyl or methoxy; and $R^{2A}$, $R^{2B}$ and $R^{2C}$ each independently represent hydrogen, methyl or methoxy.

In one embodiment, $A^1$ represents $CR^{2A}$, $A^2$ represents $CR^{2B}$ and $A^3$ represents $CR^{2C}$; $R^1$ represents cyclohexanyl, oxetanyl, tetrahydrofuranyl, tetrahydropyranyl, pyrrolidinyl, piperidinyl or tetrahydrothiopyranyl and is optionally substituted with one or two groups selected from fluoro, methyl, ethyl, hydroxyl, $NH_2$, dioxo, C(O)Me and oxetanyl, wherein the ethyl is optionally substituted with hydroxyl or methoxy; and $R^{2A}$, $R^{2B}$ and $R^{2C}$ each independently represent hydrogen, methyl or methoxy.

In one embodiment, $A^1$ represents $CR^{2A}$, $A^2$ represents $CR^{2B}$ and $A^3$ represents $CR^{2C}$; $R^1$ represents pyrrolidinyl or piperidinyl and is optionally substituted with one or two groups selected from fluoro, methyl, ethyl, hydroxyl, $NH_2$, dioxo and oxetanyl, wherein the ethyl is optionally substituted with hydroxyl or methoxy; and $R^{2A}$, $R^{2B}$ and $R^{2C}$ each independently represent hydrogen, methyl or methoxy.

In one embodiment, $A^1$ and $A^2$ both represent CH and $A^3$ represents $CR^{2C}$; $R^1$ represents cyclohexanyl, oxetanyl, tetrahydropyranyl, pyrrolidinyl, piperidinyl or tetrahydrothiopyranyl and is optionally substituted with one or two groups selected from fluoro, methyl, hydroxyl, $NH_2$, dioxo, C(O)Me and oxetanyl; and $R^{2C}$ represents hydrogen, methyl or methoxy.

In another embodiment, $A^1$ represents N, and $A^2$ and $A^3$ both represent CH; $R^1$ represents cyclohexanyl, tetrahydrofuranyl, tetrahydropyranyl or piperidinyl and is optionally substituted with hydroxyl, methyl or C(O)Me.

In one embodiment, $A^1$ represents CH or N, and $A^2$ and $A^3$ both represent CH; and $R^1$ represents a 5 or 6 membered heterocycloalkyl containing one heteroatom selected from N or O optionally substituted with fluoro or methyl.

In another embodiment, $A^1$, $A^2$ and $A^3$ each represent CH; and $R^1$ represents piperidinyl substituted with methyl.

In another embodiment, $A^1$, $A^2$ and $A^3$ each represent CH; and $R^1$ represents pyrrolidinyl substituted with fluoro.

In another embodiment, $A^1$ represents N, and $A^2$ and $A^3$ represent CH; and $R^1$ represents tetrahydrofuranyl.

In one embodiment there is provided a compound of Formula (I), or a pharmaceutically acceptable salt thereof, wherein the compound is selected from the group consisting of:

9-(1-acetylpiperidin-4-yl)-7-methyl-2-((7-methylcinnolin-6-yl)amino)-7,9-dihydro-8H-purin-8-one;

9-(1-acetylpiperidin-4-yl)-7-methyl-2-((7-methylquinoxalin-6-yl)amino)-7,9-dihydro-8H-purin-8-one;

9-(1-acetylpiperidin-4-yl)-7-methyl-2-((7-methylquinazolin-6-yl)amino)-7,9-dihydro-8H-purin-8-one;

9-(1-acetylpiperidin-4-yl)-2-((2,7-dimethylquinoxalin-6-yl)amino)-7-methyl-7,9-dihydro-8H-purin-8-one;

9-(1-acetylpiperidin-4-yl)-2-((3,7-dimethylquinoxalin-6-yl)amino)-7-methyl-7,9-dihydro-8H-purin-8-one;

9-((1r,4r)-4-hydroxycyclohexyl)-7-methyl-2-((7-methylquinolin-6-yl)amino)-7,9-dihydro-8H-purin-8-one;

9-((1r,4r)-4-hydroxycyclohexyl)-7-methyl-2-((7-methylcinnolin-6-yl)amino)-7,9-dihydro-8H-purin-8-one;

2-((4,7-dimethylquinolin-6-yl)amino)-9-((1r,4r)-4-hydroxycyclohexyl)-7-methyl-7,9-dihydro-8H-purin-8-one;

9-((1r,4r)-4-hydroxycyclohexyl)-2-((4-methoxy-7-methylquinolin-6-yl)amino)-7-methyl-7,9-dihydro-8H-purin-8-one;

9-((1r,4r)-4-hydroxycyclohexyl)-7-methyl-2-((7-methylquinoxalin-6-yl)amino)-7,9-dihydro-8H-purin-8-one;

9-((1s,4s)-4-hydroxycyclohexyl)-7-methyl-2-((7-methylquinolin-6-yl)amino)-7,9-dihydro-8H-purin-8-one;

9-((1s,4s)-4-hydroxycyclohexyl)-7-methyl-2-((7-methylcinnolin-6-yl)amino)-7,9-dihydro-8H-purin-8-one;

9-((1s,4s)-4-hydroxycyclohexyl)-7-methyl-2-((7-methylquinoxalin-6-yl)amino)-7,9-dihydro-8H-purin-8-one;

9-((1s,4s)-4-hydroxy-4-methylcyclohexyl)-7-methyl-2-((7-methylquinolin-6-yl)amino)-7,9-dihydro-8H-purin-8-one;

9-((1r,4r)-4-hydroxy-4-methylcyclohexyl)-7-methyl-2-((7-methylquinolin-6-yl)amino)-7,9-dihydro-8H-purin-8-one;

9-((1s,4s)-4-hydroxy-4-methylcyclohexyl)-7-methyl-2-((7-methylcinnolin-6-yl)amino)-7,9-dihydro-8H-purin-8-one;

9-((1r,4r)-4-hydroxy-4-methylcyclohexyl)-7-methyl-2-((7-methylcinnolin-6-yl)amino)-7,9-dihydro-8H-purin-8-one;

9-((1r,4r)-4-hydroxy-4-methylcyclohexyl)-7-methyl-2-((7-methylquinoxalin-6-yl)amino)-7,9-dihydro-8H-purin-8-one;

9-((1s,4s)-4-hydroxy-4-methylcyclohexyl)-7-methyl-2-((7-methylquinoxalin-6-yl)amino)-7,9-dihydro-8H-purin-8-one;
9-((1s,4s)-4-hydroxy-1-methylcyclohexyl)-7-methyl-2-((7-methylquinoxalin-6-yl)amino)-7,9-dihydro-8H-purin-8-one;
(S)-7-methyl-2-((7-methylcinnolin-6-yl)amino)-9-(tetrahydrofuran-3-yl)-7,9-dihydro-8H-purin-8-one;
(S)-7-methyl-2-((7-methylquinoxalin-6-yl)amino)-9-(tetrahydrofuran-3-yl)-7,9-dihydro-8H-purin-8-one;
(R)-7-methyl-2-((7-methylcinnolin-6-yl)amino)-9-(tetrahydrofuran-3-yl)-7,9-dihydro-8H-purin-8-one;
(R)-7-methyl-2-((7-methylquinoxalin-6-yl)amino)-9-(tetrahydrofuran-3-yl)-7,9-dihydro-8H-purin-8-one;
(R)-7-methyl-2-((7-methylcinnolin-6-yl)amino)-9-(tetrahydro-2H-pyran-3-yl)-7,9-dihydro-8H-purin-8-one;
(R)-7-methyl-2-((7-methylquinoxalin-6-yl)amino)-9-(tetrahydro-2H-pyran-3-yl)-7,9-dihydro-8H-purin-8-one;
(S)-7-methyl-2-((7-methylcinnolin-6-yl)amino)-9-(tetrahydro-2H-pyran-3-yl)-7,9-dihydro-8H-purin-8-one;
(S)-7-methyl-2-((7-methylquinoxalin-6-yl)amino)-9-(tetrahydro-2H-pyran-3-yl)-7,9-dihydro-8H-purin-8-one;
7-methyl-2-((7-methylcinnolin-6-yl)amino)-9-(tetrahydro-2H-pyran-4-yl)-7,9-dihydro-8H-purin-8-one;
7-methyl-2-((7-methylquinolin-6-yl)amino)-9-(tetrahydro-2H-pyran-4-yl)-7,9-dihydro-8H-purin-8-one;
7-methyl-2-((7-methylquinoxalin-6-yl)amino)-9-(tetrahydro-2H-pyran-4-yl)-7,9-dihydro-8H-purin-8-one;
7-methyl-2-((7-methylquinazolin-6-yl)amino)-9-(tetrahydro-2H-pyran-4-yl)-7,9-dihydro-8H-purin-8-one;
2-((2,7-dimethylquinoxalin-6-yl)amino)-7-methyl-9-(tetrahydro-2H-pyran-4-yl)-7,9-dihydro-8H-purin-8-one;
2-((3,7-dimethylquinoxalin-6-yl)amino)-7-methyl-9-(tetrahydro-2H-pyran-4-yl)-7,9-dihydro-8H-purin-8-one;
9-(1,1-dioxidotetrahydro-2H-thiopyran-4-yl)-7-methyl-2-((7-methylquinolin-6-yl)amino)-7,9-dihydro-8H-purin-8-one;
7-methyl-2-((7-methylquinolin-6-yl)amino)-9-(oxetan-3-yl)-7,9-dihydro-8H-purin-8-one;
7-methyl-2-((7-methylquinolin-6-yl)amino)-9-(piperidin-4-yl)-7,9-dihydro-8H-purin-8-one;
9-((3S,4R)-3-fluoropiperidin-4-yl)-7-methyl-2-((7-methylquinolin-6-yl)amino)-7,9-dihydro-8H-purin-8-one;
9-((1s,4s)-4-amino-4-methylcyclohexyl)-7-methyl-2-((7-methylquinolin-6-yl)amino)-7,9-dihydro-8H-purin-8-one;
9-((1r,4r)-4-amino-4-methylcyclohexyl)-7-methyl-2-((7-methylquinolin-6-yl)amino)-7,9-dihydro-8H-purin-8-one;
(R)-7-methyl-9-(1-methylpyrrolidin-3-yl)-2-((7-methylquinolin-6-yl)amino)-7,9-dihydro-8H-purin-8-one;
(S)-7-methyl-9-(1-methylpyrrolidin-3-yl)-2-((7-methylquinolin-6-yl)amino)-7,9-dihydro-8H-purin-8-one;
7-methyl-2-((7-methylcinnolin-6-yl)amino)-9-(1-methylpiperidin-4-yl)-7,9-dihydro-8H-purin-8-one;
7-methyl-9-(1-methylpiperidin-4-yl)-2-((7-methylquinolin-6-yl)amino)-7,9-dihydro-8H-purin-8-one;
7-methyl-9-(1-methylpiperidin-4-yl)-2-((7-methylquinoxalin-6-yl)amino)-7,9-dihydro-8H-purin-8-one;
9-((3S,4R)-3-fluoro-1-methylpiperidin-4-yl)-7-methyl-2-((7-methylquinolin-6-yl)amino)-7,9-dihydro-8H-purin-8-one;
7-methyl-2-((7-methylquinolin-6-yl)amino)-9-(1-(oxetan-3-yl)piperidin-4-yl)-7,9-dihydro-8H-purin-8-one;
9-(1-(2-hydroxyethyl)piperidin-4-yl)-7-methyl-2-((7-methylquinolin-6-yl)amino)-7,9-dihydro-8H-purin-8-one;
9-(1-(2-methoxyethyl)piperidin-4-yl)-7-methyl-2-((7-methylquinolin-6-yl)amino)-7,9-dihydro-8H-purin-8-one;
9-(1-ethylpiperidin-4-yl)-7-methyl-2-((7-methylquinolin-6-yl)amino)-7,9-dihydro-8H-purin-8-one;
9-(1-acetylpiperidin-4-yl)-7-methyl-2-((7-methylquinolin-6-yl)amino)-7,9-dihydro-8H-purin-8-one; and
9-((3R,4R)-4-fluoropyrrolidin-3-yl)-7-methyl-2-((7-methylquinolin-6-yl)amino)-7,9-dihydro-8H-purin-8-one.

In one embodiment there is provided a compound of Formula (I), or a pharmaceutically acceptable salt thereof, wherein the compound is selected from the group consisting of:
7-methyl-9-(1-methylpiperidin-4-yl)-2-((7-methylquinolin-6-yl)amino)-7,9-dihydro-8H-purin-8-one;
(S)-7-methyl-2-((7-methylcinnolin-6-yl)amino)-9-(tetrahydrofuran-3-yl)-7,9-dihydro-8H-purin-8-one; and
9-((3R,4R)-4-fluoropyrrolidin-3-yl)-7-methyl-2-((7-methylquinolin-6-yl)amino)-7,9-dihydro-8H-purin-8-one.

In one embodiment there is provided a compound of Formula (I), or a pharmaceutically acceptable salt thereof, wherein the compound is 7-methyl-9-(1-methylpiperidin-4-yl)-2-((7-methylquinolin-6-yl)amino)-7,9-dihydro-8H-purin-8-one (also referred to as Compound A).

In one embodiment there is provided a compound of Formula (I), or a pharmaceutically acceptable salt thereof, wherein the compound is (S)-7-methyl-2-((7-methylcinnolin-6-yl)amino)-9-(tetrahydrofuran-3-yl)-7,9-dihydro-8H-purin-8-one (also referred to as Compound B).

In one embodiment there is provided a compound of Formula (I), or a pharmaceutically acceptable salt thereof, wherein the compound is 9-((3R,4R)-4-fluoropyrrolidin-3-yl)-7-methyl-2-((7-methylquinolin-6-yl)amino)-7,9-dihydro-8H-purin-8-one (also referred to as Compound C).

Compounds and salts described in this specification may exist in solvated forms and unsolvated forms. For example, a solvated form may be a hydrated form, such as a hemi-hydrate, a mono-hydrate, a di-hydrate, a tri-hydrate or an alternative quantity thereof. The disclosure encompasses all such solvated and unsolvated forms of compounds of Formula (I), particularly to the extent that such forms possess DNA-PK inhibitory activity, as for example measured using the tests described herein.

Atoms of the compounds and salts described in this specification may exist as their isotopes. The disclosure encompasses all compounds of Formula (I) where an atom is replaced by one or more of its isotopes (for example a compound of Formula (I) where one or more carbon atom is an $^{11}C$ or $^{13}C$ carbon isotope, or where one or more hydrogen atoms is a $^{2}H$ or $^{3}H$ isotope, or where one or more nitrogen atoms is a $^{5}N$ isotope or where one of more oxygen atoms is an $^{17}O$ or $^{18}O$ isotope).

Certain compounds and salts described in this specification include one or more chiral (i.e. asymmetric) centres. The disclosure includes any optically active or racemic form of a compound of Formula (I) which possesses DNA-PK inhibitory activity, as for example measured using the tests described herein. To the extent a structure or chemical name in this specification does not indicate the chirality, the structure or name is intended to encompass any single stereoisomer (i.e. any single chiral isomer) corresponding to that structure or name, as well as any mixture of stereoisomers (e.g. a racemate). In some embodiments, a single stereoisomer is obtained by isolating it from a mixture of isomers (e.g. a racemate) using, for example, chiral chromatographic separation. In other embodiments, a single stereoisomer is obtained through direct synthesis from, for example, a chiral starting material.

According to one embodiment there is provided a compound of Formula (I), or a pharmaceutically acceptable salt thereof, which is a single enantiomer being in an enantiomeric excess (% ee) of ≥95%, ≥98% or ≥99%. Conveniently, the single enantiomer is present in an enantiomeric excess (% ee) of ≥99%.

According to another embodiment there is provided a pharmaceutical composition, which comprises a compound of Formula (I), which is a single enantiomer being in an enantiomeric excess (% ee) of ≥95%, ≥98% or ≥99% or a pharmaceutically acceptable salt thereof, in association with one or more pharmaceutically acceptable excipients. Conveniently, the single enantiomer is present in an enantiomeric excess (% ee) of ≥99%.

Certain compounds of Formula (I) and pharmaceutically acceptable salts of any of these compounds exist as diastereomers.

In one embodiment there is provided a compound of Formula (I), or a pharmaceutically acceptable salt thereof, which is in a diastereomeric excess (% de) of ≥95%, ≥98% or ≥99%. In one embodiment, the compound of Formula (I) or a pharmaceutically acceptable salt thereof is present in diastereomeric excess (% de) of ≥99%.

Some of the compounds of Formula (I) may be crystalline and may have more than one crystalline form. It is to be understood that the disclosure encompasses any crystalline or amorphous form, or mixtures thereof, which possess properties useful in DNA-PK inhibitory activity. It is well known how to determine the efficacy of a crystalline or amorphous form by the standard tests described hereinafter.

It is generally known that crystalline materials may be analysed using conventional techniques such as, for example, X-Ray Powder Diffraction (hereinafter XRPD) analysis and Differential Scanning Calorimetry (hereinafter DSC).

As an example, the compound of Example 44, 7-methyl-9-(1-methylpiperidin-4-yl)-2-((7-methylquinolin-6-yl)amino)-7,9-dihydro-8H-purin-8-one exhibits crystallinity and one crystalline form, Form A, has been identified.

Accordingly, in a further aspect there is provided Form A of Compound A (Example 44, 7-methyl-9-(1-methylpiperidin-4-yl)-2-((7-methylquinolin-6-yl)amino)-7,9-dihydro-8H-purin-8-one).

According to the present disclosure there is provided a crystalline form, Form A of Compound A, which has an XRPD pattern with at least one specific peak at about 2-theta=7.1°, as measured using CuKα radiation.

According to the present disclosure there is provided a crystalline form, Form A of Compound A, which has an XRPD pattern with at least one specific peak at about 2-theta=8.5°, as measured using CuKα radiation.

According to the present disclosure there is provided a crystalline form, Form A of Compound A, which has an XRPD pattern with at least two specific peaks at about 2-theta=7.1° and 8.5°, as measured using CuKα radiation.

According to the present disclosure there is provided a crystalline form, Form A of Compound A, which has an XRPD pattern with specific peaks at about 2-theta=7.1, 8.5, 12.7, 14.2, 15.4, 16.3, 18.8, 19.8, 21.5, 26.2°, as measured using CuKα radiation.

According to the present disclosure there is provided a crystalline form, Form A of Compound A, which has an XRPD pattern substantially the same as the X-ray powder diffraction pattern shown in FIG. 1.

According to the present disclosure there is provided crystalline form, Form A of Compound A, which has an XRPD pattern with at least one specific peak at 2-theta=7.1° plus or minus 0.2° 2-theta, as measured using CuKα radiation.

According to the present disclosure there is provided a crystalline form, Form A of Compound A, which has an XRPD pattern with at least one specific peak at 2-theta=8.5° plus or minus 0.2° 2-theta, as measured using CuKα radiation.

According to the present disclosure there is provided a crystalline form, Form A of Compound A, which has an XRPD with at least two specific peaks at 2-theta=7.10 and 8.5° wherein said values may be plus or minus 0.2° 2-theta, as measured using CuKα radiation.

According to the present disclosure there is provided a crystalline form, Form A of Compound A, which has an XRPD pattern with specific peaks at 2-theta=7.1, 8.5, 12.7, 14.2, 15.4, 16.3, 18.8, 19.8, 21.5, 26.2° wherein said values may be plus or minus 0.2° 2-theta, as measured using CuKα radiation.

DSC analysis of Compound A, Form A shows a melting endotherm with an onset of about 245° C. and a peak at about 246° C. (FIG. 2).

According to a further aspect there is provided Form A of Compound B (Example 21, (S)-7-methyl-2-((7-methylcinnolin-6-yl)amino)-9-(tetrahydrofuran-3-yl)-7,9-dihydro-8H-purin-8-one).

According to the present disclosure there is provided a crystalline form, Form A of Compound B, which has an XRPD pattern with at least one specific peak at about 2-theta=9.7°, as measured using CuKα radiation.

According to the present disclosure there is provided a crystalline form, Form A of Compound B, which has an XRPD pattern with at least one specific peak at about 2-theta=12.9°.

According to the present disclosure there is provided a crystalline form, Form A of Compound B, which has an XRPD with at least two specific peaks at about 2-theta=9.7° and 12.9°, as measured using CuKα radiation.

According to the present disclosure there is provided a crystalline form, Form A of Compound B, which has an XRPD pattern with specific peaks at about 2-theta=9.7, 12.5, 12.9, 15.8, 17.6, 17.9, 19.4, 21.0, 26.0, 26.4°, as measured using CuKα radiation.

According to the present disclosure there is provided crystalline form, Form A of Compound B. which has an XRPD pattern substantially the same as the XRPD pattern shown in FIG. 3.

According to the present disclosure there is provided crystalline form, Form A of Compound B, which has an XRPD pattern with at least one specific peak at 2-theta=9.7° plus or minus 0.2° 2-theta, as measured using CuKα radiation.

According to the present disclosure there is provided a crystalline form, Form A of Compound B, which has an XRPD pattern with at least one specific peak at 2-theta=12.9° plus or minus 0.2° 2-theta, as measured using CuKα radiation.

According to the present disclosure there is provided a crystalline form, Form A of Compound B, which has an XRPD pattern with at least two specific peaks at 2-theta=9.7° and 12.9° wherein said values may be plus or minus 0.2° 2-theta, as measured using CuKα radiation.

According to the present disclosure there is provided a crystalline form, Form A of Compound B, which has an XRPD pattern with specific peaks at 2-theta=9.7, 12.5, 12.9, 15.8, 17.6, 17.9, 19.4, 21.0, 26.0, 26.4° wherein said values may be plus or minus 0.2° 2-theta, as measured using CuKα radiation.

DSC analysis of Compound B, Form A shows a melting endotherm with an onset of about 227° C. and a peak at about 228° C. (FIG. 4).

According to a further aspect there is provided Form A of Compound C (Example 52, 9-((3R,4R)-4-fluoropyrrolidin-3-yl)-7-methyl-2-((7-methylquinolin-6-yl)amino)-7,9-dihydro-8H-purin-8-one).

According to the present disclosure there is provided a crystalline form, Form A of Compound C, which has an XRPD pattern with at least one specific peak at about 2-theta=7.3°, as measured using CuKα radiation.

According to the present disclosure there is provided a crystalline form, Form A of Compound C, which has an XRPD pattern with at least one specific peak at about 2-theta=15.0°.

According to the present disclosure there is provided a crystalline form, Form A of Compound C, which has an XRPD with at least two specific peaks at about 2-theta=7.3° and 15.0°, as measured using CuKα radiation.

According to the present disclosure there is provided a crystalline form, Form A of Compound C, which has an XRPD pattern with specific peaks at about 2-theta=7.3, 15.0, 14.6, 26.5, 12.2, 26.0, 17.0, 15.9, 27.3, 10.8°, as measured using CuKα radiation.

According to the present disclosure there is provided crystalline form, Form A of Compound C, which has an XRPD pattern substantially the same as the XRPD pattern shown in FIG. 5.

According to the present disclosure there is provided crystalline form, Form A of Compound C, which has an XRPD pattern with at least one specific peak at 2-theta=7.3° plus or minus 0.2° 2-theta, as measured using CuKα radiation.

According to the present disclosure there is provided a crystalline form, Form A of Compound C, which has an XRPD pattern with at least one specific peak at 2-theta=15.0° plus or minus 0.2° 2-theta, as measured using CuKα radiation.

According to the present disclosure there is provided a crystalline form, Form A of Compound C, which has an XRPD pattern with at least two specific peaks at 2-theta=7.3° and 15.0° wherein said values may be plus or minus 0.2° 2-theta, as measured using CuKα radiation.

According to the present disclosure there is provided a crystalline form, Form A of Compound C, which has an XRPD pattern with specific peaks at 2-theta=7.3, 15.0, 14.6, 26.5, 12.2, 26.0, 17.0, 15.9, 27.3, 10.8° wherein said values may be plus or minus 0.2° 2-theta, as measured using CuKα radiation.

When it is stated that the present disclosure relates to a crystalline form of Form A of Compound A, Form A of Compound B, and Form A of Compound C, the degree of crystallinity is conveniently greater than about 60%, more conveniently greater than about 80%, preferably greater than about 90% and more preferably greater than about 95%. Most preferably the degree of crystallinity is greater than about 98%.

It will be understood that the 2-theta values of the XRPD pattern may vary slightly from one machine to another or from one sample to another, and so the values quoted are not to be construed as absolute.

It is known that an XRPD pattern may be obtained which has one or more measurement errors depending on measurement conditions (such as equipment or machine used). In particular, it is generally known that intensities in an XRPD pattern may fluctuate depending on measurement conditions. Therefore it should be understood that Compound A, Form A, Compound B, Form A and Compound C, Form A of the present disclosure is not limited to the crystals that provide XRPD patterns identical to the XRPD pattern shown in FIGS. 1, 3 and 5, and any crystals providing XRPD patterns substantially the same as those shown in FIGS. 1, 3 and 5 fall within the scope of the present disclosure. A person skilled in the art of XRPD is able to judge the substantial identity of XRPD patterns.

Persons skilled in the art of XRPD will understand that the relative intensity of peaks can be affected by, for example, grains above 30 microns in size and non-unitary aspect ratios, which may affect analysis of samples. The skilled person will also understand that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.2° 2-theta, and such degree of a measurement error should be taken into account when considering the XRPD patterns in FIGS. 1, 3 and 5 and when reading Tables A, B and C. Furthermore, it should be understood that intensities might fluctuate depending on experimental conditions and sample preparation (preferred orientation).

Compounds of Formula (I) may for example be prepared by the reaction of a compound of Formula (II):

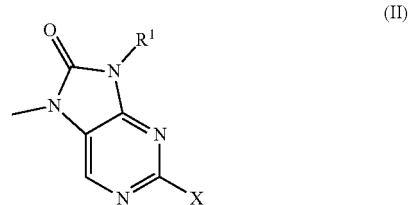

or a salt thereof, where $R^1$ is as defined in any of the embodiments herein, or a protected form thereof, and X is a leaving group (for example a halogen atom, such as a chlorine atom) with a compound of Formula (III):

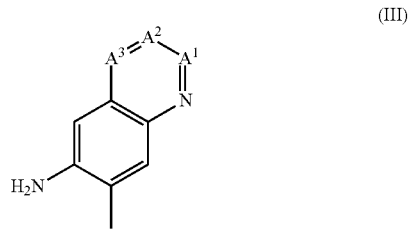

or a salt thereof, where A, $A^2$ and $A^3$ are as defined in any of the embodiments herein. The reaction is conveniently performed in a suitable solvent (for example 1,4-dioxane) in the presence of a base (for example cesium carbonate) and optionally in the presence of a suitable catalyst (for example Brettphos 3$^{rd}$ Gen) at a suitable temperature (for example a temperature in the range of about 80-100° C.).

Compounds of Formula (II) or (III), and salts thereof, are therefore useful as intermediates in the preparation of the compounds of Formula (I) and provide a further embodiment. In one embodiment there is provided a compound of Formula (II), or a salt thereof, where:
- $R^1$ represents $C_{4-6}$ cycloalkyl or a 4 to 6 membered heterocycloalkyl containing one heteroatom selected from O, S and N, wherein the $C_{4-6}$ cycloalkyl or 4 to 6 membered heterocycloalkyl is optionally substituted with one or more groups selected from fluoro, $C_{1-3}$ alkyl (optionally substituted with a group selected from hydroxyl and $C_{1-2}$ alkoxy), cyclopropyl, hydroxyl, $NH_2$, dioxo, $C(O)C_{1-2}$ alkyl, azetidinyl and oxetanyl; and
- X is a leaving group.

In one embodiment X is a halogen atom or a triflate group. In one embodiment X is a chlorine atom.

In any of the embodiments where a compound of Formula (II) or (III) or a salt thereof is mentioned it is to be understood that such salts do not need to be pharmaceutically acceptable salts.

The compounds of Formula (II) may for example be prepared by the reaction of a compound of Formula (IV):

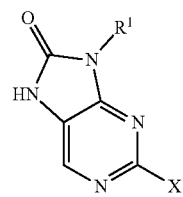

(IV)

where $R^1$ is as defined in any of the embodiments herein, and X is a leaving group (for example an iodine, bromine, or chlorine atom or a triflate group) with a methylating agent. Suitable methylating agents include methyl iodide, DMF-DMA.

The compounds of Formula (IV) may for example be prepared by the reaction of a compound of Formula (V):

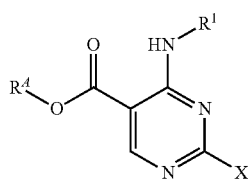

(V)

where $R^1$ is as defined in any of the embodiments herein;
$R^A$ is hydrogen; and
X is a leaving group (for example an iodine, bromine, chlorine atom or a triflate group) with diphenylphosphoryl azide (DPPA).

The reaction may be performed under standard conditions well known to those skilled in the art, for example DPPA, triethylamine, THF, reflux.

Compounds of Formula (IV) and (V) are therefore useful as intermediates in the preparation of the compounds of Formula (I) and provide a further embodiment.

Compounds of Formula (IV) and (V) can be prepared by methods similar to those shown in the Examples section.

The compound of Formula (III) may for example be prepared by the reaction of a compound of Formula (VI):

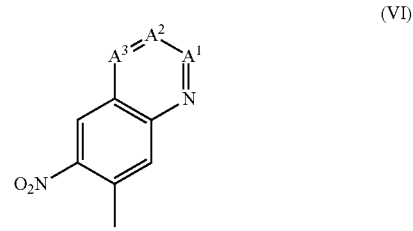

(VI)

where $A^1$, $A^2$ and $A^3$ are as defined in any of the embodiments herein, with a reducing agent. Suitable reducing agents include 10% Pd/C and hydrogen, 10% Pd/C and ammonium formate, iron/ammonium chloride.

The compound of Formula (III) for example may also be prepared by the reaction of a compound of Formula (VII):

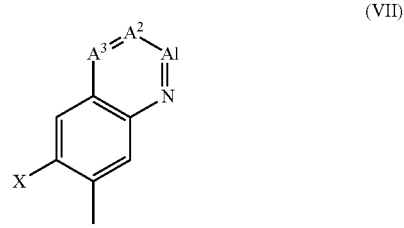

(VII)

Where $A^1$, $A^2$ and $A^3$ are as defined in any of the embodiments herein, and X is a leaving group (for example a bromine, or chlorine atom or a triflate group). The reaction is conveniently performed in a suitable solvent (for example 1,4-dioxane) in the presence of a base (for example sodium tert-butoxide) and an amine equivalent (for example benzophenone imine) and optionally in the presence of a suitable catalyst (for example Tris(dibenzylideneacetone)dipalladium) and ligand (BINAP) at a suitable temperature (for example a temperature in the range of about 80-100° C.).

The compound of Formula (III) for example may also be prepared by the reaction of a compound of Formula (VIII):

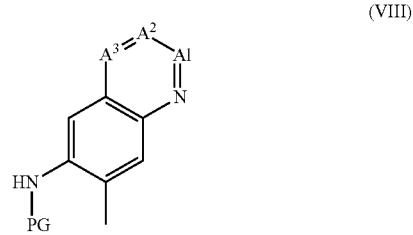

(VIII)

Where $A^1$, $A^2$ and $A^3$ are as defined in any of the embodiments herein and PG represents a suitable protecting group, for example BOC or benzophenone imine. The reaction is conveniently performed in a suitable solvent (for example methanol) in the presence of an acid (hydrochloric acid) at a suitable temperature (for example a temperature in the range of about 20° C.).

Compounds of Formula (III), (VI), (VII) and (VIII) can be prepared by methods similar to those shown in the Examples section.

It will be appreciated that certain of the various ring substituents in the compounds of the present disclosure may be introduced by standard aromatic substitution reactions or generated by conventional functional group modifications either prior to or immediately following the processes mentioned above, and as such are included in the process aspect of the disclosure. For example compounds of Formula (I) may be converted into further compounds of Formula (I) by standard aromatic substitution reactions or by conventional functional group modifications. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulfinyl or alkylsulfonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

Compounds of Formula (I), (II) and (III), and any intermediates used to make these, can be prepared by methods similar to those shown in the Examples section.

Biological Assays

The following assays were used to measure the effects of the compounds described herein: a) DNAPK enzyme potency assay; b) DNAPK cellular potency assay. During the description of the assays, generally:
 i. The following abbreviations have been used; DMSO=Dimethyl Sulphoxide; DTT=Dithiothreitol; EDTA=Ethylenediaminetetraacetic Acid, TR-FRET=Time Resolved Fluorescence Resonance Energy Transfer, ATP=Adenosine triphosphate, DTT=Dithiothreitol, DNA=Deoxyribonucleic acid, HEPES=(2-hydroxyethyl)-1-piperazineethanesulfonic acid
 ii. The $IC_{50}$ value was the concentration of test compound that inhibited 50% of biological activity.

Assay a): DNAPK Enzyme Potency Assay (DNA-PK Enz)

The inhibitory activity of compounds against DNAPK was determined by TR-FRET measuring a fluorescent labelled peptide substrate converting to a phosphorylated product. Fluorescently tagged peptide substrate were purchased from Thermo Fisher Scientific. 12 point half-log compound concentration-response curves, with a top concentration of 100 μM were generated from 10 mM stocks of compound solubilised in DMSO using an Echo 555 (Labcyte Inc., Sunnyvale, CA). All assays were preformed in white Greiner 1536 well low volume plates (Greiner Bio-One, UK), in a total reaction volume of 3 μL and 1% (v/v) final DMSO concentration. Enzymes and substrates were added separately to the compound plates and incubated at room temperature. The kinase reaction was then quenched by the addition of 3 μL of stop buffer. Stopped assay plates were read using a BMG Pherastar. $IC_{50}$ values were calculated using a Genedata Screener® software (Genedata, Inc., Basel, Switzerland).

Full length human DNAPK protein was purified from HeLa cell extract by ion exchange. Initially DNAPK protein was incubated with compound for 30 minutes at room temperature in reaction buffer (50 mM Hepes pH 7.5, 0.01% Brij-35, 10 mM $MgCl_2$, 1 mM EGTA, 1 mM DTT, 2 g/mL Calf Thymus DNA). The reaction was then initiated by the addition of ATP and fluorescently tagged peptide substrate (Fluorescein-EPPLSQEAFADLWKK, Thermo Fisher Scientific). The kinase reaction (18 μM ATP, 35 pM DNAPK, 1.6 μM peptide substrate) was quenched after 40 minutes by the addition of 3 μL of stop buffer (20 mM Tris pH7.5, 0.02% sodium azide, 0.01% Nonidet-P40, 20 m EDTA, 4 nM Tb anti-phospho-p53 [Ser15] Antibody. The reaction was incubated for a further hour and the plates were read on a BMG Pherastar.

Data was analysed and $IC_{50}$ values were calculated using Genedata Screener® software (Genedata, Inc., Basel, Switzerland). The $pIC_{50}$ values were calculated as the negative logarithm of the molar concentration of compound required for 50% reduction in measured response.

b) DNAPK Cellular Potency Assay (DNA-PK Cell)

Compounds or DMSO (dimethyl sulphoxide) were dispensed from source plates containing compounds at 10 mM in 100% (v/v) DMSO or 100% DMSO, directly into cell assay plates using an Echo 555 Acoustic dispenser (Labcyte Inc™). 10 mM compound stocks were diluted 1:100 using a fixed-tip 96-head Agilent VPrep liquid handler (Agilent Technologies, Santa Clara, CA) to give four intermediate dilutions (10 mM, 100 μM, 1 μM, 10 nM). This 1:100 intermediate dilution plate was then used by the Echo to dispense compounds and DMSO directly into the cell plates with a 12 point dose range (30, 10, 3.125, 1.25, 0.3, 0.1, 0.03125, 0.0125, 0.003, 0.001, 0.0003125, 0.00003 μM) in order to calculate compound $IC_{50}$ values, with a total DMSO concentration in the assay of 0.3% (v/v).

The DNAPK cell ELISA assay was performed in the A549 cell line. A549 cells were cultured in cell media composed of MEM-F12 (Minimum Essential Medium F12 Sigma #D6421), 10% (v/v) Foetal Calf Serum and 1% (v/v) 200 mM L-Glutamine. After harvesting, cells were dispensed into black, 384-well Costar plates (#3712, Corning) to give 15,000 cells per well in a total volume of 40 μL cell media, and were incubated overnight at 37° C., 90% relative humidity and 5% $CO_2$ in a rotating incubator. Greiner 781077 all-black high-bind 384-well ELISA plates were coated with 0.5 g/mL DNAPK antibody (Abcam #ab1832) in PBS/A overnight at 4° C. The following day the Greiner ELISA plates were washed 3× with PBS-T and blocked with 3% BSA/PBS for 2 h, before a further 3× wash with PBS-T.

Test compounds and reference controls were dosed directly into the cell plates using a Labcyte Echo 555 acoustic dispenser. The cell plates were then incubated for 1 h at 37° C. before receiving a radiation dose of 8 Gy (XRAD 320, table height 65). The cells were incubated for a further 1 h before removal of cell media. Lysis buffer (in-house preparation with addition of protease inhibitor cocktail tablets, Roche #04 693 116 001 and phosphatase inhibitor tablets, Roche #04906837001) was dispensed at 25 L/well and plates were incubated at 4° C. for 30 min. Cell lysates (20 L/well) were transferred to the DNAPK antibody-coated ELISA plates using a CyBio Felix liquid handling platform, and ELISA plates were incubated at 4° C. overnight.

The following day, ELISA plates were washed 3× with PBS-T and dispensed with in-house pS2056-DNAPK antibody (0.5 μg/mL in 3% BSA/PBS) at 20 ul/well. Plates were incubated with antibody for 2 h at room temperature (rt) before 3× wash with PBS-T. Goat anti-rabbit HRP secondary antibody (1:2000 dilution in 3% BSA/PBS; Cell Signaling #7074) was dispensed at 20 μL/well and plates were incubated at rt for 1 h before 3× wash with PBS-T.

QuantaBlu Working Substrate Solution (Thermo Scientific #15169, prepared according to manufacturer's instructions) was dispensed at 20 L/well and plates were incubated at rt for 1 h before a further 20 ul/well dispense with QuantaBlu Stop Solution provided within kit (Thermo Scientific #15169). The fluorescence intensity of individual wells was determined using a PerkinElmer EnVision plate reader.

Data was analysed and $IC_{50}$ values were calculated using Genedata Screener® software (Genedata, Inc., Basel, Switzerland). The $pIC_{50}$ values were calculated as the negative logarithm of the molar concentration of compound required for 50% reduction in measured response.

c) TTK Enzyme Assay

The inhibitory activity of compounds against TTK was determined in a LanthaScreen® Eu Kinase Binding assay run by ThermoFisher Scientific as part of their SelectScreen® Biochemical Kinase Profiling Service. The LanthaScreen® Eu Kinase Binding assay format uses binding of an Alexa Fluor® conjugate or "tracer" to a kinase, which is detected by addition of a Eu-labeled anti-tag antibody. Binding of the tracer and antibody to a kinase results in a high degree of FRET, whereas displacement of the tracer with a kinase inhibitor results in a loss of FRET. The degree of FRET measured in the assay is used to determine the binding of a compound.

10 point three-fold dilution compound concentration-response curves, with a top concentration of 10 μM were generated from 10 mM stocks of compound solubilised in DMSO. All assays were performed in white, low volume Greiner 384-well plates (cat. #784207, Greiner), in a total reaction volume of 16 μL and 1% (v/v) final DMSO concentration. 3.84 μL Kinase Buffer (50 mM HEPES pH 7.5, 0.01% BRIJ-35, 10 mM $MgCl_2$, 1 mM EGTA), 8 μL 2× Kinase/Antibody mixture (final concentrations 5 nM TTK, 2 nM Eu-anti-GST, prepared in Kinase Buffer) and 4 μL 4× AlexaFluor® labeled Tracer Solution (final concentrations 30 nM Tracer 236, prepared in Kinase Buffer) were added separately to the compound plates, placed on a plate shaker for 30 sec, and then incubated for 60 mins at room temperature. Plates were then read using a fluorescence plate reader. $IC_{50}$ values were calculated using XLfit software (IDBS Ltd, Surrey, UK), with the curve fit to model number 205 (sigmoidal dose-response model).

d) Aurora-A, Aurora-B, JAK1, JAK2, JAK3 Enzyme Assays

The inhibitory activity of compounds against AURKA, AURKB, JAK1, JAK2 and JAK3 was determined in Z'-LYTE® assays run by ThermoFisher Scientific as part of their SelectScreen® Biochemical Kinase Profiling Service. The Z'-LYTE® biochemical assay format employs a fluorescence-based, coupled-enzyme format and is based on the differential sensitivity of phosphorylated and non-phosphorylated peptides to proteolytic cleavage. The peptide substrate is labeled with two fluorophores—one at each end—that make up a FRET pair. In the primary reaction, the kinase transfers the gamma-phosphate of ATP to a single tyrosine, serine or threonine residue in a synthetic FRET-peptide. In the secondary reaction, a site-specific protease recognises and cleaves non-phosphorylated FRET-peptides. Phosphorylation of FRET-peptides suppresses cleavage by the Development Reagent. Cleavage disrupts FRET between the donor (i.e., coumarin) and acceptor (i.e., fluorescein) fluorophores on the FRET-peptide, whereas uncleaved, phosphorylated FRET-peptides maintain FRET. A ratiometric method, which calculates the ratio (the Emission Ratio) of donor emission to acceptor emission after excitation of the donor fluorophore at 400 nm, is used to quantitate reaction progress. Both cleaved and uncleaved FRET-peptides contribute to the fluorescence signals and therefore to the Emission Ratio. The extent of phosphorylation of the FRET-peptide can be calculated from the Emission Ratio. The Emission Ratio will remain low if the FRET-peptide is phosphorylated (i.e., no kinase inhibition) and will be high if the FRET-peptide is non-phosphorylated (i.e., kinase inhibition).

10 point three-fold dilution compound concentration-response curves, with a top concentration of 10 μM were generated from 10 mM stocks of compound solubilised in DMSO. All assays were performed in black, non-binding, low volume Corning 384-well plates (cat. #4514, Corning), in a total reaction volume of 10 μL and 1% (v/v) final DMSO concentration. 2.4 μL Kinase Buffer (50 mM HEPES pH 7.5, 0.01% BRIJ-35, 10 mM $MgCl_2$, 1 mM EGTA), 5 μL 2× Peptide/Kinase mixture (detailed below for each kinase) and 2.5 μL 4×ATP Solution (prepared in Kinase Buffer) were added separately to the compound plates, placed on a plate shaker for 30 sec, and then incubated for 60 mins at room temperature. The kinase reaction was then quenched by the addition of 5 μL of Development Reagent (ThermoFisher Scientific proprietary). Assay plates were placed on a plate shaker for 30 sec, incubated for 60 mins at room temperature, and then read using a fluorescence plate reader. $IC_{50}$ values were calculated using XLfit software (IDBS Ltd, Surrey, UK), with the curve fit to model number 205 (sigmoidal dose-response model).

Aurora A (AurA): The 2×AURKA (Aurora A)/Ser/Thr 01 (ThermoFisher Scientific proprietary) mixture was prepared in 50 mM HEPES pH 7.5, 0.01% BRIJ-35, 10 mM $MgCl_2$, 1 mM EGTA. The final 10 μL Kinase Reaction consisted of 15 nM AURKA (Aurora A), 2 μM Ser/Thr 01 and 10 μM ATP (Km app) in 50 mM HEPES pH 7.5, 0.01% BRIJ-35, 10 mM $MgCl_2$, 1 mM EGTA. After the 1 hour Kinase Reaction incubation, 5 μL of a 1:4096 dilution of Development Reagent was added.

Aurora B (AurB): The 2×AURKB (Aurora B)/Ser/Thr 01 (ThermoFisher Scientific proprietary) mixture was prepared in 50 mM HEPES pH 7.5, 0.01% BRIJ-35, 10 mM $MgCl_2$, 1 mM EGTA. The final 10 μL Kinase Reaction consisted of 23 nM AURKB (Aurora B), 2 μM Ser/Thr 01 and 75 μM ATP (Km app measured as 81 μM ATP) in 50 mM HEPES pH 7.5, 0.01% BRIJ-35, 10 mM $MgCl_2$, 1 mM EGTA. After the 1 hour Kinase Reaction incubation, 5 μL of a 1:4096 dilution of Development Reagent was added.

JAK1: The 2×JAK/Tyr 06 (ThermoFisher Scientific proprietary) mixture was prepared in 50 mM HEPES pH 6.5, 0.01% BRIJ-35, 10 mM $MgCl_2$, 1 mM EGTA, 0.02% NaN3. The final 10 μL Kinase Reaction consisted of 74 nM JAK, 2 μM Tyr 06 and 75 μM ATP (Km app measured as 87 μM ATP) in 50 mM HEPES pH 7.0, 0.01% BRIJ-35, 10 mM MgCl$_2$, 1 mM EGTA, 0.01% NaN3. After the 1 hour Kinase Reaction incubation, 5 µL of a 1:128 dilution of Development Reagent was added.

JAK2: The 2×JAK2/Tyr 06 (ThermoFisher Scientific proprietary) mixture was prepared in 50 mM HEPES pH 7.5, 0.01% BRIJ-35, 10 mM MgCl$_2$, 1 mM EGTA. The final 10 µL Kinase Reaction consisted of 0.27 nM JAK2, 2 µM Tyr 06 and 25 µM ATP (Km app measured as 31 µM ATP) in 50 mM HEPES pH 7.5, 0.01% BRIJ-35, 10 mM MgCl$_2$, 1 mM EGTA. After the 1 hour Kinase Reaction incubation, 5 µL of a 1:128 dilution of Development Reagent was added.

JAK3: The 2×JAK3/Tyr 06 (ThermoFisher Scientific proprietary) mixture was prepared in 50 mM HEPES pH 7.5. 0.01% BRIJ-35, 10 mM MgCl$_2$, 1 mM EGTA. The final 10 µL Kinase Reaction consisted of 2.4 nM JAK3, 2 µM Tyr 06 and 10 µM ATP (Km app measured as 14 µM ATP) in 50 mM HEPES pH 7.5, 0.0100BRIJ-35, 10 mM MgCl$_2$, 1 mM EGTA. After the 1 hour Kinase Reaction incubation, 5 µL of a 1:128 dilution of Development Reagent was added.

The examples were tested in the above assays and the following data was observed (data shown are the arithmetic mean of PIC$_{50}$ values observed from two or more experiments).

| Example | DNA-PK enz pIC50 | DNA-PK cell pIC50 | TTK enz pIC50 | JAK1 enz pIC50 | JAK2 enz pIC50 | JAK3 enz pIC50 | AurA enz pIC50 | AurB enz pIC50 |
|---|---|---|---|---|---|---|---|---|
| 1 | 10.0 | 6.7 | 5.9 | <5 | <5.2 | <5 | <5 | <5 |
| 2 | 9.8 | 7.3 | 5.8 | <5 | <5 | <5 | <5 | <5 |
| 3 | >10 | 7.2 | 5.4 | <5 | <5 | <5 | <5 | <5 |
| 4 | 9.0 | 6.6 | 6.0 | <5 | <5 | <5 | <5 | <5 |
| 5 | 9.1 | 7.0 | 5.3 | <5 | <5 | <5 | <5 | <5 |
| 6 | >10 | 8.3 | 7.2 | <5 | <5 | <5 | <5 | <5 |
| 7 | >10 | 7.3 | 6.9 | <5 | <5 | <5 | <5 | <5 |
| 8 | >10 | 8.0 | 6.2 | <5 | <5 | <5 | <5 | <5 |
| 9 | >10 | 8.1 | 6.1 | <5 | <5 | <5 | <5.1 | <5 |
| 10 | >10 | 8.0 | 6.4 | <5 | <5 | <5 | <5 | <5 |
| 11 | 9.8 | 7.7 | 6.4 | <5 | <5 | <5 | <5 | <5 |
| 12 | >10 | 7.7 | 6.3 | <5 | <5 | <5 | <5 | <5 |
| 13 | 9.7 | 7.8 | 6.5 | <5 | <5 | <5 | <5 | <5 |
| 14 | >10 | 8.0 | 7.0 | <5 | <5 | <5 | <5 | <5 |
| 15 | >10 | 7.8 | 6.6 | <5 | <5 | <5 | <5 | <5 |
| 16 | >10 | 7.8 | 6.7 | <5 | <5 | <5 | <5 | <5 |
| 17 | >10 | 7.0 | 6.5 | <5 | <5 | <5 | <5 | <5 |
| 18 | 9.6 | 7.3 | 5.8 | <5 | <5 | <5 | <5 | <5 |
| 19 | 9.8 | 7.6 | 6.7 | <5 | <5 | <5 | <5 | <5 |
| 20 | 10.0 | 7.7 | 6.4 | <5 | <5 | <5 | <5 | <5 |
| 21 | >10 | 7.8 | 6.4 | <5 | <5 | <5 | <5 | <5 |
| 22 | 9.8 | 7.6 | 5.5 | <5 | <5 | <5 | <5 | <5 |
| 23 | 9.4 | 7.2 | 5.9 | <5 | <5 | <5 | <5 | <5 |
| 24 | 9.1 | 7.1 | 5.6 | <5 | <5 | <5 | <5 | <5 |
| 25 | 9.7 | 7.4 | 6.2 | <5 | <5 | <5 | <5 | <5 |
| 26 | 9.8 | 7.4 | 5.8 | <5 | <5 | <5 | <5 | <5 |
| 27 | >10 | 7.9 | 6.4 | <5 | <5 | <5 | <5 | <5 |
| 28 | >10 | 7.8 | 6.1 | <5 | <5 | <5 | 5.3 | <5 |
| 29 | >10 | 7.6 | 6.4 | <5 | <5 | <5 | <5 | <5 |
| 30 | 9.9 | 7.9 | 6.4 | <5 | <5 | <5 | <5 | <5 |
| 31 | 9.9 | 7.6 | 5.9 | <5 | <5 | <5 | <5 | <5 |
| 32 | >10 | 7.7 | 5.8 | <5 | <5 | <5 | <5 | <5 |
| 33 | 9.3 | 6.9 | 5.9 | <5 | <5 | <5 | <5 | <5 |
| 34 | >10 | 7.5 | 5.3 | <5 | <5 | <5 | <5 | <5 |
| 35 | >10 | 7.4 | 5.9 | <5 | <5 | 5.2 | <5 | <5 |
| 36 | 9.7 | 7.5 | 6.0 | <5 | <5.1 | <5 | <5 | <5 |
| 37 | 9.2 | 6.5 | 5.7 | <5 | <5 | <5 | <5 | <5 |
| 38 | 8.0 | 5.5 | <5.1 | <5 | <5 | <5 | <5 | <5 |
| 39 | 9.0 | 7.1 | 5.4 | <5 | <5 | <5 | <5 | <5 |
| 40 | 9.5 | 6.8 | 5.8 | <5 | <5 | <5.1 | <5 | <5 |
| 41 | 8.6 | 6.2 | <5.1 | <5 | <5 | <5 | <5 | <5 |
| 42 | 8.9 | 6.5 | <5.1 | <5 | <5 | <5 | <5 | <5 |
| 43 | 7.8 | 5.7 | <5 | <5 | <5 | <5 | <5 | <5 |
| 44 | 8.5 | 6.7 | <5.1 | <5 | <5 | <5 | <5 | <5 |
| 45 | 9.2 | 7.0 | 5.2 | <5 | <5 | <5 | <5 | <5 |
| 46 | 8.1 | 6.2 | 5.4 | <5 | <5 | <5 | <5 | <5 |
| 47 | 9.0 | 6.7 | 5.8 | <5 | <5 | <5 | <5 | <5 |
| 48 | 9.0 | 6.5 | 5.9 | <5 | <5 | <5 | <5 | <5 |
| 49 | 8.8 | 6.6 | 5.7 | <5 | <5 | <5 | <5 | <5 |
| 50 | 8.4 | 6.4 | 5.2 | <5 | <5 | <5 | <5 | <5 |
| 51 | >10 | 7.9 | 6.4 | <5 | <5 | <5 | <5 | <5 |
| 52 | 9.3 | 7.0 | 5.6 | <5 | <5 | <5.1 | <5 | <5 |

From the data measured it can be seen that the Examples are DNA-PK inhibitors that are selective against these particular targets—TTK, JAK1, JAK2, JAK3, Aurora A, Aurora B. Comparing the enzyme $pIC_{50}$ values indicate that the Examples have >2.5 log units of selectivity from DNA-PK to the other targets shown. This equates to >300× fold selectivity between the $IC_{50}$ values.

Furthermore, certain DNA-PK inhibitors of Formula (I) show good volume of distribution and consequently may have longer half-life in vivo, in particular, when $R^1$ is a basic group, for example where $R^1$ is pyrrolidinyl or piperidinyl. The longer half-life means these compounds may be useful for certain combination therapy scenarios.

Pharmacokinetic data for Examples 44 and 52 are shown in Table D. Data was obtained from plasma collection up to 24 h following an acute dose of a compound of Formula (I) to either han wistar rats or beagle dogs. The han wistar rats were dosed with: i) Example 44 as either an intravenous dose of 1 mg/kg (100% deionised water pH adjusted to 3.96 using 1M HCl) or an oral dose of 5 mg/kg (5% DMSO/95% SBE-B-CD (30% w/v) in water pH adjusted to 3.87 using 1M HCl), or ii) Example 52 as either an intravenous dose of 0.5 mg/kg (5% DMSO/95% SBE-B-CD (30% w/v) in water) or an oral dose of 1 mg/kg (100% (0.5% HPMC/0.1% TWEEN in water)). The beagle dogs were dosed with: i) Example 44 (DMSO/95% SBE-B-CD (30% w/v) in water for both routes of administration) as either an intravenous dose of 0.5 mg/kg or an oral dose of 1 mg/kg, or ii) Example 52 as either an intravenous dose of 0.5 mg/kg (5% DMSO/95% SBE-B-CD (30% w/v) in water) or an oral dose of 1 mg/kg (100% (0.5% HPMC/0.1% TWEEN in water)).

TABLE D

|  | Example 44 | Example 52 |
| --- | --- | --- |
| Discrete PK Rat: | | |
| clearance (CL) | 13 mL/min/kg | 12.2 mL/min/kg |
| volume of distribution (V) | 3.4 L/kg | 1.65 L/kg |
| oral $t^{1/2}$ | 3.9 h | 3.6 h |
| iv $t^{1/2}$ | 4.3 h | 4.6 h |
| Discrete PK Dog: | | |
| clearance (CL) | 7.5 mL/min/kg | 16 mL/min/kg |
| volume of distribution (V) | 7.8 L/kg | 5.4 L/kg |
| oral $t^{1/2}$ | not determined | 6.3 h |
| iv $t^{1/2}$ | 15 h | 6.2 h |

Compounds may be further selected on the basis of further biological or physical properties which may be measured by techniques known in the art and which may be used in the assessment or selection of compounds for therapeutic or prophylactic application.

As a result of their DNA-PK inhibitory activity, the compounds of Formula (I), and pharmaceutically acceptable salts thereof are expected to be useful in therapy.

Accordingly, the compounds of the present disclosure are of value as anti-tumour agents. Particularly, the compounds of the present disclosure are of value as anti-proliferative, apoptotic and/or anti-invasive agents in the containment and/or treatment of solid and/or liquid tumour disease. Particularly, the compounds of the present disclosure are expected to be useful in the prevention or treatment of those tumours which are sensitive to inhibition of DNA-PK. Further, the compounds of the present disclosure are expected to be useful in the prevention or treatment of those tumours which are mediated alone or in part by DNA-PK. The compounds may thus be used to produce an DNA-PK enzyme inhibitory effect in a warm-blooded animal in need of such treatment.

As stated herein, inhibitors of DNA-PK should be of therapeutic value for the treatment of proliferative disease such as cancer and in particular solid tumours and their metastases, and haematological tumours.

Anti-cancer effects which are accordingly useful in the treatment of cancer in a patient include, but are not limited to, anti-tumour effects, the response rate, the time to disease progression and the survival rate. Anti-tumour effects of a method of treatment of the present disclosure include but are not limited to, inhibition of tumour growth, tumour growth delay, regression of tumour, shrinkage of tumour, increased time to regrowth of tumour on cessation of treatment, slowing of disease progression. Anti-cancer effects include prophylactic treatment as well as treatment of existing disease.

Where "cancer" is mentioned, this includes both non-metastatic cancer and also metastatic cancer, such that treating cancer involves treatment of both primary tumours and also tumour metastases.

"DNA-PK inhibitory activity" refers to a decrease in the activity of DNA-PK as a direct or indirect response to the presence of a compound of Formula (I), or pharmaceutically acceptable salt thereof, relative to the activity of DNA-PK kinase in the absence of compound of Formula (I), or pharmaceutically acceptable salt thereof. Such a decrease in activity may be due to the direct interaction of the compound of Formula (I), or pharmaceutically acceptable salt thereof with DNA-PK, or due to the interaction of the compound of Formula (I), or pharmaceutically acceptable salt thereof with one or more other factors that in turn affect DNA-PK activity. For example, the compound of Formula (I), or pharmaceutically acceptable salt thereof may decrease DNA-PK by directly binding to the DNA-PK, by causing (directly or indirectly) another factor to decrease DNA-PK activity, or by (directly or indirectly) decreasing the amount of DNA-PK present in the cell or organism.

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

In one embodiment there is provided a compound of Formula (I), or a pharmaceutically acceptable salt thereof, for use in therapy.

In one embodiment there is provided the use of the compound of Formula (I), or a pharmaceutically acceptable salt thereof, for the manufacture of a medicament.

In one embodiment there is provided a compound of Formula (I), or a pharmaceutically acceptable salt thereof, for use in the treatment of a disease mediated by DNA-PK. In one embodiment, said disease mediated by DNA-PK is cancer. In one embodiment, said cancer is a solid or haematological cancer. In one embodiment, said cancer is selected from the group consisting of breast cancer, ovarian cancer, pancreatic cancer, haematological cancer, non-small cell lung cancer, small cell lung cancer, gastric cancer and head and neck squamous cell carcinoma.

In one embodiment there is provided a compound of Formula (I), or a pharmaceutically acceptable salt thereof, for use in the treatment of cancer.

In one embodiment there is provided the use of the compound of Formula (I), or a pharmaceutically acceptable salt thereof, for the manufacture of a medicament for the treatment of a disease mediated by DNA-PK. In one embodiment, said disease mediated by DNA-PK is cancer. In one embodiment, said cancer is a solid or haematological cancer. In one embodiment, said cancer is selected from the group consisting of breast cancer, ovarian cancer, pancreatic cancer, haematological cancer, non-small cell lung cancer, small cell lung cancer, gastric cancer and head and neck squamous cell carcinoma.

In one embodiment there is provided the use of the compound of Formula (I), or a pharmaceutically acceptable salt thereof, for the manufacture of a medicament for the treatment of cancer.

In one embodiment there is provided a method for treating a disease in which inhibition of DNA-PK is beneficial in a warm-blooded animal in need of such treatment, which comprises administering to said warm-blooded animal a therapeutically effective amount of a compound of Formula (I), or a pharmaceutically acceptable salt thereof. In one embodiment, said disease is cancer. In one embodiment, said cancer is a solid or haematological cancer. In one embodiment, said cancer is selected from the group consisting of breast cancer, ovarian cancer, pancreatic cancer, haematological cancer, non small cell lung cancer, small cell lung cancer, gastric cancer and head and neck squamous cell carcinoma.

In one embodiment there is provided a method for treating cancer in a warm-blooded animal in need of such treatment, which comprises administering to said warm-blooded animal a therapeutically effective amount of a compound of Formula (I), or a pharmaceutically acceptable salt thereof.

The term "therapeutically effective amount" refers to an amount of a compound of Formula (I) as described in any of the embodiments herein which is effective to provide "therapy" in a subject, or to "treat" a disease or disorder in a subject. In the case of cancer, the therapeutically effective amount may cause any of the changes observable or measurable in a subject as described in the definition of "therapy", "treatment" and "prophylaxis" above. For example, the effective amount can reduce the number of cancer or tumour cells; reduce the overall tumour size; inhibit or stop tumour cell infiltration into peripheral organs including, for example, the soft tissue and bone; inhibit and stop tumour metastasis; inhibit and stop tumour growth; relieve to some extent one or more of the symptoms associated with the cancer; reduce morbidity and mortality; improve quality of life; or a combination of such effects. An effective amount may be an amount sufficient to decrease the symptoms of a disease responsive to inhibition of DNA-PK activity. For cancer therapy, efficacy in vivo can, for example, be measured by assessing the duration of survival, time to disease progression (TTP), the response rates (RR), duration of response, and/or quality of life. As recognized by those skilled in the art, effective amounts may vary depending on route of administration, excipient usage, and co-usage with other agents. For example, where a combination therapy is used, the amount of the compound of Formula (I) or pharmaceutically acceptable salt described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of DNA-PK activity as described above. Typically, such amounts may be determined by one skilled in the art by, for example, starting with the dosage range described in this specification for the compound of Formula (I) or pharmaceutically acceptable salt thereof and an approved or otherwise published dosage range(s) of the other pharmaceutically active compound(s).

"Warm-blooded animals" include, for example, humans.

In one embodiment there is provided a method for treating cancer in a warm-blooded animal in need of such treatment, which comprises administering to said warm-blooded animal a therapeutically effective amount of a compound of Formula (I), or a pharmaceutically acceptable salt thereof. In one embodiment, said cancer is a solid or haematological cancer. In one embodiment, said cancer is selected from the group consisting of breast cancer, ovarian cancer, pancreatic cancer, haematological cancer, non-small cell lung cancer, small cell lung cancer, gastric cancer and head and neck squamous cell carcinoma.

In any embodiment where cancer is mentioned in a general sense, said cancer may be a solid cancer or a haematological cancer, for example breast cancer, ovarian cancer, pancreatic cancer, non-small cell lung cancer, small cell lung cancer, gastric cancer and head and neck squamous cell carcinoma.

The anti-cancer treatment described in this specification may be useful as a sole therapy, or may involve, in addition to administration of the compound of Formula (I), conventional surgery, radiotherapy or chemotherapy; or a combination of such additional therapies. Such conventional surgery, radiotherapy or chemotherapy may be administered simultaneously, sequentially or separately to treatment with the compound of Formula (I).

Where a combination therapy is administered "simultaneously", this includes treatment of a patient with a single dosage form (e.g. a tablet) comprising both a compound of Formula (I), or a pharmaceutically acceptable salt thereof and an additional anti-cancer substance; and also simultaneous dosing of separate dosage forms each separately comprising one of the respective combination partners.

Where a combination therapy is administered "sequentially" or "separately", this includes treatment of a patient with a first dosage form (e.g. a tablet) comprising a compound of Formula (I), or a pharmaceutically acceptable salt thereof, followed by treatment of the same patient with a second dosage form comprising an additional anti-cancer substance; or treatment of a patient with a single dosage form (e.g. a tablet) comprising a particular anti-cancer substance, followed by treatment of the same patient with a second dosage form comprising a compound of Formula (I), or a pharmaceutically acceptable salt thereof. The interval between the sequential or separate doses may be judged by a skilled practitioner with reference to the information in this specification.

Radiotherapy may include one or more of the following categories of therapy:
    i. External radiation therapy using electromagnetic radiation, and intraoperative radiation therapy using electromagnetic radiation;

ii. Internal radiation therapy or brachytherapy; including interstitial radiation therapy or intraluminal radiation therapy; or
iii. Systemic radiation therapy, including but not limited to iodine 131 and strontium 89.

Therefore, in one embodiment there is provided a compound of Formula (I), or a pharmaceutically acceptable salt thereof, and radiotherapy, for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered in combination with radiotherapy.

In one embodiment there is provided a compound of Formula (I), or a pharmaceutically acceptable salt thereof, and radiotherapy, for use in the simultaneous, separate or sequential treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with radiotherapy. In one embodiment there is provided a method of treating cancer in a warm-blooded animal who is in need of such treatment, which comprises administering to said warm-blooded animal a compound of Formula (I), or a pharmaceutically acceptable salt thereof and radiotherapy, wherein the compound of Formula (I), or a pharmaceutically acceptable salt thereof, and radiotherapy are jointly effective in producing an anti-cancer effect.

In one embodiment there is provided a method of treating cancer in a warm-blooded animal who is in need of such treatment, which comprises administering to said warm-blooded animal a compound of Formula (I), or a pharmaceutically acceptable salt thereof and simultaneously, separately or sequentially administering radiotherapy, wherein the compound of Formula (I), or a pharmaceutically acceptable salt thereof, and radiotherapy are jointly effective in producing an anti-cancer effect. In one embodiment the cancer is a solid cancer.

In any embodiment the radiotherapy is selected from the group consisting of one or more of the categories of radiotherapy listed under points (i)-(iii) above.

Chemotherapy may include one or more of the following categories of anti-tumour substance:
i. antiproliferative/anti-neoplastic drugs and combinations thereof, as used in medical oncology, such as anti-tumour antibiotics (for example anthracyclines like adriamycin, bleomycin, doxorubicin, liposomal doxorubicin, pirarubicin, daunomycin, valrubicin, epirubicin, idarubicin, mitomycin-C, dactinomycin, amrubicin and mithramycin); and topoisomerase inhibitors (for example epipodophyllotoxins like etoposide and teniposide, amsacrine, irinotecan, topotecan and camptothecin);
ii. inhibitors of DNA repair mechanisms such as CHK kinase; ATM inhibitors (such as AZD0156 and AZD1390); inhibitors of poly (ADP-ribose) polymerase (PARP inhibitors, including olaparib); inhibitors of ATR kinase (such as cerelasertib/AZD6738); and inhibitors of WEE1 kinase (such as adavosertib/AZD1775/MK-1775); and
iii. immunotherapy approaches, including for example ex vivo and in vivo approaches to increase the immunogenicity of patient tumour cells, such as blocking antibodies to PD-L (for example durvalumab/MEDI4736).

Therefore, in one embodiment there is provided a compound of Formula (I), or a pharmaceutically acceptable salt thereof, and at least one additional anti-tumour substance, for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof is administered in combination with an additional anti-tumour substance. In one embodiment there is one additional anti-tumour substance. In one embodiment there are two additional anti-tumour substances. In one embodiment there are three or more additional anti-tumour substances.

In one embodiment there is provided a compound of Formula (I), or a pharmaceutically acceptable salt thereof, and at least one additional anti-tumour substance for use in the simultaneous, separate or sequential treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with an additional anti-tumour substance.

In one embodiment there is provided a method of treating cancer in a warm-blooded animal who is in need of such treatment, which comprises administering to said warm-blooded animal a compound of Formula (I), or a pharmaceutically acceptable salt thereof and at least one additional anti-tumour substance, wherein the amounts of the compound of Formula (I), or a pharmaceutically acceptable salt thereof, and the additional anti-tumour substance are jointly effective in producing an anti-cancer effect.

In one embodiment there is provided a method of treating cancer in a warm-blooded animal who is in need of such treatment, which comprises administering to said warm-blooded animal a compound of Formula (I), or a pharmaceutically acceptable salt thereof, and simultaneously, separately or sequentially administering at least one additional anti-tumour substance to said warm-blooded animal, wherein the amounts of the compound of Formula (I), or pharmaceutically acceptable salt thereof, and the additional anti-tumour substance are jointly effective in producing an anti-cancer effect.

In any embodiment the additional anti-tumour substance is selected from the group consisting of one or more of the anti-tumour substances listed under points (i)-(iii) above.

In one embodiment there is provided a compound of Formula (I), or a pharmaceutically acceptable salt thereof, and at least one anti-neoplastic agent for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one anti-neoplastic agent. In one embodiment the anti-neoplastic agent is selected from the list of antineoplastic agents in point (i) above.

In one embodiment there is provided a compound of Formula (I), or a pharmaceutically acceptable salt thereof, and at least one anti-neoplastic agent for use in the simultaneous, separate or sequential treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with at least one anti-neoplastic agent. In one embodiment the antineoplastic agent is selected from the list of antineoplastic agents in point (i) above.

In one embodiment there is provided a compound of Formula (I), or a pharmaceutically acceptable salt thereof, and at least one additional anti-tumour substance selected from the group consisting of doxorubicin or liposomal doxorubicin, olaparib, AZD6738 and AZD0156, for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one additional anti-tumour substance selected from the group consisting of doxorubicin, liposomal doxorubicin, olaparib, AZD6738 and AZD0156.

In one embodiment there is provided a compound of Formula (I), or a pharmaceutically acceptable salt thereof, and at least one additional anti-tumour substance selected from the group consisting of doxorubicin or liposomal doxorubicin, olaparib, AZD6738 and AZD0156, for use in the simultaneous, separate or sequential treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with at least one additional anti-tumour substance selected from the group consisting of doxorubicin, liposomal doxorubicin, olaparib, AZD6738 and AZD0156.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with olaparib. In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with olaparib.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with doxorubicin or liposomal doxorubicin. In one embodiment there is provided a compound of Formula (I), or a pharmaceutically acceptable salt thereof, for use in the treatment of cancer, where the compound of Formula (I), or a pharmaceutically acceptable salt thereof, is administered in simultaneously, separately or sequentially with doxorubicin or liposomal doxorubicin.

In one embodiment there is provided a pharmaceutical composition comprising a compound of Formula (I) and at least one additional anti-tumour substance. In one embodiment the pharmaceutical composition also comprises at least one pharmaceutically acceptable excipient.

In one embodiment there is provided a pharmaceutical composition comprising a compound of Formula (I) and at least one additional anti-tumour substance, for use in the treatment of cancer. In one embodiment the pharmaceutical composition also comprises at least one pharmaceutically acceptable excipient.

According to a further embodiment there is provided a kit comprising:
a) A compound of Formula (I), or a pharmaceutically acceptable salt thereof, in a first unit dosage form;
b) A further additional anti-tumour substance in a further unit dosage form;
c) Container means for containing said first and further unit dosage forms; and optionally
d) Instructions for use.

In one embodiment the anti-tumour substance comprises an anti-neoplastic agent.

In any embodiment where an anti-neoplastic agent is mentioned, the anti-neoplastic agent is one or more of the agents listed under point (i) above.

The compounds of Formula (I), and pharmaceutically acceptable salts thereof, may be administered as pharmaceutical compositions, comprising one or more pharmaceutically acceptable excipients.

Therefore, in one embodiment there is provided a pharmaceutical composition comprising a compound of Formula (I), or a pharmaceutically acceptable salt thereof, and at least one pharmaceutically acceptable excipients.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous or intramuscular dosing), or as a suppository for rectal dosing. The compositions may be obtained by conventional procedures using conventional pharmaceutical excipients, well known in the art. Thus, compositions intended for oral use may contain, for example, one or more colouring, sweetening, flavouring and/or preservative agents.

In one embodiment there is provided a pharmaceutical composition comprising a compound of Formula (I), or a pharmaceutically acceptable salt thereof, and at least one pharmaceutically acceptable excipients, for use in therapy.

In one embodiment there is provided a pharmaceutical composition comprising a compound of Formula (I), or a pharmaceutically acceptable salt thereof, and at least one pharmaceutically acceptable excipients, for use in the treatment of cancer. In one embodiment, said cancer is a solid cancer or a haematological cancer. In one embodiment, said cancer is selected from the group consisting of breast cancer, ovarian cancer, pancreatic cancer, haematological cancer, non small cell lung cancer, small cell lung cancer, gastric cancer and head and neck squamous cell carcinoma.

The compound of Formula (I) will normally be administered to a warm-blooded animal at a unit dose within the range 2.5-5000 mg/m$^2$ body area of the animal, or approximately 0.05-100 mg/kg, and this normally provides a therapeutically-effective dose. A unit dose form such as a tablet or capsule will usually contain, for example 0.1-250 mg of active ingredient. The daily dose will necessarily be varied depending upon the host treated, the particular route of administration, any therapies being co-administered, and the severity of the illness being treated.

EXAMPLES

The various embodiments are illustrated by the following Examples. The embodiment is not to be interpreted as being limited to the Examples.

Unless stated otherwise, starting materials were commercially available. All solvents and commercial reagents were of laboratory grade and were used as received.

General Experimental

During the preparation of the Examples, generally:
(i) operations were carried out at room temperature (rt), i.e. in the range 17 to 25° C. and under an atmosphere of an inert gas such as $N_2$ or Ar unless otherwise stated;
(ii) in general, the course of reactions was followed by thin layer chromatography (TLC) and/or analytical high performance liquid chromatography (HPLC or UPLC) which was usually coupled to a mass spectrometer (LCMS). The reaction times that are given are not necessarily the minimum attainable;
(iii) when necessary, organic solutions were dried over anhydrous $MgSO_4$ or $Na_2SO_4$, work-up procedures were carried out using traditional phase separating techniques or by using SCX as described in (xiii), evaporations were carried out either by rotary evaporation in vacuo or in a Genevac HT-4/EZ-2 or Biotage V10;
(iv) yields, where present, are not necessarily the maximum attainable, and when necessary, reactions were repeated if a larger amount of the reaction product was required;
(v) in general, the structures of the end-products of the formula (I) were confirmed by nuclear magnetic resonance (NMR) and/or mass spectral techniques; electrospray mass spectral data were typically obtained using a Waters Acquity UPLC coupled to a Waters single quadrupole mass spectrometer acquiring both positive and negative ion data, and generally, only ions relating to the parent structure are reported; proton NMR chemical shift values were measured on the delta scale using either a Bruker AV500 spectrometer operating at a field strength of 500 MHz, a Bruker AV400 operating at 400 MHz or a Bruker AV300 operating at 300 MHz. Unless otherwise stated, NMR spectra were obtained at 500 MHz in d6-dimethylsulfoxide. The following abbreviations have been used: s, singlet; d, doublet; t, triplet; q, quartet; m, multiplet; br, broad; qn, quintet;
(vi) Unless stated otherwise compounds containing an asymmetric carbon and/or sulfur atom were not resolved;
(vii) intermediates were not necessarily fully purified but their structures and purity were assessed by TLC, analytical HPLC/UPLC, and/or NMR analysis and/or mass spectrometry;
(viii) unless otherwise stated, flash column chromatography (fcc) was performed on Merck Kieselgel silica (Art. 9385) or on reversed phase silica (Fluka silica gel 90 C18) or on Silicycle cartridges (40-63 m silica, 4 to 330 g weight) or on Grace resolv cartridges (4-120 g) or on RediSep Rf 1.5 Flash columns or on RediSep Rf high performance Gold Flash columns (150-415 g weight) or on RediSep Rf Gold C18 Reversed-phase columns (20-40 m silica) either manually or automated using an Isco CombiFlash Companion system or similar system;
(ix) preparative reverse phase HPLC (RP HPLC) was performed on C18 reversed-phase silica typically using a Waters XSelect CSH C18 column (5 m silica, 30 mm diameter, 100 mm length) using decreasingly polar mixtures as eluent, for example [containing 0.1% formic acid or 0.3-5% aqueous ammonium hydroxide (d=0.91)] as solvent A and acetonitrile as solvent B; a typical procedure would be as follows: a solvent gradient over 10-20 minutes, at 40-50 mL per minute, from a 95:5 mixture of solvents A and B respectively to a 5:95 mixture of solvents A and B (or alternative ratio as appropriate).
(x) the following analytical UPLC methods were used; in general, reverse-phase C18 silica was used with a flow rate of 1 mL/minute and detection was by Electrospray Mass Spectrometry and by UV absorbance recording a wavelength range of 220-320 nm. Analytical UPLC was performed on CSH C18 reverse-phase silica, using a Waters XSelect CSH C18 column with dimensions 2.1×50 mm and particle size 1.7 micron). Gradient analysis was employed using decreasingly polar mixtures as eluent, for example decreasingly polar mixtures of water (containing 0.1% formic acid or 0.1% ammonia) as solvent A and acetonitrile as solvent B. A typical 2 minute analytical UPLC method would employ a solvent gradient over 1.3 minutes, at approximately 1 mL per minute, from a 97:3 mixture of solvents A and B respectively to a 3:97 mixture of solvents A and B.
(xi) where certain compounds were obtained as an acid-addition salt, for example a mono-hydrochloride salt or a di-hydrochloride salt, the stoichiometry of the salt was based on the number and nature of the basic groups in the compound, the exact stoichiometry of the salt was generally not determined, for example by means of elemental analysis data;
(xii) where reactions refer to the use of a microwave, one of the following microwave reactors were used: Biotage Initiator, Personal Chemistry Emrys Optimizer, Personal Chemistry Smithcreator or CEM Explorer;
(xiii) compounds were purified by strong cation exchange (SCX) chromatography using Isolute SPE flash SCX-2 or SCX-3 columns (International Sorbent Technology Limited, Mid Glamorgan, UK);
(xiv) the following preparative chiral HPLC methods were carried out using a Gilson GX-281 HPLC and a DAICEL CHIRALPAK IC (2×25 cm, 5 m), DAICEL CHIRALPAK IF (2×25 cm, um) or XBridge Prep OBD C18 Column (3×15 cm, 5 m); in general a flow rate of between 10-350 mL/minute and detection was by UV absorbance at a typical wavelength of 254 nm. A sample concentration of about 1-100 mg/mL was used in a suitable solvent mixture with an injection volume of between 0.5-10 mL and run time of between 10-150 minutes and a typical oven temperature of 25-35° C.;
(xv) the following analytical chiral HPLC methods were carried out using Shimadzu UFLC and a Daicel CHIRALPAK IC-3 (50×4.6 mm 3 um) or Daicel CHIRALPAK IF-3 (50×4.6 mm 3 μm); in general a flow rate of 1 mL/minute and detection was by UV absorbance at a typical wavelength of 254 nm. A sample concentration of about 1 mg/mL was used in a suitable solvent such as EtOH with an injection volume of about 10 μl and run time of between 10-60 minutes and a typical oven temperature of 25-35° C.;
(xvi) the following preparative chiral supercritical fluid chromatography (SFC) methods were used; in general a flow rate of about 70 mL/minute and detection was by UV absorbance at a typical wavelength of 254 nm. A sample concentration of about 100 mg/mL was used in a suitable solvent such as MeOH with an injection volume of about 0.5 mL and run time of between 10-150 minutes and a typical oven temperature of 25-35° C.;

(xvii) in general Examples and intermediate compounds were named using ACD Name, "Structure to Name" part of ChemDraw Ultra (CambridgeSoft) or Biovia Draw 2016;

(xviii) in addition to the ones mentioned above, the following abbreviations have been used:

| Ac₂O | acetic anhydride | HPLC | High-performance liquid chromatography |
|---|---|---|---|
| BINAP | 2,2'-Bis(diphenylphosphino)-1,1'-binaphthalene | iPrOH | iso-propanol |
| CDCl₃ | deuterated chloroform | MeCN | acetonitrile |
| conc. | Concentrated | MeI | iodomethane |
| DBU | 1,8-diazabicyclo[5.4.0]undec-7-ene | MeOD | D₄-methanol |
| DCM | dichloromethane | MeOH | methanol |
| DIPEA | N,N-diisopropylethylamine | MTBE | methyl tert-butyl ether |
| DMA | N,N-dimethylacetamide | m/z | mass spectrometry peak(s) |
| DMAP | 4-dimethylaminopyridine | NaH | Sodium hydride |
| DME | 1,2-dimethoxyethane | NBS | N-Bromosuccinimide |
| DMF | N,N-dimethylformamide | NH₄Cl | ammonium chloride |
| DMF-DMA | dimethylformamide dimethylacetal | NMP | 1-methylpyrrolidin-2-one |
| DMSO | Dimethylsulfoxide | rt | Room temperature |
| DSC | Differential Scanning Calorimetry | Sat. | saturated |
| Et₃N | triethylamine | SCX | Strong cation exchange |
| EtOAc | Ethyl acetate | SFC | Supercritical fluid chromatography |
| Et₂O | diethyl ether | TBAB | tetra n-butylammonium bromide |
| EtOH | ethanol | TBAF | tetra n-butylammonium fluoride |
| FA | formic acid | THF | tetrahydrofuran |
| fcc | flash column chromatography | XRPD | X-ray powder diffraction |
| h | hour(s) | | |
| RuPhos | 2-Dicyclohexylphosphino-2',6'-diisopropoxybiphenyl | | |
| RuPhos Pd G3 | (2-Dicyclohexylphosphino-2',6'-diisopropoxy-1,1'-biphenyl) [2-(2'-amino-1,1'-biphenyl)]palladium(II) methanesulfonate | | |
| Brettphos Pd G3 | [(2-Di-cyclohexylphosphino-3,6-dimethoxy-2',4',6'-triisopropyl-1,1'-biphenyl)-2-(2'-amino-1,1'-biphenyl)] palladium(II) methanesulfonate methanesulfonate | | |

(xix) For XRPD analysis the instrument used was a Bruker D4. The X-ray powder diffractogram was determined by mounting a sample of the crystalline material on a Bruker single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5418 angstroms. The collimated X-ray source was passed through an automatic variable divergence slit set at V20 and the reflected radiation directed through a 5.89 mm anti scatter slit and a 9.55 mm detector slit. Samples were measured in reflection geometry in θ-2θ configuration over the scan range 2° to 400 2θ with a nominal 0.12 second exposure per 0.02 increment. The instrument was equipped with a Position sensitive detector (Lynxeye). Persons skilled in the art of X-ray powder diffraction will understand that the relative intensity of peaks can be affected by, for example, grains above 30 microns in size and non-unitary aspect ratios that may affect analysis of samples. The skilled person will also understand that the position of reflections can be affected by the precise height at which the sample sits in the diffractometer and the zero calibration of the diffractometer. The surface planarity of the sample may also have a small effect. Hence the diffraction pattern data presented are not to be taken as absolute values; (xx) For the Differential Scanning Calorimetry the instrument used was TA Instruments Q2000 DSC. Typically less than 3 mg of material contained in a standard aluminium pan fitted with a lid was heated over the temperature range 25° C. to 300° C. at a constant heating rate of 10° C. per minute. A purge gas using nitrogen was used—flow rate 50 mL per minute. Thermal data was analysed using standard software, e.g., Universal v.4.5A from TA INSTRUMENTS®.

Intermediate 1: 5-amino-2-bromo-4-methylbenzoic acid

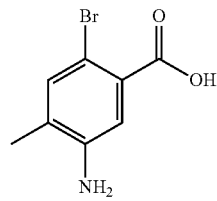

NBS (11.87 g, 66.15 mmol) was added portionwise to 3-amino-4-methylbenzoic acid (10.00 g, 66.15 mmol) in DMF (50 mL) at 5° C. over a period of 5 minutes so that the temperature did not rise above 15° C. The resulting solution was stirred at 5° C. for 1 h. The reaction mixture was poured on to ice water (250 mL) with stirring. The resulting solid was filtered, washed with ice cold water and dried to afford the title compound (15.21 g, 100%) as a pale pink solid; ¹H NMR (400 MHz, DMSO) 2.04-2.09 (3H, m), 5.21 (2H, s), 7.06 (1H, s), 7.21 (1H, d), 12.84 (1H, s).

Intermediate 2: methyl 5-amino-2-bromo-4-methylbenzoate

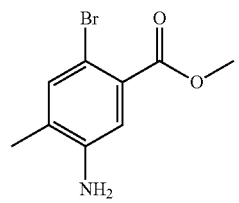

Thionyl chloride (4.80 mL, 66.11 mmol) was added dropwise to 5-amino-2-bromo-4-methylbenzoic acid (15.21 g, 66.11 mmol) in MeOH (200 mL) at 20° C. over a period of 5 minutes. The resulting solution was stirred at reflux for 2 h. The reaction mixture was allowed to cool, quenched with a small amount of water and the solvent was removed in vacuo. The reaction mixture was diluted with EtOAc (250 mL), and washed sequentially with saturated NaHCO₃ (100 mL), water (100 mL), and sat. brine (100 mL). The organic layer was passed through a phase separating filter paper and evaporated to afford the title compound (14.85 g, 92%) as a red oil; $^1$H NMR (400 MHz, DMSO) 2.06-2.11 (3H, m), 3.80 (3H, s), 5.28 (2H, s), 7.06 (1H, s), 7.22-7.28 (1H, m); m/z MH$^+$ 244.

Intermediate 3: methyl 2-bromo-5-((tert-butoxycarbonylamino))-4-methylbenzoate

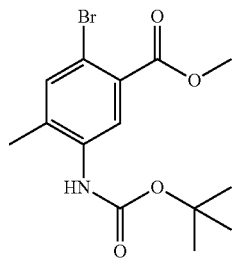

Di-tert-butyl dicarbonate (20.40 g, 93.47 mmol) was added to methyl 5-amino-2-bromo-4-methylbenzoate (15.21 g, 62.31 mmol) in ethanol (125 mL) at rt. The solution was stirred at rt for 18 h. A further 0.5 eq of di-tert-butyl dicarbonate (6.80 g, 31.15 mmol) was added and the reaction mixture was stirred at rt for a further 18 h. The EtOH was removed in vacuo and the resulting slurry was diluted with n-heptane (250 mL). The solid was filtered off, washed with n-heptane and dried to afford the title compound (14.82 g, 69%) as a grey solid; $^1$H NMR (400 MHz, DMSO) 1.48 (9H, s), 2.25 (3H, s), 3.84 (3H, s), 7.56-7.6 (1H, m), 7.89 (1H, s), 8.73 (1H, s); m/z MH$^+$ 344.

Intermediate 4: tert-butyl (4-bromo-5-formyl-2-methylphenyl)carbamate

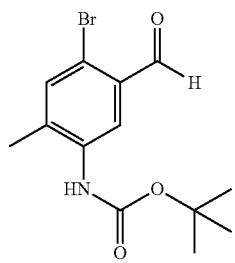 [SMILES: Cc1cc(Br)c(C=O)cc1NC(=O)OC(C)(C)C]

Diisobutylaluminium hydride (1 M, 100 mL, 100.0 mmol) was added to methyl 2-bromo-5-((tert-butoxycarbonyl)amino)-4-methylbenzoate (11.47 g, 33.33 mmol) in DCM (200 mL) at −78° C. The solution was stirred at −78° C. for 1 h. Methanol (20 mL) was slowly added to quench the reaction and the solution was warmed to rt. The reaction mixture was diluted with 0.5 M aq. HCl (250 mL) and diethyl ether (250 mL). The organic phase was isolated, washed with brine (200 mL), passed through a phase separating filter paper and the solvent was removed in vacuo to give a mixture of the desired aldehyde and alcohol. Manganese(IV) oxide (10.78 g, 124.1 mmol) was added in one portion to the mixture in DCM (260 mL) at rt. The reaction mixture was stirred at rt for 1 h. A further 5 equivalents of manganese(IV) oxide (14.48 g, 166.7 mmol) was added and the reaction mixture was stirred at rt for 1 h. The reaction mixture was filtered through Celite®, washed with DCM (500 mL) and the solvent was removed in vacuo to afford the title compound (9.97 g, 96%) as a white solid; $^1$H NMR (400 MHz, DMSO) 1.48 (9H, s), 2.29 (3H, s), 7.63-7.66 (1H, m), 7.95 (1H, s), 8.78 (1H, s), 10.14 (1H, s); m/z MH$^+$ 314.

Intermediate 5: tert-butyl N-[4-bromo-5-[(Z-2-bromovinyl]-2-methyl-phenyl]carbamate

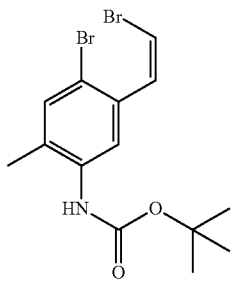 [SMILES: Cc1cc(Br)c(/C=C\Br)cc1NC(=O)OC(C)(C)C]

Potassium 2-methylpropan-2-olate (4.18 g, 37.24 mmol) was added portionwise to (bromomethyl)triphenylphosphonium bromide (16.24 g, 37.24 mmol) in THF (500 mL) at −78° C. tert-Butyl (4-bromo-5-formyl-2-methylphenyl)carbamate (9.75 g, 31.03 mmol) in THF (100 mL) was added dropwise to the resulting suspension, and the mixture was stirred for 16 h and allowed to warm slowly to rt. n-Heptane (500 mL) was added and the precipitate was filtered through celite. The solvent was removed in vacuo to give a light brown solid. The product was purified by fcc, eluting with 0-10% ethyl acetate in n-heptane, to afford the title compound (9.12 g, 75%) as a white solid; $^1$H NMR (400 MHz, DMSO) 1.47 (9H, s), 2.21 (3H, s), 6.87 (1H, d), 7.20 (1H, d), 7.51 (1H, s), 7.74 (1H, s), 8.62 (1H, s); a mass ion was not detected for this intermediate.

Intermediate 6: diethyl 6-((tert-butoxycarbonyl)amino)-7-methylcinnoline-1,2-dicarboxylate

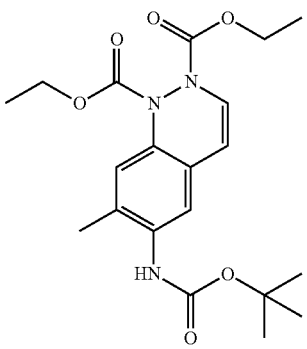 [SMILES: CCOC(=O)N1C=Cc2cc(NC(=O)OC(C)(C)C)c(C)cc2N1C(=O)OCC]

tert-Butyl N-[4-bromo-5-[(Z)-2-bromovinyl]-2-methylphenyl]carbamate (9.12 g, 23.32 mmol) was dissolved in 1,4-dioxane (150 mL) at rt under nitrogen. The reaction mixture was degassed by bubbling nitrogen through the mixture for 5 minutes. Potassium carbonate (8.06 g, 58.30 mmol), diethyl hydrazine-1,2-dicarboxylate (6.16 g, 34.98 mmol), N1,N2-dimethylethane-1,2-diamine (1.255 mL, 11.66 mmol) and copper(I) iodide (1.110 g, 5.83 mmol) were added and the resulting dark green suspension was stirred at 100° C. for 18 h. The reaction mixture was allowed to cool to rt, filtered, washed with DCM (400 mL) and the filtrate was concentrated in vacuo. The product was purified by fcc, eluting with 0-25% ethyl acetate in n-heptane. to afford the title compound (6.63 g, 70%) as a white foam; ¹H NMR (400 MHz, DMSO) 1.21 (6H, dt), 1.47 (9H, s), 2.22 (3H, s), 4.18 (4H, dq), 6.30 (1H, d), 7.11 (1H, s), 7.19 (1H, s), 7.25 (1H, s), 8.57 (1H, s); m/z MH⁺ 406.

Intermediate 7: tert-butyl (7-methylcinnolin-6-yl)carbamate

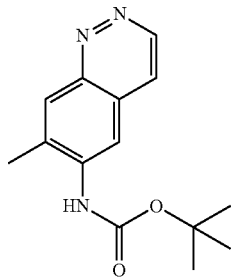 [SMILES: Cc1cc2nnccc2cc1NC(=O)OC(C)(C)C]

2 M aq. NaOH (7.95 mL, 15.91 mmol) was added to diethyl 6-((tert-butoxycarbonyl)amino)-7-methylcinnoline-1,2-dicarboxylate (2.15 g, 3.18 mmol) in EtOH (25 mL) at rt. The reaction mixture was stirred at rt for 18 h, then was concentrated in vacuo. The reaction mixture was diluted with EtOAc (100 mL), and the organic layer was isolated and washed sequentially with water (50 mL) and sat. brine (50 mL). The organic layer was passed through a phase separating filter paper, concentrated in vacuo, then purified by fcc, eluting with 0-100% EtOAc in n-heptane, to afford the title compound (0.370 g, 45%) as an orange foam; ¹H NMR (400 MHz, DMSO) 1.53 (9H, s), 2.54 (3H, d), 8.09 (1H, dd), 8.24 (2H, d), 8.89 (1H, s), 9.19 (1H, d); m/z MH⁺ 260.

Intermediate 8: 7-methylcinnolin-6-amine

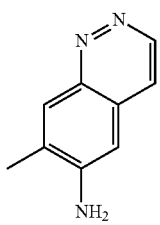

4 M HCl in 1,4-dioxane (1.54 mL, 6.17 mmol) was added to tert-butyl (7-methylcinnolin-6-yl)carbamate (320 mg, 1.23 mmol) in MeOH (5 mL) at rt and the reaction mixture was stirred at rt for 18 h, then was concentrated in vacuo to afford the title compound (245 mg, 100%) as a bright orange solid; ¹H NMR (400 MHz, DMSO) 2.42 (3H, d), 6.96 (1H, s), 7.91 (2H, s), 8.10 (1H, s), 8.22 (1H, d), 8.86 (1H, d); m/z MH⁺ 160.

Intermediate 9: N-(7-methyl-6-quinolyl)-1,1-diphenyl-methanimine

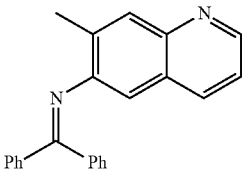 [SMILES: Cc1cc2ncccc2cc1N=C(c1ccccc1)c1ccccc1]

Pd₂(dba)₃ (0.918 g, 1.13 mmol) and sodium tert-butoxide (6.49 g, 67.54 mmol) were added to a degassed suspension of 6-bromo-7-methylquinoline (10 g, 45.03 mmol), diphenylmethanimine (8.31 mL, 49.53 mmol) and rac-BINAP (1.40 g, 2.25 mmol) in toluene (172 mL). The reaction was heated at 90° C. for 1 h. The reaction mixture was allowed to cool to rt, diluted with EtOAc (200 mL) and washed with water (100 mL). The aqueous layer was extracted with EtOAc (2×100 mL), then the combined organic layers were passed through a phase separating filter paper and the solvent was removed in vacuo. The crude product was purified by fcc, eluting with 0-100% EtOAc in n-heptane, to afford the title compound (14.30 g, 99%) as an orange solid; ¹H NMR (400 MHz, DMSO) 2.35-2.4 (3H, m), 6.92 (1H, s), 7.20 (2H, dd), 7.25-7.34 (4H, m), 7.49-7.55 (2H, m), 7.58 (1H, ddd), 7.72-7.79 (3H, m), 7.94-8.02 (1H, m), 8.66 (1H, dd); m/z MH⁺ 323.

Intermediate 10: 7-methylquinolin-6-amine

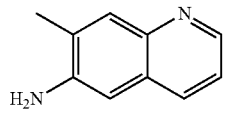

2 M aq. HCl (93.0 mL, 186.1 mmol) was added to N-(7-methyl-6-quinolyl)-1,1-diphenyl-methanimine (15.00 g, 46.52 mmol) in THF (35 mL) and the reaction mixture was stirred for 1 h.

The reaction was diluted with EtOAc (100 mL) and the layers were separated. The aqueous layer was further extracted with EtOAc (50 mL). The aqueous phase was neutralised with 2 M aq. NaOH and the resulting solid was collected by filtration, washed with a small volume of water and dried to afford the title compound (6.70 g, 91%) as a cream solid; ¹H NMR (400 MHz, DMSO) 2.25-2.32 (3H, m), 5.35 (2H, s), 6.87 (1H, s), 7.22 (1H, dd), 7.61 (1H, s), 7.87-7.98 (1H, m), 8.46 (1H, dd); m/z MH⁺ 159.

Intermediate 11: 6-bromo-4-methoxy-7-methylquinoline

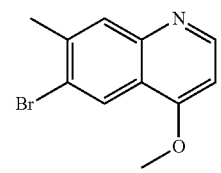

Sodium methanolate (221 mg, 4.09 mmol) was added in one portion to 6-bromo-4-chloro-7-methylquinoline (350 mg, 1.36 mmol) in methanol (8 mL) at rt. The reaction mixture was stirred at 65° C. for 1 day, then was allowed to cool to rt. The reaction mixture was diluted with EtOAc (75 mL) and washed with water (20 mL) and sat. brine (20 mL). The organic phase was dried over MgSO$_4$, filtered and concentrated in vacuo to afford the title compound (275 mg, 80%) as a cream solid; $^1$H NMR (400 MHz, DMSO) 2.54 (3H, s), 4.05 (3H, s), 7.03 (1H, d), 7.94 (1H, s), 8.30 (1H, s), 8.74 (1H, d); m/z MH$^+$ 252.

Intermediate 12: 4-methoxy-7-methylquinolin-6-amine

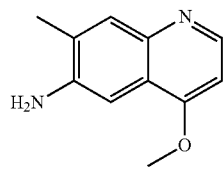

Brettphos precat G3 (126 mg, 0.14 mmol) was added in one portion to 6-bromo-4-methoxy-7-methylquinoline (350 mg, 1.39 mmol), cesium carbonate (905 mg, 2.78 mmol) and ammonia 0.5 M in 1,4-dioxane (5.55 mL, 2.78 mmol) in dioxane (9 mL) at rt. The reaction mixture was heated in a microwave reactor at 100° C. for 3 days. The reaction mixture was filtered and the solid was washed with DCM (50 mL). The organic layers were combined and concentrated in vacuo, then purified by fcc, eluting with 0-5% MeOH in DCM, to afford the title compound (200 mg, 77%) as a white solid; $^1$H NMR (400 MHz, DMSO) 2.27 (3H, s), 3.96 (3H, s), 5.30 (2H, s), 6.75 (1H, d), 7.15 (1H, s), 7.55 (1H, s), 8.33 (1H, d); m/z MH$^+$ 189.

Intermediate 13: N-(4-chloro-7-methyl-6-quinolyl)-1,1-diphenylmethanimine

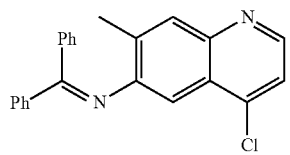 [SMILES: Cc1cc2nccc(Cl)c2cc1N=C(c1ccccc1)c1ccccc1]

Pd$_2$(dba)$_3$ (23.8 mg, 0.03 mmol) and sodium tert-butoxide (169 mg, 1.75 mmol) were added to a degassed suspension of 6-bromo-4-chloro-7-methylquinoline (300 mg, 1.17 mmol), diphenylmethanimine (216 µl, 1.29 mmol) and rac-BINAP (36.4 mg, 0.06 mmol) in toluene (4.46 mL). The reaction mixture was heated at 90° C. for 1 h, then was allowed to cool to rt, diluted with EtOAc and washed with water. The aqueous layer was extracted with EtOAc, then the combined organic layers were dried over MgSO$_4$, concentrated in vacuo and purified by fcc, eluting with 0-25% EtOAc in n-heptane, to afford the title compound (408 mg, 98%) as a yellow gum; $^1$H NMR (400 MHz, DMSO) 2.43 (3H, s), 7.14 (3H, s), 7.23 (3H, s), 7.28 (1H, d), 7.38-7.56 (3H, m), 7.84 (3H, d), 8.55 (1H, d); m/z MH$^+$ 357.

Intermediate 14: N-(4,7-dimethyl-6-quinolyl)-1,1-diphenylmethanimine

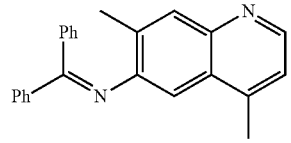 [SMILES: Cc1cc2nccc(C)c2cc1N=C(c1ccccc1)c1ccccc1]

PdCl$_2$(dppf)-CH$_2$Cl$_2$ adduct (37.3 mg, 0.05 mmol) was added in one portion to a degassed mixture of 2,4,6-trimethyl-1,3,5,2,4,6-trioxatriborinane (0.192 mL, 1.37 mmol), N-(4-chloro-7-methyl-6-quinolyl)-1,1-diphenylmethanimine (326 mg, 0.91 mmol) and cesium carbonate (595 mg, 1.83 mmol) in 1,4-dioxane (12 mL) at rt. The resulting suspension was stirred in a capped vial at 120° C. for 15 h. The reaction was allowed to cool to rt and was filtered, then evaporated to dryness and purified by fcc, eluting with 0-40% EtOAc in n-heptane, to afford the title compound (254 mg, 83%) as a yellow gum; $^1$H NMR (400 MHz, DMSO) 2.38 (3H, d), 2.43 (3H, d), 6.86 (1H, s), 6.94-7.07 (1H, m), 7.13 (2H, dd), 7.18-7.24 (3H, m), 7.38-7.59 (3H, m), 7.74-7.94 (3H, m), 8.55 (1H, d); m/z MH$^+$ 337.

Intermediate 15: 4,7-dimethylquinolin-6-amine

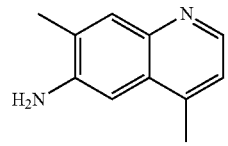

2 M aq. HCl (0.092 mL, 3.02 mmol) was added to N-(4,7-dimethyl-6-quinolyl)-1,1-diphenylmethanimine (254 mg, 0.75 mmol) in THF (2 mL) and the reaction mixture was stirred for 1 h. Water was added to the mixture (to dissolve the solid) and the solution was loaded onto a 10 g SCX-2 column. Benzophenone was washed away with MeOH (2× column volumes) then the column was eluted with 1 M NH$_3$ in MeOH to afford the title compound (129 mg, 99%) as a cream solid; $^1$H NMR (400 MHz, DMSO) 2.29 (3H, d), 2.52 (3H, s), 5.37 (2H, s), 7.00 (1H, s), 7.04-7.13 (1H, m), 7.51-7.66 (1H, m), 8.33 (1H, d); m/z MH$^+$ 173.

Intermediate 16: 6-chloro-7-nitroquinoxaline

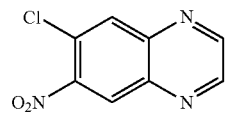 [SMILES: O=[N+]([O-])c1cc2nccnc2cc1Cl]

Oxalaldehyde (40% in water, 4.26 mL, 37.32 mmol) was added to 4-chloro-5-nitrobenzene-1,2-diamine (5.00 g, 26.65 mmol) in ethanol (100 mL) at rt. The resulting solution was heated at reflux for 1 h. The reaction mixture was cooled to rt and the resulting precipitate was filtered off and dried to afford the title compound (4.50 g, 81%) as a brown solid; ¹H NMR (400 MHz, DMSO) 8.57 (1H, s), 8.91 (1H, s), 9.15 (1H, d), 9.17 (1H, d); m/z MH⁺ 210.

Intermediate 17: 6-methyl-7-nitroquinoxaline

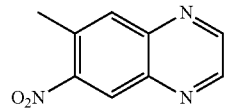

2,4,6-Trimethyl-1,3,5,2,4,6-trioxatriborinane (2.97 mL, 21.27 mmol) was added to 6-chloro-7-nitroquinoxaline (3.43 g, 16.37 mmol) in 1,4-dioxane (50 mL) and water (5 mL) at rt. K₂CO₃ (6.79 g, 49.10 mmol) and dichloro 1,1'-bis(diphenylphosphino) ferrocene palladium (II) (1.197 g, 1.64 mmol) were added and the reaction mixture was heated at reflux for 2 h. The reaction mixture was allowed to cool to rt, diluted with EtOAc (100 mL), washed with water (50 mL) and sat. brine (50 mL), and the organic layer was filtered through a phase separating filter paper and concentrated in vacuo to afford the crude product (2.50 g, 85% if pure) which was used directly in the next step; ¹H NMR (400 MHz, DMSO) 2.65 (3H, s), 8.19 (1H, s), 8.66 (1H, s), 9.04 (2H, dd); m/z MH⁺ 190.

Intermediate 18: 7-methylquinoxalin-6-amine

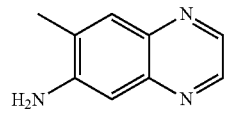

Iron (4.43 g, 79.29 mmol) and ammonia hydrochloride (0.707 g, 13.22 mmol) were added to 6-methyl-7-nitroquinoxaline (2.50 g, 13.22 mmol) in EtOH (85 mL) and water (15 mL) at rt. The resulting mixture was heated at 100° C. for 1 h. The reaction mixture was allowed to cool to rt, filtered and washed with EtOH. The filtrate was concentrated in vacuo and the crude product was purified by fcc, eluting with 0-5% MeOH in DCM to afford the title compound (1.80 g, 86%) as a yellow solid; ¹H NMR (400 MHz, DMSO) 2.24-2.38 (3H, m), 5.83 (2H, s), 7.02 (1H, s), 7.61-7.68 (1H, m), 8.44 (1H, d), 8.57 (1H, d); m/z MH⁺ 160.

Intermediates 19 and 20: 7-chloro-2-methyl-6-nitroquinoxaline (major) and 6-chloro-2-methyl-7-nitroquinoxaline (minor)

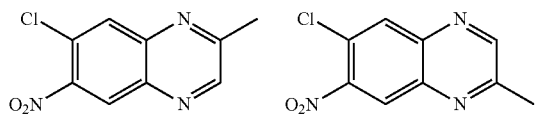

2-Oxopropanal (4.80 g, 26.65 mmol) was added to 4-chloro-5-nitrobenzene-1,2-diamine (5.00 g, 26.65 mmol) in EtOH (100 mL) at rt. The reaction solution was heated at reflux for 1 h. The reaction mixture was allowed to cool to rt and the resulting precipitate was isolated by filtration and dried in vacuo to give a 6:1 mixture of 7-chloro-2-methyl-6-nitroquinoxaline (major) and 6-chloro-2-methyl-7-nitroquinoxaline (4.67 g, 78% total for both isomers); ¹H NMR (400 MHz, DMSO, major isomer) 2.78 (3H, s), 8.43 (1H, s), 8.84 (1H, s), 9.05 (1H, s); m/z [M-H]⁻ 222.

Intermediates 21 and 22: 2,7-dimethyl-6-nitroquinoxaline (major) and 2,6-dimethyl-7-nitroquinoxaline (minor)

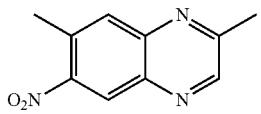 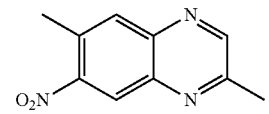

2,4,6-Trimethyl-1,3,5,2,4,6-trioxatriborinane (1.60 mL, 11.40 mmol) was added to a 6:1 mixture of 7-chloro-2-methyl-6-nitroquinoxaline and 6-chloro-2-methyl-7-nitroquinoxaline (2.04 g, 9.12 mmol) in 1,4-dioxane (50 mL) and water (5 mL) at rt. Potassium carbonate (3.15 g, 22.81 mmol) and dichloro 1,1'-bis(diphenylphosphino) ferrocene palladium (II) (Pd106) (0.57 g, 0.76 mmol) were added and the reaction mixture was heated at reflux for 2 h. The reaction was cooled, diluted with EtOAc (100 mL) and filtered. The filtrate was washed with water (50 mL) and sat. brine (50 mL). The organic layer was isolated, filtered through a phase separating filter paper, concentrated in vacuo and purified by fcc, eluting with 0-50% EtOAc in n-heptane to afford the title compounds as a 6:1 mixture of isomers (1.01 g, 65% total) as a tan solid; ¹H NMR (400 MHz, DMSO, major isomer) 2.69 (3H, s), 2.76 (3H, s), 8.10 (1H, s), 8.66 (1H, s), 8.98 (1H, s); m/z MH⁺ 204.

Intermediates 23 and 24: 2,7-dimethylquinoxalin-6-amine (major) and 3,7-dimethylquinoxalin-6-amine (minor)

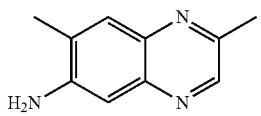 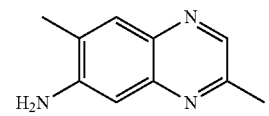

Iron (1.43 g, 25.69 mmol) and ammonia hydrochloride (229 mg, 4.28 mmol) were added to a 6:1 mixture of 2,7-dimethyl-6-nitroquinoxaline and 3,7-dimethylquinoxalin-6-amine (1.01 g, 4.28 mmol) in EtOH (30 mL) and water (5 mL) at rt under nitrogen. The resulting mixture was stirred at 100° C. for 1 h. The reaction mixture was cooled, filtered and washed with EtOH. The solvent was removed in vacuo and the crude product was purified by fcc, elution gradient 0 to 5% MeOH in DCM, to afford the title compounds (600 mg, 81%) as a brown solid (5:1 mixture); ¹H NMR for major isomer (400 MHz, DMSO) 2.30 (3H, s), 2.56 (3H, s), 5.63 (2H, s), 7.01 (1H, s), 7.56 (1H, s), 8.50 (1H, s); m/z MH⁺ 174.

Intermediate 25: 5-chloroquinazolin-6-amine

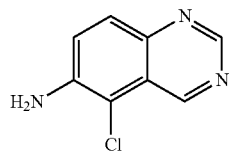 [SMILES: Nc1ccc2ncncc2c1Cl]

N-Chlorosuccinimide (4.47 g, 33.48 mmol) was added in one portion to quinazolin-6-amine (4.86 g, 33.48 mmol) in DCM (150 mL) at 25° C. The resulting solution was stirred at 25° C. for 16 h. The solvent was removed under reduced pressure and the residue was purified by fcc, elution gradient 0 to 30% EtOAc in petroleum ether. Pure fractions were evaporated to dryness to afford the title compound (6.30 g, 105%) as a pale yellow solid; $^1$H NMR (400 MHz, DMSO) 6.31 (2H, s), 7.60 (1H, d), 7.76 (1H, d), 9.04 (1H, s), 9.41 (1H, s) m/z MH$^+$ 180.

Intermediate 26: 7-bromo-5-chloroquinazolin-6-amine

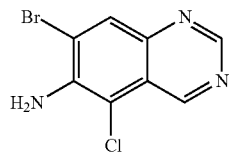

NBS (5.00 g, 28.09 mmol) was added in one portion to 5-chloroquinazolin-6-amine (6.10 g, 33.96 mmol) in DCM (150 mL) at rt. The resulting solution was stirred at rt for 16 h. The reaction mixture was quenched with sat. aq. Na$_2$CO$_3$ (200 mL), extracted with DCM (4×200 mL), and the combined organic layers were dried over MgSO$_4$, filtered and evaporated. The crude product was purified by fcc, elution gradient 0 to 20% EtOAc in petroleum ether, to afford the title compound (0.91 g, 10%) as a grey solid; $^1$H NMR (400 MHz, CDCl$_3$) 5.03 (2H, s), 8.22 (1H, s), 9.19 (1H, s), 9.56 (1H, s); m/z MH$^+$ 258.

Intermediate 27: 5-chloro-7-methylquinazolin-6-amine

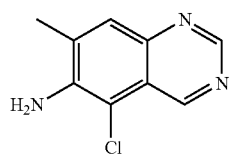

Pd(Ph$_3$P)$_4$ (384 mg, 0.33 mmol) was added in one portion to 7-bromo-5-chloroquinazolin-6-amine (860 mg, 3.33 mmol), trimethylboroxine (2506 mg, 9.98 mmol) and K$_2$CO$_3$ (920 mg, 6.65 mmol) in THF (15 mL) at rt. The reaction mixture was stirred at 80° C. for 48 h, then allowed to cool to rt and purified by fcc, elution gradient 0 to 30% EtOAc in petroleum ether, to afford the title compound (540 mg, 84%) as a pale yellow solid; $^1$H NMR (400 MHz, DMSO) 2.43 (3H, d), 6.03 (2H, s), 7.68 (1H, s), 9.02 (1H, s), 9.38 (1H, s); m/z MH$^+$ 194.

Intermediate 28: 7-methylquinazolin-6-amine

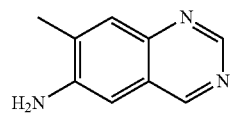

Pd/C 10% (500 mg, 4.70 mmol), 5-chloro-7-methylquinazolin-6-amine (500 mg, 2.58 mmol) and Et$_3$N (0.720 mL, 5.16 mmol) in MeOH (25 mL) was stirred under 3 atm of hydrogen at rt for 3 days. The reaction mixture was filtered through celite, and concentrated in vacuo. The resulting crude product was purified by flash C18-flash chromatography, elution gradient 0 to 30% MeCN in water to afford the title compound (80 mg, 19%) as a yellow solid; $^1$H NMR (400 MHz, DMSO) 2.32 (3H, d), 5.71 (2H, s), 6.95 (1H, s), 7.62 (1H, s), 8.86 (1H, s), 9.14 (1H, s); m/z MH$^+$ 160.

Intermediate 29: ethyl 2-chloro-4-((tetrahydro-2H-pyran-4-yl)amino)pyrimidine-5-carboxylate

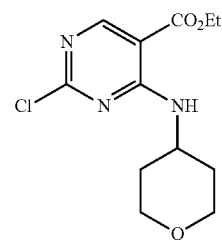 [SMILES: CCOC(=O)c1cnc(Cl)nc1NC1CCOCC1]

Potassium carbonate (62.50 g, 452.41 mmol) was added to ethyl 2,4-dichloropyrimidine-5-carboxylate (40.00 g, 180.97 mmol) and tetrahydro-2H-pyran-4-amine hydrochloride (24.90 g, 181.0 mmol) in acetonitrile (1 L). The reaction mixture was stirred at rt for 16 h. The resulting precipitate was collected by filtration, washed with THF (750 mL) and the combined organic layers were concentrated in vacuo. The crude product was purified by fcc, elution gradient 0 to 2% THF in DCM, to afford the title compound (37.74 g, 73%) as a pale yellow solid; $^1$H NMR (400 MHz, DMSO) 1.32 (3H, t), 1.54-1.63 (2H, m), 1.85-1.89 (2H, m), 3.43-3.49 (2H, m), 3.83-3.88 (2H, m), 4.12-4.26 (1H, m), 4.29-4.34 (2H, m), 8.34 (1H, d), 8.64 (1H, s); m/z MH$^+$ 286.

Intermediate 30: 2-chloro-4-((tetrahydro-2H-pyran-4-yl)amino)pyrimidine-5-carboxylic acid

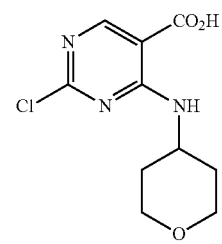 [SMILES: O=C(O)c1cnc(Cl)nc1NC1CCOCC1]

A solution of LiOH (13.11 g, 547.37 mmol) in water (800 mL) was added to a stirred solution of ethyl 2-chloro-4-((tetrahydro-2H-pyran-4-yl)amino)pyrimidine-5-carboxylate (78.20 g, 273.7 mmol) in THF (800 mL). The reaction mixture was stirred at rt for 3 h, then partially concentrated in vacuo and acidified with 2 M aq. HCl. The resulting precipitate was collected by filtration, washed with water (500 mL) and dried in vacuo to afford the title compound (66.4 g, 92%) as a white solid; $^1$H NMR (300 MHz, DMSO) 1.48-1.61 (2H, m), 1.85-1.89 (2H, m), 3.41-3.49 (2H, m), 3.81-3.87 (2H, m), 4.10-4.22 (1H, m), 8.54 (1H, d), 8.59 (1H, s); m/z MH$^+$ 258.

Intermediate 31: 2-chloro-9-(tetrahydro-2H-pyran-4-yl)-7,9-dihydro-8H-purin-8-one

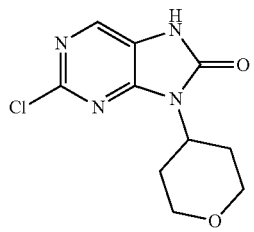 [SMILES: O=c1[nH]c2cnc(Cl)nc2n1C1CCOCC1]

Triethylamine (25.4 g, 251.5 mmol) was added to 2-chloro-4-((tetrahydro-2H-pyran-4-yl)amino)pyrimidine-5-carboxylic acid (64.8 g, 251.5 mmol) and diphenylphosphoryl azide (69.2 g, 251.5 mmol) in DMA (330 mL). The reaction mixture was stirred at rt for 1 h, then stirred at 120° C. for 16 h. The reaction mixture was poured into ice (2 L), the precipitate was collected by filtration, washed with water (400 mL) and dried in vacuo to afford the title compound (44.8 g, 70%) as a white solid; $^1$H NMR (400 MHz, DMSO) 1.66-1.70 (2H, m), 2.39-2.47 (2H, m), 3.45 (2H, t), 3.95-3.99 (2H, m), 4.38-4.46 (1H, m), 8.14 (1H, s), 11.65 (1H, s); m/z MH$^+$ 255.

Intermediate 32: 2-chloro-7-methyl-9-(tetrahydro-2H-pyran-4-yl)-7,9-dihydro-8H-purin-8-one

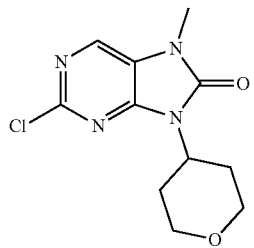 [SMILES: Cn1c(=O)n(C2CCOCC2)c2nc(Cl)ncc21]

A solution of NaOH (31.0 g, 775.50 mmol) in water (80 mL) was added to a stirred solution of 2-chloro-9-(tetrahydro-2H-pyran-4-yl)-7,9-dihydro-8H-purin-8-one (39.5 g, 155.1 mmol) and MeI (48.5 mL, 775.5 mmol) in THF (720 mL). The reaction mixture was stirred at rt for 16 h. The reaction mixture was partially concentrated in vacuo, then diluted with water. The resulting precipitate was collected by filtration, washed with water (300 mL) and dried in vacuo to afford the title compound (32.5 g, 69%) as a white solid; $^1$H NMR (400 MHz, DMSO) 1.67-1.71 (2H, m), 2.39-2.48 (2H, m), 3.37 (3H, s), 3.46 (2H, t), 3.96-3.99 (2H, m), 4.42-4.50 (1H, m), 8.37 (1H, s); m/z MH$^+$ 269.

Intermediate 33: ethyl 2-chloro-4-(((1s,4s)-4-hydroxycyclohexyl)amino)pyrimidine-5-carboxylate

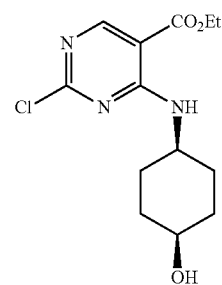 [SMILES: CCOC(=O)c1cnc(Cl)nc1N[C@H]1CC[C@@H](O)CC1]

Potassium carbonate (78.00 g, 565.5 mmol) was added to ethyl 2,4-dichloropyrimidine-5-carboxylate (50.00 g, 226.2 mmol) and (1s,4s)-4-aminocyclohexan-1-ol hydrochloride (34.30 g, 226.2 mmol) in acetonitrile (700 mL) at rt under air. The reaction mixture was stirred at rt for 16 h, then filtered through a Celite® pad. The filtrate was partially concentrated in vacuo and the resulting precipitate was collected by filtration, washed with MeCN (100 mL) and dried in vacuo to afford the title compound (41.0 g, 61%) as a white solid; $^1$H NMR (400 MHz, DMSO) 1.32 (3H, t), 1.42-1.58 (2H, m), 1.60-1.75 (6H, m), 3.66 (1H, d), 4.06 (1H, dd), 4.33 (2H, q), 4.57 (1H, d), 8.46 (1H, d), 8.63 (1H, s); m/z MH$^+$ 300.

Intermediate 34: 2-chloro-4-(((1s,4s)-4-hydroxycyclohexyl)amino)pyrimidine-5-carboxylic acid

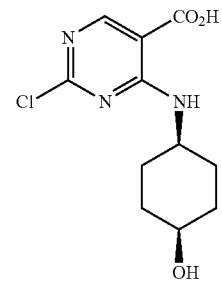 [SMILES: O=C(O)c1cnc(Cl)nc1N[C@H]1CC[C@@H](O)CC1]

LiOH (9.75 g, 407.00 mmol) was added to ethyl 2-chloro-4-(((1s,4s)-4-hydroxycyclohexyl)amino)pyrimidine-5-carboxylate (61.0 g, 203.50 mmol) in THF (400 mL) and water (400 mL) at rt under air. The reaction mixture was stirred at rt for 16 h, then partially concentrated in vacuo and acidified to pH~2 with 2 M aq. HCl. The resulting precipitate was collected by filtration, washed with water (500 mL) and dried in vacuo to afford the title compound (52 g, 94%) as a white solid; $^1$H NMR (400 MHz, DMSO) 1.51 (2H, d), 1.58-1.75 (6H, m), 3.66 (1H, s), 4.00-4.07 (1H, m), 4.56 (1H, s), 8.59 (1H, s), 8.69 (1H, d), 13.82 (1H, s); m/z MH$^+$ 272.

Intermediate 35: 2-chloro-9-((1s,4s)-4-hydroxycyclohexyl)-7,9-dihydro-8H-purin-8-one

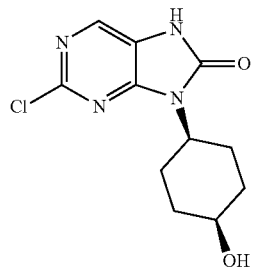 [SMILES: O=c1[nH]c2cnc(Cl)nc2n1[C@H]1CC[C@@H](O)CC1]

Triethylamine (28.2 mL, 202.4 mmol) was added to 2-chloro-4-(((1s,4s)-4-hydroxycyclohexyl)amino)pyrimidine-5-carboxylic acid (55.0 g, 202.4 mmol) in acetonitrile (550 mL) at rt under air. The reaction mixture was stirred at rt for 15 min. DPPA (55.7 g, 202.4 mmol) was added, and the reaction mixture was stirred at rt for 30 min and then heated at 90° C. for 6 h. The reaction mixture was allowed to cool to rt and poured into water (4 L). The precipitate was collected by filtration, washed with water (1 L) and dried in vacuo to afford the title compound (34.9 g, 64.1%) as a white solid; m/z MH$^+$ 269.

Intermediate 36: 2-chloro-9-((1s,4s)-4-hydroxycyclohexyl)-7-methyl-7,9-dihydro-8H-purin-8-one

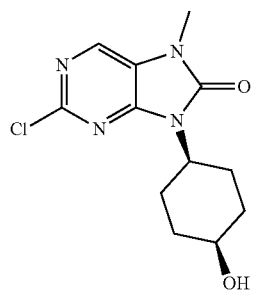 [SMILES: Cn1c(=O)n([C@H]2CC[C@@H](O)CC2)c2nc(Cl)ncc21]

Iodomethane (31.70 g, 223.30 mmol) was added to 2-chloro-9-((1s,4s)-4-hydroxycyclohexyl)-7,9-dihydro-8H-purin-8-one (30.00 g, 111.65 mmol), NaOH (22.33 g, 558.24 mmol) in THF (300 mL) and water (150 mL) at 25° C. The reaction mixture was stirred at 25° C. for 16 h. The reaction mixture was concentrated in vaccuo. The precipitate was collected by filtration, washed with water (250 mL) and dried in vacuo to afford the title compound (24.02 g, 76%) as a white solid; $^1$H NMR (400 MHz, DMSO) 1.43-1.61 (4H, m), 1.79 (2H, d), 2.54-2.68 (2H, m), 3.34 (3H, s), 3.87 (1H, s), 4.15-4.21 (1H, m), 4.46 (1H, d), 8.34 (1H, s); m/z MH$^+$ 283.

Intermediate 37: ethyl 2-chloro-4-(((1r,4r)-4-hydroxycyclohexyl)amino)pyrimidine-5-carboxylate

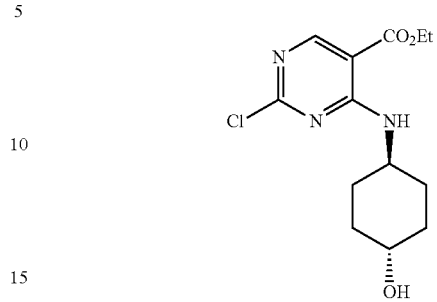

DIPEA (35.10 g, 271.5 mmol) was added dropwise to ethyl 2,4-dichloropyrimidine-5-carboxylate (40 g, 181.0 mmol) and (1r,4r)-4-aminocyclohexan-1-ol (20.84 g, 181.0 mmol) in acetonitrile (1.25 L) at 0° C. The reaction mixture was allowed to warm to rt, then stirred at rt for 16 h. The resulting precipitate was collected by filtration, washed with THF (500 mL) and the combined organic layers were isolated and concentrated in vacuo. The resulting crude product was purified by fcc, elution gradient 0 to 3% THF in DCM, to afford the title compound (42.0 g, 77%) as a pale yellow solid; $^1$H NMR (300 MHz, DMSO) 1.23-1.45 (7H, m), 1.82-1.95 (4H, m), 3.47-3.48 (1H, m), 3.86-3.95 (1H, m), 4.27-4.34 (2H, m), 4.63 (1H, d), 8.26 (1H, d), 8.60 (1H, s); m/z MH$^+$ 300.

Intermediate 38: 2-chloro-4-(((1r,4r)-4-hydroxycyclohexyl)amino)pyrimidine-5-carboxylic acid

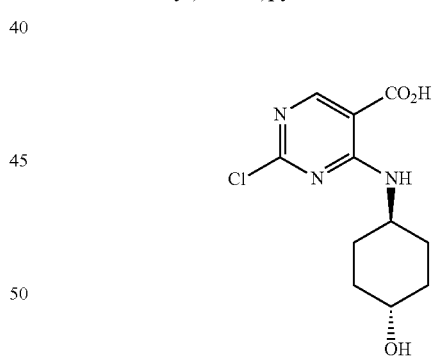

A solution of LiOH (6.71 g, 280.23 mmol) in water (420 mL) was added to a stirred solution of ethyl 2-chloro-4-(((1r,4r)-4-hydroxycyclohexyl)amino)pyrimidine-5-carboxylate (42.00 g, 140.1 mmol) in THF (420 mL). The reaction mixture was stirred at rt for 16 h, then partially concentrated in vacuo and acidified with 2 M aq. HCl. The resulting precipitate was collected by filtration, washed with water (350 mL) and dried in vacuo to afford the title compound (34.29 g, 90%) as a white solid, which was used without further purification; $^1$H NMR (300 MHz, DMSO) 1.24-1.43 (4H, m), 1.84 (2H, d), 1.94 (2H, d), 3.44-3.50 (1H, m), 3.88-3.90 (1H, m), 8.47 (1H, d), 8.58 (1H, s), 13.79 (1H, s), 1 exchangeable proton not visible; m/z MH$^+$ 272.

Intermediate 39: 2-chloro-9-((1r,4r-4-hydroxycyclo-hexyl)-79-dihydro-8H-purin-8-one

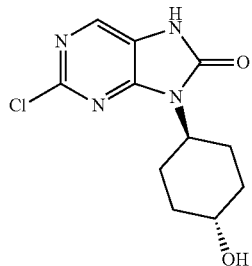 [SMILES: O=c1[nH]c2cnc(Cl)nc2n1[C@H]1CC[C@H](O)CC1]

Diphenylphosphoryl azide (38.3 g, 139.1 mmol) was added dropwise to 2-chloro-4-(((1r,4r)-4-hydroxycyclohexyl)amino)pyrimidine-5-carboxylic acid (36.0 g, 132.5 mmol), and triethylamine (18.47 mL, 132.50 mmol) in THF (800 mL) was added at rt. The reaction mixture was stirred at 100° C. for 12 h, then was allowed to cool to rt, concentrated in vacuo and the residue was diluted with water (700 mL). The solid was collected by filtration, dried in vacuo and triturated with DCM to afford the title compound (18.36 g, 51%) as a white solid; m/z MH$^+$ 269.

Intermediate 40: 2-chloro-9-((1r,4r)-4-hydroxycyclo-hexyl)-7-methyl-7,9-dihydro-8H-purin-8-one

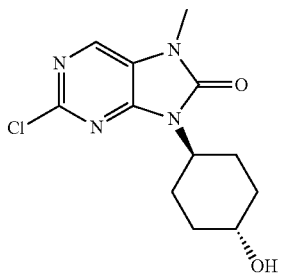 [SMILES: Cn1c(=O)n([C@H]2CC[C@H](O)CC2)c2nc(Cl)ncc21]

Sodium hydroxide (26.0 g, 651.28 mmol) in water (350 mL) was added in one portion to 2-chloro-9-((1r,4r)-4-hydroxycyclohexyl)-7,9-dihydro-8H-purin-8-one (35.0 g, 130.3 mmol) and methyl iodide (40.7 mL, 651.3 mmol) in THF (700 mL) at rt. The reaction mixture was stirred at rt for 16 h, then was partially concentrated in vacuo and the resulting solid was isolated by filtration and dried in vacuo to afford the title compound (31.6 g, 86%) as a light yellow solid; $^1$H NMR (300 MHz, DMSO) 1.16-1.45 (2H, m), 1.61-1.81 (2H, m), 1.87-2.03 (2H, m), 2.15-2.39 (2H, m), 3.35 (3H, s), 3.40-3.60 (1H, m), 4.00-4.28 (1H, m), 4.70 (1H, d), 8.35 (1H, s); m/z MH$^+$ 283.

Intermediate 41: ethyl (S)-2-chloro-4-((tetrahydro-2H-pyran-3-yl)amino)pyrimidine-5-carboxylate

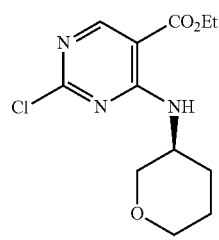 [SMILES: CCOC(=O)c1cnc(Cl)nc1N[C@H]1CCCOC1]

(S)-Tetrahydro-2H-pyran-3-amine hydrochloride (1.99 g, 14.48 mmol) in MeCN (10 mL) was added dropwise to a mixture of DIPEA (6.30 mL, 36.19 mmol) and ethyl 2,4-dichloropyrimidine-5-carboxylate (3.20 g, 14.48 mmol) in MeCN (60 mL) at 0° C. over a period of 5 min under air. The reaction mixture was stirred for 4 h, slowly allowing to warm to rt, then was stirred at rt for 18 h and concentrated in vacuo, diluted with EtOAc (100 mL), and washed with water then with sat. brine. The organic layer was dried over MgSO$_4$, filtered and concentrated in vacuo, and purified by fcc, eluting with 0-40% EtOAc in n-heptane, to afford the title compound (3.24 g, 78%) as a yellow oil; $^1$H NMR (400 MHz, DMSO) 1.32 (3H, t), 1.49-1.6 (1H, m), 1.63-1.79 (2H, m), 1.83-1.94 (1H, m), 3.48 (1H, dd), 3.54-3.65 (2H, m), 3.74 (1H, dd), 4.08-4.19 (1H, m), 4.33 (2H, q), 8.57 (1H, d), 8.64 (1H, s); m/z [M-H]$^-$ 284.

Intermediate 42: 2-chloro-4-[[(3S)-tetrahydropyran-3-yl]amino]pyrimidine-5-carboxylic acid

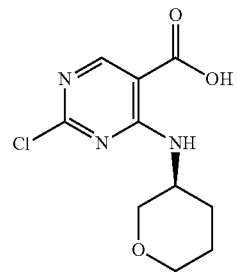 [SMILES: O=C(O)c1cnc(Cl)nc1N[C@H]1CCCOC1]

Lithium hydroxide hydrate (0.933 g, 22.23 mmol) was added in one portion to ethyl (S)-2-chloro-4-((tetrahydro-2H-pyran-3-yl)amino)pyrimidine-5-carboxylate (3.241 g, 11.12 mmol) in THF (20 mL) and water (20 mL) at 0° C. The reaction mixture was allowed to warm to rt and stirred at rt for 16 h. The reaction mixture was partially concentrated in vacuo, then was acidified with 2 M aq. HCl. The resulting precipitate was collected by filtration, washed with water (50 mL) and air dried overnight. The resulting white solid was further dried in vacuo at 50° C. for 24 h to afford the title compound (2.40 g, 84%) as a white solid; $^1$H NMR (400 MHz, DMSO) 1.55 (1H, dq), 1.61-1.77 (2H, m), 1.85-1.95 (1H, m), 3.45 (1H, dd), 3.59 (2H, t), 3.75 (1H, dd), 4.06-4.16 (1H, m), 8.60 (1H, s), 8.76 (1H, d), 13.62 (1H, s); m/z MH$^+$ 258.

Intermediate 43: (S)-2-chloro-9-(tetrahydro-2H-pyran-3-yl)-7,9-dihydro-8H-purin-8-one

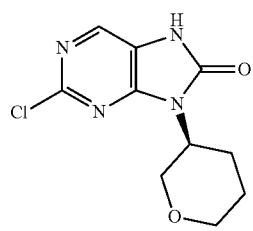

Diphenylphosphoryl azide (2.00 mL, 9.29 mmol) was added in one portion to a solution of 2-chloro-4-[[(3S)-tetrahydropyran-3-yl]amino]pyrimidine-5-carboxylic acid (2.40 g, 9.29 mmol) and triethylamine (1.30 mL, 9.29 mmol) in THF (50 mL) at rt. The reaction mixture was stirred at 80° C. for 24 h. The reaction mixture was allowed to cool to rt then was poured into water (40 mL), then was partially concentrated in vacuo causing a white precipitate to form which was isolated by filtration, dried in vacuo, washed with water, air dried, then dried in vacuo at 50° C. to afford the title compound (1.84 g, 78%) as a white solid; $^1$H NMR (400 MHz, DMSO) 1.61-1.82 (2H, m), 1.88-1.99 (1H, m), 2.4-2.49 (1H, m), 3.3-3.37 (1H, m), 3.78-3.93 (3H, m), 4.2-4.32 (1H, m), 8.13 (1H, s), 11.63 (1H, s); m/z MH$^+$ 255.

Intermediate 44: 2-chloro-7-methyl-9-[(3S)-tetrahydropyran-3-yl]purin-8-one

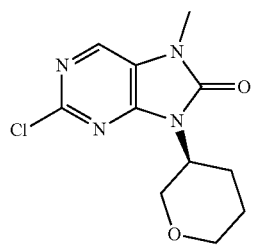 [SMILES: Cn1c(=O)n([C@H]2CCCOC2)c2nc(Cl)ncc21]

Sodium hydride (60%) (0.434 g, 10.86 mmol) was added portionwise to (S)-2-chloro-9-(tetrahydro-2H-pyran-3-yl)-7,9-dihydro-8H-purin-8-one (1.843 g, 7.24 mmol) in DMF (25 mL) at 0° C. The reaction mixture was stirred for 30 minutes then iodomethane (1.36 mL, 21.71 mmol) was added dropwise. The reaction mixture was stirred at 0° C. for 1 h, then was quenched with water (50 mL) and the resulting precipitate was filtered off and dried in vacuo to afford the title compound (1.62 g, 83%) as a cream solid; $^1$H NMR (400 MHz, DMSO) 1.64-1.82 (2H, m), 1.9-1.98 (1H, m), 2.41-2.48 (1H, m), 3.32-3.38 (4H, m), 3.79-3.91 (3H, m), 4.25-4.34 (1H, m), 8.35 (1H, s); m/z MH$^+$ 269.

Intermediate 45: ethyl 2-chloro-4-[[(3R)-tetrahydropyran-3-yl]amino]pyrimidine-5-carboxylate

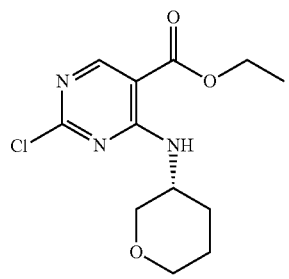 [SMILES: CCOC(=O)c1cnc(Cl)nc1N[C@@H]1CCCOC1]

(R)-tetrahydro-2H-pyran-3-amine hydrochloride (1.00 g, 7.27 mmol) in acetonitrile (5 mL) was added dropwise to a mixture of DIPEA (3.16 mL, 18.17 mmol) and ethyl 2,4-dichloropyrimidine-5-carboxylate (1.606 g, 7.27 mmol) in acetonitrile (30 mL) at 0° C. over a period of 5 minutes under air. The reaction mixture was stirred for 4 h, slowly allowing to warm to rt and then stirred at rt overnight. The reaction mixture was concentrated in vacuo, diluted with EtOAc (100 mL), and washed with water then sat. brine. The organic layer was isolated and dried over MgSO$_4$, filtered and concentrated in vacuo. The resulting crude product was purified by fcc, elution gradient 0 to 50% EtOAc in n-heptane, to afford the title compound (0.936 g, 45%) as a yellow oil; $^1$H NMR (400 MHz, DMSO) 1.33 (3H, t), 1.57 (1H, dt), 1.71 (2H, dtd), 1.91 (1H, ddt), 3.48 (1H, dd), 3.55-3.66 (2H, m), 3.75 (1H, dd), 4.11-4.2 (1H, m), 4.33 (2H, q), 8.58 (1H, d), 8.65 (1H, s); m/z MH$^+$ 286.

Intermediate 46: 2-chloro-4-[[(3R)-tetrahydropyran-3-yl]amino]pyrimidine-5-carboxylic acid

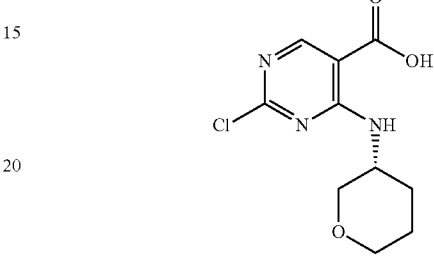

Lithium hydroxide hydrate (276 mg, 6.57 mmol) was added in one portion to ethyl 2-chloro-4-[[(3R)-tetrahydropyran-3-yl]amino]pyrimidine-5-carboxylate (939 mg, 3.29 mmol) in THF (1.23 mL) and water (4.10 mL) at rt. The reaction mixture was stirred at rt for 30 min, then was partially concentrated in vacuo and acidified with 2 M aq. HCl. The resulting solid was isolated by filtration and dried at 45° C. in vacuo overnight to afford the title compound (806 mg, 95%) as a white solid; $^1$H NMR (400 MHz, DMSO) 1.56 (1H, dq), 1.70 (2H, ddt), 1.91 (1H, ddt), 3.46 (1H, dd), 3.60 (2H, t), 3.76 (1H, dd), 4.12 (1H, d), 8.61 (1H, s), 8.77 (1H, d), one exchangeable proton not observed; m/z MH$^+$ 258.

Intermediate 47: 2-chloro-9-[(3R)-tetrahydropyran-3-yl]-7H-purin-8-one

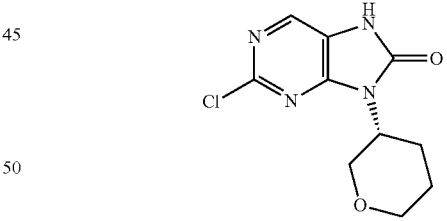

Diphenylphosphoryl azide (0.674 mL, 3.13 mmol) was added in one portion to a solution of 2-chloro-4-[[(3R)-tetrahydropyran-3-yl]amino]pyrimidine-5-carboxylic acid (806 mg, 3.13 mmol) and triethylamine (0.436 mL, 3.13 mmol) in THF (17.3 mL) at rt. The reaction mixture was heated at 80° C. for 24 h, then was allowed to cool to rt and poured into water (20 mL). The resulting mixture was partially concentrated in vacuo and the resulting precipitate was isolated by filtration, washed with water, air dried for 2 h, then in vacuo overnight at 45° C. to afford the title compound (565 mg, 71%) as a white solid; $^1$H NMR (400 MHz, DMSO) 1.64-1.83 (2H, m), 1.93 (1H, d), 2.4-2.49 (1H, m), 3.35 (1H, dd), 3.8-3.92 (3H, m), 4.21-4.36 (1H, m), 8.13 (1H, s), 11.64 (1H, s); m/z MH$^+$ 255.

Intermediate 48: 2-chloro-7-methyl-9-[(3R)-tetrahydropyran-3-yl]purin-8-one

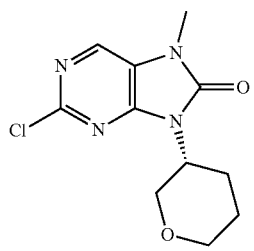 [SMILES: Cn1c(=O)n([C@@H]2CCCOC2)c2nc(Cl)ncc21]

Sodium hydride (60%) (133 mg, 3.33 mmol) was added portionwise to 2-chloro-9-[(3R)-tetrahydropyran-3-yl]-7H-purin-8-one (565 mg, 2.22 mmol) in DMF (5.13 mL) at 0° C. The reaction mixture was stirred for 30 min then iodomethane (0.42 mL, 6.66 mmol) was added dropwise. The reaction mixture was stirred at 0° C. for 1 h, then was quenched with water (50 mL) and the resulting precipitate was isolated by filtration and dried in vacuo to afford the title compound (535 mg, 90%) as a white solid; $^1$H NMR (400 MHz, DMSO) 1.73 (2H, dddd), 1.94 (1H, d), 2.41-2.49 (1H, m), 3.36 (4H, s), 3.81-3.92 (3H, m), 4.24-4.36 (1H, m), 8.36 (1H, s); m/z MH$^+$ 269.

Intermediate 49: ethyl 2-chloro-4-[(4-oxocyclohexyl)amino]pyrimidine-5-carboxylate

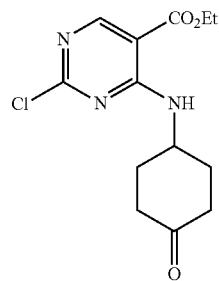 [SMILES: CCOC(=O)c1cnc(Cl)nc1NC1CCC(=O)CC1]

DIPEA (4.19 mL, 24.0 mmol) was added dropwise to ethyl 2,4-dichloropyrimidine-5-carboxylate (4.42 g, 20.0 mmol) and 4-aminocyclohexan-1-one hydrochloride (2.99 g, 20.0 mmol) in acetonitrile (100 mL) at 0° C. over a period of 2 min. The reaction mixture was allowed to warm to rt then stirred at rt for 16 h, then concentrated in vacuo and purified by fcc, elution gradient 0 to 5% EtOAc in DCM, to afford the title compound (3.42 g, 57%) as a white solid; $^1$H NMR (400 MHz, CDCl$_3$) 1.41 (3H, t), 1.82-1.97 (2H, m), 2.28-2.41 (2H, m), 2.44-2.62 (4H, m), 4.38 (2H, q), 4.52-4.66 (1H, m), 8.51-8.59 (1H, m), 8.71 (1H, s); m/z MH$^+$ 298.

Intermediate 50: 2-chloro-4-((4-oxocyclohexyl)amino)pyrimidine-5-carboxylic acid

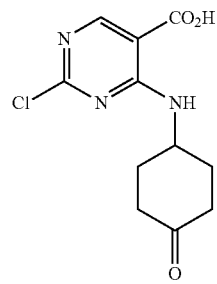 [SMILES: O=C1CCC(Nc2nc(Cl)ncc2C(=O)O)CC1]

LiOH (0.502 g, 20.96 mmol) was added in one portion to ethyl 2-chloro-4-[(4-oxocyclohexyl)amino]pyrimidine-5-carboxylate (3.12 g, 10.48 mmol) in THF (25 mL) and water (25 mL) at 0° C. The reaction mixture was stirred at rt for 48 h, then was partially concentrated in vacuo and acidified with 2 M aq. HCl. The resulting precipitate was isolated by filtration, washed with water (20 mL) and dried in vacuo to afford the title compound (2.80 g, 99%) as a white solid; $^1$H NMR (400 MHz, DMSO) 1.80-1.98 (2H, m), 2.11-2.31 (4H, m), 2.50-2.63 (2H, m), 4.38-4.52 (1H, m), 8.62 (2H, d), 13.81 (1H, s); m/z MH$^+$ 270.

Intermediate 51: 2-chloro-9-(4-oxocyclohexyl)-7,9-dihydro-8H-purin-8-one

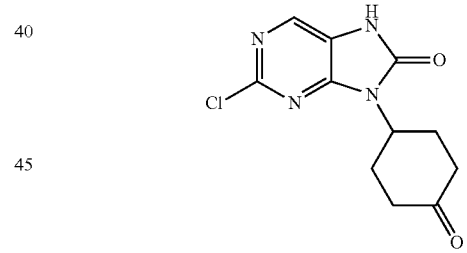

Diphenylphosphoryl azide (4.00 mL, 18.54 mmol) was added in one portion to 2-chloro-4-((4-oxocyclohexyl)amino)pyrimidine-5-carboxylic acid (5.00 g, 18.54 mmol) and Et$_3$N (2.58 mL, 18.54 mmol) in THF (80 mL) at rt. The reaction mixture was heated at 80° C. for 16 h, then was allowed to cool to rt and was concentrated in vacuo. The resulting crude product was purified by fcc, elution gradient 0 to 40% EtOAc in DCM, to afford the title compound (3.50 g, 71%) as a white solid; $^1$H NMR (400 MHz, DMSO) 2.03-2.14 (2H, m), 2.25-2.35 (2H, m), 2.54-2.64 (2H, m), 2.64-2.77 (2H, m), 4.72-4.85 (1H, m), 8.15 (1H, s), 11.65-11.71 (1H, m); m/z MH$^+$ 267.

Intermediate 52: 2-chloro-7-methyl-9-(4-oxocyclohexyl)-7,9-dihydro-8H-purin-8-one

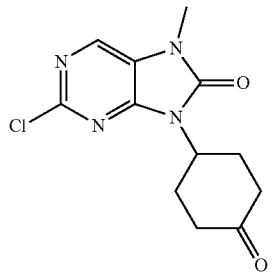 [SMILES: Cn1c(=O)n(C2CCC(=O)CC2)c2nc(Cl)ncc21]

NaH (0.525 g, 13.12 mmol) was added in one portion to 2-chloro-9-(4-oxocyclohexyl)-7,9-dihydro-8H-purin-8-one (3.50 g, 13.12 mmol) in DMF (50 mL) at 0° C. The reaction mixture was allowed to warm to rt and was stirred at rt for 30 min. MeI (2.462 mL, 39.37 mmol) was added and the reaction mixture was stirred at rt for 16 h, then was poured into water (150 mL). The resulting recipitate was isolated by filtration, washed with water (50 mL) and dried in vacuo to afford the title compound (3.30 g, 90%) as a white solid; $^1$H NMR (400 MHz, DMSO) 2.03-2.14 (2H, m), 2.26-2.37 (2H, m), 2.53-2.65 (2H, m), 2.65-2.77 (2H, m), 3.37 (3H, s), 4.76-4.89 (1H, m), 8.38 (1H, s); m/z MH$^+$ 281.

Intermediate 53: 2-chloro-9-(4-hydroxy-4-methylcyclohexyl)-7-methyl-7,9-dihydro-8H-purin-8-one

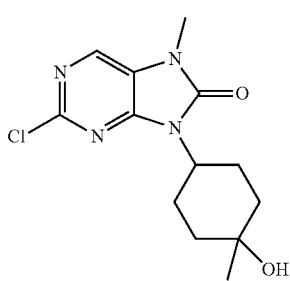 [SMILES: Cn1c(=O)n(C2CCC(C)(O)CC2)c2nc(Cl)ncc21]

Methyl magnesium bromide (3M, 0.89 mL, 2.67 mmol) was added to 2-chloro-7-methyl-9-(4-oxocyclohexyl)-7,9-dihydro-8H-purin-8-one (500 mg, 1.78 mmol) in THF (10 mL) at 0° C. The reaction mixture was allowed to warm to rt and was stirred at rt for 4 h, then was concentrated in vacuo. The resulting crude product was purified by C18-flash chromatography, elution gradient 0 to 100% MeOH in water, to afford the title compound (400 mg, 76%) as a white solid (mixture of diastereoisomers); $^1$H NMR (major diastereoisomer) (300 MHz, CDCl$_3$) 1.30 (3H, s), 1.47 (1H, s), 1.51-1.92 (6H, m), 2.44-2.83 (2H, m), 3.44 (3H, s), 4.26-4.50 (1H, m), 8.01 (1H, s); m/z MH$^+$ 297.

Intermediate 54: ethyl 2-chloro-4-(((1s,4s)-4-hydroxy-4-methylcyclohexyl)amino)-pyrimidine-5-carboxylate

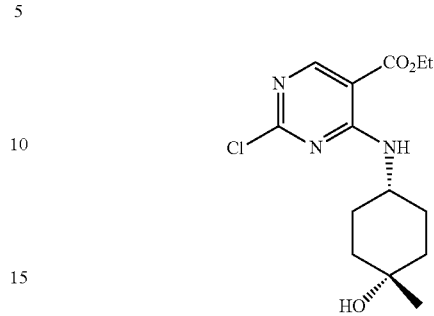

DIPEA (8.76 mL, 50.31 mmol) was added dropwise to a mixture of (1s,4s)-4-amino-1-methylcyclohexan-1-ol (5.00 g, 38.70 mmol) and ethyl 2,4-dichloropyrimidine-5-carboxylate (8.55 g, 38.70 mmol) in acetonitrile (143 mL) at −5° C. over a period of 15 min under air. The reaction mixture was stirred for 2 h, then was slowly allowed to warm to rt, concentrated in vacuo, diluted with EtOAc (200 mL), and washed with water then with sat. brine. The organic layer was dried over MgSO$_4$, filtered and concentrated in vacuo. The resulting crude mixture was suspended in DCM (20 mL), and the resulting solid was isolated by filtration and was washed with DCM (5 mL) to afford title compound (3.8 g). The filtrate was purified by fcc, elution gradient 0 to 70% EtOAc in n-heptane, to afford additional title compound (5.3 g). Both batches were combined to afford the title compound (9.10 g, 75%) as a white solid; $^1$H NMR (400 MHz, DMSO) 1.13 (3H, s), 1.32 (3H, t), 1.43 (2H, td), 1.53-1.61 (2H, m), 1.69 (4H, tt), 3.85-3.99 (1H, m), 4.15 (1H, s), 4.32 (2H, q), 8.27 (1H, d), 8.62 (1H, s); m/z MH$^+$ 314.

Intermediate 55: 2-chloro-4-(((1s,4s)-4-hydroxy-4-methylcyclohexyl)amino)pyrimidine-5-carboxylic acid

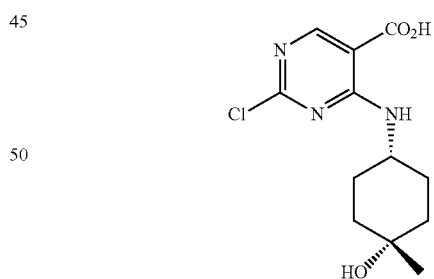

Lithium hydroxide hydrate (2.17 g, 51.63 mmol) was added in one portion to ethyl 2-chloro-4-(((1s,4s)-4-hydroxy-4-methylcyclohexyl)amino)-pyrimidine-5-carboxylate (8.10 g, 25.81 mmol) in THF (97 mL) and water (32.3 mL) at rt. The reaction mixture was stirred at rt for 3 h, then was partially concentrated in vacuo, and acidified with 2 M aq. HCl, and the resulting solid was isolated by filtration to afford the title compound (7.35 g, 100%) as a white solid; $^1$H NMR (400 MHz, DMSO) 1.13 (3H, s), 1.43 (2H, td), 1.52-1.75 (6H, m), 3.89 (1H, qd), 4.15 (1H, s), 8.50 (1H, d), 8.58 (1H, s), 13.75 (1H, s); m/z MH$^+$ 286.

Intermediate 56: 2-chloro-9-((1s,4s)-4-hydroxy-4-methylcyclohexyl)-7,9-dihydro-8H-purin-8-one

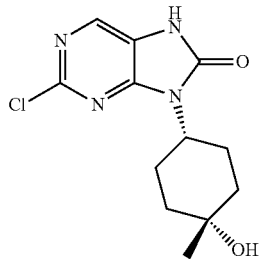 [SMILES: C[C@]1(O)CC[C@@H](n2c(=O)[nH]c3cnc(Cl)nc32)CC1]

Diphenylphosphoryl azide (4.79 mL, 22.22 mmol) was added in one portion to a solution of 2-chloro-4-(((1s,4s)-4-hydroxy-4-methylcyclohexyl)amino)pyrimidine-5-carboxylic acid (6.35 g, 22.22 mmol) and triethylamine (3.10 mL, 22.22 mmol) in THF (123 mL) at rt. The reaction mixture was heated at 80° C. for 24 h, then was allowed to cool to rt and poured into water (100 mL). The resulting mixture was partially concentrated in vacuo, and the resulting precipitate was isolated by filtration, washed with water, then dried in vacuo at 45° C. to afford the title compound (5.39 g, 86%) as a white solid; $^1$H NMR (400 MHz, DMSO) 1.15 (3H, s), 1.39-1.52 (4H, m), 1.66 (2H, d), 2.54-2.71 (2H, m), 4.10 (2H, qd), 8.11 (1H, s), 11.55 (1H, s); m/z MH$^+$ 283.

Intermediate 57: 2-chloro-9-((1s,4s)-4-hydroxy-4-methylcyclohexyl)-7-methyl-7,9-dihydro-8H-purin-8-one

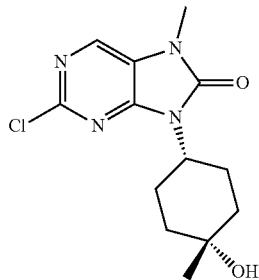 [SMILES: Cn1c(=O)n([C@H]2CC[C@@](C)(O)CC2)c2nc(Cl)ncc21]

2 M aq. sodium hydroxide (37.5 mL, 74.98 mmol) was added in one portion to 2-chloro-9-((1s,4s)-4-hydroxy-4-methylcyclohexyl)-7,9-dihydro-8H-purin-8-one (4.24 g, 15.00 mmol) and iodomethane (4.69 mL, 74.98 mmol) in THF (73.2 mL) at rt under air. The reaction mixture was stirred at rt for 3 h, then was partially concentrated in vacuo. The resulting white precipitate was isolated by filtration, washed with water and dried in vacuo at 45° C. to afford the title compound (3.64 g, 82%) as a white solid; $^1$H NMR (400 MHz, DMSO) 1.15 (3H, s), 1.47 (4H, d), 1.66 (2H, d), 2.58-2.65 (2H, m), 3.36 (3H, s), 4.1-4.19 (2H, m), 8.33 (1H, s); m/z MH$^+$ 297.

Intermediate 58: ethyl 2-chloro-4-(((1r,4r)-4-hydroxy-4-methylcyclohexyl)amino)-pyrimidine-5-carboxylate

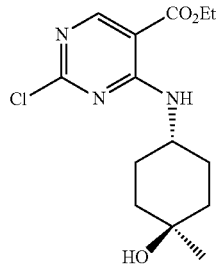 [SMILES: CCOC(=O)c1cnc(Cl)nc1N[C@H]1CC[C@](C)(O)CC1]

DIPEA (17.53 mL, 100.62 mmol) was added dropwise to a mixture of (1r,4r)-4-amino-1-methylcyclohexan-1-ol (10.00 g, 77.40 mmol) and ethyl 2,4-dichloropyrimidine-5-carboxylate (17.11 g, 77.40 mmol) in acetonitrile (300 mL) at −5° C. over 5 min under air. The reaction mixture was stirred for 18 h, slowly allowing to warm to rt, then was concentrated in vacuo, diluted with EtOAc (200 mL), and washed with water then with sat. brine. The organic layer was dried over MgSO$_4$, filtered and concentrated in vacuo. The resulting crude product was purified by fcc, elution gradient 0 to 50% EtOAc in n-heptane, to afford the title compound (17.85 g, 74%) as a white solid; $^1$H NMR (400 MHz, DMSO) 1.16 (3H, s), 1.32 (3H, t), 1.46-1.58 (6H, m), 1.82-1.94 (2H, m), 4.06 (1H, dq), 4.26 (1H, s), 4.32 (2H, q), 8.45 (1H, d), 8.61 (1H, s); m/z MH$^+$ 314.

Intermediate 59: 2-chloro-4-(((1r,4r)-4-hydroxy-4-methylcyclohexyl)amino)pyrimidine-5-carboxylic acid

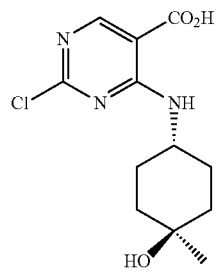 [SMILES: C[C@]1(O)CC[C@H](Nc2nc(Cl)ncc2C(=O)O)CC1]

Lithium hydroxide hydrate (4.77 g, 113.77 mmol) was added in one portion to ethyl 2-chloro-4-(((1r,4r)-4-hydroxy-4-methylcyclohexyl)amino)-pyrimidine-5-carboxylate (17.85 g, 56.89 mmol) in THF (213 mL) and water (71.1 mL) at rt. The reaction mixture was stirred at rt for 30 min, then was partially concentrated in vacuo and acidified with 2 M aq. HCl. The resulting precipitate was isolated by filtration to afford the title compound (14.78 g, 91%) as a white solid; $^1$H NMR (400 MHz, DMSO) 1.16 (3H, s), 1.43-1.56 (6H, m), 1.89 (2H, dt), 3.96-4.12 (1H, m), 4.26 (1H, s), 8.58 (1H, s), 8.69 (1H, d), 13.73 (1H, s); m/z MH$^+$ 286.

Intermediate 60: 2-chloro-9-((1r,4r)-4-hydroxy-4-methylcyclohexyl)-7,9-dihydro-8H-purin-8-one

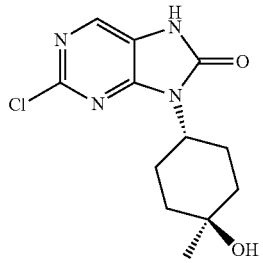 [SMILES: C[C@]1(O)CC[C@H](n2c(=O)[nH]c3cnc(Cl)nc32)CC1]

Diphenylphosphoryl azide (11.15 mL, 51.73 mmol) was added in one portion to a solution of 2-chloro-4-(((1r,4r)-4-hydroxy-4-methylcyclohexyl)amino)pyrimidine-5-carboxylic acid (14.78 g, 51.73 mmol) and triethylamine (7.21 mL, 51.73 mmol) in THF (286 mL) at rt. The reaction mixture was stirred at 80° C. for 24 h., then was allowed to cool to rt then poured into water (200 mL). The resulting mixture was partially concentrated in vacuo. The resulting precipitate was isolated by filtration, washed with water and dried in vacuo at 45° C. to afford the title compound (12.53 g, 86%) as a white solid; $^1$H NMR (400 MHz, DMSO) 1.27 (3H, s), 1.53 (2H, td), 1.6-1.72 (4H, m), 2.24-2.44 (2H, m), 4.15 (1H, tt), 4.41 (1H, s), 8.12 (1H, s), 11.60 (1H, s); m/z MH$^+$ 283.

Intermediate 61: 2-chloro-9-((1r,4r)-4-hydroxy-4-methylcyclohexyl)-7-methyl-7,9-dihydro-8H-purin-8-one

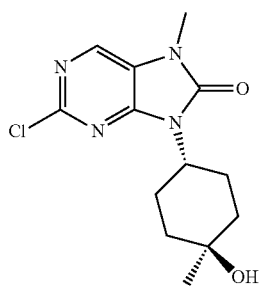 [SMILES: Cn1c(=O)n([C@H]2CC[C@](C)(O)CC2)c2nc(Cl)ncc21]

2M Sodium hydroxide (44.8 mL, 89.66 mmol) was added in one portion to 2-chloro-9-((1r,4r)-4-hydroxy-4-methylcyclohexyl)-7,9-dihydro-8H-purin-8-one (5.07 g, 17.93 mmol) and iodomethane (5.61 mL, 89.66 mmol) in THF (88 mL) at rt under air. The reaction mixture was stirred at rt for 5 h, then was partially concentrated in vacuo. The resulting solid was isolated by filtration, washed with water and dried in vacuo 45° C. to afford the title compound (4.00 g, 75%) as a white solid; $^1$H NMR (400 MHz, DMSO) 1.27 (3H, s), 1.46-1.6 (2H, m), 1.67 (4H, d), 2.33 (2H, ddd), 3.36 (3H, s), 4.19 (1H, ddt), 4.45 (1H, s), 8.35 (1H, s); m/z MH$^+$ 297.

Intermediate 62: ethyl 2-chloro-4-((4-hydroxy-1-methylcyclohexyl)amino)pyrimidine-5-carboxylate

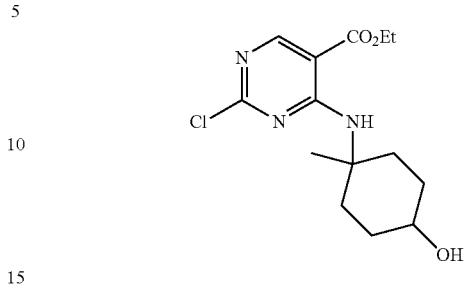

DIPEA (4.28 mL, 24.49 mmol) was added dropwise to ethyl 2,4-dichloropyrimidine-5-carboxylate (2.46 g, 11.13 mmol) and 4-amino-4-methyl-cyclohexanol hydrochloride (2.00 g, 11.13 mmol) in acetonitrile (40 mL) at 0° C. over 5 min. The reaction mixture was allowed to warm to rt, then stirred at rt for 6 h and concentrated in vacuo, diluted with EtOAc (300 mL) and washed with sat. brine (100 mL×2). The organic layer was dried over MgSO$_4$, filtered and concentrated in vacuo. The resulting crude product was purified by fcc, elution gradient 0 to 20% EtOAc in n-heptane, to afford the title compound (2.82 g, 81%) as a pale yellow gum; $^1$H NMR (400 MHz, DMSO) 1.36-1.44 (3H, m), 1.44-1.58 (6H, m), 1.57-1.71 (1H, m), 1.72-2.13 (3H, m), 2.41-2.54 (2H, m), 3.63-3.75 (1H, m), 4.30-4.42 (2H, m), 8.52-8.59 (1H, m), 8.67 (1H, d); m/z MH$^+$ 314.

Intermediate 63: 2-chloro-4-((4-hydroxy-1-methylcyclohexyl)amino)pyrimidine-5-carboxylic acid

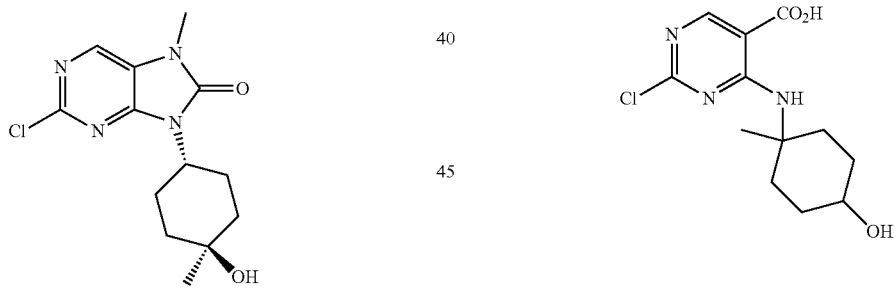

LiOH (0.43 g, 17.97 mmol) was added in one portion to ethyl 2-chloro-4-((4-hydroxy-1-methylcyclohexyl)amino)pyrimidine-5-carboxylate (2.82 g, 8.99 mmol) in THF (25 mL) and water (25 mL) at 0° C. The reaction mixture was allowed to warm to rt and was stirred at rt for 5 h, then was partially concentrated in vacuo and acidified with 2 M aq. HCl. The resulting precipitate was isolated by filtration, washed with water (20 mL) and dried in vacuo to afford the title compound (2.17 g, 85%) as a white solid; $^1$H NMR (400 MHz, DMSO) 1.18-1.32 (2H, m), 1.34-1.52 (5H, m), 1.52-1.79 (2H, m), 2.21-2.30 (2H, m), 3.37-3.49 (1H, m), 4.55 (1H, s), 8.59 (1H, d), 8.74 (1H, s), 13.85 (1H, s); m/z MH$^+$ 286.

Intermediate 64: 2-chloro-9-(4-hydroxy-1-methylcyclohexyl)-7,9-dihydro-8H-purin-8-one

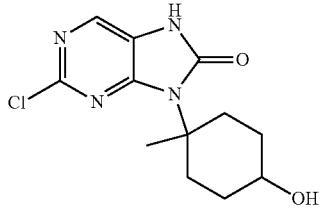 [SMILES: CC1(n2c(=O)[nH]c3cnc(Cl)nc32)CCC(O)CC1]

Diphenylphosphoryl azide (1.64 mL, 7.59 mmol) was added in one portion to 2-chloro-4-((4-hydroxy-1-methylcyclohexyl)amino)pyrimidine-5-carboxylic acid (2.17 g, 7.59 mmol) and Et$_3$N (1.06 mL, 7.59 mmol) in THF (20 mL) at rt. The reaction mixture was heated at 80° C. for 2 days, then was concentrated in vacuo. The resulting crude product was purified by fcc, elution gradient 0 to 50% EtOAc in DCM, to afford the title compound (1.79 g, 83%) as a white solid; $^1$H NMR (400 MHz, DMSO) 1.09-1.25 (2H, m), 1.34-1.64 (5H, m), 1.65-1.77 (2H, m), 3.17 (2H, d), 3.41-3.57 (1H, m), 4.07-4.15 (1H, m), 8.10 (1H, d), 11.61 (1H, s); m/z MH$^+$ 283.

Intermediates 65 and 66: 2-chloro-9-((1s,4s)-4-hydroxy-1-methylcyclohexyl)-7-methyl-7,9-dihydro-8H-purin-8-one and 2-chloro-9-((1r,4r)-4-hydroxy-1-methylcyclohexyl)-7-methyl-7,9-dihydro-8H-purin-8-one

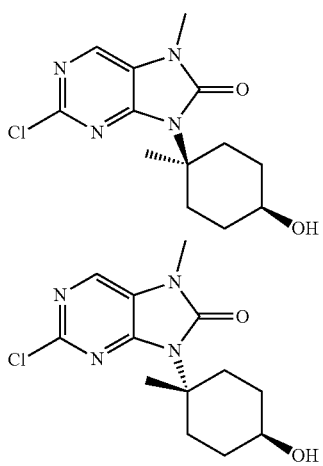

A solution of NaOH (1.27 g, 31.66 mmol) in water (24 mL) was added to a stirred mixture of 2-chloro-9-(4-hydroxy-1-methylcyclohexyl)-7,9-dihydro-8H-purin-8-one (1.79 g, 6.33 mmol), iodomethane (1.97 mL, 31.66 mmol) and tetrabutylammonium bromide (0.204 g, 0.63 mmol) in DCM (40 mL) at rt. The reaction mixture was stirred at rt for 16 h, then was extracted with DCM (3×50 mL). The combined organic layers were dried over MgSO$_4$, filtered and concentrated in vacuo. The resulting crude product was purified by fcc, elution gradient 0 to 40% EtOAc in DCM, to afford the title compounds:

Minor product 2-chloro-9-((1s,4s)-4-hydroxy-1-methylcyclohexyl)-7-methyl-7,9-dihydro-8H-purin-8-one (0.26 g, 14%) as a white solid; $^1$H NMR (400 MHz, CDCl$_3$) 1.66 (3H, s), 1.67-1.85 (4H, m), 2.19-2.31 (2H, m), 2.91-3.02 (2H, m), 3.41 (3H, s), 3.89-3.99 (1H, m), 7.99 (1H, s), one exchangeable proton missing; m/z MH$^+$ 297.

Major product 2-chloro-9-((1r,4r)-4-hydroxy-1-methylcyclohexyl)-7-methyl-7,9-dihydro-8H-purin-8-one (1.440 g, 77% as a white solid; $^1$H NMR (400 MHz, CDCl$_3$) 1.42-1.50 (2H, m), 1.51 (3H, s), 1.58-1.88 (2H, m), 1.88-2.00 (2H, m), 3.40 (3H, s), 3.52-3.63 (2H, m), 3.72-3.84 (1H, m), 7.99 (1H, s), one exchangeable proton missing; m/z MH$^+$ 297.

Intermediate 67: 2-chloro-7-methyl-9-(1-methyl-4-oxocyclohexyl)-7,9-dihydro-8H-purin-8-one

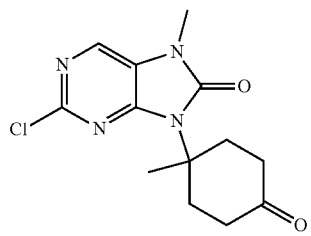 [SMILES: Cn1c(=O)n(C2(C)CCC(=O)CC2)c2nc(Cl)ncc21]

Dess-Martin periodinane (1.07 g, 2.53 mmol) was added to 2-chloro-9-((1r,4r)-4-hydroxy-1-methylcyclohexyl)-7-methyl-7,9-dihydro-8H-purin-8-one (0.50 g, 1.68 mmol) in DCM (10 mL). The reaction mixture was stirred at rt for 4 h, then was quenched with sat. aq. NaHCO$_3$ (20 mL) and extracted with DCM (3×20 mL). The combined organic layers were dried over Na$_2$SO$_4$, filtered and concentrated in vacuo. The resulting crude product was purified by flash C18-flash chromatography, elution gradient 0 to 50% MeOH in water, to afford the title compound (0.43 g, 87%) as a white solid; $^1$H NMR (400 MHz, DMSO) 1.52 (3H, s), 1.88-2.05 (2H, m), 2.11-2.25 (2H, m), 2.37-2.49 (2H, m), 3.34 (3H, s), 3.45-3.60 (2H, m), 8.37 (1H, s); m/z MH$^+$ 295.

Intermediate 68: 2-chloro-9-((1s,4s)-4-hydroxy-1-methylcyclohexyl)-7-methyl-7,9-dihydro-8H-purin-8-one

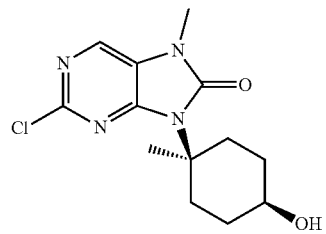 [SMILES: Cn1c(=O)n([C@]2(C)CC[C@H](O)CC2)c2nc(Cl)ncc21]

Sodium borohydride (135 mg, 3.56 mmol) was added to 2-chloro-7-methyl-9-(1-methyl-4-oxocyclohexyl)-7,9-dihydro-8H-purin-8-one (700 mg, 2.37 mmol) in MeOH (15 mL) at rt. The reaction mixture was stirred for 2 h at rt then was quenched with sat. aq. NH$_4$Cl (1 mL) and concentrated in vacuo. The resulting crude mixture was purified by fcc, elution gradient 0 to 40% DCM in EtOAc, to afford the title compound (50 mg, 7%) as a white solid; $^1$H NMR (400 MHz, DMSO) 1.43-1.53 (5H, m), 1.54-1.65 (2H, m), 2.01-

2.13 (2H, m), 2.79-2.84 (2H, m), 3.32 (3H, s), 3.59-3.70 (1H, m), 4.51 (1H, d), 8.33 (1H, s); m/z MH+ 297.

Intermediate 69: ethyl 2-chloro-4-[[(3R)-tetrahydrofuran-3-yl]amino]pyrimidine-5-carboxylate

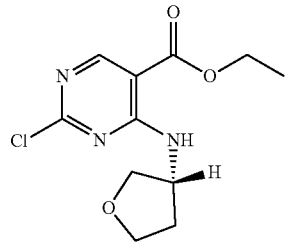 [SMILES: CCOC(=O)c1cnc(Cl)nc1N[C@@H]1CCOC1]

DIPEA (4.74 mL, 27.14 mmol) was added to ethyl 2,4-dichloropyrimidine-5-carboxylate (5.00 g, 22.62 mmol) and (R)-tetrahydrofuran-3-amine (1.97 g, 22.62 mmol) in MeCN (100 mL) at 0° C. The reaction mixture was allowed to warm to rt and was stirred at rt for 4 h, then was concentrated in vacuo. The resulting crude product was purified by fcc, elution gradient 0 to 9% EtOAc in petroleum ether, to afford the title compound (4.90 g, 80%) as a yellow solid; $^1$H NMR (400 MHz, CDCl$_3$) 1.40 (3H, t), 1.80-1.98 (1H, m), 2.29-2.46 (1H, m), 3.69-3.78 (1H, m), 3.79-3.93 (1H, m), 3.95-4.05 (2H, m), 4.36 (2H, q), 4.68-4.90 (1H, m), 8.55 (1H, s), 8.66-8.71 (1H, m); m/z MH+ 272.

Intermediate 70: 2-chloro-4-[[(3R)-tetrahydrofuran-3-yl]amino]pyrimidine-5-carboxylic acid

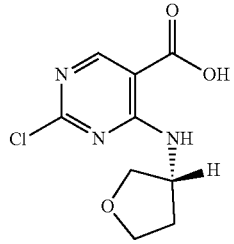 [SMILES: O=C(O)c1cnc(Cl)nc1N[C@@H]1CCOC1]

A solution of LiOH (0.864 g, 36.07 mmol) in water (40.0 mL) was added to a stirred solution of ethyl 2-chloro-4-[[(3R)-tetrahydrofuran-3-yl]amino]pyrimidine-5-carboxylate (4.90 g, 18.03 mmol) in THF (40 mL) at 0° C. The reaction mixture was allowed to warm to rt and was stirred at rt for 3 h, then was partially concentrated in vacuo and acidified with 2 M aq. HCl. The resulting precipitate was isolated by filtration, washed with water (20 mL) and dried in vacuo to afford the title compound (3.90 g, 89%) as a white solid; $^1$H NMR (400 MHz, CDCl$_3$) 2.01-2.14 (1H, m), 2.40-2.54 (1H, m), 3.89-4.23 (4H, m), 5.01-5.13 (1H, m), 8.78 (1H, s), 9.08 (1H, d), one exchangeable proton not observed; m/z MH+ 244.

Intermediate 71: 2-chloro-9-[(3R)-tetrahydrofuran-3-yl]-7H-purin-8-one

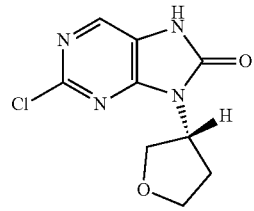

Diphenylphosphoryl azide (3.45 mL, 16.01 mmol) was added to 2-chloro-4-[[(3R)-tetrahydrofuran-3-yl]amino]pyrimidine-5-carboxylic acid (3.90 g, 16.01 mmol) and triethylamine (2.23 mL, 16.01 mmol) in THF (70 mL). The reaction mixture was heated at 80° C. for 24 h, then was concentrated in vacuo. The resulting crude product was purified by fcc, elution gradient 0 to 50% EtOAc in DCM, to afford the title compound (3.20 g, 83%) as a white solid; $^1$H NMR (400 MHz, DMSO) 2.16-2.30 (1H, m), 2.35-2.48 (1H, m), 3.81-3.94 (2H, m), 3.94-4.02 (1H, m), 4.05-4.15 (1H, m), 4.91-5.03 (1H, m), 8.14 (1H, s), 11.68 (1H, s); m/z MH+ 241.

Intermediate 72: 2-chloro-7-methyl-9-[(3R)-tetrahydro-3-furanyl]-7,9-dihydro-8H-purin-8-one

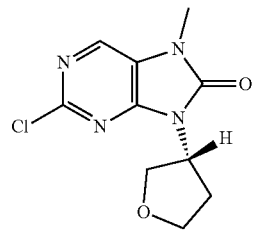 [SMILES: Cn1c(=O)n([C@@H]2CCOC2)c2nc(Cl)ncc21]

NaH (0.532 g, 13.30 mmol) was added to 2-chloro-9-[(3R)-tetrahydrofuran-3-yl]-7H-purin-8-one (3.2 g, 13.30 mmol) in DMF (40 mL) at 0° C. The reaction mixture was stirred at 0° C. for 1 h, then MeI (5.66 g, 39.89 mmol) was added and the reaction mixture was stirred at rt for 5 h, then concentrated in vacuo. The crude product was purified by fcc, elution gradient 0 to 50% EtOAc in DCM, to afford the title compound (3.20 g, 94%) as a yellow solid; $^1$H NMR (300 MHz, MeOD) 2.28-2.47 (1H, m), 2.50-2.67 (1H, m), 3.46 (3H, s), 3.94-4.15 (3H, m), 4.23-4.37 (1H, m), 5.08-5.24 (1H, m), 8.23 (1H, s); m/z MH+ 255.

Intermediate 73: ethyl 2-chloro-4-[[(3S)-tetrahydrofuran-3-yl]amino]pyrimidine-5-carboxylate

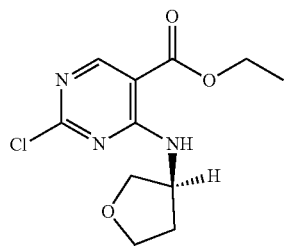 [SMILES: CCOC(=O)c1cnc(Cl)nc1N[C@H]1CCOC1]

DIPEA (4.74 mL, 27.14 mmol) was added dropwise to ethyl 2,4-dichloropyrimidine-5-carboxylate (5 g, 22.62 mmol) and (S)-tetrahydrofuran-3-amine (1.97 g, 22.62 mmol) in acetonitrile (100 mL) at 0° C. over a period of 2 min. The reaction mixture was allowed to warm to rt then was stirred at rt for 16 h and concentrated in vacuo. The resulting crude product was purified by fcc, elution gradient 0 to 5% EtOAc in petroleum ether, to afford the title compound (4.60 g, 75%) as a white solid; $^1$H NMR (400 MHz, DMSO) 1.32 (3H, t), 1.83-1.95 (1H, m), 2.21-2.35 (1H, m), 3.61-3.69 (1H, m), 3.69-3.92 (3H, m), 4.27-4.37 (2H, m), 4.57-4.68 (1H, m), 8.44 (1H, d), 8.63 (1H, s); m/z MH$^+$ 272.

Intermediate 74: 2-chloro-4-[[(3S)-tetrahydrofuran-3-yl]amino]pyrimidine-5-carboxylic acid

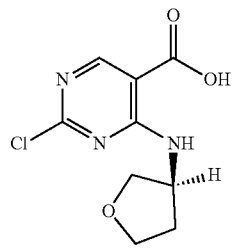 [SMILES: O=C(O)c1cnc(Cl)nc1N[C@H]1CCOC1]

LiOH (0.811 g, 33.86 mmol) was added in one portion to ethyl 2-chloro-4-[[(3S)-tetrahydrofuran-3-yl]amino]pyrimidine-5-carboxylate (4.60 g, 16.93 mmol) in THF (50 mL) and water (25 mL) at 0° C. The reaction mixture was allowed to warm to rt, stirred at rt for 2 h, partially concentrated in vacuo and acidified with 2 M aq. HCl. The resulting precipitate was isolated by filtration, washed with water (20 mL) and dried in vacuo to afford the title compound (3.50 g, 85%) as a white solid; H NMR (400 MHz, DMSO) 1.81-1.93 (1H, m), 2.21-2.35 (1H, m), 3.60-3.68 (1H, m), 3.69-3.94 (3H, m), 4.56-4.68 (1H, m), 8.63 (2H, d), 13.84 (1H, s); m/z MH$^+$ 244.

Intermediate 75: 2-chloro-9-[(3S)-tetrahydro-3-furanyl]-7,9-dihydro-8H-purin-8-one

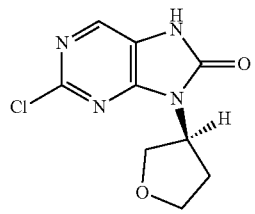 [SMILES: O=c1[nH]c2cnc(Cl)nc2n1[C@H]1CCOC1]

Diphenylphosphoryl azide (3.10 mL, 14.37 mmol) was added in one portion to 2-chloro-4-[[(3S)-tetrahydrofuran-3-yl]amino]pyrimidine-5-carboxylic acid (3.5 g, 14.4 mmol) and Et$_3$N (2.00 mL, 14.4 mmol) in THF (100 mL) at rt. The reaction mixture was heated at 80° C. for 2 days. The solvent was removed under reduced pressure. The resulting crude product was purified by fcc, elution gradient 0 to 50% EtOAc in petroleum ether, to afford the title compound (3.20 g, 93%) as a white solid; $^1$H NMR (400 MHz, DMSO) 2.16-2.32 (1H, m), 2.35-2.48 (1H, m), 3.81-3.92 (2H, m), 3.97 (1H, t), 4.10 (1H, q), 4.91-5.03 (1H, m), 8.14 (1H, s), 11.66 (1H, s); m/z MH$^+$ 241.

Intermediate 76: 2-chloro-7-methyl-9-[(3S)-tetrahydro-3-furanyl]-7,9-dihydro-8H-purin-8-one

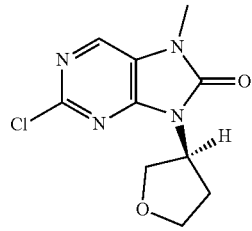

NaH (0.532 g, 13.30 mmol) was added in one portion to 2-chloro-9-[(3S)-tetrahydro-3-furanyl]-7,9-dihydro-8H-purin-8-one (3.2 g, 13.30 mmol) in DMF (30 mL) at 0° C. The reaction mixture was stirred at rt for 30 min. MeI (2.49 mL, 39.9 mmol) was added. The reaction mixture was stirred at rt for 16 h, then was quenched with water (5 mL) and concentrated in vacuo. The crude product was purified by fcc, elution gradient 0 to 40% EtOAc in petroleum ether, to afford the title compound (2.90 g, 86%) as a yellow solid; $^1$H NMR (400 MHz, DMSO) 2.18-2.32 (1H, m), 2.35-2.48 (1H, m), 3.36 (3H, s), 3.82-3.94 (2H, m), 3.98 (1H, t), 4.11 (1H, q), 4.95-5.07 (1H, m), 8.36 (1H, s); m/z MH$^+$ 255.

Intermediate 77: ethyl 2-chloro-4-[(1,1-dioxothian-4-yl)amino]pyrimidine-5-carboxylate

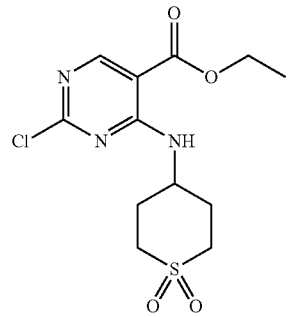 [SMILES: CCOC(=O)c1cnc(Cl)nc1NC1CCS(=O)(=O)CC1]

DIPEA (7.68 mL, 44.0 mmol) was added dropwise to ethyl 2,4-dichloropyrimidine-5-carboxylate (4.42 g, 20.0 mmol) and 4-aminotetrahydro-2H-thiopyran 1,1-dioxide hydrochloride (3.71 g, 20.0 mmol) in acetonitrile (80 mL) at 0° C. over a period of 5 min. The resulting mixture was stirred at rt for 6 h, then was concentrated in vacuo, diluted with EtOAc (500 mL), and washed with sat. brine (100 mL×2). The organic layer was isolated and dried over MgSO$_4$, filtered and concentrated in vacuo. The resulting crude product was purified by fcc, elution gradient 0 to 6% EtOAc in DCM, to afford the title compound (2.40 g, 36%) as a white solid. $^1$H NMR (400 MHz, CDCl$_3$) 1.42 (3H, t), 2.23-2.38 (2H, m), 2.40-2.51 (2H, m), 3.10-3.27 (4H, m), 4.34-4.50 (3H, m), 8.57 (1H, d), 8.73 (1H, s); m/z MH$^+$ 334.

Intermediate 78: 2-chloro-4-[(1,1-dioxothian-4-yl)amino]pyrimidine-5-carboxylic acid

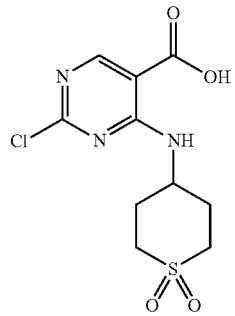 [SMILES: O=C(O)c1cnc(Cl)nc1NC1CCS(=O)(=O)CC1]

LiOH (0.344 g, 14.38 mmol) was added in one portion to ethyl 2-chloro-4-[(1,1-dioxothian-4-yl)amino]pyrimidine-5-carboxylate (2.40 g, 7.19 mmol) in THF (25 mL) and water (25 mL) at 0° C. The reaction mixture was stirred at rt for 5 h, then was partially concentrated in vacuo and acidified with 2 M aq. HCl. The resulting precipitate was collected by filtration, washed with water (50 mL) and dried in vacuo to afford the title compound (2.08 g, 95%) as a white solid; $^1$H NMR (400 MHz, DMSO) 2.00-2.15 (2H, m), 2.18-2.30 (2H, m), 3.02-3.14 (2H, m), 3.34-3.55 (2H, m), 4.27-4.42 (1H, m), 8.57 (1H, d), 8.61 (1H, s), 13.84 (1H, s); m/z MH$^+$ 306.

Intermediate 79: 2-chloro-9-(1,1-dioxothian-4-yl)-7H-purin-8-one

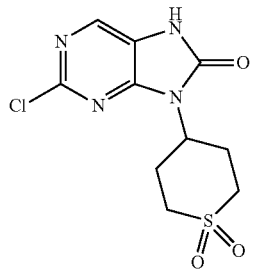 [SMILES: O=c1[nH]c2cnc(Cl)nc2n1C1CCS(=O)(=O)CC1]

Diphenylphosphoryl azide (1.46 mL, 6.80 mmol) was added in one portion to 2-chloro-4-[(1,1-dioxothian-4-yl)amino]pyrimidine-5-carboxylic acid (2.08 g, 6.80 mmol) and triethylamine (0.948 mL, 6.80 mmol) in THF (40 mL) at rt. The reaction mixture was stirred at 80° C. for 2 days, then was poured into water (75 mL). The resulting precipitate was collected by filtration, washed with water (25 mL) and dried in vacuo to afford the title compound (1.72 g, 84%) as a white solid; $^1$H NMR (400 MHz, DMSO) 2.05-2.15 (2H, m), 2.81-3.03 (2H, m), 3.07-3.23 (2H, m), 3.43-3.56 (2H, m), 4.59-4.72 (1H, m), 8.15 (1H, s), 11.69 (1H, s); m/z MH$^+$ 303.

Intermediate 80: 2-chloro-9-(1,1-dioxidotetrahydro-2H-thiopyran-4-yl)-7-methyl-7,9-dihydro-8H-purin-8-one

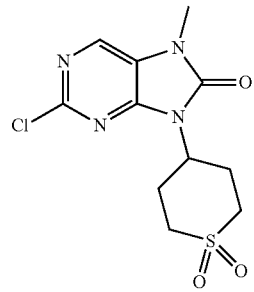 [SMILES: Cn1c(=O)n(C2CCS(=O)(=O)CC2)c2nc(Cl)ncc21]

NaH (0.337 g, 8.42 mmol) was added in one portion to 2-chloro-9-(1,1-dioxothian-4-yl)-7H-purin-8-one (1.70 g, 5.62 mmol) in DMF (25 mL) at rt, and the reaction mixture was stirred at rt for 30 min. MeI (0.53 mL, 8.42 mmol) was added, and the reaction mixture was stirred at rt for 2 h, then was diluted with water (50 mL). The resulting precipitate was collected by filtration, washed with water (20 mL) and dried in vacuo to afford the title compound (1.67 g, 94%) as a white solid; $^1$H NMR (400 MHz, DMSO) 2.05-2.15 (2H, m), 2.81-2.96 (2H, m), 3.09-3.21 (2H, m), 3.36 (3H, s), 3.44-3.57 (2H, m), 4.64-4.77 (1H, m), 8.38 (1H, s); m/z MH$^+$ 317.

Intermediate 81: 2-chloro-5-nitro-N-(oxetan-3-yl)pyrimidin-4-amine

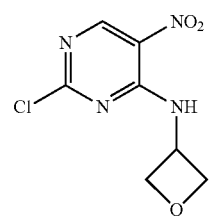 [SMILES: O=[N+]([O-])c1cnc(Cl)nc1NC1COC1]

Oxetan-3-amine (1.507 g, 20.62 mmol) was added dropwise to 2,4-dichloro-5-nitropyrimidine (4.00 g, 20.62 mmol) and DIPEA (4.67 mL, 26.81 mmol) in DCM (100 mL) at −78° C. The reaction mixture was allowed to warm to rt and was stirred at rt for 2 h, then was washed sequentially with water (100 mL) and sat. brine (100 mL). The organic layer was filtered through a phase separating filter paper and concentrated in vacuo. The resulting crude product was purified by fcc, elution gradient 0 to 100% EtOAc in n-heptane, to afford the title compound (3.70 g, 78%) as a white solid; $^1$H NMR (400 MHz, DMSO) 4.71 (2H, t), 4.77 (2H, t), 5.09 (1H, qd), 9.06 (1H, s), 9.34 (1H, d).

Intermediate 82: 2-chloro-N4-(oxetan-3-yl)pyrimidine-4,5-diamine

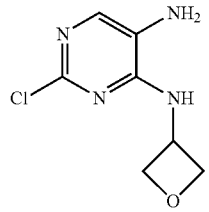 [SMILES: Nc1cnc(Cl)nc1NC1COC1]

Platinum (10% on carbon) (0.313 g, 1.60 mmol) was added to 2-chloro-5-nitro-N-(oxetan-3-yl)pyrimidin-4-amine (3.70 g, 16.04 mmol) in EtOAc (50 mL) at rt. The reaction mixture was purged with hydrogen and stirred under hydrogen at rt for 18 h. The reaction mixture was diluted with MeOH (to solubilise the product) and filtered, washing the precipitate with MeOH. The combined MeOH layers were concentrated in vacuo to afford the title compound (3.10 g, 96%) as an off-white solid; $^1$H NMR (400 MHz, DMSO) 4.49 (2H, t), 4.83 (2H, t), 4.9-5.06 (3H, m), 7.45 (1H, s), 7.50 (1H, d); m/z MH$^+$ 201.

Intermediate 83: 2-chloro-9-(oxetan-3-yl)-7,9-dihydro-8H-purin-8-one

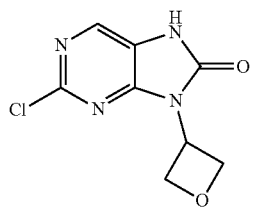 [SMILES: O=c1[nH]c2cnc(Cl)nc2n1C1COC1]

2-Chloro-N4-(oxetan-3-yl)pyrimidine-4,5-diamine (3.10 g, 15.45 mmol) was placed in a flask in THF (100 mL) at rt. Di(1H-imidazol-1-yl)methanone (4.01 g, 24.72 mmol) was added and the reaction mixture was heated at reflux for 1 h, then was allowed to cool to rt and was partially concentrated (50%) in vacuo. The resulting precipitate was isolated by filtration and dried in vacuo to afford the title compound (2.75 g, 79%) as a white solid; $^1$H NMR (400 MHz, DMSO) 4.77 (2H, dd), 5.24 (2H, t), 5.46 (1H, p), 8.15 (1H, s), 11.68 (1H, s); m/z MH$^+$ 227.

Intermediate 84: 2-chloro-7-methyl-9-(oxetan-3-yl)-7,9-dihydro-8H-purin-8-one

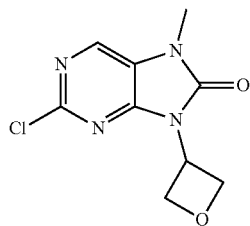 [SMILES: Cn1c(=O)n(C2COC2)c2nc(Cl)ncc21]

Sodium hydride (60%) (0.73 g, 18.20 mmol) was added portionwise to 2-chloro-9-(oxetan-3-yl)-7,9-dihydro-8H-purin-8-one (2.75 g, 12.13 mmol) in DMF (25 mL) at rt. The reaction mixture was stirred for 30 min, then cooled to 0° C. and iodomethane (2.28 mL, 36.40 mmol) was added dropwise. The resulting solution was stirred at rt for 1 h. The reaction mixture was poured into water, the solid was filtered off and dried to the title compound (2.80 g, 96%) as a cream solid; $^1$H NMR (400 MHz, DMSO) 3.36 (3H, s), 4.79 (2H, dd), 5.23 (2H, t), 5.50 (1H, p), 8.38 (1H, s); m/z MH$^+$ 241.

Intermediate 85: ethyl 4-[(1-tert-butoxycarbonyl-4-piperidyl)amino]-2-chloro-pyrimidine-5-carboxylate

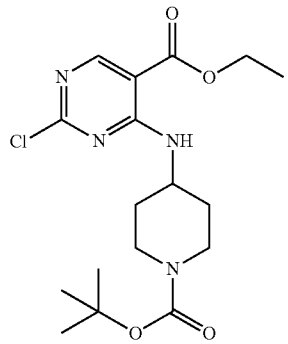 [SMILES: CCOC(=O)c1cnc(Cl)nc1NC1CCN(C(=O)OC(C)(C)C)CC1]

DIPEA (20.49 mL, 117.63 mmol) was added dropwise to a mixture of tert-butyl 4-aminopiperidine-1-carboxylate (18.12 g, 90.48 mmol) and ethyl 2,4-dichloropyrimidine-5-carboxylate (20.00 g, 90.48 mmol) in acetonitrile (334 mL) at −5° C. over a period of 15 min under air. The reaction mixture was stirred for 2 h, slowly allowing to warm to rt, then was concentrated in vacuo, diluted with EtOAc (300 mL), and washed with water then sat. brine. The organic layer was dried over MgSO$_4$, filtered and concentrated in vacuo. The resulting crude product was purified by fcc, elution gradient 0 to 40% EtOAc in n-heptane, to afford the title compound (24.56 g, 71%) as a pale yellow solid; $^1$H NMR (400 MHz, DMSO) 1.32 (3H, t), 1.41 (9H, s), 1.43-1.53 (2H, m), 1.84-1.91 (2H, m), 2.9-3.03 (2H, m), 3.87 (2H, d), 4.17 (1H, ddt), 4.32 (2H, q), 8.31 (1H, d), 8.64 (1H, s); m/z MH$^+$ 385.

Intermediate 86: 4-((1-(tert-butoxycarbonyl)piperidin-4-yl)amino)-2-chloropyrimidine-5-carboxylic acid

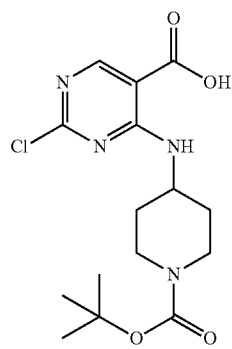 [SMILES: CC(C)(C)OC(=O)N1CCC(Nc2nc(Cl)ncc2C(=O)O)CC1]

Lithium hydroxide hydrate (5.36 g, 127.63 mmol) was added in one portion to ethyl 4-[(1-tert-butoxycarbonyl-4-piperidyl)amino]-2-chloro-pyrimidine-5-carboxylate (24.56 g, 63.82 mmol) in THF (239 mL) and water (80 mL) at 20° C. The resulting solution was stirred at 25° C. for 3 h. The organic solvent was removed under reduced pressure. The resulting mixture was acidified with 2M HCl. The resulting white solid was filtered to afford the title compound (22.72 g, 100%) as a white solid; $^1$H NMR (400 MHz, DMSO) 1.37-1.51 (11H, m), 1.89 (2H, dd), 2.97 (2H, s), 3.86 (2H, d), 4.14 (1H, qd), 8.56 (1H, d), 8.60 (1H, s); m/z MH$^+$ 357.

Intermediate 87: tert-butyl 4-(2-chloro-8-oxo-7,8-dihydro-9H-purin-9-yl)piperidine-1-carboxylate

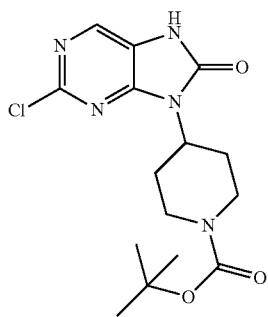 [SMILES: CC(C)(C)OC(=O)N1CCC(n2c(=O)[nH]c3cnc(Cl)nc32)CC1]

Diphenylphosphoryl azide (13.72 mL, 63.68 mmol) was added in one portion to a solution of 4-((1-(tert-butoxycarbonyl)piperidin-4-yl)amino)-2-chloropyrimidine-5-carboxylic acid (22.72 g, 63.68 mmol) and triethylamine (8.88 mL, 63.68 mmol) in THF (352 mL) at rt. The reaction mixture was heated at 80° C. for 24 h, allowed to cool to rt, then poured into water (200 mL) and partially concentrated in vacuo. The resulting precipitate was isolated by filtration, washed with water and dried in vacuo to afford the title compound (23.56 g, 105%) as a white solid which was used in the next step without purification; $^1$H NMR (400 MHz, DMSO) 1.44 (9H, s), 1.68-1.8 (2H, m), 2.19-2.36 (2H, m), 2.87 (2H, s), 4.07 (2H, d), 4.38 (1H, tt), 8.14 (1H, s), 11.63 (1H, s); m/z MH$^+$ 354.

Intermediate 88: tert-butyl 4-(2-chloro-7-methyl-8-oxo-7,8-dihydro-9H-purin-9-yl)piperidine-1-carboxylate

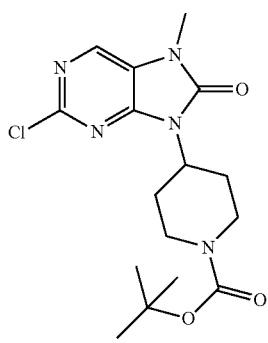 [SMILES: Cn1c(=O)n(C2CCN(C(=O)OC(C)(C)C)CC2)c2nc(Cl)ncc21]

2 M aq. NaOH (159 mL, 317.97 mmol) was added in one portion to tert-butyl 4-(2-chloro-8-oxo-7,8-dihydro-9H-purin-9-yl)piperidine-1-carboxylate (22.50 g, 63.59 mmol) and iodomethane (19.88 mL, 317.97 mmol) in THF (310 mL) at rt under air. The reaction mixture was stirred at rt for 3 h, then was partially concentrated in vacuo. The resulting precipitate was collected by filtration, washed with water and dried in vacuo at 45° C. to afford the title compound (17.98 g, 77%) as a white solid; $^1$H NMR (400 MHz, DMSO) 1.44 (9H, s), 1.7-1.78 (2H, m), 2.26 (2H, qd), 2.88 (2H, s), 3.36 (3H, s), 4.07 (2H, d), 4.42 (1H, tt), 8.36 (1H, s); m/z MH$^+$ 368.

Intermediate 89: 2-chloro-7-methyl-9-(piperidin-4-yl)-7,9-dihydro-8H-purin-8-one hydrochloride

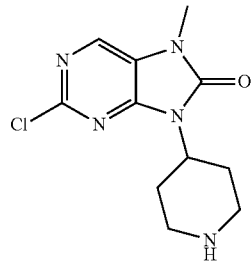

4 M HCl in 1,4-dioxane (6.80 mL, 27.19 mmol) was added to tert-butyl 4-(2-chloro-7-methyl-8-oxo-7,8-dihydro-9H-purin-9-yl)piperidine-1-carboxylate (2.0 g, 5.44 mmol) in methanol (25 mL) at rt and the reaction mixture was stirred at rt for 1 h, then was concentrated in vacuo. The resulting solid was triturated with EtOAc and a small amount of methanol to afford the title compound (1.61 g, 97%) as the HCl salt; $^1$H NMR (400 MHz, DMSO) 1.97 (2H, d), 2.58 (2H, dd), 3.04-3.16 (2H, m), 3.37 (3H, s), 3.41 (2H, d), 4.58 (1H, ddd), 8.39 (1H, s), 8.52 (1H, s), 9.08 (1H, s); m/z MH$^+$ 268.

Intermediate 90: 2-chloro-7-methyl-9-(1-methylpiperidin-4-yl)-7,9-dihydro-8H-purin-8-one

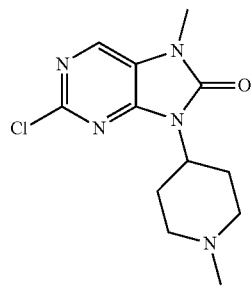 [SMILES: CN1CCC(n2c(=O)n(C)c3cnc(Cl)nc32)CC1]

Formaldehyde (37% in water) (0.20 mL, 2.72 mmol) was added in one portion to tert-butyl 4-(2-chloro-7-methyl-8-oxo-7,8-dihydro-9H-purin-9-yl)piperidine-1-carboxylate (500 mg, 1.36 mmol) in formic acid (2 mL) at rt. The reaction mixture was heated at 55° C. for 18 h, then was allowed to cool to rt, concentrated in vacuo, and taken up in sat. aq. NaHCO$_3$ (20 mL) and EtOAc (20 mL). The organic layer was isolated and passed through a phase separating filter and concentrated in vacuo to afford the title compound (200 mg, 52%) as a cream solid; $^1$H NMR (400 MHz, DMSO) 1.62-1.72 (2H, m), 1.94-2.04 (2H, m), 2.21 (3H, s), 2.45 (2H, td), 2.85-2.93 (2H, m), 3.36 (3H, s), 4.1-4.23 (1H, m), 8.35 (1H, s); m/z MH⁺ 282.

Intermediate 91: 9-(1-acetylpiperidin-4-yl)-2-chloro-7-methyl-7,9-dihydro-8H-purin-8-one

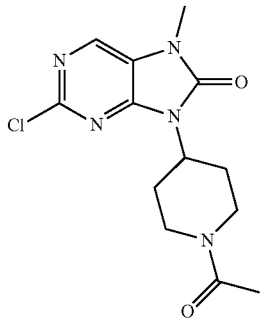 [SMILES: CC(=O)N1CCC(n2c(=O)n(C)c3cnc(Cl)nc32)CC1]

Acetyl chloride (0.472 mL, 6.62 mmol) in DCM (5 mL) was added to triethylamine (2.51 mL, 18.04 mmol) and 2-chloro-7-methyl-9-(piperidin-4-yl)-7,9-dihydro-8H-purin-8-one hydrochloride (1.61 g, 5.29 mmol) in DCM (50 mL) at 0° C. and the reaction mixture was stirred at rt for 1 h. The reaction mixture was diluted with DCM (50 mL), washed sequentially with water (50 mL) and sat. brine (40 mL). The organic layer was isolated and passed through a phase separating filter and concentrated in vacuo to afford the title compound (1.36 g, 83%) as a beige solid; ¹H NMR (400 MHz, DMSO) 1.80 (2H, t), 2.06 (3H, s), 2.18 (1H, qd), 2.26-2.38 (1H, m), 2.66 (1H, t), 3.20 (1H, t), 3.36 (3H, s), 3.96 (1H, d), 4.4-4.6 (2H, m), 8.37 (1H, s); m/z MH⁺ 310.

Intermediate 92: tert-butyl (4-(benzylamino)-1-methylcyclohexyl)carbamate

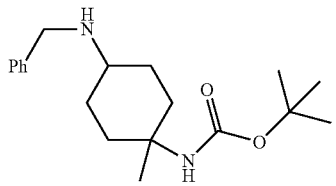

Benzylamine (2.309 mL, 21.12 mmol) was added in one portion to tert-butyl (1-methyl-4-oxocyclohexyl)carbamate (4 g, 17.60 mmol) in DCM (45 mL) at rt. The reaction mixture was stirred at rt for 2 h. Sodium triacetoxyborohydride (7.46 g, 35.20 mmol) and AcOH (0.050 mL, 0.88 mmol) were added, and the reaction mixture was stirred at rt for 16 h, then was quenched with sat. aq. Na₂CO₃ (100 mL) and extracted with EtOAc (3×100 mL). The combined organic layers were dried over MgSO₄, filtered and concentrated in vacuo. The resulting crude product was purified by fcc, elution gradient 0 to 50% EtOAc in petroleum ether, to afford the title compound (5.60 g, 100%) as a colourless oil; ¹H NMR (300 MHz, CDCl₃) 1.17-1.54 (15H, m), 1.73-1.89 (3H, m), 2.00-2.16 (1H, m), 2.44-2.69 (1H, m), 3.80 (2H, d), 4.40-4.49 (1H, m), 7.18-7.41 (5H, m), NH protons not observed; m/z MH⁺ 319.

Intermediate 93: tert-butyl (4-amino-1-methylcyclohexyl)carbamate

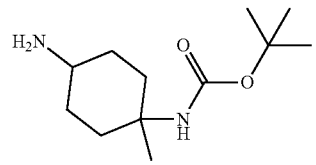 [SMILES: CC1(NC(=O)OC(C)(C)C)CCC(N)CC1]

Pd/C 10% (1.00 g, 9.40 mmol) and tert-butyl (4-(benzylamino)-1-methylcyclohexyl)carbamate (5.60 g, 17.58 mmol) in ethanol (50 mL) was stirred under 3 atm of hydrogen at rt for 30 h. The reaction mixture was filtered through Celite® and concentrated in vacuo to afford the title compound (4.06 g, 101%) as a pale yellow oil; ¹H NMR (400 MHz, CDCl₃) 1.26-1.34 (5H, m), 1.42 (9H, s), 1.59-1.86 (5H, m), 2.00-2.12 (1H, m), 2.70-2.75 (1H, m), 3.45 (2H, s), 4.42 (1H, d).

Intermediate 94: ethyl 4-((4-((tert-butoxycarbonyl)amino)-4-methylcyclohexyl)amino)-2-chloropyrimidine-5-carboxylate

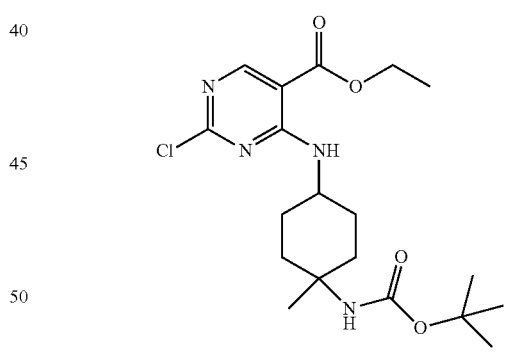

DIPEA (3.69 mL, 21.12 mmol) was added dropwise to ethyl 2,4-dichloropyrimidine-5-carboxylate (3.89 g, 17.60 mmol) and tert-butyl (4-amino-1-methylcyclohexyl)carbamate (4.02 g, 17.6 mmol) in acetonitrile (80 mL) at 0° C. over a period of 2 min. The reaction mixture was stirred at rt for 16 h and concentrated in vacuo. The resulting crude product was purified by fcc, elution gradient 0 to 10% EtOAc in petroleum ether, to afford the title compound (6.0 g, 83%) as a pale yellow gum; ¹H NMR (400 MHz, CDCl₃) 1.33-1.43 (6H, m), 1.43-1.64 (11H, m), 1.70-1.82 (1H, m), 1.85-2.01 (4H, m), 2.17 (1H, s), 4.07-4.24 (2H, m), 4.30-4.42 (2H, m), 8.24-8.57 (1H, m), 8.67 (1H, s); m/z MH⁺ 413.

Intermediate 95: 4-((4-((tert-butoxycarbonyl)amino)-4-methylcyclohexyl)amino)-2-chloropyrimidine-5-carboxylic acid

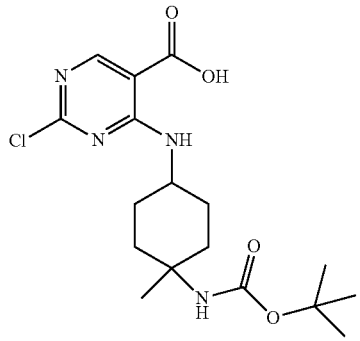 [SMILES: CC1(NC(=O)OC(C)(C)C)CCC(Nc2nc(Cl)ncc2C(=O)O)CC1]

LiOH (0.696 g, 29.06 mmol) was added in one portion to ethyl 4-((4-((tert-butoxycarbonyl)amino)-4-methylcyclohexyl)amino)-2-chloropyrimidine-5-carboxylate (6.0 g, 14.5 mmol) in THF (50 mL) and water (50 mL) at 0° C. The reaction mixture was stirred at rt for 5 h, then was partially concentrated in vacuo and acidified with 2 M aq. HCl. The resulting precipitate was isolated by filtration, washed with water (20 mL) and dried in vacuo to afford the title compound (5.24 g, 94%) as a white solid; $^1$H NMR (400 MHz, DMSO) 1.16-1.63 (16H, m), 1.67-1.89 (3H, m), 2.08-2.18 (1H, m), 3.82-4.08 (1H, m), 6.44 (1H, d), 8.56 (1H, s), 8.57-8.82 (1H, m); m/z MH$^+$ 385.

Intermediate 96: tert-butyl (4-(2-chloro-8-oxo-7,8-dihydro-9H-purin-9-yl)-1-methylcyclohexyl)carbamate

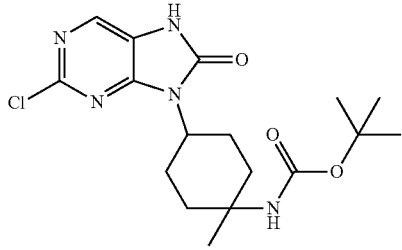 [SMILES: CC1(NC(=O)OC(C)(C)C)CCC(n2c(=O)[nH]c3cnc(Cl)nc32)CC1]

Diphenylphosphoryl azide (2.91 mL, 13.51 mmol) was added in one portion to 4-((4-((tert-butoxycarbonyl)amino)-4-methylcyclohexyl)amino)-2-chloropyrimidine-5-carboxylic acid (5.20 g, 13.51 mmol) and triethylamine (1.88 mL, 13.51 mmol) in THF (50 mL) at rt. The reaction mixture was heated at 80° C. for 2 days, then was allowed to cool to rt and poured into water (150 mL). The resulting precipitate was isolated by filtration, washed with water (25 mL) and dried in vacuo to afford the title compound (4.53 g, 88%) as a white solid; $^1$H NMR (400 MHz, DMSO) 1.24 (3H, d), 1.34-1.51 (10H, m), 1.58-1.80 (3H, m), 1.93 (1H, d), 2.27-2.46 (3H, m), 4.07-4.20 (1H, m), 6.52 (1H, d), 8.12 (1H, d), 11.62 (1H, d); m/z MH$^+$ 382.

Intermediate 97: tert-butyl (4-(2-chloro-7-methyl-8-oxo-7,8-dihydro-9H-purin-9-yl)-1-methylcyclohexyl)

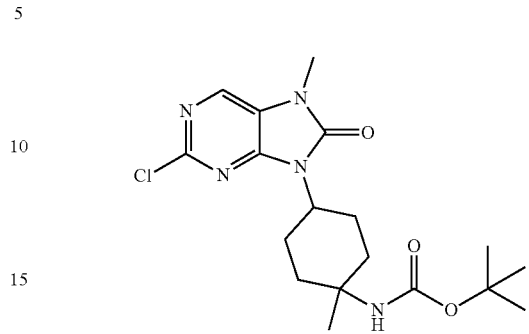

DMF-DMA (2.01 mL, 15.0 mmol) was added in one portion to tert-butyl (4-(2-chloro-8-oxo-7,8-dihydro-9H-purin-9-yl)-1-methylcyclohexyl)carbamate (1.909 g, 5.00 mmol) in DMF (20 mL) at rt. The reaction mixture was heated at 80° C. for 6 h, allowed to cool to rt then quenched with water (100 mL) and extracted with EtOAc (3×50 mL). The combined organic layers were dried over MgSO$_4$, filtered and concentrated in vacuo. The resulting crude product was purified by fcc, elution gradient 0 to 30% EtOAc in petroleum ether, to afford the title compound (1.540 g, 78%) as a pale yellow solid; $^1$H NMR (400 MHz, CDCl$_3$) 1.36-1.55 (14H, m), 1.59-1.80 (2H, m), 1.99-2.09 (1H, m), 2.25-2.34 (1H, m), 2.49-2.66 (2H, m), 3.45 (3H, d), 4.29-4.47 (1H, m), 4.58 (1H, d), 8.01 (1H, d); m/z MH$^+$ 396.

Intermediate 98: ethyl 4-(((3S,4R)-1-(tert-butoxycarbonyl)-3-fluoropiperidin-4-yl)amino)-2-chloropyrimidine-5-carboxylate

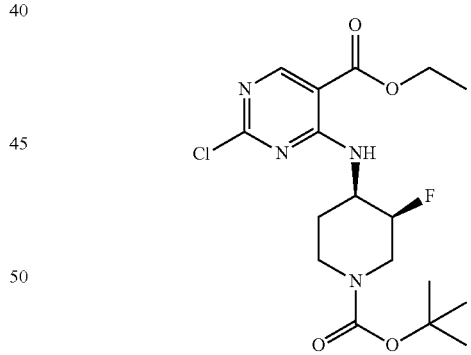

DIPEA (5.19 mL, 29.78 mmol) was added portionwise to ethyl 2,4-dichloropyrimidine-5-carboxylate (5.06 g, 22.91 mmol) and tert-butyl (3S,4R)-4-amino-3-fluoropiperidine-1-carboxylate (5.00 g, 22.91 mmol) in acetonitrile (100 mL) at 0° C. The reaction mixture was stirred at rt for 4 h, then concentrated in vacuo, diluted with EtOAc (200 mL) and washed sequentially with water (100 mL) and sat. brine (100 mL). The organic layer was filtered through a phase separating filter paper and concentrated in vacuo. The resulting crude product was purified by fcc, elution gradient 0 to 50% EtOAc in n-heptane, to afford the title compound (4.87 g, 53%) as a white crystalline solid; H NMR (400 MHz, DMSO) 1.32 (3H, t), 1.41 (9H, s), 1.56-1.67 (1H, m), 1.82

(1H, d), 2.93 (1H, s), 4.01 (1H, s), 4.33 (5H, q), 4.86 (1H, d), 8.53 (1H, d), 8.69 (1H, s); m/z MH+ 403.

Intermediate 99: 4-(((3S,4R)-1-(tert-butoxycarbonyl)-3-fluoropiperidin-4-yl)amino)-2-chloropyrimidine-5-carboxylic acid

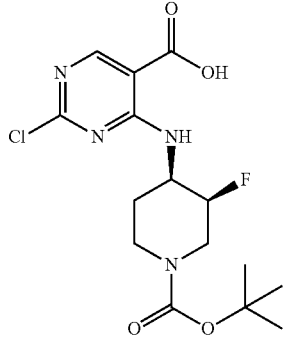 [SMILES: CC(C)(C)OC(=O)N1CC[C@@H](Nc2nc(Cl)ncc2C(=O)O)[C@@H](F)C1]

Lithium hydroxide hydrate (0.99 g, 23.58 mmol) in water (45 mL), was added to ethyl 4-(((3S,4R)-1-(tert-butoxycarbonyl)-3-fluoropiperidin-4-yl)amino)-2-chloropyrimidine-5-carboxylate (4.75 g, 11.79 mmol) in THF (45 mL) at rt. The reaction mixture was stirred at rt for 1 h, then was partially concentrated in vacuo and acidified with 2 M aq. HCl. The resulting precipitate was filtered, washed with water and dried to give the title compound (4.24 g, 96%) as a white solid; $^1$H NMR (400 MHz, DMSO) 1.41 (9H, s), 1.60 (2H, d), 1.82 (1H, d), 4.01 (1H, s), 4.18-4.49 (3H, m), 4.85 (1H, d), 8.64 (1H, s), 8.79 (1H, s); m/z MH+ 375.

Intermediate 100: tert-butyl(3S,4R)-4-(2-chloro-8-oxo-7,8-dihydro-9H-purin-9-yl)-3-fluoropiperidine-1-carboxylate

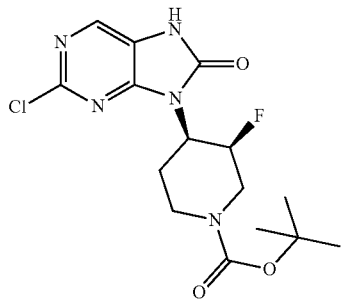 [SMILES: CC(C)(C)OC(=O)N1CC[C@@H](n2c(=O)[nH]c3cnc(Cl)nc32)[C@@H](F)C1]

Diphenylphosphoryl azide (2.44 mL, 11.31 mmol) was added to 4-(((3S,4R)-1-(tert-butoxycarbonyl)-3-fluoropiperidin-4-yl)amino)-2-chloropyrimidine-5-carboxylic acid (4.24 g, 11.31 mmol) and triethylamine (1.58 mL, 11.31 mmol) in THF (75 mL) at rt. The reaction mixture was stirred at 80° C. for 16 h. The reaction mixture was allowed to cool to rt and water (150 mL) was added, and was partially concentrated in vacuo. The resulting solid was isolated by filtration and dried in vacuo to afford the title compound (3.94 g, 94%) as a white solid; $^1$H NMR (400 MHz, DMSO) 1.43 (9H, s), 1.82 (1H, d), 4.09-4.37 (4H, m), 4.53 (1H, ddd), 4.82 (2H, d), 8.17 (1H, s), 11.71 (1H, s); m/z MH+ 372.

Intermediate 101: tert-butyl (3S,4R)-4-(2-chloro-7-methyl-8-oxo-7,8-dihydro-9H-purin-9-yl)-3-fluoropiperidine-1-carboxylate

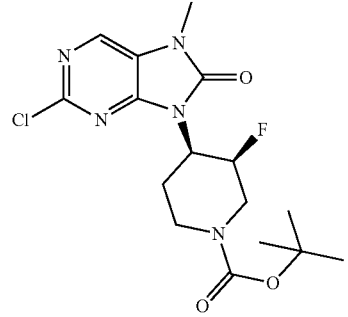 [SMILES: Cn1c(=O)n([C@@H]2CCN(C(=O)OC(C)(C)C)C[C@@H]2F)c2nc(Cl)ncc21]

2 M aq. NaOH (23.13 mL, 46.26 mmol) was added in one portion to tert-butyl (3S,4R)-4-(2-chloro-8-oxo-7,8-dihydro-9H-purin-9-yl)-3-fluoropiperidine-1-carboxylate (3.44 g, 9.25 mmol) and iodomethane (2.89 mL, 46.26 mmol) in THF (50 mL) at rt under air. The reaction mixture was stirred at rt for 3 h, then was concentrated in vacuo and diluted with water (50 mL). The resulting precipitate was isolated by filtration and washed with water to afford the title compound (2.08 g, 58%) as a pale orange solid; $^1$H NMR (400 MHz, DMSO) 1.43 (9H, s), 1.82 (1H, d), 3.03-3.15 (2H, m), 3.38 (3H, s), 4.09-4.36 (3H, m), 4.58 (1H, ddt), 4.82 (1H, d), 8.39 (1H, s); m/z MH+ 386.

Intermediate 102: ethyl 4-[[(3R)-1-tert-butoxycarbonylpyrrolidin-3-yl]amino]-2-chloro-pyrimidine-5-carboxylate

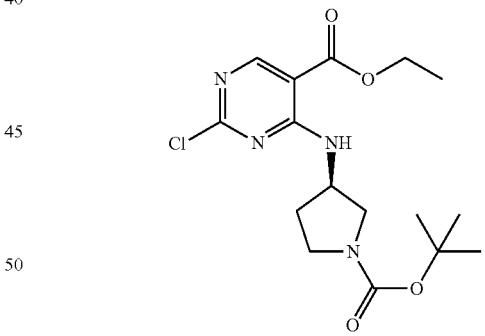

DIPEA (6.59 mL, 37.83 mmol) was added dropwise to a mixture of tert-butyl (R)-3-aminopyrrolidine-1-carboxylate (5.42 g, 29.10 mmol) and ethyl 2,4-dichloropyrimidine-5-carboxylate (6.43 g, 29.10 mmol) in acetonitrile (108 mL) at −5° C. over a period of 15 min under air. The reaction mixture was stirred for 2 h, slowly allowing to warm to rt. The reaction mixture was concentrated in vacuo, diluted with EtOAc (100 mL), and washed with water then sat. brine. The organic layer was dried over MgSO$_4$, filtered and concentrated in vacuo. The resulting crude product was purified by fcc, eluting with 0-70% EtOAc in n-heptane, to afford the title compound (7.92 g, 73%) as a pale yellow solid. $^1$H NMR (400 MHz, DMSO) 1.32 (3H, t), 1.41 (9H, s), 1.92-2.03 (1H, m), 2.19 (1H, s), 3.21 (1H, dd), 3.37 (2H, t), 3.62 (1H, dd), 4.32 (2H, q), 4.59 (1H, s), 8.39 (1H, d), 8.65 (1H, s); m/z MH+ 371.

Intermediate 103: 4-[[(3R)-1-tert-butoxycarbonylpyrrolidin-3-yl]amino]-2-chloro-pyrimidine-5-carboxylic acid

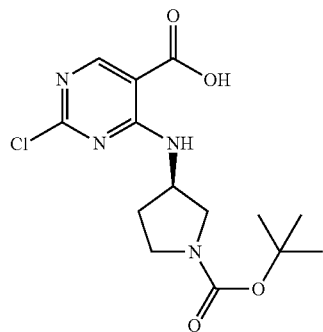 [SMILES: CC(C)(C)OC(=O)N1CC[C@@H](Nc2nc(Cl)ncc2C(=O)O)C1]

Lithium hydroxide hydrate (1.79 g, 42.71 mmol) was added in one portion to ethyl 4-[[(3R)-1-tert-butoxycarbonylpyrrolidin-3-yl]amino]-2-chloro-pyrimidine-5-carboxylate (7.92 g, 21.36 mmol) in THF (80 mL) and water (26.7 mL) at rt. The reaction mixture was stirred at rt for 3 h, then partially concentrated in vacuo and acidified with 2 M aq. HCl. The resulting white solid was isolated by filtration and dried in vacuo at 45° C. in to afford the title compound (7.07 g, 97%) as a white solid; ¹H NMR (400 MHz, DMSO) 1.41 (9H, s), 1.95 (1H, s), 2.19 (1H, s), 3.20 (1H, dd), 3.37 (2H, t), 3.62 (1H, dd), 4.57 (1H, s), 8.61 (1H, s), 8.67 (1H, d), 13.80 (1H, s); m/z MH+ 343.

Intermediate 104: tert-butyl (3R)-3-(2-chloro-8-oxo-7H-purin-9-yl)pyrrolidine-1-carboxylate

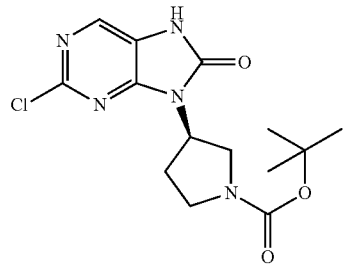 [SMILES: CC(C)(C)OC(=O)N1CC[C@@H](n2c(=O)[nH]c3cnc(Cl)nc32)C1]

Diphenylphosphoryl azide (4.44 mL, 20.63 mmol) was added in one portion to a solution of 4-[[(3R)-1-tert-butoxycarbonylpyrrolidin-3-yl]amino]-2-chloro-pyrimidine-5-carboxylic acid (7.07 g, 20.63 mmol) and triethylamine (2.87 mL, 20.63 mmol) in THF (114 mL) at rt. The resulting solution was stirred at 80° C. for 24 h. The mixture was allowed to cool then was poured into water (100 mL), no precipitate formed. The solvent was removed in vacuo causing a white precipitate to form in the water. Precipitate filtered off under vacuum, washed with water, air dried in vacuo for 30 minutes, then placed in vacuum oven for 4 h at 45° C. to afford the title compound (5.45 g, 78%) as a white solid which was used in the next step without purification. ¹H NMR (400 MHz, DMSO) 1.42 (9H, d), 2.19 (1H, s), 2.50 (1H, s) 3.37 (1H, s), 3.53-3.67 (2H, m), 3.68-3.74 (1H, m), 4.94 (1H, q), 8.14 (1H, s), 11.64 (1H, s); m/z [M-H]⁻ 338.

Intermediate 105: tert-butyl (3R)-3-(2-chloro-7-methyl-8-oxo-purin-9-yl)pyrrolidine-1-carboxylate

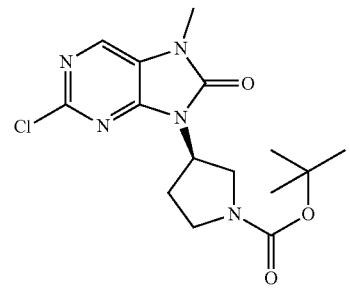 [SMILES: Cn1c(=O)n([C@@H]2CCN(C(=O)OC(C)(C)C)C2)c2nc(Cl)ncc21]

2M Sodium hydroxide (36.8 mL, 73.6 mmol) was added in one portion to tert-butyl (3R)-3-(2-chloro-8-oxo-7H-purin-9-yl)pyrrolidine-1-carboxylate (5.00 g, 14.72 mmol) and iodomethane (4.60 mL, 73.58 mmol) in THF (71.8 mL) at rt under air. The reaction mixture was stirred at rt for 3 h, then partially concentrated in vacuo and extracted with DCM (100 mL). The organic layer was isolated and passed through a phase separating filter, then concentrated in vacuo to afford the title compound (5.17 g, 99%) as a yellow gum. ¹H NMR (400 MHz, DMSO) 1.42 (9H, d), 2.21 (1H, s), 2.53 (1H, d), 3.36 (4H, s), 3.5-3.75 (3H, m), 4.91-5.07 (1H, m), 8.37 (1H, s); m/z MH+ 354.

Intermediate 106: ethyl 4-[[(3S)-1-tert-butoxycarbonylpyrrolidin-3-yl]amino]-2-chloro-pyrimidine-5-carboxylate

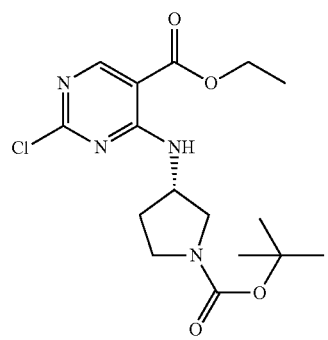 [SMILES: CCOC(=O)c1cnc(Cl)nc1N[C@H]1CCN(C(=O)OC(C)(C)C)C1]

tert-Butyl (S)-3-aminopyrrolidine-1-carboxylate (5.00 g, 26.84 mmol) was added slowly to ethyl 2,4-dichloropyrimidine-5-carboxylate (5.93 g, 26.84 mmol) and DIPEA (6.08 mL, 34.90 mmol) in acetonitrile (100 mL) at 0° C. The reaction mixture was allowed to warm to rt and was stirred at rt for 4 h, then concentrated in vacuo, diluted with EtOAc (200 mL) and washed sequentially with water (100 mL) and sat. brine (100 mL). The organic layer was filtered through a phase separating filter paper and concentrated in vacuo. The resulting crude product was purified by fcc, elution gradient 0 to 50% EtOAc in n-heptane, to afford the title compound (5.40 g, 54%) as a white solid; H NMR (400 MHz, DMSO) 1.32 (3H, t), 1.41 (9H, s), 1.99 (1H, d), 2.19

(1H, s), 3.21 (1H, dd), 3.37 (2H, t), 3.62 (1H, dd), 4.32 (2H, q), 4.59 (1H, s), 8.39 (1H, d), 8.65 (1H, s); m/z [M-H]⁻ 369.

Intermediate 107: 4-[[(3S)-1-tert-butoxycarbonylpyrrolidin-3-yl]amino]-2-chloro-pyrimidine-5-carboxylic acid

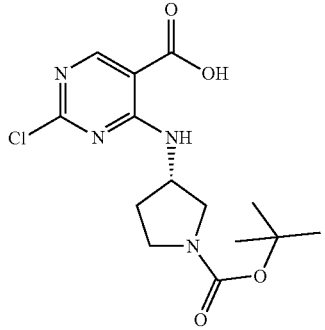 [SMILES: CC(C)(C)OC(=O)N1CC[C@H](Nc2nc(Cl)ncc2C(=O)O)C1]

Lithium hydroxide hydrate (1.22 g, 29.12 mmol) in water (50 mL) was added to ethyl 4-[[(3S)-1-tert-butoxycarbonylpyrrolidin-3-yl]amino]-2-chloro-pyrimidine-5-carboxylate (5.40 g, 14.56 mmol) in THF (50 mL) at rt. The reaction mixture was stirred at rt for 2 h, then was partially concentrated in vacuo, acidified with 2 M aq. HCl, and extracted into DCM (100 mL). The organic layer was washed with brine (50 mL), passed through a phase separating filter paper and concentrated in vacuo to afford the title compound (4.95 g, 99%); ¹H NMR (400 MHz, DMSO) 1.41 (9H, s), 1.95 (1H, s), 2.19 (1H, s), 3.37 (2H, t), 3.59-3.64 (2H, m), 4.57 (1H, s), 8.61 (2H, s), 13.80 (1H, s); m/z MH⁺ 343.

Intermediate 108: tert-butyl(3S)-3-(2-chloro-8-oxo-7H-purin-9-yl)pyrrolidine-1-carboxylate

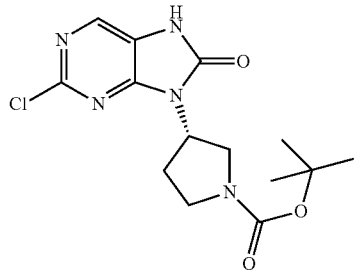 [SMILES: CC(C)(C)OC(=O)N1CC[C@H](n2c(=O)[nH]c3cnc(Cl)nc32)C1]

Diphenylphosphoryl azide (3.08 mL, 14.29 mmol) was added to 4-[[(3S)-1-tert-butoxycarbonylpyrrolidin-3-yl]amino]-2-chloro-pyrimidine-5-carboxylic acid (4.90 g, 14.29 mmol) and triethylamine (1.99 mL, 14.29 mmol) in THF (50 mL) at rt. The reaction mixture was heated at reflux for 16 h, allowed to cool to rt and diluted with water (100 mL). The resulting precipitate was isolated by filtration, washed with water and dried in vacuo to afford the title compound (4.35 g, 90%) as a white solid; ¹H NMR (400 MHz, DMSO) 1.41 (9H, s), 2.19 (1H, s), 3.37 (1H, d), 3.5-3.67 (3H, m), 3.67-3.74 (1H, m), 4.89-5.01 (1H, m), 8.14 (1H, s), 11.66 (1H, s); m/z MH⁺ 340.

Intermediate 109: tert-butyl (3S)-3-(2-chloro-7-methyl-8-oxo-purin-9-yl)pyrrolidine-1-carboxylate

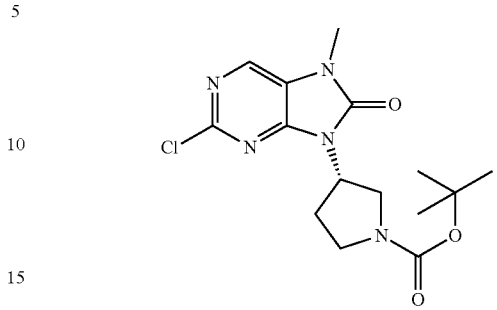

Sodium hydride (60%) (0.662 g, 16.55 mmol) was added portionwise to tert-butyl (3S)-3-(2-chloro-8-oxo-7H-purin-9-yl)pyrrolidine-1-carboxylate (3.75 g, 11.04 mmol) in DMF (30 mL) at rt. The reaction mixture was stirred for 1 h, then cooled to 0° C. and iodomethane (2.07 mL, 33.11 mmol) was added dropwise. The reaction mixture was allowed to warm to rt then was stirred at rt for 1 h. The reaction mixture was diluted with EtOAc (100 mL) and washed sequentially with water (3×50 mL) and sat. brine (50 mL). The organic layer was passed through a phase separating filter paper and concentrated in vacuo. The resulting crude product was triturated with EtOAc to afford the title compound (1.65 g, 42%) as a yellow solid. ¹H NMR (400 MHz, DMSO) 1.42 (9H, d), 2.21 (1H, s), 2.47 (1H, d), 3.36 (4H, s), 3.61 (2H, d), 3.70 (1H, dd), 4.92-5.04 (1H, m), 8.37 (1H, s); m/z MH⁺ 354.

Intermediate 110: tert-butyl 4-(7-methyl-2-((7-methylquinolin-6-yl)amino)-8-oxo-7,8-dihydro-9H-purin-9-yl)piperidine-1-carboxylate

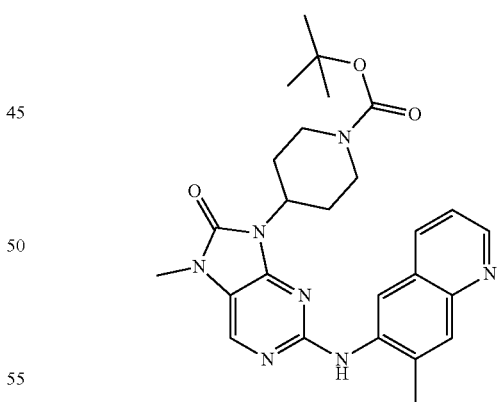

Cesium carbonate (33.4 g, 102.4 mmol) was added to 7-methylquinolin-6-amine (5.40 g, 34.1 mmol) and tert-butyl 4-(2-chloro-7-methyl-8-oxo-7,8-dihydro-9H-purin-9-yl)piperidine-1-carboxylate (12.56 g, 34.13 mmol) in 2-methyl tetrahydrofuran (110 mL). Nitrogen was bubbled through the reaction mixture for 5 min. 2,2'-Bis(diphenylphosphanyl)-1,1'-binaphthalene (1.06 g, 1.71 mmol) and diacetoxypalladium (0.192 g, 0.85 mmol) were added and the reaction mixture was heated at 80° C. for 1 h, then allowed to cool to rt. The reaction mixture was cooled to rt, filtered and the solid was washed with 10% MeOH in DCM (100 mL). The filtrate was concentrated in vacuo. The crude material was purified by fcc, elution gradient 0 to 100% (10% MeOH in EtOAc) in n-heptane, to afford the title compound (14.70 g, 88%) as a cream solid; $^1$H NMR (400 MHz, DMSO) 1.35 (9H, s), 1.78 (2H, d), 2.36 (2H, qd), 2.50 (3H, s), 2.84 (2H, s), 3.30 (3H, s), 4.05-4.17 (2H, m), 4.37 (1H, tt), 7.38 (1H, dd), 7.84 (1H, s), 8.07-8.15 (1H, m), 8.16 (1H, s), 8.30 (1H, s), 8.51 (1H, s), 8.72 (1H, dd); m/z MH$^+$ 490.

Intermediate 111: tert-butyl (3R)-3-[7-methyl-2-[(7-methyl-6-quinolyl)amino]-8-oxo-purin-9-yl]pyrrolidine-1-carboxylate

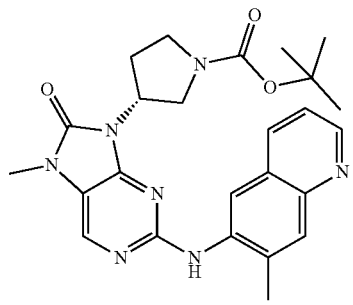 [SMILES: Cc1cc2ncccc2cc1Nc1ncc2c(n1)n([C@@H]1CCN(C(=O)OC(C)(C)C)C1)c(=O)n2C]

Cesium carbonate (368 mg, 1.13 mmol) was added in one portion to 7-methylquinolin-6-amine (89 mg, 0.57 mmol) and tert-butyl (3R)-3-(2-chloro-7-methyl-8-oxo-purin-9-yl)pyrrolidine-1-carboxylate (200 mg, 0.57 mmol) in 1,4-dioxane (3.2 mL) at 20° C. and degassed by bubbling nitrogen through the mixture for 5 minutes. Brettphos precat G3 (25.6 mg, 0.03 mmol) was added and the reaction was heated at 100° C. for 2 h. The reaction mixture was filtered hot and the filtercup washed through with DCM (20 mL). The DCM layer was evaporated and the residue was absorbed onto silica then purified by fcc (12 g Interchim column), elution gradient 0 to 5% MeOH in DCM to afford the title compound (174 mg, 64.7%) as a yellow gum; $^1$H NMR (400 MHz, DMSO) 1.37 (9H, s), 2.18 (1H, d), 2.5 (3H, s), 2.64-2.76 (1H, m), 3.33 (4H, s), 3.53 (1H, s), 3.64 (1H, s), 3.75 (1H, s), 4.96 (1H, s), 7.38 (1H, dd), 7.85 (1H, s), 8.12 (1H, s), 8.18 (1H, s), 8.30 (1H, d), 8.54 (1H, d), 8.73 (1H, dd); m/z MH$^+$ 476.

Intermediate 112: tert-butyl(3S)-3-[7-methyl-2-[(7-methyl-6-quinolyl)amino]-8-oxo-purin-9-yl]pyrrolidine-1-carboxylate

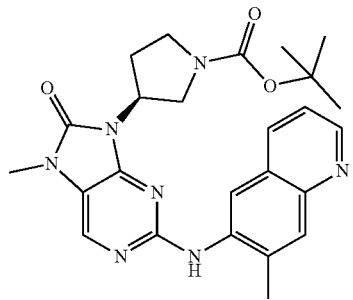 [SMILES: Cc1cc2ncccc2cc1Nc1ncc2c(n1)n([C@H]1CCN(C(=O)OC(C)(C)C)C1)c(=O)n2C]

Cesium carbonate (368 mg, 1.13 mmol) was added to 7-methylquinolin-6-amine (71.5 mg, 0.45 mmol) and tert-butyl (3S)-3-(2-chloro-7-methyl-8-oxo-purin-9-yl)pyrrolidine-1-carboxylate (200 mg, 0.57 mmol) in 1,4-dioxane (5 mL). Brettphos precat G3 (25.6 mg, 0.03 mmol) was added and the reaction mixture was heated at 100° C. for 1 h. A further 5% of Brettphos precat G3 catalyst was added and the reaction mixture was stirred for 1 h, then was allowed to cool to rt, filtered and the solid was washed with DCM (10 mL). The combined organic layers were concentrated in vacuo and the resulting crude product was purified by fcc, elution gradient 0 to 10% MeOH in DCM, to afford the title compound (80 mg, 30%) as a cream solid; $^1$H NMR (400 MHz, CDCl$_3$) 1.47 (9H, d), 2.23 (1H, s), 2.59 (3H, s), 2.91 (1H, dq), 3.43 (4H, s), 3.66-3.91 (2H, m), 4.02 (1H, d), 5.10 (1H, s), 7.08 (1H, d), 7.31 (1H, s), 7.92 (1H, s), 7.97 (1H, s), 8.04 (1H, s), 8.69 (1H, d), 8.75 (1H, dd); m/z MH$^+$ 476.

Intermediate 113: tert-butyl 4-(7-methyl-2-((7-methylcinnolin-6-yl)amino)-8-oxo-7,8-dihydro-9H-purin-9-yl)piperidine-1-carboxylate

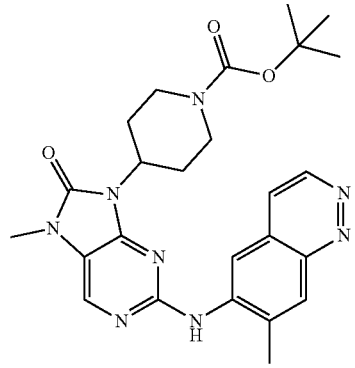 [SMILES: Cc1cc2nnccc2cc1Nc1ncc2c(n1)n(C1CCN(C(=O)OC(C)(C)C)CC1)c(=O)n2C]

Cesium carbonate (531 mg, 1.63 mmol) was added to 7-methylcinnolin-6-amine (130 mg, 0.82 mmol) and tert-butyl 4-(2-chloro-7-methyl-8-oxo-7,8-dihydro-9H-purin-9-yl)piperidine-1-carboxylate (300 mg, 0.82 mmol) in 1,4-dioxane (6 mL). Brettphos precat G3 (37 mg, 0.04 mmol) was added and the reaction mixture was stirred at 100° C. for 1 h. Additional 5% of Brettphos precat G3 catalyst was added and the reaction mixture was heated at 100° C. for 2 h. A further 5% catalyst was added and the reaction mixture was heated at 100° C. for 16 h. A further 5% catalyst was added and the reaction mixture was heated at 100° C. for 1 h. The reaction mixture was allowed to cool to rt and filtered, and the solid was washed with 10% MeOH in DCM (3 mL). The combined organic layers were concentrated in vacuo, and the resulting crude mixture was purified by fcc, elution gradient 0 to 10% MeOH in DCM, to afford the title compound (138 mg, 35%) as a brown oil; $^1$H NMR (400 MHz, DMSO) 1.33 (9H, s), 1.80 (2H, d), 2.08 (2H, s), 2.63 (3H, s), 2.88 (2H, s), 3.37 (3H, s), 4.11 (2H, s), 4.40 (1H, d), 7.88 (1H, d), 8.24 (1H, s), 8.28 (1H, s), 8.52 (1H, s), 8.68 (1H, s), 9.10 (1H, d); m/z MH$^+$ 491.

Intermediate 114: tert-butyl (3S,4R)-3-fluoro-4-(7-methyl-2-((7-methylquinolin-6-yl)amino)-8-oxo-7,8-dihydro-9H-purin-9-yl)piperidine-1-carboxylate

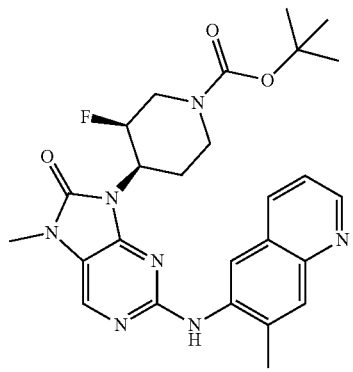 [SMILES: Cc1cc2ncccc2cc1Nc1ncc2c(n1)n([C@@H]1CCN(C(=O)OC(C)(C)C)C[C@@H]1F)c(=O)n2C]

Cesium carbonate (760 mg, 2.33 mmol) was added to 7-methylquinolin-6-amine (123 mg, 0.78 mmol) and tert-butyl (3S,4R)-4-(2-chloro-7-methyl-8-oxo-7,8-dihydro-9H-purin-9-yl)-3-fluoropiperidine-1-carboxylate (300 mg, 0.78 mmol) in 2-methyl tetrahydrofuran (4 mL). The solution was degassed by bubbling nitrogen through the reaction mixture for 5 minutes. 2,2'-Bis(diphenylphosphanyl)-1,1'-binaphthalene (24.2 mg, 0.04 mmol) and diacetoxypalladium (4.36 mg, 0.02 mmol) were added and the reaction mixture was heated at 80° C. for 3 h, then allowed to cool to rt, concentrated in vacuo, taken up in DCM (3 mL) and filtered. The filtrate was purified by fcc, elution gradient 0 to 10% methanol in DCM, to afford the title compound (132 mg, 33%) as a golden solid; $^1$H NMR (400 MHz, DMSO) 1.21-1.51 (9H, m), 1.88 (1H, d), 2.96 (1H, s), 3.11-3.29 (2H, m), 3.30 (3H, s), 3.36 (3H, s), 4.17 (1H, s), 4.31 (1H, s), 4.53 (1H, dd), 4.88 (1H, d), 7.36 (1H, dd), 7.83 (1H, s), 8.10 (1H, d), 8.21 (1H, s), 8.38 (1H, s), 8.49 (1H, s), 8.72 (1H, dd); m/z MH$^+$ 508.

Intermediate 115: 7-methyl-2-[(7-methyl-6-quinolyl)amino]-9-[(3R)-pyrrolidin-3-yl]purin-8-one

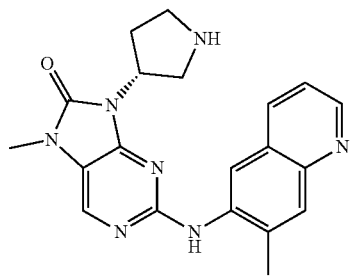 [SMILES: Cc1cc2ncccc2cc1Nc1ncc2c(n1)n([C@@H]1CCNC1)c(=O)n2C]

4 M HCl in 1,4-dioxane (0.45 mL, 1.83 mmol) was added to tert-butyl (3R)-3-[7-methyl-2-[(7-methyl-6-quinolyl)amino]-8-oxo-purin-9-yl]pyrrolidine-1-carboxylate (174 mg, 0.37 mmol) in methanol (2.2 mL) at rt and the reaction mixture was stirred at rt for 1 h. The mixture was diluted with water (3 mL) to dissolve solids then loaded onto a 5 g SCX column washing with MeOH, then eluting with 1 N NH$_3$ in MeOH. The solvent was removed in vacuo to afford the title compound (122 mg, 89%) as a yellow gum, used directly in the next step; m/z [M-H]$^-$ 374.

Intermediate 116: 7-methyl-2-[(7-methyl-6-quinolyl)amino]-9-[(3S)-pyrrolidin-3-yl]purin-8-one

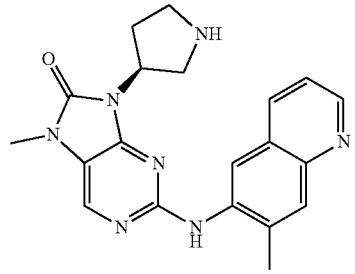 [SMILES: Cc1cc2ncccc2cc1Nc1ncc2c(n1)n([C@H]1CCNC1)c(=O)n2C]

4 M HCl in 1,4-dioxane (0.21 mL, 0.84 mmol) was added to tert-butyl (3)-3-[7-methyl-2-[(7-methyl-6-quinolyl)amino]-8-oxo-purin-9-yl]pyrrolidine-1-carboxylate (80 mg, 0.17 mmol) in methanol (1 mL) at rt and the reaction mixture was stirred at rt for 2 h, then was concentrated in vacuo to afford the HCl salt of the title compound (70 mg, 101%) as a pale yellow solid; $^1$H NMR (400 MHz, DMSO) 2.32-2.41 (2H, m), 2.73 (3H, s), 3.32 (1H, dd), 3.37 (3H, s), 3.57 (2H, q), 3.77 (1H, d), 5.11-5.22 (1H, m), 7.95 (1H, dd), 8.23 (1H, s), 8.26 (1H, s), 8.78 (1H, s), 9.07 (2H, dd), 9.51 (2H, s), 9.84 (1H, s); m/z [M-H]$^-$ 374.

Intermediate 117: 7-methyl-2-((7-methylcinnolin-6-yl)amino)-9-(piperidin-4-yl)-7,9-dihydro-8H-purin-8-one

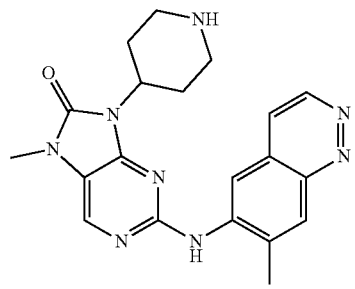 [SMILES: Cc1cc2nnccc2cc1Nc1ncc2c(n1)n(C1CCNCC1)c(=O)n2C]

4 M HCl in 1,4-dioxane (0.262 mL, 1.05 mmol) was added to tert-butyl 4-(7-methyl-2-((7-methylcinnolin-6-yl)amino)-8-oxo-7,8-dihydro-9H-purin-9-yl)piperidine-1-carboxylate (103 mg, 0.21 mmol) in methanol (1.2 mL) at rt and the reaction mixture was stirred at rt for 1 h, then was concentrated in vacuo and loaded onto a 5 g SCX column, washing with MeOH, then eluting with 1N NH$_3$/MeOH. The solvent was removed in vacuo, MeCN (3 mL) was added and concentrated in vacuo to afford the title compound (61 mg, 74%) as a brown solid; $^1$H NMR (400 MHz, DMSO) 1.75 (2H, d), 2.53 (2H, s), 2.63 (1H, s), 2.65 (3H, s), 3.1-3.19 (3H, m), 3.37 (3H, s), 4.32 (1H, t), 8.08 (1H, d), 8.24 (1H, s), 8.28 (1H, s), 8.63 (1H, s), 8.75 (1H, s), 9.12 (1H, d) m/z MH$^+$ 391.

Intermediate 118: ethyl 4-(((3R,4R)-1-(tert-butoxy-carbonyl)-4-fluoropyrrolidin-3-yl)amino)-2-chloro-pyrimidine-5-carboxylate

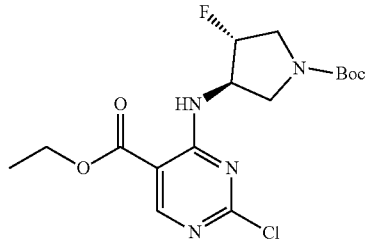 [SMILES: CCOC(=O)c1cnc(Cl)nc1N[C@@H]1CN(C(=O)OC(C)(C)C)C[C@H]1F]

DIPEA (7.33 mL, 41.97 mmol) was added in one portion to a stirred solution of ethyl 2,4-dichloropyrimidine-5-carboxylate (4.64 g, 20.98 mmol), and tert-butyl (3R,4R)-3-amino-4-fluoropyrrolidine-1-carboxylate (sourced commercially) (4.5 g, 22.03 mmol) in MeCN (100 mL) at rt. The reaction mixture was stirred at rt for 13 h. The reaction mixture was combined with a smaller scale reaction mixture that used similar reagents and conditions (max 2.26 mmol of desired product) and concentrated in vacuo. The resulting crude product was purified by fcc, elution gradient 0 to 30% EtOAc in petroleum ether, to afford the title compound (7.60 g, 84% overall) as a white solid. $^1$H NMR (400 MHz, DMSO) 1.31 (3H, q), 1.43 (9H, s), 3.39-3.80 (4H, m), 4.21-4.38 (2H, m), 4.70 (1H, s), 5.26 (1H, d), 8.34 (1H, d), 8.69 (1H, s); m/z MH$^+$ 389.

Intermediate 119: 4-(((3R,4R)-1-(tert-butoxycarbonyl)-4-fluoropyrrolidin-3-yl)amino)-2-chloropyrimidine-5-carboxylic acid

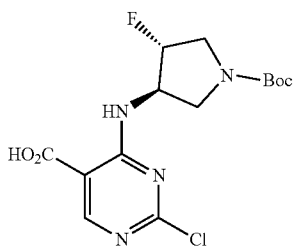 [SMILES: CC(C)(C)OC(=O)N1C[C@@H](F)[C@H](Nc2nc(Cl)ncc2C(=O)O)C1]

A solution of lithium hydroxide (0.91 g, 38.06 mmol) in water (150 mL) was added in one portion to a stirred solution of ethyl 4-(((3R,4R)-1-(tert-butoxycarbonyl)-4-fluoropyrrolidin-3-yl)amino)-2-chloropyrimidine-5-carboxylate (7.40 g, 19.03 mmol) in THF (150 mL) at rt. The reaction mixture was stirred at rt for 16 h, then concentrated in vacuo, diluted with water (100 mL) and acidified to pH 2 using 2 M aq. HCl. The resulting precipitate was collected and dried under vacuum to afford the title compound (6.10 g, 89%) as a white solid. $^1$H NMR (400 MHz, DMSO) 1.43 (9H, s), 3.39-3.81 (5H, m), 4.67 (1H, s), 5.25 (1H, d), 8.64 (1H, s), 13.78 (1H, br s); m/z MH$^+$ 361.

Intermediate 120: tert-butyl (3R,4R)-3-(2-chloro-8-oxo-7,8-dihydro-9H-purin-9-yl)-4-fluoropyrrolidine-1-carboxylate

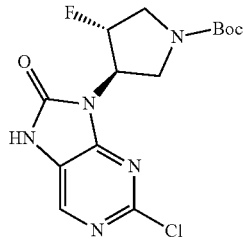 [SMILES: CC(C)(C)OC(=O)N1C[C@@H](F)[C@H](n2c(=O)[nH]c3cnc(Cl)nc32)C1]

Diphenylphosphonic azide (3.57 g, 12.97 mmol) was added in one portion to 4-(((3R,4R)-1-(tert-butoxycarbonyl)-4-fluoropyrrolidin-3-yl)amino)-2-chloropyrimidine-5-carboxylic acid (3.90 g, 10.81 mmol), and Et$_3$N (4.52 mL, 32.43 mmol) in toluene (140 mL) at rt. The reaction mixture was heated at 100° C. for 16 h, then was allowed to cool to rt. The reaction mixture was combined with a smaller scale reaction mixture that used similar reagents and conditions (max 4.16 mmol of desired product) and the resulting mixture was diluted with DCM (200 mL). The organic layer was isolated and washed with sat. brine, then dried over Na$_2$SO$_4$, filtered and concentrated in vacuo. The resulting crude product was purified by fcc, elution gradient 0 to 5% MeOH in DCM, to afford the title compound (3.50 g, 67% overall) as a brown oil. $^1$H NMR (400 MHz, DMSO) 1.43 (9H, s), 3.53-4.06 (4H, m), 5.03 (1H, d), 5.44-5.64 (1H, m), 8.18 (1H, s), 11.82 (1H, s); m/z MH$^+$ 358.

Intermediate 121: tert-butyl (3R,4R)-3-(2-chloro-7-methyl-8-oxo-7,8-dihydro-9H-purin-9-yl)-4-fluoropyrrolidine-1-carboxylate

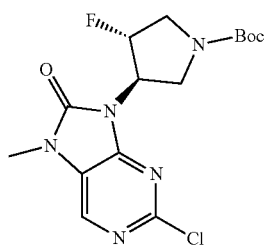 [SMILES: Cn1c(=O)n([C@@H]2CN(C(=O)OC(C)(C)C)C[C@H]2F)c2nc(Cl)ncc21]

60% w/w sodium hydride in mineral oil (0.67 g, 16.77 mmol) was added portionwise to tert-butyl (3R,4R)-3-(2-chloro-8-oxo-7,8-dihydro-9H-purin-9-yl)-4-fluoropyrrolidine-1-carboxylate (4.00 g, 11.18 mmol) in DMF (100 mL) at 0° C. and the reaction mixture was stirred at 0° C. for 10 min. Iodomethane (1.40 mL, 22.36 mmol) was added and the reaction mixture was stirred at rt for 1 h. The reaction mixture was combined with a smaller scale reaction mixture that used similar reagents and conditions (max 1.40 mmol of desired product). The resulting mixture was poured into water (1 L) and the resulting precipitate was collected by filtration and dried under vacuum, then triturated with MTBE and purified by fcc, elution gradient 0 to 3% MeOH in DCM, to afford the title compound (1.80 g, 39% overall) as a yellow solid. $^1$H NMR (400 MHz, DMSO) 1.43 (9H, s), 3.36 (3H, s), 3.51-4.02 (4H, m), 5.06 (1H, d), 5.36-5.68 (1H, m), 8.40 (1H, s); m/z MH+ 372.

Intermediate 122: tert-butyl (3R,4R)-3-fluoro-4-(7-methyl-2-((7-methylquinolin-6-yl)amino)-8-oxo-7,8-dihydro-9H-purin-9-yl)pyrrolidine-1-carboxylate

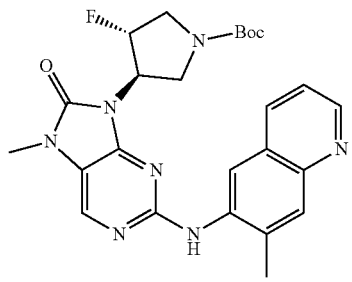 [SMILES: Cc1cc2ncccc2cc1Nc1ncc2c(n1)n([C@@H]1CN(C(=O)OC(C)(C)C)C[C@H]1F)c(=O)n2C]

Brettphos Pd G3 (0.51 g, 0.56 mmol) was added in one portion to a stirred mixture of tert-butyl (3R,4R)-3-(2-chloro-7-methyl-8-oxo-7,8-dihydro-9H-purin-9-yl)-4-fluoropyrrolidine-1-carboxylate (1.60 g, 4.30 mmol), $Cs_2CO_3$ (3.51 g, 10.76 mmol) and 7-methylquinolin-6-amine (0.72 g, 4.52 mmol) in 1,4-dioxane (60 mL) at rt. The reaction mixture was heated at 100° C. for 16 h. The mixture was allowed to cool to rt and diluted with DCM (200 mL). The resulting mixture was washed with sat. brine, and the resulting organic layer was isolated and dried over $Na_2SO_4$, filtered and concentrated in vacuo. The resulting crude product was purified by fcc, elution gradient 0 to 2% MeOH in DCM, to afford the title compound (1.80 g, 85%) as a yellow solid. $^1$H NMR (400 MHz, DMSO) 1.35 (9H, s), 3.30 (3H, s), 3.31 (3H, s), 3.22-3.94 (4H, m), 5.02 (1H, d), 5.57 (1H, ddt), 7.38 (1H, dd), 7.83 (1H, s), 8.06-8.30 (3H, m), 8.62 (1H, d), 8.72 (1H, dd); m/z MH+ 494.

Example 1: 9-(1-acetylpiperidin-4-yl)-7-methyl-2-((7-methylcinnolin-6-yl)amino)-7,9-dihydro-8H-purin-8-one

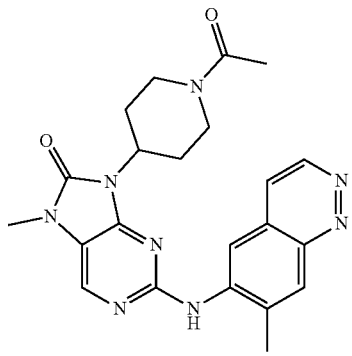 [SMILES: CC(=O)N1CCC(n2c(=O)n(C)c3cnc(Nc4cc5ccnnc5cc4C)nc32)CC1]

Cesium carbonate (210 mg, 0.65 mmol) was added to 9-(1-acetylpiperidin-4-yl)-2-chloro-7-methyl-7,9-dihydro-8H-purin-8-one (100 mg, 0.32 mmol) and 7-methylcinnolin-6-amine (51.4 mg, 0.32 mmol) in 1,4-dioxane (3 mL). Brettphos Pd G3 (14.6 mg, 0.02 mmol) was added and the resulting suspension was stirred at 100° C. for 1 h. A further 5% Brettphos Pd G3 catalyst was added and the reaction mixture was heated at 100° C. for 2 h, then a further 5% Pd catalyst was added and the reaction mixture was heated at 100° C. for 16 h. The reaction mixture was allowed to cool to rt and was concentrated in vacuo. The residue was taken up in DMF (2 mL), filtered and purified by preparative HPLC. The residue was dissolved in DCM (1 mL) and a few drops of n-heptane were added. The solvent was removed in vacuo to give a yellow oil. Acetonitrile (2 mL) was added and the solid was isolated by filtration and dried in vacuo to afford the title compound (8.0 mg, 6%) as a yellow solid; $^1$H NMR (400 MHz, DMSO) 1.84 (2H, s), 1.95 (3H, s), 2.62 (5H, s), 3.1-3.24 (2H, m), 3.36 (3H, s), 3.96 (1H, d), 4.48 (1H, t), 4.59 (1H, d), 7.86 (1H, d), 8.23 (1H, s), 8.27 (1H, s), 8.49 (1H, s), 8.73 (1H, s), 9.09 (1H, d); m/z MH+ 433.

Example 2: 9-(1-acetylpiperidin-4-yl)-7-methyl-2-((7-methylquinoxalin-6-yl)amino)-7,9-dihydro-8H-purin-8-one

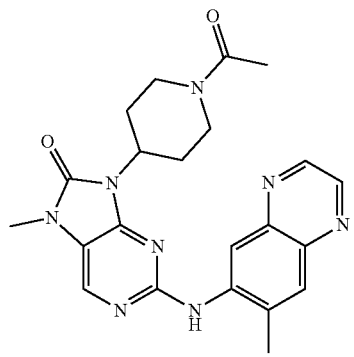 [SMILES: CC(=O)N1CCC(n2c(=O)n(C)c3cnc(Nc4cc5nccnc5cc4C)nc32)CC1]

Cesium carbonate (210 mg, 0.65 mmol) was added to 9-(1-acetylpiperidin-4-yl)-2-chloro-7-methyl-7,9-dihydro-8H-purin-8-one (100 mg, 0.32 mmol) and 7-methylquinoxalin-6-amine (51.4 mg, 0.32 mmol) in 1,4-dioxane (3 mL). Brettphos Pd G3 (14.6 mg, 0.02 mmol) was added and the resulting suspension was stirred at 100° C. for 1 h. A further 5 mol % Brettphos Pd G3 (14.6 mg, 0.02 mmol) was added and the reaction mixture was heated at 100° C. for 2 h. A further 5 mol % Brettphos Pd G3 (14.6 mg, 0.02 mmol) was added and the reaction mixture was heated at 100° C. for 1 h. The reaction mixture was allowed to cool to rt and was concentrated in vacuo. The residue was diluted with DMF (2 mL), filtered and purified by preparative HPLC. DCM (2 mL) and a few drops of diethyl ether were added, and the mixture was concentrated in vacuo to afford the title compound (27 mg, 19%) as a green solid; $^1$H NMR (400 MHz, DMSO) 1.76 (1H, d), 1.85 (1H, d), 1.98 (3H, s), 2.15-2.27 (1H, m), 2.55 (5H, s), 3.15 (1H, t), 3.34 (3H, s), 3.96 (1H, d), 4.39-4.49 (1H, m), 4.52 (1H, d), 7.89 (1H, s), 8.22 (1H, s), 8.55 (1H, s), 8.66 (1H, s), 8.73 (1H, d), 8.76 (1H, d); m/z MH+ 433.

Example 3: 9-(1-acetylpiperidin-4-yl)-7-methyl-2-((7-methylquinazolin-6-yl)amino)-7,9-dihydro-8H-purin-8-one

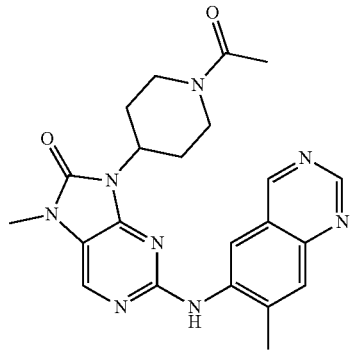 [SMILES: CC(=O)N1CCC(n2c(=O)n(C)c3cnc(Nc4cc5cncnc5cc4C)nc32)CC1]

RuPhos Pd G3 (9.2 mg, 11 mol) was added to 9-(1-acetylpiperidin-4-yl)-2-chloro-7-methyl-7,9-dihydro-8H-purin-8-one (68.1 mg, 0.22 mmol), 7-methylquinazolin-6-amine (35 mg, 0.22 mmol), RuPhos (10.3 mg, 0.02 mmol) and Cs$_2$CO$_3$ (215 mg, 0.66 mmol) in 1,4-dioxane (1 mL) under nitrogen. The reaction mixture was heated at 100° C. for 16 h, then was allowed to cool to rt and was concentrated in vacuo and purified by preparative HPLC to afford the title compound (22 mg, 23%) as a white solid; $^1$H NMR (400 MHz, DMSO) 1.74-1.87 (2H, m), 1.95 (3H, s), 2.16-2.31 (1H, m), 2.34-2.49 (1H, m), 2.53-2.67 (4H, m), 3.09-3.21 (1H, m), 3.34 (3H, s), 3.95 (1H, d), 4.38-4.48 (1H, m), 4.48-4.58 (1H, m), 7.86 (1H, s), 8.20 (1H, s), 8.43 (1H, s), 8.78 (1H, s), 9.13 (1H, s), 9.36 (1H, s); m/z MH$^+$ 433.

Example 4: 9-(1-acetylpiperidin-4-yl)-2-((2,7-dimethylquinoxalin-6-yl)amino)-7-methyl-7,9-dihydro-8H-purin-8-one

Example 5: 9-(1-acetylpiperidin-4-yl)-2-((3,7-dimethylquinoxalin-6-yl)amino)-7-methyl-7,9-dihydro-8H-purin-8-one

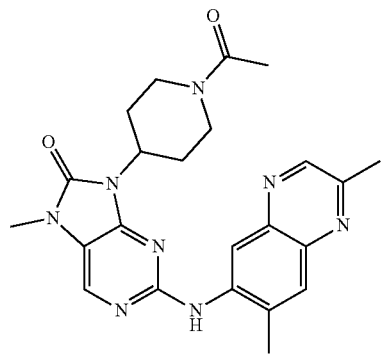

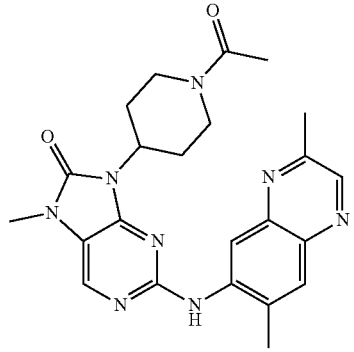

Cesium carbonate (1.05 g, 3.23 mmol) was added to 9-(1-acetylpiperidin-4-yl)-2-chloro-7-methyl-7,9-dihydro-8H-purin-8-one (500 mg, 1.61 mmol), a mixture of 2,7-dimethylquinoxalin-6-amine (224 mg, 1.29 mmol) and 3,7-dimethylquinoxalin-6-amine (55.9 mg, 0.32 mmol) in 1,4-dioxane (10 mL). Brettphos Pd G3 (73.2 mg, 0.08 mmol) was added and the reaction mixture was heated at 100° C. for 1 h. A further 5 mol % Brettphos Pd G3 (73.2 mg, 0.08 mmol) was added and the reaction mixture was heated at 100° C. for 1 h, then was allowed to cool to rt, filtered and washed with DCM (10 mL). The filtrate was concentrated in vacuo and was purified by fcc, elution gradient 0 to 10% MeOH in DCM, to afford the title compounds as a mixture. Examples 4 and 5 were separated by SFC to afford the title compounds 4 (62 mg, 10%) as a cream solid and 5 (20 mg, 3%) as a cream solid.

Example 4: $^1$H NMR (400 MHz, DMSO) 1.75 (1H, d), 1.84 (1H, d), 1.98 (3H, s), 2.21 (1H, qd), 2.45 (1H, dd), 2.52 (3H, s), 2.54-2.64 (1H, m), 2.66 (3H, s), 3.13 (1H, d), 3.34 (3H, s), 3.96 (1H, d), 4.44 (1H, tt), 4.52 (1H, d), 7.77-7.81 (1H, m), 8.19 (1H, s), 8.45 (1H, s), 8.61 (1H, s); m/z MH$^+$ 447.

Example 5: $^1$H NMR (400 MHz, DMSO) 1.77 (1H, d), 1.85 (1H, d), 1.94 (3H, s), 2.15-2.27 (1H, m), 2.4-2.48 (1H, m), 2.52 (3H, s), 2.57-2.64 (1H, m), 2.66 (3H, s), 3.13 (1H, d), 3.34 (3H, s), 3.94 (1H, d), 4.45 (1H, ddd), 4.53 (1H, d), 7.83 (1H, s), 8.20 (1H, s), 8.39 (1H, s), 8.63 (2H, d); m/z MH$^+$ 447.

Example 6: 9-((1r,4r)-4-hydroxycyclohexyl)-7-methyl-2-((7-methylquinolin-6-yl)amino)-7,9-dihydro-8H-purin-8-one

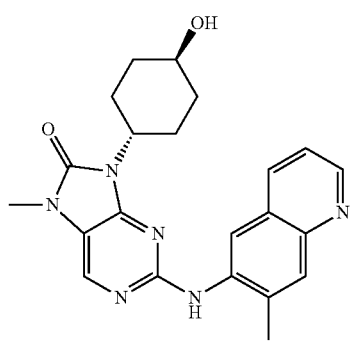 [SMILES: Cc1cc2ncccc2cc1Nc1ncc2c(n1)n([C@H]1CC[C@H](O)CC1)c(=O)n2C]

RuPhos Pd G3 (40.1 mg, 0.04 mmol) was added to 2-chloro-9-((1r,4r)-4-hydroxycyclohexyl)-7-methyl-7,9-dihydro-8H-purin-8-one (125 mg, 0.44 mmol), 7-methylquinolin-6-amine (70 mg, 0.44 mmol) and Cs₂CO₃ (288 mg, 0.88 mmol) in 1,4-dioxane (4 mL). The reaction mixture was heated at 100° C. for 16 h, then was allowed to cool to rt, filtered and the solid was washed with MeOH (10 mL). The combined organic layers were concentrated in vacuo, and purified by preparative HPLC to afford the title compound (20 mg, 11%) as a white solid; ¹H NMR (300 MHz, DMSO) 1.18-1.37 (2H, m), 1.67-1.78 (2H, m), 1.87-1.98 (2H, m), 2.28-2.43 (2H, m), 2.51 (3H, s), 3.32 (3H, s), 3.35-3.37 (1H, m), 4.06-4.24 (1H, m), 4.66 (1H, d), 7.42 (1H, dd), 7.85 (1H, s), 8.08-8.14 (1H, m), 8.14-8.21 (1H, m), 8.29 (1H, s), 8.61 (1H, s), 8.74 (1H, dd); m/z MH⁺ 405.

Example 7: 9-((1r,4r)-4-hydroxycyclohexyl)-7-methyl-2-((7-methylcinnolin-6-yl)amino)-7,9-dihydro-8H-purin-8-one

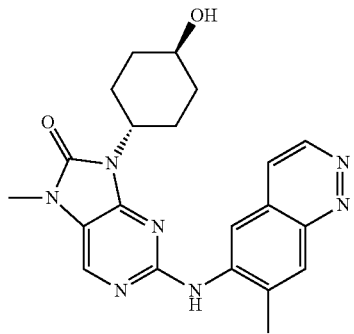 [SMILES: Cc1cc2nnccc2cc1Nc1ncc2c(n1)n([C@H]1CC[C@H](O)CC1)c(=O)n2C]

Cesium carbonate (230 mg, 0.71 mmol) was added to 2-chloro-9-((1r,4r)-4-hydroxycyclohexyl)-7-methyl-7,9-dihydro-8H-purin-8-one (100 mg, 0.35 mmol) and 7-methylcinnolin-6-amine (56.3 mg, 0.35 mmol) in 1,4-dioxane (2 mL). The reaction mixture was degassed with nitrogen and Brettphos Pd G3 (32 mg, 0.04 mmol) was added. The reaction mixture was heated at 100° C. for 2 h. A further 5% of Brettphos Pd G3 was added and stirred for 1 h. The reaction mixture was allowed to cool to rt and was concentrated. The resulting crude product was purified by preparative HPLC. The pure fractions were combined and partially concentrated, and the product crystallised out of water, which was isolated by filtration and dried in vacuo to afford the title compound (30 mg, 21%) as a beige solid; ¹H NMR (400 MHz, DMSO) 1.32 (2H, q), 1.76 (2H, d), 1.96 (2H, d), 2.3-2.44 (2H, m), 2.64 (3H, s), 3.35 (3H, s), 3.43 (1H, s), 4.20 (1H, ddd), 4.67 (1H, d), 7.88 (1H, d), 8.26 (2H, s), 8.52 (1H, s), 8.71 (1H, s), 9.15 (1H, d); m/z MH⁺ 406.

Example 8: 2-((4,7-dimethylquinolin-6-yl)amino)-9-((1r,4r)-4-hydroxycyclohexyl)-7-methyl-7,9-dihydro-8H-purin-8-one

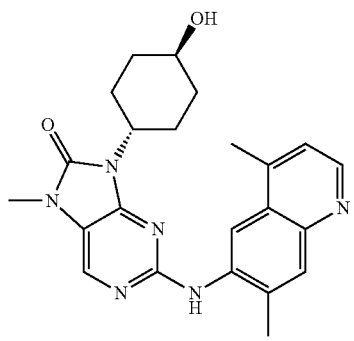 [SMILES: Cc1cc2nccc(C)c2cc1Nc1ncc2c(n1)n([C@H]1CC[C@H](O)CC1)c(=O)n2C]

Cesium carbonate (488 mg, 1.50 mmol) was added in one portion to 4,7-dimethylquinolin-6-amine (129 mg, 0.75 mmol) and 2-chloro-9-((1r,4r)-4-hydroxycyclohexyl)-7-methyl-7,9-dihydro-8H-purin-8-one (212 mg, 0.75 mmol) in 1,4-dioxane (5 mL) at rt and the reaction mixture was degassed by bubbling nitrogen through the mixture for 5 minutes. Brettphos Pd G3 (67.9 mg, 0.07 mmol) was added and the reaction mixture was heated at 100° C. for 4 h, then was allowed to cool to rt, diluted with DCM and filtered through celite. The DCM layer was concentrated in vacuo and purified by fcc, elution gradient 0 to 5% MeOH in DCM, to afford the title compound (175 mg, 56%) as a cream solid; ¹H NMR (400 MHz, DMSO) 1.26 (2H, q), 1.71 (2H, d), 1.90 (2H, d), 2.22-2.38 (2H, m), 2.50 (3H, s), 2.59-2.66 (3H, m), 3.32 (3H, s), 3.33-3.37 (1H, m), 4.18 (1H, ddd), 4.61 (1H, d), 7.26-7.31 (1H, m), 7.84 (1H, s), 8.14 (1H, s), 8.40 (1H, s), 8.56 (1H, s), 8.60 (1H, d); m/z MH⁺ 419.

Example 9: 9-((1r,4r)-4-hydroxycyclohexyl)-2-((4-methoxy-7-methylquinolin-6-yl)amino)-7-methyl-7,9-dihydro-8H-purin-8-one

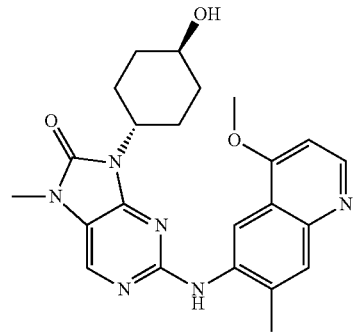 [SMILES: COc1ccnc2cc(C)c(Nc3ncc4c(n3)n([C@H]3CC[C@H](O)CC3)c(=O)n4C)cc12]

Cesium carbonate (346 mg, 1.06 mmol) was added in one portion to 4-methoxy-7-methylquinolin-6-amine (100 mg, 0.53 mmol) and 2-chloro-9-((1r,4r)-4-hydroxycyclohexyl)-7-methyl-7,9-dihydro-8H-purin-8-one (150 mg, 0.53 mmol) in 1,4-dioxane (4 mL) at rt and the reaction mixture was degassed by bubbling nitrogen through the mixture for 5 minutes. Brettphos Pd G3 (48.1 mg, 0.05 mmol) was added and the reaction mixture was heated at 100° C. for 18 h, then was allowed to cool to rt, diluted with DCM and filtered through celite. The DCM layer was concentrated in vacuo and purified by fcc, elution gradient 0 to 5% MeOH in DCM, to afford the title compound (70 mg, 30%) as a cream solid; ¹H NMR (400 MHz, DMSO) 1.26 (2H, q), 1.70 (2H, d), 1.89 (2H, d), 2.32 (3H, q), 2.48 (3H, s), 3.32 (3H, s), 4.02 (3H, s), 4.09-4.19 (1H, m), 4.58 (1H, d), 6.92 (1H, d), 7.78 (1H, s), 8.14 (1H, s), 8.46 (1H, s), 8.51 (1H, s), 8.58 (1H, d); m/z MH⁺ 435.

Example 10: 9-((1r,4r)-4-hydroxycyclohexyl)-7-methyl-2-((7-methylquinoxalin-6-yl)amino)-7,9-dihydro-8H-purin-8-one

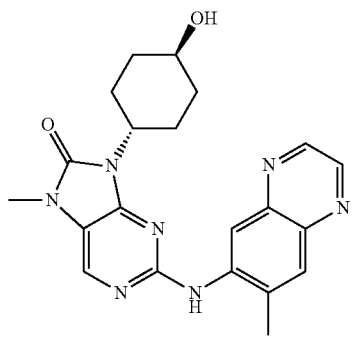 [SMILES: Cc1cc2nccnc2cc1Nc1ncc2c(n1)n([C@H]1CC[C@H](O)CC1)c(=O)n2C]

Cesium carbonate (1.73 g, 5.31 mmol) was added to 2-chloro-9-((1r,4r)-4-hydroxycyclohexyl)-7-methyl-7,9-dihydro-8H-purin-8-one (750 mg, 2.65 mmol) and 7-methylquinoxalin-6-amine (422 mg, 2.65 mmol) in 1,4-dioxane (15 mL). Brettphos Pd G3 (120 mg, 0.13 mmol) was added and the reaction mixture was heated at 100° C. for 2 h, then was allowed to cool to rt, filtered and the solid was washed with DCM (10 mL). The combined DCM layers were concentrated in vacuo and purified by fcc, elution gradient 0 to 10% MeOH in DCM. The resulting solid was suspended in MeCN (50 mL). The suspension was heated at reflux, then allowed to cool to rt, filtered, washed with a small amount of MeCN and the solid was dried at 45° C. in vacuo to afford the title compound (460 mg, 43%) as a yellow solid; $^1$H NMR (400 MHz, DMSO) 1.29 (2H, q), 1.73 (2H, d), 1.94 (2H, d), 2.41 (2H, d), 2.58 (3H, s), 3.34 (3H, s), 3.54 (1H, d), 4.13-4.24 (1H, m), 4.60 (1H, d), 7.90 (1H, s), 8.22 (1H, s), 8.61 (1H, s), 8.69 (1H, s), 8.73 (1H, d), 8.80 (1H, d); m/z MH$^+$ 406.

Example 11: 9-((1s,4s)-4-hydroxycyclohexyl)-7-methyl-2-((7-methylquinolin-6-yl)amino)-7,9-dihydro-8H-purin-8-one

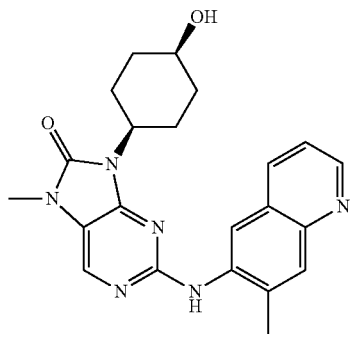 [SMILES: Cc1cc2ncccc2cc1Nc1ncc2c(n1)n([C@H]1CC[C@@H](O)CC1)c(=O)n2C]

BrettPhos Pd G3 (64.1 mg, 0.07 mmol) was added to 2-chloro-9-((1s,4s)-4-hydroxycyclohexyl)-7-methyl-7,9-dihydro-8H-purin-8-one (100 mg, 0.35 mmol), 7-methylquinolin-6-amine (84 mg, 0.53 mmol) and Cs$_2$CO$_3$ (346 mg, 1.06 mmol) in 1,4-dioxane (3 mL). The reaction mixture was heated at 100° C. for 16 h. The reaction mixture was cooled to rt and directly purified by fcc, elution gradient 0 to 35% MeCN in water (with 0.1% FA), then further purified by preparative HPLC to afford the title compound (45 mg, 32%) as a white solid; $^1$H NMR (400 MHz, DMSO) 1.47-1.61 (4H, m), 1.79-1.89 (2H, m), 2.52 (3H, s), 2.67-2.82 (2H, m), 3.33 (3H, s), 3.87-3.94 (1H, m), 4.15-4.28 (1H, m), 4.48 (1H, d), 7.38 (1H, dd), 7.83 (1H, s), 8.16 (1H, s), 8.32 (1H, dd), 8.38 (1H, s), 8.47 (1H, s), 8.70 (1H, dd); m/z MH$^+$ 405.

Example 12: 9-((1s,4s)-4-hydroxycyclohexyl)-7-methyl-2-((7-methylcinnolin-6-yl)amino)-7,9-dihydro-8H-purin-8-one

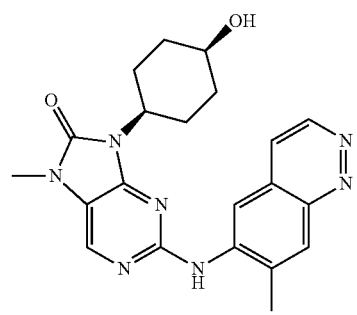 [SMILES: Cc1cc2nnccc2cc1Nc1ncc2c(n1)n([C@H]1CC[C@@H](O)CC1)c(=O)n2C]

Cesium carbonate (230 mg, 0.71 mmol) was added to 2-chloro-9-((1s,4s)-4-hydroxycyclohexyl)-7-methyl-7,9-dihydro-8H-purin-8-one (100 mg, 0.35 mmol) and 7-methylcinnolin-6-amine (56.3 mg, 0.35 mmol) in 1,4-dioxane (2 mL). The reaction mixture was degassed with nitrogen and Brettphos Pd G3 (16.0 mg, 0.02 mmol) was added. The reaction mixture was heated at 100° C. for 2 h. A further 5% Pd catalyst was added and the reaction mixture was heated at 100° C. for 2 h, then was allowed to cool to rt, was concentrated in vacuo and purified by preparative HPLC, then further purified by trituration with MeCN to afford the title compound (35 mg, 24%) as a beige solid; $^1$H NMR (400 MHz, DMSO) 1.58 (4H, q), 1.87 (2H, d), 2.65 (3H, s), 2.79 (2H, q), 3.37 (3H, s), 3.95 (1H, s), 4.25 (1H, t), 4.56 (1H, d), 8.18 (1H, d), 8.23 (1H, s), 8.28 (1H, s), 8.49 (1H, s), 8.74 (1H, s), 9.10 (1H, d); m/z MH$^+$ 406.

Example 13: 9-((1s,4s)-4-hydroxycyclohexyl)-7-methyl-2-((7-methylquinoxalin-6-yl)amino)-7,9-dihydro-8H-purin-8-one

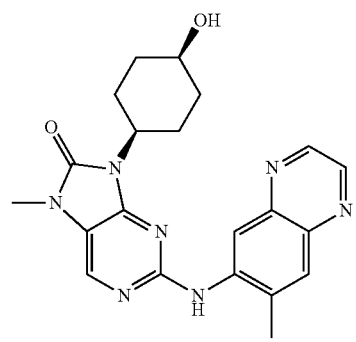 [SMILES: Cc1cc2nccnc2cc1Nc1ncc2c(n1)n([C@H]1CC[C@@H](O)CC1)c(=O)n2C]

Cesium carbonate (230 mg, 0.71 mmol) was added to 2-chloro-9-((1s,4s)-4-hydroxycyclohexyl)-7-methyl-7,9-dihydro-8H-purin-8-one (100 mg, 0.35 mmol) and 7-methylquinoxalin-6-amine (56.3 mg, 0.35 mmol) in 1,4-dioxane (2 mL). The reaction mixture was degassed with nitrogen and Brettphos Pd G3 (16.0 mg, 0.02 mmol) was added. The reaction mixture was heated at 100° C. for 2 h. Additional Brettphos Pd G3 (16.0 mg, 0.02 mmol) was added and then the reaction mixture was heated at 100° C. for 1 h, then allowed to cool to rt and concentrated in vacuo. The residue was diluted with MeOH (3 mL), filtered and purified by preparative HPLC. The pure fractions were combined and partially concentrated. The resulting precipitate was isolated by filtration and dried in vacuo to afford the title compound (65 mg, 45%) as a yellow solid; $^1$H NMR (400 MHz, DMSO) 1.45-1.61 (4H, m), 1.83 (2H, d), 2.58 (3H, s), 2.66-2.79 (2H, m), 3.34 (3H, s), 3.91 (1H, s), 4.25 (1H, td), 4.34 (1H, d), 7.90 (1H, s), 8.20 (1H, s), 8.54 (1H, s), 8.70 (1H, s), 8.73 (1H, d), 8.79 (1H, d); m/z MH$^+$ 406.

Example 14: 9-((1s,4s)-4-hydroxy-4-methylcyclohexyl)-7-methyl-2-((7-methylquinolin-6-yl)amino)-7,9-dihydro-8H-purin-8-one Example 15: 9-((1r,4r)-4-hydroxy-4-methylcyclohexyl)-7-methyl-2-((7-methylquinolin-6-yl)amino)-7,9-dihydro-8H-purin-8-one

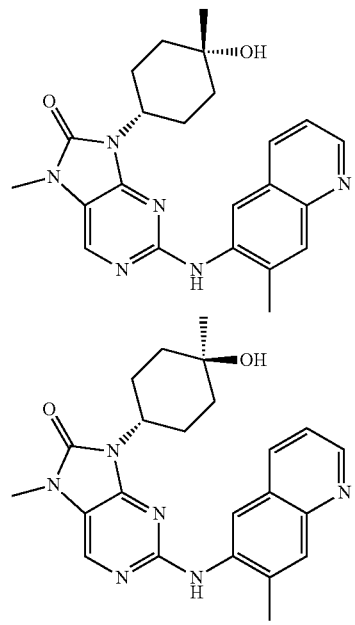

RuPhos Pd G3 (169 mg, 0.20 mmol) and 2-dicyclohexylphosphino-2',6'-di-i-propoxy-1,1'-biphenyl (94 mg, 0.20 mmol) were added to 2-chloro-9-(4-hydroxy-4-methylcyclohexyl)-7-methyl-7,9-dihydro-8H-purin-8-one (300 mg, 1.01 mmol), 7-methylquinolin-6-amine (240 mg, 1.52 mmol) and Cs$_2$CO$_3$ (988 mg, 3.03 mmol) in 1,4-dioxane (5 mL). The reaction mixture was heated at 100° C. for 5 h, then allowed to cool to rt and directly purified by fcc, elution gradient 0 to 32% MeCN in water (with 0.1% FA), then further purified by preparative HPLC to afford 14 (102 mg, 24%) as a white solid and 15 (36 mg, 9%) as a white solid.

Example 14: $^1$H NMR (400 MHz, DMSO) 1.17 (3H, s), 1.37-1.56 (4H, m), 1.66-1.75 (2H, m), 2.52 (3H, s), 2.65-2.80 (2H, m), 3.32 (3H, s), 4.11-4.24 (2H, m), 7.39 (1H, dd), 7.83 (1H, s), 8.15 (1H, s), 8.31 (1H, dd), 8.38 (1H, s), 8.45 (1H, s), 8.71 (1H, dd); m/z MH$^+$ 419.

Example 15: $^1$H NMR (400 MHz, DMSO) 0.69 (3H, s), 1.35-1.48 (2H, m), 1.48-1.62 (4H, m), 2.18-2.34 (2H, m), 2.46 (3H, s), 3.31 (3H, s), 4.03-4.16 (1H, m), 4.31 (1H, s), 7.41 (1H, dd), 7.85 (1H, s), 8.08 (1H, s), 8.15 (2H, d), 8.68 (1H, s), 8.74 (1H, dd); m/z MH$^+$ 419.

Example 16: 9-((1s,4s)-4-hydroxy-4-methylcyclohexyl)-7-methyl-2-((7-methylcinnolin-6-yl)amino)-7,9-dihydro-8H-purin-8-one Example 17: 9-((1r,4r)-4-hydroxy-4-methylcyclohexyl)-7-methyl-2-((7-methylcinnolin-6-yl)amino)-7,9-dihydro-8H-purin-8-one

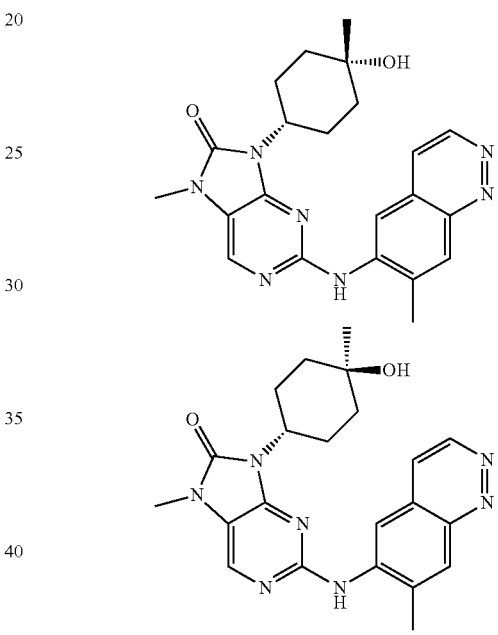

Cesium carbonate (220 mg, 0.67 mmol) was added to 2-chloro-9-((1s,4s)-4-hydroxy-4-methylcyclohexyl)-7-methyl-7,9-dihydro-8H-purin-8-one (100 mg, 0.34 mmol) and 7-methylcinnolin-6-amine (53.6 mg, 0.34 mmol) in 1,4-dioxane (2 mL). Brettphos Pd G3 (15.3 mg, 0.02 mmol) was added and the reaction mixture was heated at 100° C. for 2 h. A further 5% catalyst was added and the reaction mixture was heated at 100° C. for 2 h, then was allowed to cool to rt and was concentrated in vacuo. The residue was diluted with DCM (3 mL), filtered and purified by fcc, elution gradient 0 to 10% MeOH in DCM, to afford example 16 (15 mg, 11%) as a light brown solid and example 17 (25 mg, 18%) as a beige solid.

Example 16: $^1$H NMR (400 MHz, DMSO) 1.19 (3H, s), 1.50 (4H, q), 1.73 (2H, d), 2.64 (3H, s), 2.76 (2H, q), 3.36 (3H, s), 4.21 (2H, s), 8.15 (1H, d), 8.22 (1H, s), 8.27 (1H, s), 8.47 (1H, s), 8.72 (1H, s), 9.10 (1H, d); m/z MH$^+$ 420.

Example 17: $^1$H NMR (400 MHz, DMSO) 0.85 (3H, s), 1.42-1.54 (2H, m), 1.57-1.69 (4H, m), 2.27-2.4 (2H, m), 2.57-2.64 (3H, m), 3.35 (3H, s), 4.17 (1H, dq), 4.34 (1H, s), 7.92 (1H, dd), 8.25 (2H, d), 8.33 (1H, s), 8.79 (1H, s), 9.15 (1H, d); m/z MH$^+$ 420.

Example 18: 9-((1r,4r)-4-hydroxy-4-methylcyclohexyl)-7-methyl-2-((7-methylquinoxalin-6-yl)amino)-7,9-dihydro-8H-purin-8-one Example 19: 9-((1s,4s)-4-hydroxy-4-methylcyclohexyl)-7-methyl-2-((7-methylquinoxalin-6-yl)amino)-7,9-dihydro-8H-purin-8-one

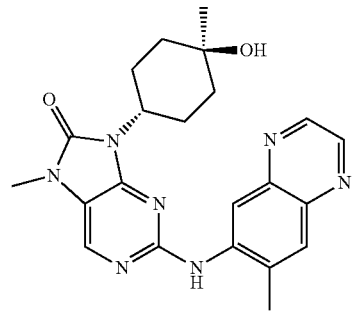

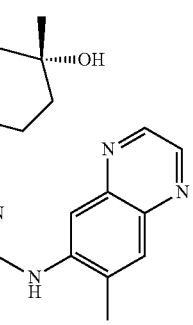

Cesium carbonate (220 mg, 0.67 mmol) was added to 2-chloro-9-((1r,4r)-4-hydroxy-4-methylcyclohexyl)-7-methyl-7,9-dihydro-8H-purin-8-one (100 mg, 0.34 mmol) and 7-methylquinoxalin-6-amine (53.6 mg, 0.34 mmol) in 1,4-dioxane (2 mL). The reaction was degassed and Brettphos Pd G3 (15.3 mg, 0.02 mmol) was added. The reaction mixture was heated at 100° C. for 2 h. A further 5 mol % Brettphos Pd G3 (15.3 mg, 0.02 mmol) was added and the reaction mixture was heated at 100° C. for 2 h, then was allowed to cool to rt and concentrated in vacuo. The residue was diluted with MeOH (3 mL), filtered and purified by preparative HPLC. The pure fractions were combined and partially concentrated in vacuo and the resulting precipitate was isolated by filtration and dried in vacuo to afford example 18 (35 mg, 25%) as a yellow solid and example 19 (55 mg, 39%) as a beige solid.

Example 18: $^1$H NMR (400 MHz, DMSO) 0.82 (3H, s), 1.4-1.51 (2H, m), 1.59 (4H, t), 2.22-2.4 (2H, m), 2.54 (3H, s), 3.34 (3H, s), 4.14 (1H, ddt), 4.30 (1H, s), 7.88-7.95 (1H, m), 8.21 (1H, s), 8.41 (1H, s), 8.71 (1H, s), 8.75 (1H, d), 8.79 (1H, d); m/z MH$^+$ 420.

Example 19: $^1$H NMR (400 MHz, DMSO) 1.16 (3H, s), 1.38-1.55 (4H, m), 1.68 (2H, d), 2.57 (3H, s), 2.66-2.78 (2H, m), 3.33 (3H, s), 4.10 (1H, d), 4.20 (1H, td), 7.89 (1H, s), 8.19 (1H, s), 8.50 (1H, s), 8.69-8.74 (2H, m), 8.78 (1H, d); m/z MH$^+$ 420.

Example 20: 9-((1s,4s)-4-hydroxy-1-methylcyclohexyl)-7-methyl-2-((7-methylquinoxalin-6-yl)amino)-7,9-dihydro-8H-purin-8-one

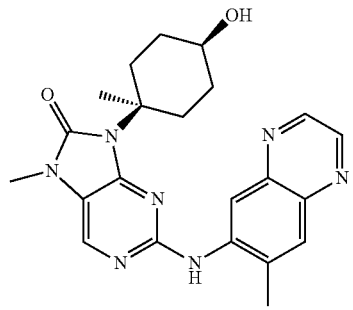 [SMILES: Cc1cc2nccnc2cc1Nc1ncc2c(n1)n([C@]1(C)CC[C@H](O)CC1)c(=O)n2C]

RuPhos Pd G3 (14.1 mg, 0.02 mmol) was added to 2-chloro-9-((1s,4s)-4-hydroxy-1-methylcyclohexyl)-7-methyl-7,9-dihydro-8H-purin-8-one (50 mg, 0.17 mmol), 7-methylquinoxalin-6-amine (26.8 mg, 0.17 mmol), Cs$_2$CO$_3$ (453 mg, 1.39 mmol) and RuPhos (15.7 mg, 0.03 mmol) in 1,4-dioxane (2 mL). The reaction mixture was heated at 100° C. for 16 h, then was concentrated in vacuo. The residue was purified by fcc, elution gradient 0 to 50% MeCN in water, to afford the title compound (45 mg, 64%) as a yellow solid; $^1$H NMR (400 MHz, DMSO) 1.44-1.56 (5H, m), 1.56-1.66 (2H, m), 1.99-2.11 (2H, m), 2.57 (3H, s), 2.90-2.95 (2H, m), 3.30 (3H, s), 3.62-3.68 (1H, m), 4.47 (1H, s), 7.89 (1H, s), 8.22 (1H, s), 8.51 (1H, s), 8.56 (1H, s), 8.73 (1H, d), 8.79 (1H, d); m/z MH$^+$ 420.

Example 21: (S)-7-methyl-2-((7-methylcinnolin-6-yl)amino)-9-(tetrahydrofuran-3-yl)-7,9-dihydro-8H-purin-8-one

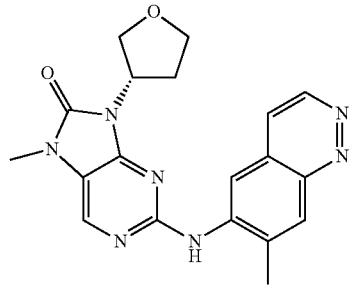 [SMILES: Cc1cc2nnccc2cc1Nc1ncc2c(n1)n([C@H]1CCOC1)c(=O)n2C]

RuPhos Pd G3 (263 mg, 0.31 mmol) and 2-dicyclohexylphosphino-2',6'-di-i-propoxy-1,1'-biphenyl (147 mg, 0.31 mmol) were added to 2-chloro-7-methyl-9-[(3S)-tetrahydro-3-furanyl]-7,9-dihydro-8H-purin-8-one (960 mg, 3.77 mmol), 7-methylcinnolin-6-amine (500 mg, 3.14 mmol) and Cs$_2$CO$_3$ (3.07 g, 9.42 mmol) in 1,4-dioxane (15 mL). The reaction mixture was heated at 100° C. for 16 h, then was allowed to cool to rt and directly purified by fcc, elution gradient 0 to 40% MeCN in water, then further purified by preparative HPLC to afford the title compound (847 mg, 72%) as a light yellow solid; $^1$H NMR (300 MHz, DMSO) 2.27-2.35 (1H, m), 2.36-2.48 (1H, m), 2.62 (3H, s), 3.35 (3H, s), 3.74-3.88 (1H, m), 3.92-4.19 (3H, m), 4.97-5.15 (1H, m), 7.94 (1H, d), 8.22 (1H, s), 8.27 (1H, s), 8.63 (1H, s), 8.67 (1H, s), 9.13 (1H, d); m/z MH$^+$ 378.

Form A

The final product, (S)-7-methyl-2-((7-methylcinnolin-6-yl)amino)-9-(tetrahydrofuran-3-yl)-7,9-dihydro-8H-purin-8-one, was analysed by XRPD and DSC and found to be crystalline. XRPD of a sample of the material gave rise to a diffraction pattern as shown in FIG. 3. (S)-7-methyl-2-((7-methylcinnolin-6-yl)amino)-9-(tetrahydrofuran-3-yl)-7,9-dihydro-8H-purin-8-one, Form A is characterised by at least one peak at a 2θ value 9.7° or 12.9° measured using CuKα radiation. The ten most prominent peaks of the XRPD are shown in Table A.

TABLE A

Ten most prominent XRPD peaks for Form A, (S)-7-methyl-2-((7-methylcinnolin-6-yl)amino)-9-(tetrahydrofuran-3-yl)-7,9-dihydro-8H-purin-8-one

| Angle 2-Theta (2θ) | Intensity % |
|---|---|
| 9.7 | 100.0 |
| 12.9 | 14.7 |
| 17.9 | 11.9 |
| 12.5 | 11.0 |
| 21.0 | 11.0 |
| 17.6 | 10.9 |
| 19.4 | 10.4 |
| 26.4 | 6.5 |
| 26.0 | 5.5 |
| 15.8 | 5.1 | wherein the 2-theta values are +/− 0.2°.

Example 22: (S)-7-methyl-2-((7-methylquinoxalin-6-yl)amino)-9-(tetrahydrofuran-3-yl)-7,9-dihydro-8H-purin-8-one

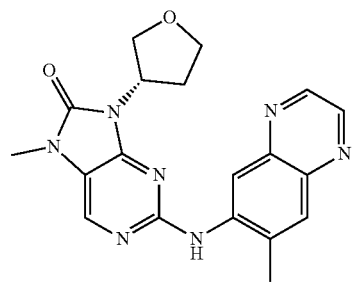 [SMILES: Cc1cc2nccnc2cc1Nc1ncc2c(n1)n([C@H]1CCOC1)c(=O)n2C]

RuPhos Pd G3 (32.8 mg, 0.04 mmol) and 2-dicyclohexylphosphino-2',6'-di-i-propoxy-1,1'-biphenyl (18.3 mg, 0.04 mmol) were added to 2-chloro-7-methyl-9-[(3S)-tetrahydro-3-furanyl]-7,9-dihydro-8H-purin-8-one (100 mg, 0.39 mmol), 7-methylquinoxalin-6-amine (68.8 mg, 0.43 mmol) and Cs$_2$CO$_3$ (384 mg, 1.18 mmol) in 1,4-dioxane (2 mL). The reaction mixture was heated at 100° C. for 16 h. The reaction mixture was allowed to cool to rt and directly purified by fcc, elution gradient 0 to 70% MeCN in water, then further purified by preparative HPLC to afford the title compound (44 mg, 30%) as a yellow solid; $^1$H NMR (300 MHz, DMSO) 2.18-2.32 (1H, m), 2.51-2.62 (4H, m), 3.35 (3H, s), 3.76-3.84 (1H, m), 3.88 (1H, dd), 3.97 (1H, t), 4.11 (1H, q), 4.92-5.05 (1H, m), 7.91 (1H, d), 8.24 (1H, s), 8.58 (1H, s), 8.66 (1H, s), 8.74 (1H, d), 8.80 (1H, d); m/z MH$^+$ 378.

Example 23: (R)-7-methyl-2-((7-methylcinnolin-6-yl)amino)-9-(tetrahydrofuran-3-yl)-7,9-dihydro-8H-purin-8-one

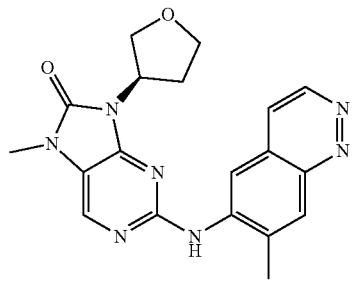 [SMILES: Cc1cc2nnccc2cc1Nc1ncc2c(n1)n([C@@H]1CCOC1)c(=O)n2C]

RuPhos Pd G3 (26.3 mg, 0.03 mmol) and 2-dicyclohexylphosphino-2',6'-di-i-propoxy-1,1'-biphenyl (14.7 mg, 0.03 mmol) were added to 2-chloro-7-methyl-9-[(3R)-tetrahydro-3-furanyl]-7,9-dihydro-8H-purin-8-one (96 mg, 0.38 mmol), 7-methylcinnolin-6-amine (50 mg, 0.31 mmol) and Cs$_2$CO$_3$ (205 mg, 0.63 mmol) in 1,4-dioxane (1.5 mL). The reaction mixture was heated at 100° C. for 16 h. The reaction was allowed to cool to rt and directly purified by fcc, elution gradient 0 to 40% MeCN in water, then further purified by preparative HPLC to afford the title compound (60 mg, 51%) as a pink solid; $^1$H NMR (400 MHz, DMSO) 2.21-2.35 (1H, m), 2.38-2.51 (1H, m), 2.64 (3H, d), 3.37 (3H, s), 3.76-3.86 (1H, m), 3.99-4.15 (3H, m), 5.02-5.14 (1H, m), 7.96 (1H, d), 8.24 (1H, s), 8.30 (1H, s), 8.69 (2H, d), 9.15 (1H, d); m/z MH$^+$ 378.

Example 24: (R)-7-methyl-2-((7-methylquinoxalin-6-yl)amino)-9-(tetrahydrofuran-3-yl)-7,9-dihydro-8H-purin-8-one

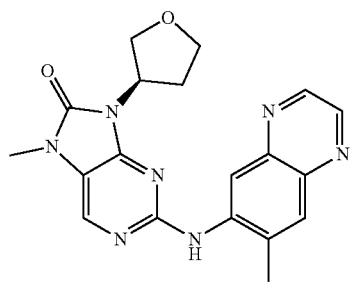 [SMILES: Cc1cc2nccnc2cc1Nc1ncc2c(n1)n([C@@H]1CCOC1)c(=O)n2C]

RuPhos Pd G3 (32.8 mg, 0.04 mmol) and 2-dicyclohexylphosphino-2',6'-di-i-propoxy-1,1'-biphenyl (18.32 mg, 0.04 mmol) were added to 2-chloro-7-methyl-9-[(3R)-tetrahydro-3-furanyl]-7,9-dihydro-8H-purin-8-one (100 mg, 0.39 mmol), 7-methylquinoxalin-6-amine (68.8 mg, 0.43 mmol) and Cs$_2$CO$_3$ (256 mg, 0.79 mmol) in 1,4-dioxane (3 mL). The reaction mixture was heated at 100° C. for 3 h. The reaction was allowed to cool to rt and directly purified by fcc, elution gradient 0-34% MeCN in water, then further purified by preparative HPLC to afford the title compound (71 mg, 48%) as a white solid; $^1$H NMR (400 MHz, DMSO) 2.14-2.33 (1H, m), 2.50-2.62 (4H, m), 3.33 (3H, s), 3.72-4.02 (3H, m), 4.03-4.17 (1H, m), 4.89-5.05 (1H, m), 7.89 (1H, d), 8.23 (1H, s), 8.57 (1H, s), 8.64 (1H, s), 8.72 (1H, d), 8.78 (1H, d); m/z MH$^+$ 378.

Example 25: (R)-7-methyl-2-((7-methylcinnolin-6-yl)amino)-9-(tetrahydro-2H-pyran-3-yl)-7,9-dihydro-8H-purin-8-one

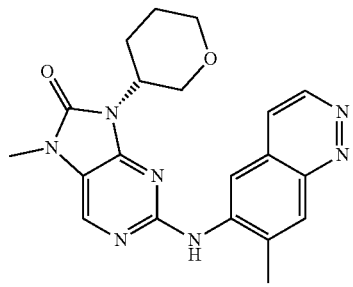

Cesium carbonate (243 mg, 0.74 mmol) was added to 2-chloro-7-methyl-9-[(3R)-tetrahydropyran-3-yl]purin-8-one (100 mg, 0.37 mmol) and 7-methylcinnolin-6-amine (59.2 mg, 0.37 mmol) in 1,4-dioxane (2 mL). The reaction was degassed with nitrogen and Brettphos Pd G3 (16.9 mg, 0.02 mmol) was added. The reaction mixture was heated at 100° C. for 2 h. A further 5% Pd catalyst was added and the reaction mixture was stirred at 100° C. for 2 h. The reaction mixture was allowed to cool to rt and was concentrated in vacuo. The residue was diluted with DMF (3 mL), filtered and purified by preparative HPLC to afford the title compound (30 mg, 21%) as a brown solid; $^1$H NMR (400 MHz, DMSO) 1.70 (1H, d), 1.79 (1H, d), 1.97 (1H, d), 2.64 (3H, s), 3.2-3.3 (2H, m), 3.36 (3H, s), 3.85 (2H, d), 3.99 (1H, t), 4.29-4.4 (1H, m), 7.92 (1H, d), 8.27 (2H, s), 8.52 (1H, s), 8.76 (1H, s), 9.16 (1H, d); m/z MH$^+$ 392.

Example 26: (R)-7-methyl-2-((7-methylquinoxalin-6-yl)amino)-9-(tetrahydro-2H-pyran-3-yl)-7,9-dihydro-8H-purin-8-one

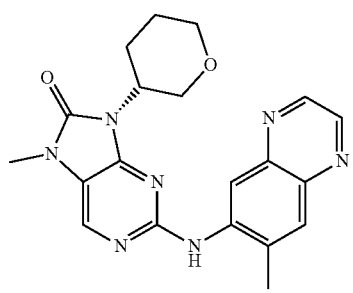

Cesium carbonate (243 mg, 0.74 mmol) was added to 2-chloro-7-methyl-9-[(3R)-tetrahydropyran-3-yl]purin-8-one (100 mg, 0.37 mmol) and 7-methylquinoxalin-6-amine (59.2 mg, 0.37 mmol) in 1,4-dioxane (2 mL). The reaction was degassed with nitrogen and Brettphos Pd G3 (16.9 mg, 0.02 mmol) was added. The reaction mixture was heated at 100° C. for 2 h. A further 5 mol % Brettphos precat G3 (16.87 mg, 0.02 mmol) was added and the reaction mixture was heated at 100° C. for 2 h. The reaction mixture was allowed to cool to rt and was concentrated in vacuo. The residue was diluted with DMF (3 mL), filtered and purified by preparative HPLC. Pure fractions were combined and partially concentrated and the resulting precipitate was isolated by filtration and dried in vacuo to afford the title compound (50 mg, 34%); $^1$H NMR (400 MHz, DMSO) 1.71 (2H, dt), 1.94 (1H, d), 2.59 (4H, s), 3.35 (3H, s), 3.41 (1H, td), 3.79-3.9 (2H, m), 4.05 (1H, t), 4.33 (1H, ddt), 7.91 (1H, s), 8.25 (1H, s), 8.65 (1H, s), 8.7-8.76 (2H, m), 8.79 (1H, d); m/z MH$^+$ 392.

Example 27: (S)-7-methyl-2-((7-methylcinnolin-6-yl)amino)-9-(tetrahydro-2H-pyran-3-yl)-7,9-dihydro-8H-purin-8-one

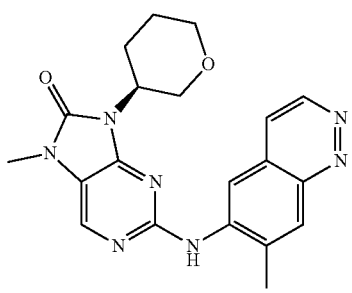 [SMILES: Cc1cc2nnccc2cc1Nc1ncc2c(n1)n([C@H]1CCCOC1)c(=O)n2C]

Cesium carbonate (1.21 g, 3.72 mmol) was added to 2-chloro-7-methyl-9-[(3S)-tetrahydropyran-3-yl]purin-8-one (500 mg, 1.86 mmol) and 7-methylcinnolin-6-amine (296 mg, 1.86 mmol) in 1,4-dioxane (12 mL). The reaction was degassed with nitrogen and Brettphos Pd G3 (84 mg, 0.09 mmol) was added. The reaction mixture was heated at 100° C. for 24 h. The reaction mixture was filtered whilst hot, then the solid was washed with DCM (10 mL). The combined organic layers were concentrated in vacuo. The resulting crude product was purified by fcc, elution gradient 0 to 5% MeOH in DCM, then further purified by preparative HPLC. The resulting solid was stirred overnight in MeCN then filtered to afford the title compound (153 mg, 21%) as a light brown solid; $^1$H NMR (400 MHz, DMSO) 1.63-1.83 (2H, m), 1.97 (1H, d), 2.53-2.58 (1H, m), 2.64 (3H, s), 3.25 (1H, td), 3.35 (3H, s), 3.82-3.9 (2H, m), 3.99 (1H, t), 4.34 (1H, ddt), 7.91 (1H, dd), 8.26 (2H, d), 8.52 (1H, s), 8.75 (1H, s), 9.15 (1H, d); m/z MH$^+$ 392.

Example 28: (S)-7-methyl-2-((7-methylquinoxalin-6-yl)amino)-9-(tetrahydro-2H-pyran-3-yl)-7,9-dihydro-8H-purin-8-one

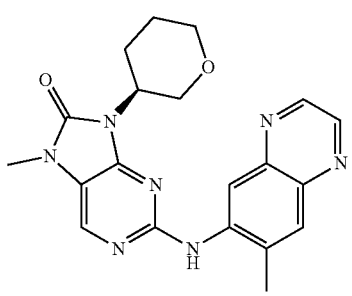 [SMILES: Cc1cc2nccnc2cc1Nc1ncc2c(n1)n([C@H]1CCCOC1)c(=O)n2C]

Cesium carbonate (243 mg, 0.74 mmol) was added to 2-chloro-7-methyl-9-[(3S)-tetrahydropyran-3-yl]purin-8-one (100 mg, 0.37 mmol) and 7-methylquinoxalin-6-amine (59.2 mg, 0.37 mmol) in 1,4-dioxane (2 mL). The reaction was degassed with nitrogen and Brettphos Pd G3 (16.9 mg, 0.02 mmol) was added. The reaction mixture was heated at 100° C. for 2 h. A further 5 mol % Brettphos precat G3 (16.9 mg, 0.02 mmol) was added and the reaction mixture was heated at 100° C. for 2 h. The reaction mixture was allowed to cool to rt and was concentrated in vacuo. The residue was diluted with DMF (3 mL), filtered and purified by preparative HPLC. The combined pure fractions were partially concentrated in vacuo and the resulting solid was isolated by filtration and dried in vacuo to give the title compound (65 mg, 45%) as a light brown solid; $^1$H NMR (400 MHz, DMSO) 1.70 (2H, dt), 1.93 (1H, d), 2.59 (4H, s), 3.35 (3H, s), 3.36-3.46 (1H, m), 3.8-3.9 (2H, m), 4.05 (1H, t), 4.33 (1H, ddd), 7.91 (1H, s), 8.25 (1H, s), 8.66 (1H, s), 8.71-8.75 (2H, m), 8.79 (1H, d); m/z MH$^+$ 392.

Example 29: 7-methyl-2-((7-methylcinnolin-6-yl)amino)-9-(tetrahydro-2H-pyran-4-yl)-7,9-dihydro-8H-purin-8-one

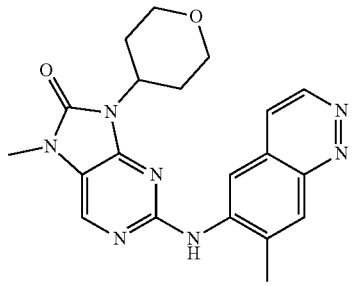 [SMILES: Cc1cc2nnccc2cc1Nc1ncc2c(n1)n(C1CCOCC1)c(=O)n2C]

Cesium carbonate (243 mg, 0.74 mmol) was added to 2-chloro-7-methyl-9-(tetrahydro-2H-pyran-4-yl)-7,9-dihydro-8H-purin-8-one (100 mg, 0.37 mmol) and 7-methylcinnolin-6-amine (59.2 mg, 0.37 mmol) in 1,4-dioxane (2 mL). The reaction was degassed with nitrogen and Brettphos Pd G3 (16.9 mg, 0.02 mmol) was added. The reaction mixture was heated at 100° C. for 2 h. A further 5% catalyst was added and the reaction mixture was heated at 100° C. for 2 h, then was allowed to cool to rt and concentrated in vacuo. The residue was diluted with MeOH (3 mL), filtered and purified by preparative HPLC, then by trituration with MeCN to afford the title compound (15 mg, 10%) as a beige solid; $^1$H NMR (400 MHz, DMSO) 1.75 (2H, d), 2.58-2.71 (5H, m), 3.37 (3H, s), 3.49 (2H, t), 4.03 (2H, dd), 4.51 (1H, ddd), 7.95 (1H, d), 8.25 (1H, s), 8.29 (1H, s), 8.70 (2H, d), 9.14 (1H, d); m/z MH$^+$ 392.

Example 30: 7-methyl-2-((7-methylquinolin-6-yl)amino)-9-(tetrahydro-2H-pyran-4-yl)-7,9-dihydro-8H-purin-8-one

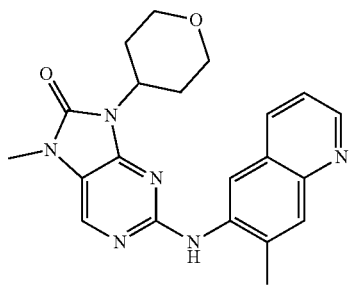 [SMILES: Cc1cc2ncccc2cc1Nc1ncc2c(n1)n(C1CCOCC1)c(=O)n2C]

RuPhos Pd G3 (218 mg, 0.24 mmol) was added to 2-dicyclohexylphosphino-2',6'-di-i-propoxy-1,1'-biphenyl (112 mg, 0.24 mmol), 7-methylquinolin-6-amine (380 mg, 2.40 mmol), 2-chloro-7-methyl-9-(tetrahydro-2H-pyran-4-yl)-7,9-dihydro-8H-purin-8-one (645 mg, 2.40 mmol) and Cs$_2$CO$_3$ (1.56 g, 4.80 mmol) in 1,4-dioxane (4 mL). The reaction mixture was heated at 100° C. for 16 h, then was allowed to cool to rt, filtered and the solid was washed with MeOH (10 mL). The combined organic layers were concentrated in vacuo, and purified by preparative HPLC to afford the title compound (208 mg, 22%) as a white solid; $^1$H NMR (300 MHz, DMSO) 1.64-1.76 (2H, m), 2.52 (3H, s), 2.54-2.71 (2H, m), 3.33 (3H, s), 3.44 (2H, dd), 3.92-4.04 (2H, m), 4.36-4.53 (1H, m), 7.41 (1H, dd), 7.84 (1H, s), 8.17 (1H, s), 8.19 (1H, d), 8.44 (1H, s), 8.55 (1H, s), 8.71 (1H, dd); m/z MH$^+$ 391.

Example 31: 7-methyl-2-((7-methylquinoxalin-6-yl)amino)-9-(tetrahydro-2H-pyran-4-yl)-7,9-dihydro-8H-purin-8-one

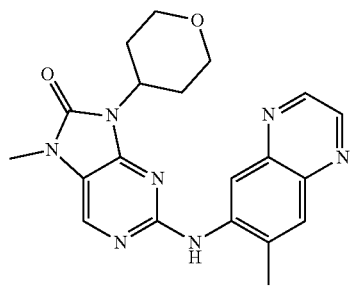 [SMILES: Cc1cc2nccnc2cc1Nc1ncc2c(n1)n(C1CCOCC1)c(=O)n2C]

Cesium carbonate (1.81 g, 5.58 mmol) was added to 2-chloro-7-methyl-9-(tetrahydro-2H-pyran-4-yl)-7,9-dihydro-8H-purin-8-one (750 mg, 2.79 mmol) and 7-methylquinoxalin-6-amine (444 mg, 2.79 mmol) in 1,4-dioxane (2 mL). Brettphos Pd G3 (127 mg, 0.14 mmol) was added and the reaction mixture was heated at 100° C. for 2 h, then allowed to cool to rt, filtered and the solid was washed with DCM (10 mL). The combined organic layers were concentrated in vacuo and purified by fcc, elution gradient 0 to 10% MeOH in DCM, and triturated with MeCN to afford the title compound (340 mg, 31%) as a pale yellow solid; $^1$H NMR (400 MHz, DMSO) 1.68-1.75 (2H, m), 2.54-2.63 (5H, m), 3.35 (3H, s), 3.43 (2H, t), 3.98 (2H, dd), 4.46 (1H, ddt), 7.91 (1H, s), 8.22 (1H, s), 8.60 (1H, s), 8.65 (1H, s), 8.74 (1H, d), 8.79 (1H, d); m/z MH$^+$ 392.

Example 32: 7-methyl-2-((7-methylquinazolin-6-yl)amino)-9-(tetrahydro-2H-pyran-4-yl)-7,9-dihydro-8H-purin-8-one

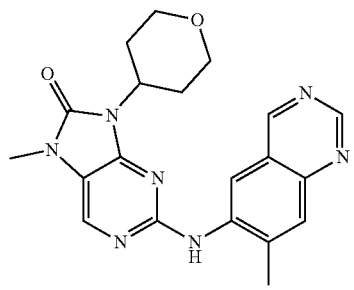 [SMILES: Cc1cc2ncncc2cc1Nc1ncc2c(n1)n(C1CCOCC1)c(=O)n2C]

RuPhos Pd G3 (9.2 mg, 11.0 mol) was added to 2-chloro-7-methyl-9-(tetrahydro-2H-pyran-4-yl)-7,9-dihydro-8H-purin-8-one (59.1 mg, 0.22 mmol), 7-methylquinazolin-6-amine (35 mg, 0.22 mmol), RuPhos (10.3 mg, 0.02 mmol) and $Cs_2CO_3$ (215 mg, 0.66 mmol) in 1,4-dioxane (1 mL). The reaction mixture was heated at 100° C. for 16 h, then was allowed to cool to rt and was concentrated in vacuo. The resulting crude product was purified by fcc, elution gradient 0 to 40% MeCN in water eluent with 0.1% $NH_4HCO_3$, then further purified by preparative HPLC to afford the title compound (16 mg, 19%) as a white solid; $^1$H NMR (400 MHz, DMSO) 1.68-1.77 (2H, m), 2.54-2.70 (5H, m), 3.35 (3H, s), 3.41-3.52 (2H, m), 3.96-4.05 (2H, m), 4.41-4.54 (1H, m), 7.87 (1H, s), 8.23 (1H, s), 8.67 (1H, s), 8.73 (1H, s), 9.12 (1H, s), 9.40 (1H, s); m/z MH$^+$ 392.

Example 33:2-((2,7-dimethylquinoxalin-6-yl)amino)-7-methyl-9-(tetrahydro-2H-pyran-4-yl)-7,9-dihydro-8H-purin-8-one Example 34:2-((3,7-dimethylquinoxalin-6-yl)amino)-7-methyl-9-(tetrahydro-2H-pyran-4-yl)-7,9-dihydro-8H-purin-8-one

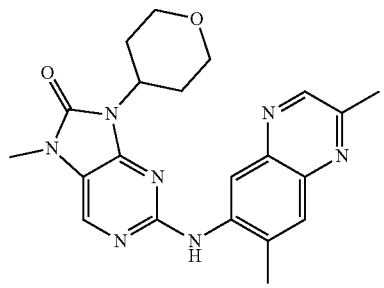

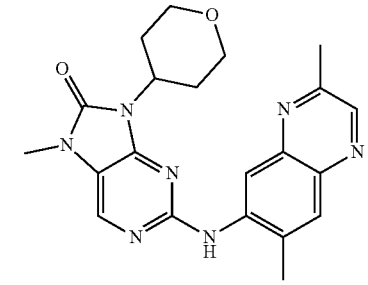

Cesium carbonate (1.21 mg, 3.72 mmol) was added to 2-chloro-7-methyl-9-(tetrahydro-2H-pyran-4-yl)-7,9-dihydro-8H-purin-8-one (500 mg, 1.86 mmol), a mixture of 2,7-dimethylquinoxalin-6-amine (258 mg, 1.49 mmol) and 3,7-dimethylquinoxalin-6-amine (64.5 mg, 0.37 mmol) in 1,4-dioxane (10 mL). Brettphos Pd G3 (84 mg, 0.09 mmol) was added and the reaction mixture was heated at 100° C. for 1 h. A further 5 mol % Brettphos precat G3 (84 mg, 0.09 mmol) was added and the reaction mixture was stirred for 1 h then was allowed to cool to rt, filtered and the solid was washed with DCM (10 mL). The combined filtrate was concentrated in vacuo and the crude product was purified by fcc, elution gradient 0 to 10% MeOH in DCM, then by trituration with EtOAc to afford a mixture of the title compounds. The isomers were separated by SFC to afford 33 (125 mg, 17%) as a cream solid and 34 (25 mg, 3%) as a cream solid.

Example 33: $^1$H NMR (400 MHz, DMSO) 1.66-1.74 (2H, m), 2.53-2.62 (5H, m), 2.66 (3H, s), 3.34 (3H, s), 3.42 (2H, t), 3.97 (2H, dd), 4.45 (1H, tt), 7.76-7.82 (1H, m), 8.18 (1H, s), 8.48 (1H, s), 8.60 (1H, s), 8.70 (1H, s); m/z MH$^+$ 406.

Example 34: $^1$H NMR (400 MHz, DMSO) 1.71 (2H, d), 2.53-2.63 (5H, m), 2.65 (3H, s), 3.35 (3H, s), 3.43 (2H, t), 3.98 (2H, dd), 4.46 (1H, ddd), 7.84 (1H, s), 8.20 (1H, s), 8.51 (1H, s), 8.60 (1H, s), 8.64 (1H, s); m/z MH$^+$ 406.

Example 35: 9-(1,1-dioxidotetrahydro-2H-thiopyran-4-yl)-7-methyl-2-((7-methylquinolin-6-yl)amino)-7,9-dihydro-8H-purin-8-one

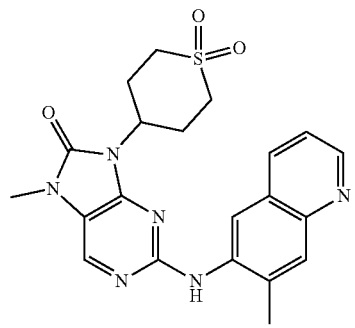 [SMILES: Cc1cc2ncccc2cc1Nc1ncc2c(n1)n(C1CCS(=O)(=O)CC1)c(=O)n2C]

RuPhos Pd G3 (26.4 mg, 0.03 mmol) was added to 2-chloro-9-(1,1-dioxidotetrahydro-2H-thiopyran-4-yl)-7-methyl-7,9-dihydro-8H-purin-8-one (100 mg, 0.32 mmol), 7-methylquinolin-6-amine (59.9 mg, 0.38 mmol), RuPhos (14.7 mg, 0.03 mmol) and $Cs_2CO_3$ (309 mg, 0.95 mmol) in 1,4-dioxane (2 mL). The reaction mixture was heated at 100° C. for 16 h. The reaction was cooled to rt and the mixture was purified by flash C18-flash chromatography, elution gradient 0 to 50% MeCN in water, then further purified by preparative HPLC to afford the title compound (42 mg, 30%) as a white solid; $^1$H NMR (400 MHz, DMSO) 2.14 (2H, d), 2.52 (3H, s), 3.00 (2H, q), 3.17 (2H, d), 3.34 (3H, s), 3.42-3.55 (2H, m), 4.60-4.73 (1H, m), 7.39 (1H, dd), 7.85 (1H, s), 8.20 (1H, s), 8.30-8.33 (1H, m), 8.34 (1H, s), 8.46 (1H, s), 8.72 (1H, dd); m/z, MH$^+$ 439.

Example 36: 7-methyl-2-((7-methylquinolin-6-yl)amino)-9-(oxetan-3-yl)-7,9-dihydro-8H-purin-8-one

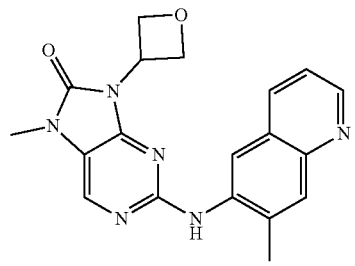 [SMILES: Cc1cc2ncccc2cc1Nc1ncc2c(n1)n(C1COC1)c(=O)n2C]

Cesium carbonate (271 mg, 0.83 mmol) was added to 2-chloro-7-methyl-9-(oxetan-3-yl)-7,9-dihydro-8H-purin-8-one (100 mg, 0.42 mmol) and 7-methylquinolin-6-amine (65.7 mg, 0.42 mmol) in 1,4-dioxane (2 mL). The reaction was degassed with nitrogen and Brettphos Pd G3 (18.8 mg, 0.02 mmol) was added. The reaction mixture was heated at 100° C. for 1 h. Additional 5% of Pd catalyst was added and the reaction mixture was stirred for 1 h at 100° C. A further 2 equivalents of cesium carbonate and 5% of Pd catalyst were added and the reaction mixture was heated at 100° C. for 18 h, then was allowed to cool to rt and concentrated in vacuo. The residue was diluted with DCM (3 mL), filtered and purified by fcc, elution gradient 0 to 8% MeOH in DCM, to afford the title compound (15 mg, 10%) as an off-white solid; $^1$H NMR (400 MHz, DMSO) 2.52 (3H, d), 3.33 (3H, s), 4.83 (2H, dd), 5.36 (2H, t), 5.49 (1H, qn), 7.39 (1H, dd), 7.84 (1H, s), 8.17 (1H, d), 8.21 (1H, s), 8.51 (1H, s), 8.57 (1H, s), 8.71 (1H, dd); m/z MH$^+$ 363.

Example 37: 7-methyl-2-((7-methylquinolin-6-yl)amino)-9-(piperidin-4-yl)-7,9-dihydro-8H-purin-8-one

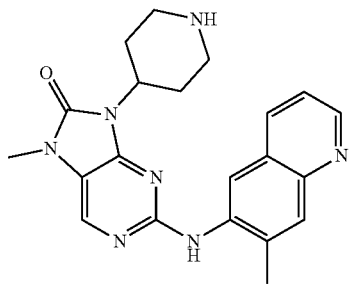 [SMILES: Cc1cc2ncccc2cc1Nc1ncc2c(n1)n(C1CCNCC1)c(=O)n2C]

4 M HCl in 1,4-dioxane (0.23 mL, 0.92 mmol) was added to tert-butyl 4-(7-methyl-2-((7-methylquinolin-6-yl)amino)-8-oxo-7,8-dihydro-9H-purin-9-yl)piperidine-1-carboxylate (90 mg, 0.18 mmol) in methanol (1 mL) at rt and the reaction mixture was stirred at rt for 1 h. The solvent was removed in vacuo, and the residue was loaded onto a 5 g SCX column, washing with MeOH, then eluting with 1N NH$_3$/MeOH. The solvent was removed in vacuo, and MeCN (2 mL) was added and concentrated in vacuo to afford the title compound (62 mg, 87%) as a yellow solid; $^1$H NMR (400 MHz, DMSO) 1.71 (2H, d), 2.45 (2H, dt), 2.53 (3H, s), 2.61 (2H, t), 3.10 (2H, d), 3.33 (3H, s), 4.27 (1H, ddd), 7.40 (1H, dd), 7.85 (1H, s), 8.16 (1H, s), 8.27 (1H, d), 8.47 (2H, d), 8.72 (1H, dd); m/z MH$^+$ 390.

Example 38: 9-((3S,4R)-3-fluoropiperidin-4-yl)-7-methyl-2-((7-methylquinolin-6-yl)amino)-7,9-dihydro-8H-purin-8-one

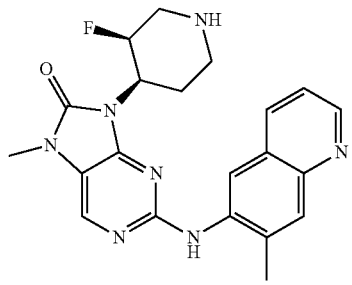 [SMILES: Cc1cc2ncccc2cc1Nc1ncc2c(n1)n([C@@H]1CCNC[C@@H]1F)c(=O)n2C]

4 M HC in 1,4-dioxane (1.00 mL, 4.00 mmol) was added to tert-butyl (3S,4R)-3-fluoro-4-(7-methyl-2-((7-methylquinolin-6-yl)amino)-8-oxo-7,8-dihydro-9H-purin-9-yl)piperidine-1-carboxylate (85 mg, 0.17 mmol) in methanol (3 mL) at rt and the reaction mixture was stirred at rt for 1 h, then was concentrated in vacuo. 1 M ammonia in methanol (1.5 mL) and water (1 mL) were added and the resulting solid was isolated by filtration to afford the title compound (50 mg, 73%) as a white solid; $^1$H NMR (400 MHz, DMSO) 1.77 (1H, d), 2.06 (1H, s), 2.52 (3H, s), 2.62 (1H, d), 2.82 (1H, dd), 3.04 (1H, d), 3.20 (2H, d), 3.36 (3H, s), 4.35-4.5 (1H, m), 4.73 (1H, d), 7.40 (1H, dd), 7.84 (1H, s), 8.20 (2H, s), 8.47 (2H, d), 8.72 (1H, dd); m/z MH$^+$ 408.

Example 39:9-((1s,4s)-4-amino-4-methylcyclohexyl)-7-methyl-2-((7-methylquinolin-6-yl)amino)-7,9-dihydro-8H-purin-8-one Example 40:9-((1r,4r)-4-amino-4-methylcyclohexyl)-7-methyl-2-((7-methylquinolin-6-yl)amino)-7,9-dihydro-8H-purin-8-one

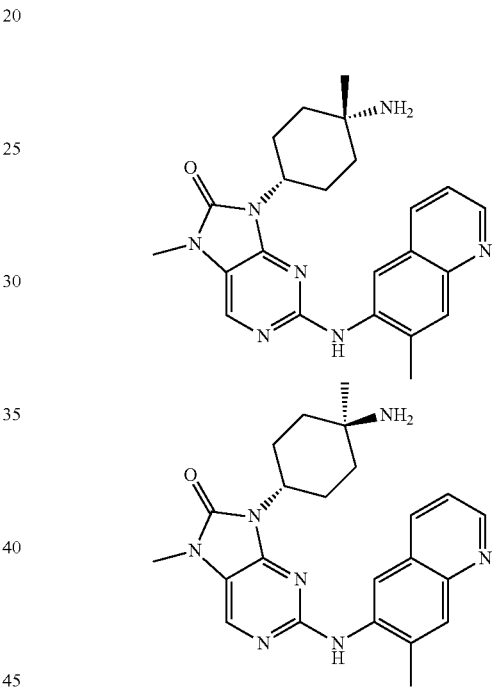

3rd Generation RuPhos precatalyst (84 mg, 0.10 mmol) and RuPhos (47.1 mg, 0.10 mmol) were added to tert-butyl (4-(2-chloro-7-methyl-8-oxo-7,8-dihydro-9H-purin-9-yl)-1-methylcyclohexyl) (400 mg, 1.01 mmol), 7-methylquinolin-6-amine (240 mg, 1.52 mmol) and Cs$_2$CO$_3$ (988 mg, 3.03 mmol) in 1,4-dioxane (5 mL). The reaction mixture was stirred at 100° C. for 16 h, then was allowed to cool to rt and was concentrated in vacuo to afford tert-butyl (1-methyl-4-(7-methyl-2-((7-methylquinolin-6-yl)amino)-8-oxo-7,8-dihydro-9H-purin-9-yl)cyclohexyl)carbamate as a yellow gum that was used without further purification. 4 M HCl in 1,4-dioxane (10 mL, 40 mmol) was added dropwise to the crude mixture and the reaction mixture was stirred at rt for 3 h, then directly purified by flash C18-flash chromatography, elution gradient 0 to 70% MeCN in water, then further purified by preparative HPLC to afford Example 39 (48 mg, 11%) as a white solid and Example 40 (46 mg, 11%) as a yellow solid.

Example 39: $^1$H NMR (300 MHz, DMSO) 1.03 (3H, s), 1.32-1.59 (6H, m), 2.49 (4H, s), 2.51-2.59 (1H, m), 3.32

(3H, s), 4.02-4.19 (1H, m), 7.40 (1H, dd), 7.84 (1H, s), 8.14 (1H, s), 8.19 (1H, d), 8.23 (1H, s), 8.60 (1H, s), 8.73 (1H, dd); m/z MH+ 418.

Example 40: ¹H NMR (300 MHz, DMSO) 0.61 (3H, s), 1.20-1.39 (2H, m), 1.39-1.59 (4H, m), 2.18-2.39 (2H, m), 2.46 (3H, s), 3.31 (3H, s), 3.98-4.16 (1H, m), 7.40 (1H, dd), 7.84 (1H, s), 8.08 (1H, d), 8.15 (2H, d), 8.67 (1H, s), 8.74 (1H, dd); m/z MH+ 418.

Example 41: (R)-7-methyl-9-(1-methylpyrrolidin-3-yl)-2-((7-methylquinolin-6-yl)amino)-7,9-dihydro-8H-purin-8-one

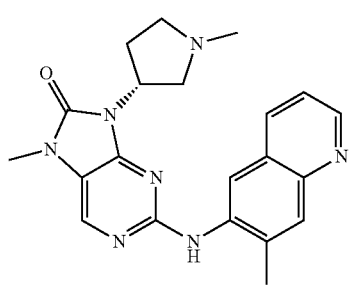 [SMILES: Cc1cc2ncccc2cc1Nc1ncc2c(n1)n([C@@H]1CCN(C)C1)c(=O)n2C]

Sodium triacetoxyborohydride (138 mg, 0.65 mmol) was added to 7-methyl-2-[(7-methyl-6-quinolyl)amino]-9-[(3R)-pyrrolidin-3-yl]purin-8-one (122 mg, 0.32 mmol), formaldehyde (37% aq. solution) (0.048 mL, 0.65 mmol) and acetic acid (0.074 mL, 1.30 mmol) in DCM (1 mL) at rt and the reaction mixture was stirred at rt for 24 h then was concentrated in vacuo. The residue was purified by preparative HPLC to afford the title compound (32 mg, 25%) as a white solid; ¹H NMR (400 MHz, DMSO) 2.07-2.18 (4H, m), 2.27 (1H, ddd), 2.41 (1H, q), 2.48 (3H, s), 2.59-2.7 (2H, m), 2.90 (1H, t), 3.32 (3H, s), 4.85 (1H, dtd), 7.41 (1H, dd), 7.86 (1H, s), 8.15 (1H, s), 8.17-8.22 (2H, m), 8.58 (1H, s), 8.74 (1H, dd); m/z [M-H]⁻ 388.

Example 42: (S)-7-methyl-9-(1-methylpyrrolidin-3-yl)-2-((7-methylquinolin-6-yl)amino)-7,9-dihydro-8H-purin-8-one

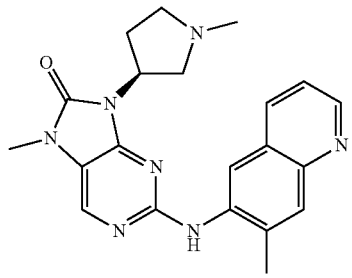 [SMILES: Cc1cc2ncccc2cc1Nc1ncc2c(n1)n([C@H]1CCN(C)C1)c(=O)n2C]

Sodium triacetoxyborohydride (51.5 mg, 0.24 mmol) was added to a mixture of formaldehyde (37% solution in water, 19.7 mg, 0.24 mmol) and 7-methyl-2-[(7-methyl-6-quinolyl)amino]-9-[(3S)-pyrrolidin-3-yl]purin-8-one, HCl (50 mg, 0.12 mmol) in MeOH at rt. The reaction mixture was stirred at rt for 30 min. A further 2 eq of sodium triacetoxyborohydride (51.5 mg, 0.24 mmol) was added and the reaction mixture was stirred for 30 min, concentrated in vacuo and purified by preparative HPLC to afford the title compound (20 mg, 42%) as a white solid; ¹H NMR (400 MHz, DMSO) 2.13 (4H, s), 2.22-2.31 (1H, m), 2.41 (1H, q), 2.48-2.49 (3H, m), 2.64 (2H, dq), 2.90 (1H, t), 3.32 (3H, s), 4.85 (1H, dtd), 7.41 (1H, dd), 7.86 (1H, s), 8.15 (1H, s), 8.19 (2H, d), 8.58 (1H, s), 8.74 (1H, dd); m/z MH+ 390.

Example 43: 7-methyl-2-((7-methylcinnolin-6-yl)amino)-9-(1-methylpiperidin-4-yl)-7,9-dihydro-8H-purin-8-one

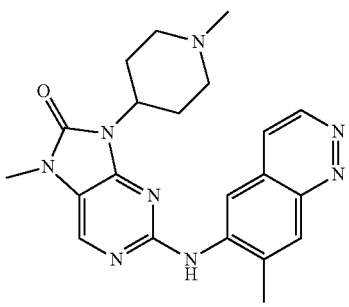 [SMILES: Cc1cc2nnccc2cc1Nc1ncc2c(n1)n(C1CCN(C)CC1)c(=O)n2C]

Sodium triacetoxyborohydride (60.8 mg, 0.29 mmol) was added to 7-methyl-2-((7-methylcinnolin-6-yl)amino)-9-(piperidin-4-yl)-7,9-dihydro-8H-purin-8-one (56 mg, 0.14 mmol), formaldehyde (37% aq. solution) (0.021 mL, 0.29 mmol) and acetic acid (0.033 mL, 0.57 mmol) in DCM (1 mL) at rt and the reaction mixture was stirred for 3.5 h, then was concentrated in vacuo and purified by preparative HPLC to afford the title compound (22 mg, 38%) as a white solid; ¹H NMR (400 MHz, DMSO) 1.73 (2H, d), 2-2.08 (3H, m), 2.29 (3H, s), 2.64-2.66 (3H, m), 2.72 (1H, d), 2.95 (2H, d), 3.37 (3H, s), 4.17-4.27 (1H, m), 8.07 (1H, d), 8.24 (1H, s), 8.29 (1H, s), 8.64 (1H, s), 8.84 (1H, s), 9.14 (1H, d); m/z MH+ 405.

Example 44: 7-methyl-9-(1-methylpiperidin-4-yl)-2-((7-methylquinolin-6-yl)amino)-7,9-dihydro-8H-purin-8-one

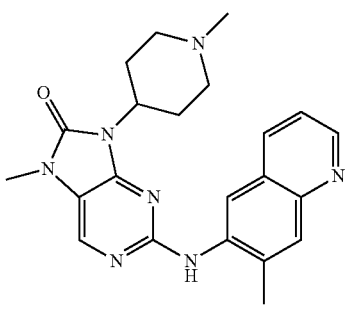 [SMILES: Cc1cc2ncccc2cc1Nc1ncc2c(n1)n(C1CCN(C)CC1)c(=O)n2C]

Paraformaldehyde (568 mg, 1.46 mmol) was added to 7-methyl-2-((7-methylquinolin-6-yl)amino)-9-(piperidin-4-yl)-7,9-dihydro-8H-purin-8-one (568 mg, 1.46 mmol) in MeOH (6 mL). The reaction mixture was stirred at rt for 30 min. Sodium cyanotrihydroborate (275 mg, 4.38 mmol) was added at rt, then the reaction mixture was heated at 80° C. for 30 min, then allowed to cool to rt and concentrated in vacuo. The resulting crude product was purified by fcc, elution gradient 0-10% MeOH in (0.5% NH₃ in DCM) to afford the title compound (390 mg, 66%) as a white solid. ¹H NMR (400 MHz, DMSO) 1.67-1.71 (2H, m), 1.99-2.08 (2H, m), 2.25 (3H, s), 2.54 (3H, s), 2.60-2.74 (2H, m), 2.92 (2H, d), 3.34 (3H, s), 4.12-4.22 (1H, m), 7.34-7.42 (1H, m), 7.84 (1H, s), 8.18 (1H, s), 8.28-8.30 (1H, m), 8.50 (1H, s), 8.58 (1H, s), 8.70-8.72 (1H, m); m/z MH+ 404.

Form A

The final product, 7-methyl-9-(1-methylpiperidin-4-yl)-2-((7-methylquinolin-6-yl)amino)-7,9-dihydro-8H-purin-8-one, was analysed by XRPD and DSC and found to be crystalline. XRPD of a sample of the material gave rise to the diffraction pattern as shown in FIG. 1. 7-methyl-9-(1-methylpiperidin-4-yl)-2-((7-methylquinolin-6-yl)amino)-7,9-dihydro-8H-purin-8-one, Form A is characterised by at least one peak at a 2θ value of 7.1° or 8.5° measured using CuKα radiation.

The ten most prominent peaks of the XRPD are shown in Table B.

TABLE B

Ten most prominent XRPD peaks for Form A, 7-methyl-9-(1-methylpiperidin-4-yl)-2-((7-methylquinolin-6-yl)amino)-7,9-dihydro-8H-purin-8-one

| Angle 2-Theta (2θ) | Intensity % |
|---|---|
| 8.5 | 100.0 |
| 7.1 | 51.2 |
| 18.8 | 47.1 |
| 21.5 | 44.8 |
| 15.4 | 39.1 |
| 26.2 | 37.5 |
| 16.3 | 29.7 |
| 14.2 | 21.0 |
| 12.7 | 17.8 |
| 19.8 | 17.4 | wherein the 2-theta values are +/− 0.2°.

Example 45: 7-methyl-9-(1-methylpiperidin-4-yl)-2-((7-methylquinoxalin-6-yl)amino)-7,9-dihydro-8H-purin-8-one

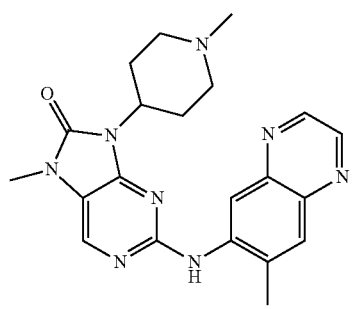 [SMILES: Cc1cc2nccnc2cc1Nc1ncc2c(n1)n(C1CCN(C)CC1)c(=O)n2C]

RuPhos Pd G3 (47.5 mg, 0.06 mmol) and RuPhos (26.5 mg, 0.06 mmol) were added to 2-chloro-7-methyl-9-(1-methylpiperidin-4-yl)-7,9-dihydro-8H-purin-8-one (80 mg, 0.28 mmol), 7-methylquinoxalin-6-amine (54.2 mg, 0.34 mmol) and Cs₂CO₃ (185 mg, 0.57 mmol) in 1,4-dioxane (6 mL) at rt. The reaction mixture was heated at 100° C. for 4 h, then was allowed to cool to rt, concentrated in vacuo and the residue was purified by fcc, elution gradient 0 to 10% MeOH in DCM then further purified by preparative HPLC to afford the title compound (49 mg, 43%) as a yellow solid; ¹H NMR (400 MHz, DMSO) 1.68 (2H, d), 1.97 (2H, t), 2.17 (3H, s), 2.52-2.63 (5H, m), 2.88 (2H, d), 3.34 (3H, s), 4.11-4.25 (1H, m), 7.90 (1H, s), 8.20 (1H, s), 8.62 (2H, d), 8.73 (1H, d), 8.79 (1H, d); m/z MH+ 405.

Example 46: 9-((3S,4R)-3-fluoro-1-methylpiperidin-4-yl)-7-methyl-2-((7-methylquinolin-6-yl)amino)-7,9-dihydro-8H-purin-8-one

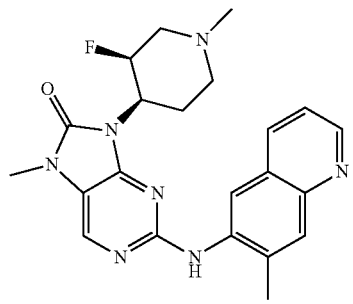 [SMILES: Cc1cc2ncccc2cc1Nc1ncc2c(n1)n([C@@H]1CCN(C)C[C@@H]1F)c(=O)n2C]

Sodium triacetoxyborohydride (118 mg, 0.55 mmol) was added to a suspension of formaldehyde (37% solution in water, 90 mg, 1.11 mmol) and 9-((3S,4R)-3-fluoropiperidin-4-yl)-7-methyl-2-((7-methylquinolin-6-yl)amino)-7,9-dihydro-8H-purin-8-one (113 mg, 0.28 mmol) in iPrOH (2 mL) at rt. MeOH (1 mL) was added, and the reaction mixture was stirred at rt for 30 min. Sodium triacetoxyborohydride (59 mg, 0.27 mmol) was added and the reaction mixture was stirred at rt for 30 min. The reaction mixture was quenched with sat. aq. NaHCO₃ (2 mL), and extracted with EtOAc (2×2 mL). The combined organic layers were washed with sat. brine (1 mL), passed through a phase separating filter paper and concentrated in vacuo. MeCN (3 mL) was added to the resulting solid, and the solid was isolated by filtration to afford the title compound (25 mg, 21%) as a yellow solid; ¹H NMR (400 MHz, DMSO) 1.03-1.11 (1H, m), 1.83 (1H, s), 2.29 (3H, s), 2.53 (3H, s), 2.89 (1H, s), 3.18 (1H, s), 3.36 (3H, s), 3.44-3.57 (1H, m), 4.25-4.41 (1H, m), 4.56-4.72 (1H, m), 4.85 (1H, d), 7.40 (1H, dd), 7.83 (1H, s), 8.21 (1H, s), 8.25 (1H, d), 8.46 (1H, s), 8.58 (1H, s), 8.71 (1H, dd); m/z MH+ 422.

Example 47: 7-methyl-2-((7-methylquinolin-6-yl)amino)-9-(1-(oxetan-3-yl)piperidin-4-yl)-7,9-dihydro-8H-purin-8-one

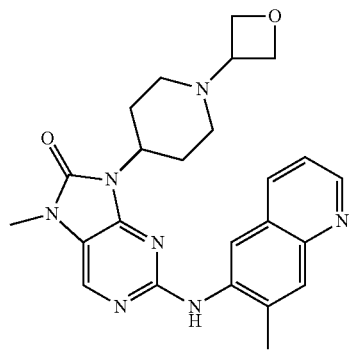 [SMILES: Cc1cc2ncccc2cc1Nc1ncc2c(n1)n(C1CCN(C3COC3)CC1)c(=O)n2C]

Oxetan-3-one (30.5 mg, 0.42 mmol) was added to 7-methyl-2-((7-methylquinolin-6-yl)amino)-9-(piperidin-4-yl)-7,9-dihydro-8H-purin-8-one (150 mg, 0.39 mmol) in MeOH (5 mL). The reaction mixture was heated at 60° C. for 1 h. NaBH₃CN (36.3 mg, 0.58 mmol) was added and the reaction mixture was heated at 60° C. for 16 h, then was allowed to cool to rt and poured into water (125 mL) and extracted with DCM (3×125 mL). The combined organic layers were dried over Na₂SO₄, filtered and evaporated, then purified by preparative HPLC to afford the title compound (21 mg, 12%) as a white solid; ¹H NMR (400 MHz, DMSO) 1.91-2.08 (2H, d), 2.33-2.53 (2H, t), 2.56 (3H, d), 2.67-2.71 (2H, m), 2.89 (2H, d), 3.33 (3H, s), 3.44-3.47 (1H, m), 4.22-4.23 (1H, m), 4.48-4.59 (2H, t), 4.61-4.62 (2H, t), 7.42-7.45 (1H, m), 7.85 (1H, s), 8.21 (1H, s), 8.48 (1H, s), 8.52-8.54 (1H, m), 8.71-8.75 (2H, m); m/z MH⁺ 446.

Example 48: 9-(1-(2-hydroxyethyl)piperidin-4-yl)-7-methyl-2-((7-methylquinolin-6-yl)amino)-7,9-dihydro-8H-purin-8-one

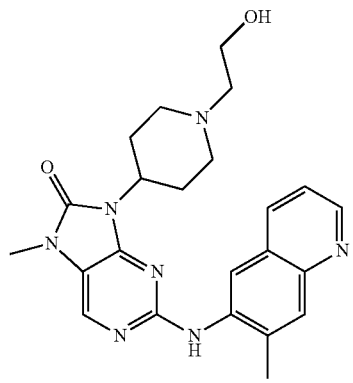 [SMILES: Cc1cc2ncccc2cc1Nc1ncc2c(n1)n(C1CCN(CCO)CC1)c(=O)n2C]

2-Bromoethan-1-ol (52.9 mg, 0.42 mmol) was added to 7-methyl-2-((7-methylquinolin-6-yl)amino)-9-(piperidin-4-yl)-7,9-dihydro-8H-purin-8-one (150 mg, 0.39 mmol) and DIPEA (0.202 mL, 1.16 mmol) in iPrOH (3 mL). The reaction mixture was heated at 80° C. for 16 h, allowed to cool to rt and concentrated in vacuo. The resulting crude product was purified by preparative HPLC to afford the title compound (18 mg, 11%) as a white solid; ¹H NMR (300 MHz, CD₃OD) 1.81-1.85 (2H, m), 2.25-2.59 (2H, m), 2.59-2.65 (5H, m), 2.74-2.88 (2H, m), 3.16-3.20 (2H, m), 3.42 (3H, s), 3.73 (2H, t), 4.31-4.41 (1H, m), 7.43-7.47 (1H, m), 7.87 (1H, s), 8.09 (1H, s), 8.34-8.37 (1H, m), 8.67-8.69 (2H, m); m/z MH⁺ 434.

Example 49: 9-(1-(2-methoxyethyl)piperidin-4-yl)-7-methyl-2-((7-methylquinolin-6-yl)amino)-7,9-dihydro-8H-purin-8-one

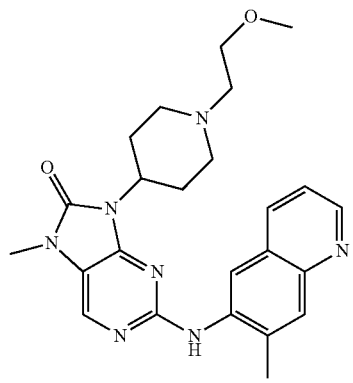 [SMILES: COCCN1CCC(n2c(=O)n(C)c3cnc(Nc4cc5cccnc5cc4C)nc32)CC1]

1-Bromo-2-methoxyethane (58.9 mg, 0.42 mmol) was added to 7-methyl-2-((7-methylquinolin-6-yl)amino)-9-(piperidin-4-yl)-7,9-dihydro-8H-purin-8-one (150 mg, 0.39 mmol) and DIPEA (0.202 mL, 1.16 mmol) in iPrOH (5 mL). The reaction mixture was heated at 80° C. for 16 h. The reaction mixture was allowed to cool to rt and directly purified by preparative HPLC to afford the title compound (26 mg, 15%) as a yellow solid; ¹H NMR (300 MHz, CDCl₃) 1.69 (2H, d), 2.27 (2H, s), 2.64 (3H, s), 2.73 (2H, s), 2.92 (2H, s), 3.19 (2H, d), 3.21-3.63 (6H, m), 3.63-3.68 (2H, m), 4.40 (1H, t), 7.15 (1H, s), 7.28-7.34 (1H, m), 7.96 (2H, d), 8.30 (1H, d), 8.76-8.78 (1H, m), 8.97 (1H, s); m/z MH⁺ 448.

Example 50: 9-(1-ethylpiperidin-4-yl)-7-methyl-2-((7-methylquinolin-6-yl)amino)-7,9-dihydro-8H-purin-8-one

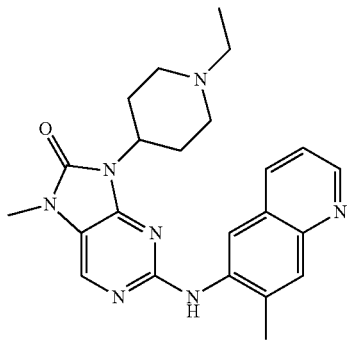 [SMILES: CCN1CCC(n2c(=O)n(C)c3cnc(Nc4cc5cccnc5cc4C)nc32)CC1]

Acetaldehyde (18.7 mg, 0.42 mmol) was added to 7-methyl-2-((7-methylquinolin-6-yl)amino)-9-(piperidin-4-yl)-7,9-dihydro-8H-purin-8-one (150 mg, 0.39 mmol) in MeOH (5 mL). The reaction mixture was stirred at rt for 1 h. NaBH₃CN (36.9 mg, 0.58 mmol) was added and the reaction mixture was stirred at rt for 1 h, then was poured into water (150 mL) and extracted with DCM (3×150 mL). The combined organic layers were dried over Na₂SO₄, filtered and concentrated in vacuo, then purified by preparative HPLC to afford the title compound (49 mg, 31%) as a yellow solid; ¹H NMR (300 MHz, CDCl₃) 1.22 (3H, s), 1.85-1.88 (2H, d), 2.15 (2H, s), 2.57-2.63 (5H, s), 2.91 (2H, s), 3.20 (2H, s), 3.46 (3H, s), 4.41-4.45 (1H, m), 7.16 (1H, s), 7.28-7.33 (1H, m), 7.95 (2H, d), 8.35-8.37 (1H, m), 8.77 (1H, s), 9.01 (1H, s); m/z MH⁺ 418.

Example 51: 9-(1-acetylpiperidin-4-yl)-7-methyl-2-((7-methylquinolin-6-yl)amino)-7,9-dihydro-8H-purin-8-one

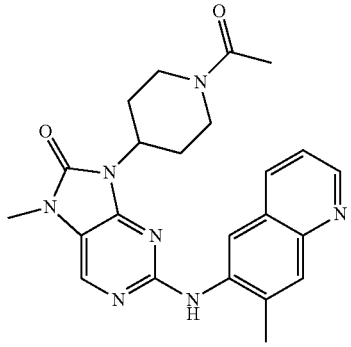 [SMILES: CC(=O)N1CCC(n2c(=O)n(C)c3cnc(Nc4cc5cccnc5cc4C)nc32)CC1]

Cesium carbonate (3.09 g, 9.49 mmol) was added to 9-(1-acetylpiperidin-4-yl)-2-chloro-7-methyl-7,9-dihydro-8H-purin-8-one (840 mg, 2.71 mmol) and and 7-methylquinolin-6-amine hydrochloride (528 mg, 2.71 mmol) in 1,4-dioxane (15 mL). Brettphos Pd G3 (123 mg, 0.14 mmol) was added and the reaction mixture was heated at 100° C. for 1 h, then allowed to cool to rt, filtered and washed with DCM (10 mL). The combined filtrate was concentrated in vacuo and the residue was purified by fcc, eluent 0-10% MeOH in DCM. The resulting oil was taken up in MeCN (20 mL), and the resulting suspension was heated briefly at reflux, then allowed cool to rt. The resulting precipitate was isolated by filtration, washed with a small amount of MeCN and dried in vacuo to afford the title compound (550 mg, 47.0%) as a pale yellow solid; $^1$H NMR (400 MHz, DMSO) 1.81 (2H, t), 1.93 (3H, s), 2.21-2.32 (1H, m), 2.38-2.47 (1H, m), 2.52 (3H, s), 2.62 (1H, t), 3.15 (1H, t), 3.34 (3H, s), 3.94 (1H, d), 4.44 (1H, ddd), 4.57 (1H, d), 7.39 (1H, dd), 7.85 (1H, s), 8.13 (1H, d), 8.17 (1H, s), 8.29 (1H, s), 8.59 (1H, s), 8.74 (1H, dd); m/z MH$^+$ 432.

Example 52: 9-((3R,4R)-4-fluoropyrrolidin-3-yl)-7-methyl-2-((7-methylquinolin-6-yl)amino)-7,9-dihydro-8H-purin-8-one

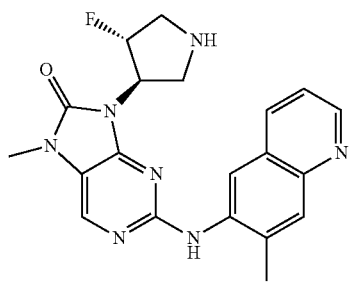 [SMILES: Cc1cc2ncccc2cc1Nc1ncc2c(n1)n([C@@H]1CNC[C@H]1F)c(=O)n2C]

4 M HCl in 1,4-dioxane (11.40 mL, 45.59 mmol) was added in one portion to a stirred solution of tert-butyl (3R,4R)-3-fluoro-4-(7-methyl-2-((7-methylquinolin-6-yl)amino)-8-oxo-7,8-dihydro-9H-purin-9-yl)pyrrolidine-1-carboxylate (1.5 g, 3.04 mmol) in 1,4-dioxane (50 mL) at rt, and the reaction mixture was stirred at rt for 12 h then concentrated in vacuo. The resulting residue was diluted with DCM (200 mL), then basified with 7 M NH$_3$ in MeOH (10 mL). The mixture was washed with sat. brine, dried over Na$_2$SO$_4$, filtered and concentrated in vacuo. The resulting crude product was purified by preparative HPLC (XBridge Prep C18 OBD column, 5 silica, 19 mm diameter, 150 mm length), using decreasingly polar mixtures of water (containing 0.1% NH$_4$HCO$_3$) and MeCN as eluents, then triturated with MeCN to afford one batch of the title compound. The liquors from the trituration were purified by preparative HPLC (Column: XBridge Shield RP18 OBD Column 19*250 mm, 10 um; Mobile Phase A:Water (10 mmol/L NH$_4$HCO$_3$), Mobile Phase B: ACN; Flow rate: 25 mL/min; Gradient: 25% B to 35% B in 7 min; 254; 220 nm; Rt: 6.83 min), to afford additional title compound. The two batches were combined to afford the title compound (620 mg, 52%) as a white solid. $^1$H NMR (300 MHz, DMSO, 23° C.) 2.49 (3H, s), 2.80-3.02 (2H, m), 3.02-3.31 (2H, m), 3.34 (3H, s), 4.75 (1H, dt), 5.57 (1H, dd), 7.41 (1H, dd), 7.86 (1H, s), 8.12-8.25 (3H, m), 8.67 (1H, s), 8.74 (1H, dd), one NH missing; m/z MH$^+$ 394.

Form A

The final product, 9-((3R,4R)-4-fluoropyrrolidin-3-yl)-7-methyl-2-((7-methylquinolin-6-yl)amino)-7,9-dihydro-8H-purin-8-one, was analysed by XRPD and found to be crystalline. XRPD of a sample of the material gave rise to the diffraction pattern as shown in FIG. 5. 9-((3R,4R)-4-fluoropyrrolidin-3-yl)-7-methyl-2-((7-methylquinolin-6-yl)amino)-7,9-dihydro-8H-purin-8-one, Form A is characterised by at least one peak at a 2θ value of 7.3° or 15.0° measured using CuKα radiation. The ten most prominent peaks of the XRPD are shown in Table C.

TABLE C

Ten most prominent XRPD peaks for Form A, 9-((3R, 4R)-4-fluoropyrrolidin-3-yl)-7-methyl-2-((7-methylquinolin-6-yl)amino)-7,9-dihydro-8H-purin-8-one in order of intensity with the first value being the greatest intensity

| Angle 2-Theta (2θ) |
|---|
| 7.3 |
| 15.0 |
| 14.6 |
| 26.5 |
| 12.2 |
| 26.0 |
| 17.0 |
| 15.9 |
| 27.3 |
| 10.8 | wherein the 2-theta values are +/− 0.2°.

REFERENCES

An J et al. DNA-PKcs plays a dominant role in the regulation of H2AX phosphorylation in response to DNA damage and cell cycle progression. BMC Mol Biol 2010; 11: 18

Ashley A K. DNA-PK phosphorylation of RPA32 Ser4/Ser8 regulates replication stress checkpoint activation, fork restart, homologous recombination and mitotic catastrophe. DNA Repair 2014; 21: 131-139

Buisson R et al. Distinct but concerted roles of ATR, DNA-PK and Chk1 in countering replication stress during S phase. Molecular Cell 2015; 59: 1011-1024

Chan D W et al. Autophosphorylation of the DNA-dependent protein kinase catalytic subunit is required for rejoining of DNA double-strand breaks. Genes Dev 2002; 16: 2333-2338

Ciszewski W M et al. DNA-PK inhibition by NU7441 sensitizes breast cancer cells to ionizing radiation and doxorubicin. Breast Cancer Res Treat 2014; 143: 47-55

Deitlein F et al. A functional cancer genomics screen identifies a druggable synthetic lethal interaction between MSH3 and PRKDC. Cancer Discovery 2014; 4: 592-605

Douglas P et al. Identification of in vitro and in vivo phosphorylation sites in the catalytic subunit of the DNA dependent protein kinase. Biochem J 2002; 368: 243-251

Escribano-Diaz C. et a. A cell cycle dependent regulatory circuit composed of 53BP1-RIF1 and BRCA1-CtIP controls DNA repair pathway choice. Mol Cell 2013; 49: 872-883

Goodwin J F and Knudsen K E. Beyond DNA repair: DNA-PK function in cancer. Cancer Discovery 2014; 4: 1126-1139

Goodwin J F et al. A hormone-DNA repair circuit governs the response to genotoxic insult. Cancer Discovery 2013; 3: 1254-1271

Hartlerode A J and Scully R. Mechanisms of double-strand break repair in somatic mammalian cells. Biochem J 2009; 423: 157-168

Lin Y-F et al. DNA-PKcs is required to maintain stability of Chk1 and claspin for optimal replication stress response. Nucleic Acids Res 2014; 42: 4463-4473

Medunjanin S et al. Interaction of the double strand break repair kinase DNA-PK and estrogen receptor alpha. Mol Biol Cell 2010; 21: 1620-1628

Munck J M et al. Chemosensitization of cancer cells by KU-0060648, a dual inhibitor of DNA-PK and PI-3K. Mol Cancer Ther 2012; 11: 1789-1798

Neal J A and Meek K. Choosing the right path: does DNA-PK help make the decision? Mutat Res 2011; 711: 73-86

Riabinska A et al. Therapeutic targeting of a robust non-oncogene addiction to PRKDC in ATM-defective tumors. Science Translational Medicine 2013; 189: 189ra78

San Filippo J et al. Mechanism of ukaryotic homologous recombination. Annu Rev Biochem 2008; 77: 229-257

Smith G C M and Jackson S P. The DNA dependent protein kinase. Genes and Development 1999; 13: 916-934

Symington L S and Gautier J. Double strand break end resection and repair pathway choice. Annu Rev Genet 2011; 45: 247-271

Willmore E et al. A novel DNA-dependent protein kinase inhibitor, NU7026, potentiates the cytotoxicity of topoisomerase II poisons used in the treatment of leukemia Blood 2004; 103: 4659-4665

Yoo S and Dynan W S. Geometry of a complex formed by double strand break repair proteins at a single DNA end: recruitment of DNA-PKcs induces inward translocation of Ku protein. Nucleic Acids Res 1999; 27: 4679-4686

The invention claimed is:

1. A compound of Formula (I):

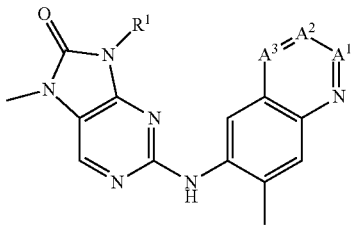

(I)

or a pharmaceutically acceptable salt thereof, wherein:
$A^1$ represents N or $CR^{2A}$, $A^2$ represents N or $CR^{2B}$ and $A^3$ represents N or $CR^{2C}$, where no more than one of $A^1$, $A^2$ and $A^3$ represent N;
$R^1$ represents $C_{4-6}$ cycloalkyl or a 4 to 6 membered heterocycloalkyl containing one heteroatom selected from O, S and N, wherein the $C_{4-6}$ cycloalkyl or 4 to 6 membered heterocycloalkyl is optionally substituted with one or more groups selected from fluoro, $C_{1-3}$ alkyl (optionally substituted with a group selected from hydroxyl and $C_{1-2}$ alkoxy), cyclopropyl, hydroxyl, $NH_2$, dioxo, $C(O)C_{1-2}$ alkyl, azetidinyl and oxetanyl;
$R^{2A}$, $R^{2B}$ and $R^{2C}$ each independently represent hydrogen, methyl or methoxy.

2. The compound of Formula (I), or a pharmaceutically acceptable salt thereof, as claimed in claim 1, wherein $A^1$ represents $CR^{2A}$, $A^2$ represents $CR^{2B}$ and $A^3$ represents $CR^{2C}$.

3. The compound of Formula (I), or a pharmaceutically acceptable salt thereof, as claimed in claim 1, wherein $R^{2A}$, $R^{2B}$ and $R^{2C}$ each represent hydrogen.

4. The compound of Formula (I), or a pharmaceutically acceptable salt thereof, as claimed in claim 1, wherein $R^1$ is selected from cyclohexanyl, piperidinyl, tetrahydrofuranyl, tetrahydropyranyl, tetrahydrothiopyranyl, oxetanyl and pyrrolidinyl.

5. The compound of Formula (I), or a pharmaceutically acceptable salt thereof, as claimed in claim 1, wherein $R^1$ is optionally substituted with one or more groups selected from fluoro, methyl, ethyl, hydroxyl, $NH_2$, dioxo, C(O)Me and oxetanyl, wherein the ethyl is optionally substituted with hydroxyl or methoxy.

6. The compound of Formula (I), or a pharmaceutically acceptable salt thereof, as claimed in claim 1, wherein $R^1$ is selected from piperidinyl and pyrrolidinyl.

7. The compound of Formula (I), or a pharmaceutically acceptable salt thereof, as claimed in claim 1, wherein $R^1$ is optionally substituted with one or more groups selected from fluoro, methyl, ethyl, hydroxyl, $NH_2$ and oxetanyl.

8. The compound of Formula (I), or a pharmaceutically acceptable salt thereof, as claimed in claim 1, wherein $R^1$ is pyrrolidin-3-yl.

9. The compound of Formula (I), or a pharmaceutically acceptable salt thereof, as claimed in claim 1, wherein $R^1$ is 4-fluoropyrrolidin-3-yl.

10. The compound of Formula (I), or a pharmaceutically acceptable salt thereof, as claimed in claim 1, wherein the compound is selected from the group consisting of:
9-(1-acetylpiperidin-4-yl)-7-methyl-2-((7-methylcinnolin-6-yl)amino)-7,9-dihydro-8H-purin-8-one;
9-(1-acetylpiperidin-4-yl)-7-methyl-2-((7-methylquinoxalin-6-yl)amino)-7,9-dihydro-8H-purin-8-one;
9-(1-acetylpiperidin-4-yl)-7-methyl-2-((7-methylquinazolin-6-yl)amino)-7,9-dihydro-8H-purin-8-one;
9-(1-acetylpiperidin-4-yl)-2-((2,7-dimethylquinoxalin-6-yl)amino)-7-methyl-7,9-dihydro-8H-purin-8-one;
9-(1-acetylpiperidin-4-yl)-2-((3,7-dimethylquinoxalin-6-yl)amino)-7-methyl-7,9-dihydro-8H-purin-8-one;
9-((1r,4r)-4-hydroxycyclohexyl)-7-methyl-2-((7-methylquinolin-6-yl)amino)-7,9-dihydro-8H-purin-8-one;
9-((1r,4r)-4-hydroxycyclohexyl)-7-methyl-2-((7-methylcinnolin-6-yl)amino)-7,9-dihydro-8H-purin-8-one;
2-((4,7-dimethylquinolin-6-yl)amino)-9-((1r,4r)-4-hydroxycyclohexyl)-7-methyl-7,9-dihydro-8H-purin-8-one;
9-((1r,4r)-4-hydroxycyclohexyl)-2-((4-methoxy-7-methylquinolin-6-yl)amino)-7-methyl-7,9-dihydro-8H-purin-8-one;
9-((1r,4r)-4-hydroxycyclohexyl)-7-methyl-2-((7-methylquinoxalin-6-yl)amino)-7,9-dihydro-8H-purin-8-one;
9-((1s,4s)-4-hydroxycyclohexyl)-7-methyl-2-((7-methylquinolin-6-yl)amino)-7,9-dihydro-8H-purin-8-one;
9-((1s,4s)-4-hydroxycyclohexyl)-7-methyl-2-((7-methylcinnolin-6-yl)amino)-7,9-dihydro-8H-purin-8-one;
9-((1s,4s)-4-hydroxycyclohexyl)-7-methyl-2-((7-methylquinoxalin-6-yl)amino)-7,9-dihydro-8H-purin-8-one;
9-((1s,4s)-4-hydroxy-4-methylcyclohexyl)-7-methyl-2-((7-methylquinolin-6-yl)amino)-7,9-dihydro-8H-purin-8-one;
9-((1r,4r)-4-hydroxy-4-methylcyclohexyl)-7-methyl-2-((7-methylquinolin-6-yl)amino)-7,9-dihydro-8H-purin-8-one;

9-((1s,4s)-4-hydroxy-4-methylcyclohexyl)-7-methyl-2-((7-methylcinnolin-6-yl)amino)-7,9-dihydro-8H-purin-8-one;
9-((1r,4r)-4-hydroxy-4-methylcyclohexyl)-7-methyl-2-((7-methylcinnolin-6-yl)amino)-7,9-dihydro-8H-purin-8-one;
9-((1r,4r)-4-hydroxy-4-methylcyclohexyl)-7-methyl-2-((7-methylquinoxalin-6-yl)amino)-7,9-dihydro-8H-purin-8-one;
9-((1s,4s)-4-hydroxy-4-methylcyclohexyl)-7-methyl-2-((7-methylquinoxalin-6-yl)amino)-7,9-dihydro-8H-purin-8-one;
9-((1s,4s)-4-hydroxy-1-methylcyclohexyl)-7-methyl-2-((7-methylquinoxalin-6-yl)amino)-7,9-dihydro-8H-purin-8-one;
(S)-7-methyl-2-((7-methylcinnolin-6-yl)amino)-9-(tetrahydrofuran-3-yl)-7,9-dihydro-8H-purin-8-one;
(S)-7-methyl-2-((7-methylquinoxalin-6-yl)amino)-9-(tetrahydrofuran-3-yl)-7,9-dihydro-8H-purin-8-one;
(R)-7-methyl-2-((7-methylcinnolin-6-yl)amino)-9-(tetrahydrofuran-3-yl)-7,9-dihydro-8H-purin-8-one;
(R)-7-methyl-2-((7-methylquinoxalin-6-yl)amino)-9-(tetrahydrofuran-3-yl)-7,9-dihydro-8H-purin-8-one;
(R)-7-methyl-2-((7-methylcinnolin-6-yl)amino)-9-(tetrahydro-2H-pyran-3-yl)-7,9-dihydro-8H-purin-8-one;
(R)-7-methyl-2-((7-methylquinoxalin-6-yl)amino)-9-(tetrahydro-2H-pyran-3-yl)-7,9-dihydro-8H-purin-8-one;
(S)-7-methyl-2-((7-methylcinnolin-6-yl)amino)-9-(tetrahydro-2H-pyran-3-yl)-7,9-dihydro-8H-purin-8-one;
(S)-7-methyl-2-((7-methylquinoxalin-6-yl)amino)-9-(tetrahydro-2H-pyran-3-yl)-7,9-dihydro-8H-purin-8-one;
7-methyl-2-((7-methylcinnolin-6-yl)amino)-9-(tetrahydro-2H-pyran-4-yl)-7,9-dihydro-8H-purin-8-one;
7-methyl-2-((7-methylquinolin-6-yl)amino)-9-(tetrahydro-2H-pyran-4-yl)-7,9-dihydro-8H-purin-8-one;
7-methyl-2-((7-methylquinoxalin-6-yl)amino)-9-(tetrahydro-2H-pyran-4-yl)-7,9-dihydro-8H-purin-8-one;
7-methyl-2-((7-methylquinazolin-6-yl)amino)-9-(tetrahydro-2H-pyran-4-yl)-7,9-dihydro-8H-purin-8-one;
2-((2,7-dimethylquinoxalin-6-yl)amino)-7-methyl-9-(tetrahydro-2H-pyran-4-yl)-7,9-dihydro-8H-purin-8-one;
2-((3,7-dimethylquinoxalin-6-yl)amino)-7-methyl-9-(tetrahydro-2H-pyran-4-yl)-7,9-dihydro-8H-purin-8-one;
9-(1,1-dioxidotetrahydro-2H-thiopyran-4-yl)-7-methyl-2-((7-methylquinolin-6-yl)amino)-7,9-dihydro-8H-purin-8-one;
7-methyl-2-((7-methylquinolin-6-yl)amino)-9-(oxetan-3-yl)-7,9-dihydro-8H-purin-8-one;
7-methyl-2-((7-methylquinolin-6-yl)amino)-9-(piperidin-4-yl)-7,9-dihydro-8H-purin-8-one;
9-((3S,4R)-3-fluoropiperidin-4-yl)-7-methyl-2-((7-methylquinolin-6-yl)amino)-7,9-dihydro-8H-purin-8-one;
9-((1s,4s)-4-amino-4-methylcyclohexyl)-7-methyl-2-((7-methylquinolin-6-yl)amino)-7,9-dihydro-8H-purin-8-one;
9-((1r,4r)-4-amino-4-methylcyclohexyl)-7-methyl-2-((7-methylquinolin-6-yl)amino)-7,9-dihydro-8H-purin-8-one;
(R)-7-methyl-9-(1-methylpyrrolidin-3-yl)-2-((7-methylquinolin-6-yl)amino)-7,9-dihydro-8H-purin-8-one;
(S)-7-methyl-9-(1-methylpyrrolidin-3-yl)-2-((7-methylquinolin-6-yl)amino)-7,9-dihydro-8H-purin-8-one;
7-methyl-2-((7-methylcinnolin-6-yl)amino)-9-(1-methylpiperidin-4-yl)-7,9-dihydro-8H-purin-8-one;
7-methyl-9-(1-methylpiperidin-4-yl)-2-((7-methylquinolin-6-yl)amino)-7,9-dihydro-8H-purin-8-one;
7-methyl-9-(1-methylpiperidin-4-yl)-2-((7-methylquinoxalin-6-yl)amino)-7,9-dihydro-8H-purin-8-one;
9-((3S,4R)-3-fluoro-1-methylpiperidin-4-yl)-7-methyl-2-((7-methylquinolin-6-yl)amino)-7,9-dihydro-8H-purin-8-one;
7-methyl-2-((7-methylquinolin-6-yl)amino)-9-(1-(oxetan-3-yl)piperidin-4-yl)-7,9-dihydro-8H-purin-8-one;
9-(1-(2-hydroxyethyl)piperidin-4-yl)-7-methyl-2-((7-methylquinolin-6-yl)amino)-7,9-dihydro-8H-purin-8-one;
9-(1-(2-methoxyethyl)piperidin-4-yl)-7-methyl-2-((7-methylquinolin-6-yl)amino)-7,9-dihydro-8H-purin-8-one;
9-(1-ethylpiperidin-4-yl)-7-methyl-2-((7-methylquinolin-6-yl)amino)-7,9-dihydro-8H-purin-8-one;
9-(1-acetylpiperidin-4-yl)-7-methyl-2-((7-methylquinolin-6-yl)amino)-7,9-dihydro-8H-purin-8-one; and
9-((3R,4R)-4-fluoropyrrolidin-3-yl)-7-methyl-2-((7-methylquinolin-6-yl)amino)-7,9-dihydro-8H-purin-8-one.

11. The compound of Formula (I) as claimed in claim 1, wherein the compound is 9-((3R,4R)-4-fluoropyrrolidin-3-yl)-7-methyl-2-((7-methylquinolin-6-yl)amino)-7,9-dihydro-8H-purin-8-one or a pharmaceutically acceptable salt thereof.

12. The compound of Formula (I) as claimed in claim 1, wherein the compound is 9-((3R,4R)-4-fluoropyrrolidin-3-yl)-7-methyl-2-((7-methylquinolin-6-yl)amino)-7,9-dihydro-8H-purin-8-one.

13. A crystalline compound of Formula (I), as claimed in claim 1, wherein the compound is 9-((3R,4R)-4-fluoropyrrolidin-3-yl)-7-methyl-2-((7-methylquinolin-6-yl)amino)-7,9-dihydro-8H-purin-8-one.

14. A crystalline compound of Formula (I), as claimed in claim 13, wherein the compound has an XRPD substantially as shown in FIG. 5 as measured using CuKα radiation.

15. A crystalline compound of Formula (I), as claimed in claim 1, wherein the compound is 7-methyl-9-(1-methylpiperidin-4-yl)-2-((7-methylquinolin-6-yl)amino)-7,9-dihydro-8H-purin-8-one.

16. A crystalline compound of Formula (I), as claimed in claim 15, wherein the compound has an XRPD substantially as shown in FIG. 1 as measured using CuKα radiation.

17. A crystalline compound of Formula (I), as claimed in claim 1, wherein the compound is (S)-7-methyl-2-((7-methylcinnolin-6-yl)amino)-9-(tetrahydrofuran-3-yl)-7,9-dihydro-8H-purin-8-one.

18. A crystalline compound of Formula (I), as claimed in claim 17, wherein the compound has an XRPD substantially as shown in FIG. 3 as measured using CuKα radiation.

19. A pharmaceutical composition which comprises a compound of Formula (I), or a pharmaceutically acceptable salt thereof, as claimed in claim 1, and at least one pharmaceutically acceptable excipient.

20. A method for treatment of cancer in a warm-blooded animal in need of such treatment, which comprises administering to said warm-blooded animal a therapeutically effective amount of a compound of Formula (I), or a pharmaceutically acceptable salt thereof, as claimed in claim 1.

21. The method for treatment of cancer as claimed in claim 20, wherein the compound of Formula (I), or a pharmaceutically acceptable salt thereof, is administered in combination with radiotherapy.

22. The method for treatment of cancer as claimed in claim 20, wherein the compound of Formula (I), or a pharmaceutically acceptable salt thereof, is administered in combination with an anti-tumour substance selected from the group consisting of doxorubicin, liposomal doxorubicin, olaparib, AZD6738 and AZD0156.

* * * * *